United States Patent
Jacoby et al.

(10) Patent No.: US 10,711,283 B2
(45) Date of Patent: *Jul. 14, 2020

(54) PRIMARY CELL GENE EDITING

(71) Applicant: PACT PHARMA, INC., South San Francisco, CA (US)

(72) Inventors: Kyle Jacoby, Burlingame, CA (US); Alex Franzusoff, El Granada, CA (US)

(73) Assignee: PACT PHARMA, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/782,450

(22) Filed: Feb. 5, 2020

(65) Prior Publication Data
US 2020/0181650 A1 Jun. 11, 2020

Related U.S. Application Data

(63) Continuation of application No. 16/552,714, filed on Aug. 27, 2019, now Pat. No. 10,584,357, which is a continuation of application No. PCT/US2018/058230, filed on Oct. 30, 2018.

(60) Provisional application No. 62/579,113, filed on Oct. 30, 2017, provisional application No. 62/579,114, filed on Oct. 30, 2017.

(51) Int. Cl.
| | |
|---|---|
| *C12N 15/90* | (2006.01) |
| *C12N 15/62* | (2006.01) |
| *C12N 15/85* | (2006.01) |
| *C12N 15/113* | (2010.01) |
| *C07K 14/725* | (2006.01) |
| *A61K 35/17* | (2015.01) |

(52) U.S. Cl.
CPC .............. *C12N 15/90* (2013.01); *A61K 35/17* (2013.01); *C07K 14/7051* (2013.01); *C12N 15/113* (2013.01); *C12N 15/62* (2013.01); *C12N 15/85* (2013.01); *C12N 15/907* (2013.01); *C07K 2319/02* (2013.01); *C07K 2319/50* (2013.01); *C12N 2310/20* (2017.05); *C12N 2310/315* (2013.01); *C12N 2310/344* (2013.01); *C12N 2310/346* (2013.01); *C12N 2320/51* (2013.01)

(58) Field of Classification Search
CPC .................................................. C12N 15/907
See application file for complete search history.

(56) References Cited

U.S. PATENT DOCUMENTS

| | | | |
|---|---|---|---|
| 7,709,224 B2 | 5/2010 | Fang et al. | |
| 8,895,020 B2 | 11/2014 | Hansen et al. | |
| 8,992,937 B2 | 3/2015 | Hansen et al. | |
| 9,540,657 B2 | 1/2017 | Yu et al. | |
| 10,584,357 B2 * | 3/2020 | Jacoby | C12N 15/90 |
| 2018/0289741 A1 | 10/2018 | Nicholson et al. | |

FOREIGN PATENT DOCUMENTS

| | | |
|---|---|---|
| WO | WO 2014/153470 A2 | 9/2014 |
| WO | WO 2016/069282 A1 | 5/2016 |
| WO | WO 2016/071343 A1 | 5/2016 |
| WO | WO 2017/062451 A1 | 4/2017 |
| WO | WO 2017/156484 A1 | 9/2017 |
| WO | WO 2019/084552 A1 | 5/2019 |

OTHER PUBLICATIONS

U.S. Appl. No. 16/552,714 (2019/0376091 A1), filed Aug. 27, 2019 (Dec. 12, 2019).
U.S. Appl. No. 16/552,714, Jan. 31, 2020 Notice of Allowance.
U.S. Appl. No. 16/552,714, Nov. 27, 2019 Response to Non-Final Office Action.
U.S. Appl. No. 16/552,714, Nov. 21, 2019 Applicant Initiated Interview Summary.
U.S. Appl. No. 16/552,714, Oct. 23, 2019 Non-Final Office Action.
Barsov et al., "Transduction of SIV-Specific TCR Genes into Rhesus Macaque CD8+ T Cells Conveys the Ability to Suppress SIV Replication," PLoS ONE, 6(8):e23703 (2011).
Chung et al., "Functional three-domain single-chain T-cell receptors," Proc. Natl. Acad. Sci., 91:12654-12658 (1994).
Foley et al., "HCV T Cell Receptor Chain Modifications to Enhance Expression, Pairing, and Antigen Recognition in T Cells for Adoptive Transfer," Molecular Therapy—Oncolytics, 5:105-115 (2017).
Kitz, "Generation and analysis of T cell receptor transgenic rats to model CNS autoimmunity," PhD Dissertation 2013. Georg-August University School of Science (GAUSS) Gottingen, Germany. (125 pages).
Knipping et al., "Genome-wide Specificity of Highly Efficient TALENs and CRISPR/Cas9 for T Cell Receptor Modification," Molecular Therapy—Methods and Clinical Development, 4:213-224 (2017).
Okamoto et al., "A Promising Vector for TCR Gene Therapy: Differential Effect of siRNA, 2A Peptide, and Disulfide Bond on the Introduced TCR Expression," Molecular Therapy—Nucleic Acids, 1:e63 (2012).
Schober et al., "Orthotopic replacement of T-cell receptor α- and β-chains with preservation of near-physiological T-cell function," Nature Biomedical Engineering, (2019).

\* cited by examiner

*Primary Examiner* — Scott Long
(74) *Attorney, Agent, or Firm* — Baker Botts L.L.P.

(57) ABSTRACT

Methods and compositions are provided for nuclease-mediated gene editing of primary cells without the use of viral mediated delivery. Methods of treatments using edited primary cells are also provided.

25 Claims, 40 Drawing Sheets
Specification includes a Sequence Listing.

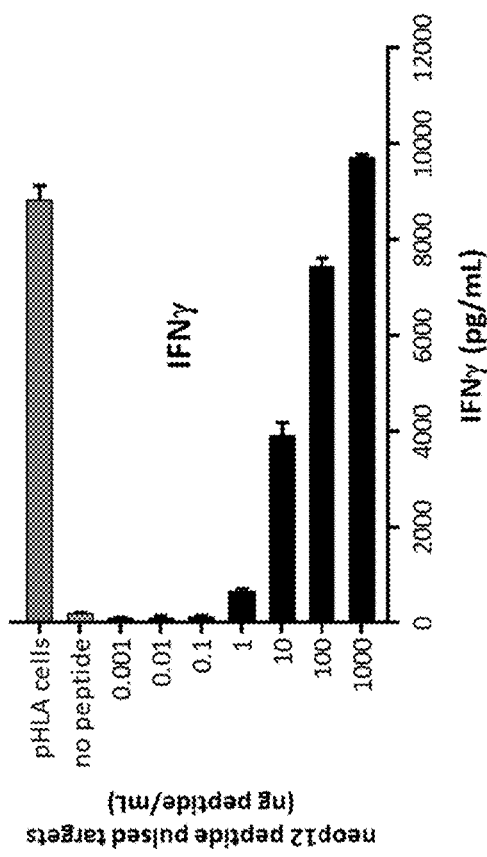
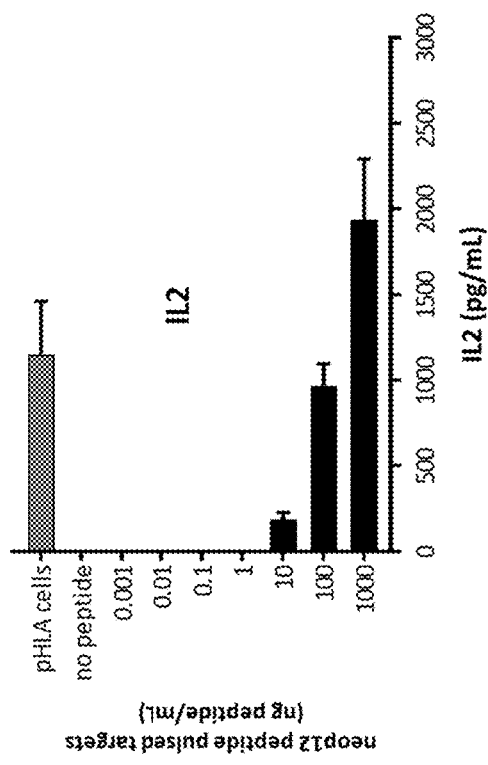
Fig. 26A
Fig. 26B

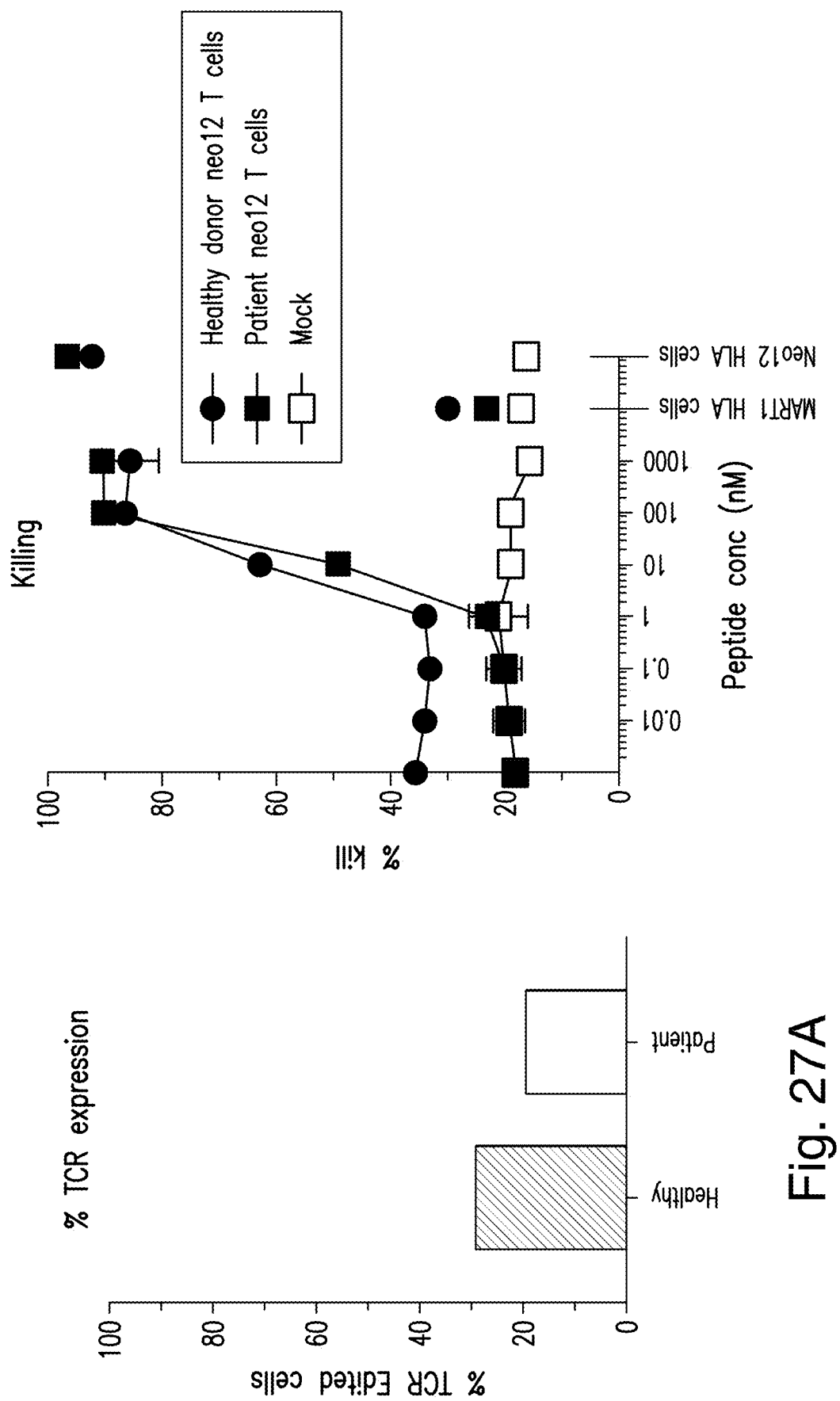

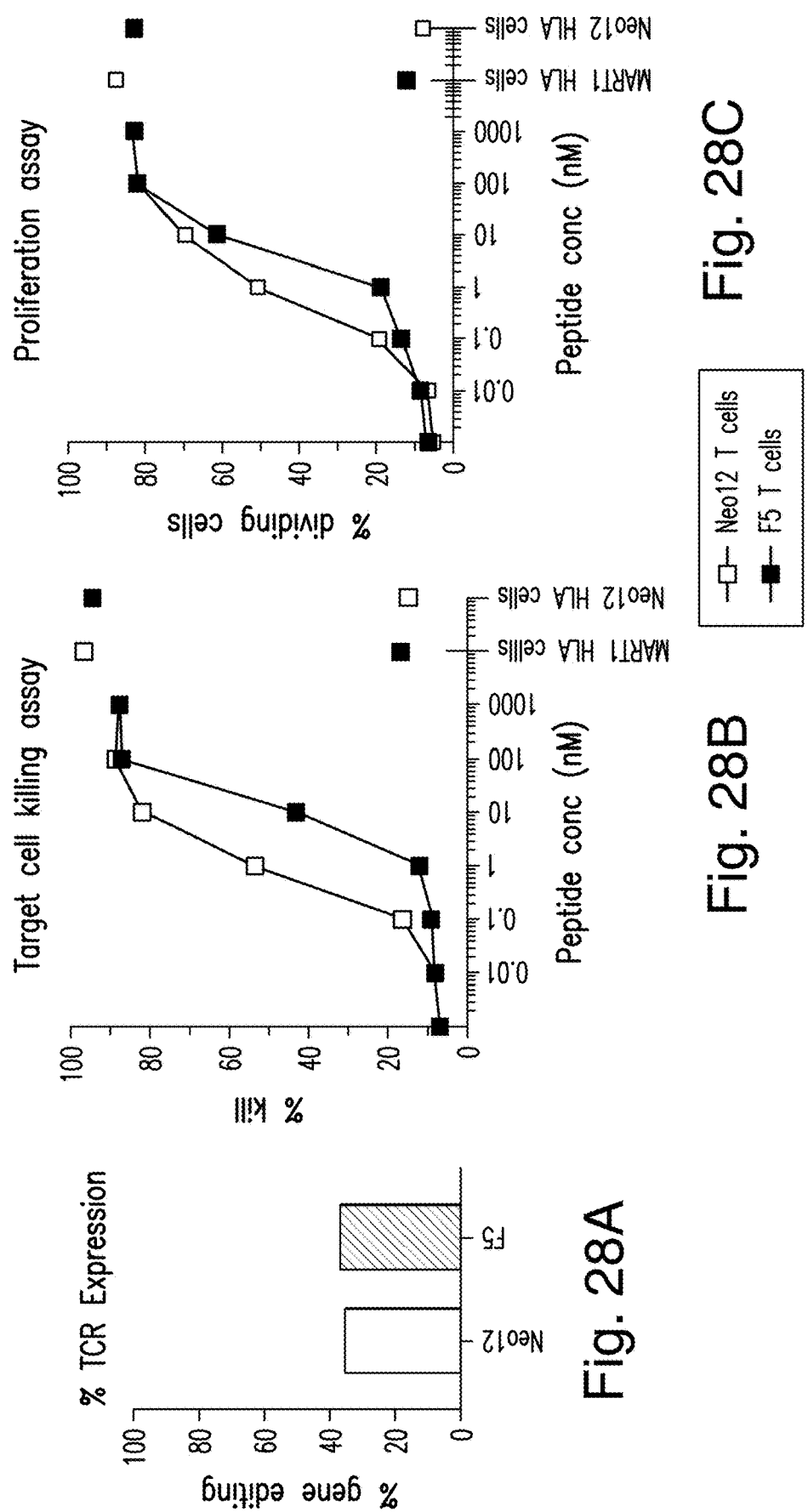

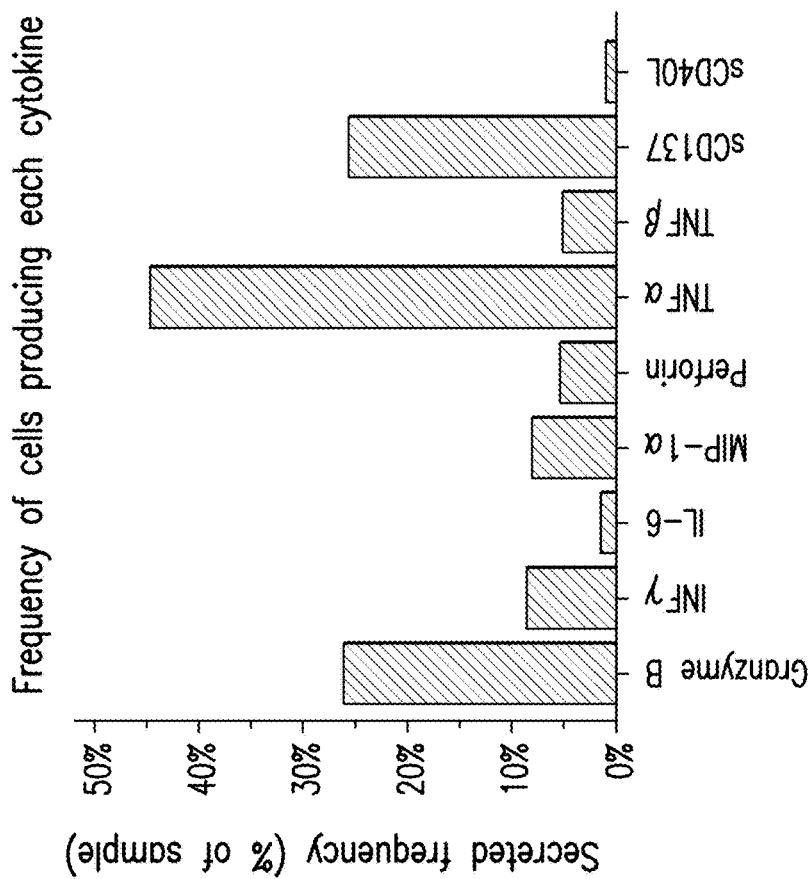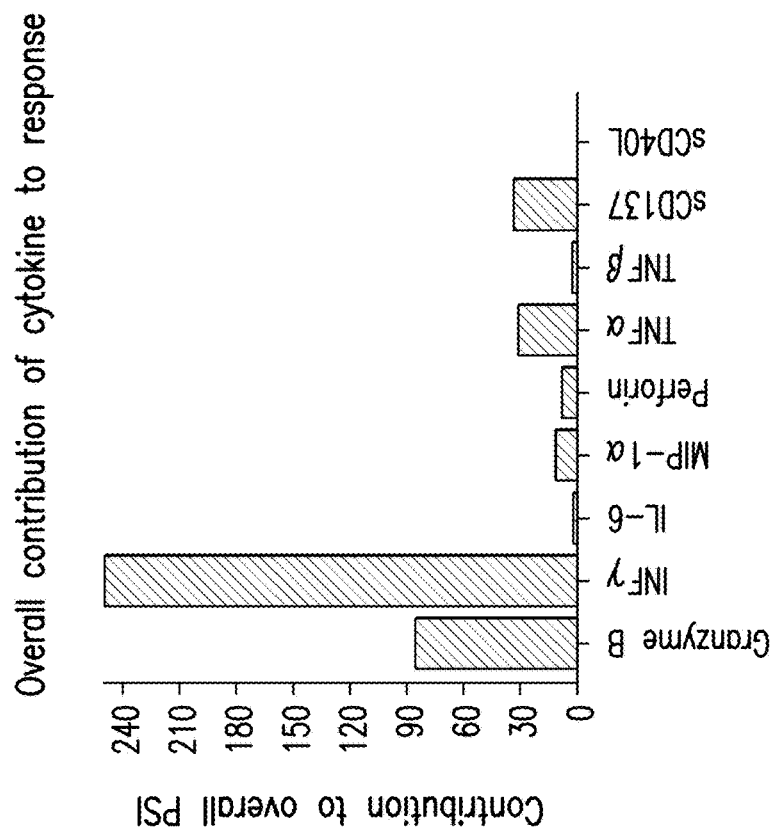
Fig. 30C

```
SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgctaatcct ccggcaaacc                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcttcaaca tcgccagcct                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagccatctg ttgtttgccc                                               20
```

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agctttctgg cgtccttaga at                                              22

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Leu Ala Gly Ile Gly Ile Leu Thr Val
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Leu Thr His Arg Val Asp Val Ile
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Leu Leu Met Trp Ile Thr Gln Val
1               5

<210> SEQ ID NO 8
<211> LENGTH: 4373
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ccgcctaatg agcgggcttt ttttttggctt gttgtccaca accgttaaac cttaaaagct     60
ttaaaagcct tatatattct ttttttttctt ataaaactta aaaccttaga ggctatttaa    120
gttgctgatt tatattaatt ttattgttca aacatgagag cttagtacgt gaaacatgag    180
agcttagtac gttagccatg agagcttagt acgttagcca tgagggttta gttcgttaaa    240
catgagagct tagtacgtta aacatgagag cttagtacgt actatcaaca ggttgaactg    300
ctgatccacg ttgtggtaga attggtaaag agagtcgtgt aaaatatcga gttcgcacat    360

-continued

```
cttgttgtct gattattgat ttttggcgaa accatttgat catatgacaa gatgtgtatc    420
taccttaact taatgatttt gataaaaatc attaggtacc acattaaaaa cacaaaatcc    480
tacggaaata ctgaagaatg agtctcagca ctaaggaaaa gcctccagca gctcctgctt    540
tctgagggtg aaggatagac gctgtggctc tgcatgactc actagcactc tatcacggcc    600
atattctggc agggtcagtg gctccaacta acatttgttt ggtactttac agtttattaa    660
atagatgttt atatggagaa gctctcattt ctttctcaga agagcctggc taggaaggtg    720
gatgaggcac catattcatt ttgcaggtga aattcctgag atgtaaggag ctgctgtgac    780
ttgctcaagg ccttatatcg agtaaacggt agtgctgggg cttagacgca ggtgttctga    840
tttatagttc aaaacctcta tcaatgagag agcaatctcc tggtaatgtg atagatttcc    900
caacttaatg ccaacatacc ataaacctcc cattctgcta atgcccagcc taagttgggg    960
agaccactcc agattccaag atgtacagtt tgctttgctg ggccttttc ccatgcctgc    1020
ctttactctg ccagagttat attgctgggg ttttgaagaa gatcctatta aataaaagaa    1080
taagcagtat tattaagtag ccctgcattt caggtttcct tgagtggcag gccaggcctg    1140
gccgtgaacg ttcactgaaa tcatggcctc ttggccaaga ttgatagctt gtgcctgtcc    1200
ctgagtccca gtccatcacg agcagctggt ttctaagatg ctatttcccg tataaagcat    1260
gagaccgtga cttgccagcc ccacagagcc ccgcccttgt ccatcactgg catctggact    1320
ccagcctggg ttggggcaaa gagggaaatg agatcatgtc ctaaccctga tcctcttgtc    1380
ccacagatat ccagaaccct gaccctgccg tgtaccagct gagagactct aaatccagtg    1440
acaagtctgt ctgcctattc gaattcggct ccggagccac taacttctcc ctgttgaaac    1500
aggctggcga tgttgaagaa aaccccggtc ctatggccca gtccaagcac ggcctgacca    1560
aggagatgac catgaagtac cgcatggagg gctgcgtgga cggccacaag ttcgtgatca    1620
ccggcgaggg catcggctac cccttcaagg gcaagcaggc catcaacctg tgcgtggtgg    1680
agggcggccc cttgcccttc gccgaggaca tcttgtccgc cgccttcatg tacggcaacc    1740
gcgtgttcac cgagtacccc caggacatcg tggactactt caagaactcc tgccccgccg    1800
gatacacctg ggaccgctcc ttcctgttcg aggacggcgc cgtgtgcatc tgcaacgccg    1860
acatcaccgt cagcgtggag gagaactgca tgtaccacga gtccaagttc tacggcgtga    1920
acttccccgc cgacggcccc gtgatgaaga agatgaccga caactgggag ccctcctgcg    1980
agaagatcat ccccgtgccc aagcagggca tcttgaaggg cgacgtcagc atgtacctgc    2040
tgctgaagga cggtggccgc ttgcgctgcc agttcgacac cgtgtacaag gccaagtccg    2100
tgccccgcaa gatgcccgac tggcacttca tccagcacaa gctgacccgc gaggaccgca    2160
gcgacgccaa gaaccagaag tggcacctga ccgagcacgc catcgcctcc ggctccgcct    2220
tgcccgggc caagcggggc agcggcgcca ccaacttcag cctgctgaag caggccggcg    2280
acgtggagga gaaccccggc cctatggggg caggtccac cggccgcgct atggacgggc    2340
cgcgcctgct gctgttgctg cttctgggg tgtcccttgg aggtgccaag gaggcatgcc    2400
ccacaggcct gtacacacac agcggtgagt gctgcaaagc ctgcaacctg ggcgagggtg    2460
tggcccagcc ttgtggagcc aaccagaccg tgtgtgagcc ctgcctggac agcgtgacgt    2520
tctccgacgt ggtgagcgcg accgagccgt gcaagccgtg caccgagtgc gtgggctcc    2580
agagcatgtc ggcgccgtgc gtggaggccg acgacgccgt gtgccgctgc gcctacggct    2640
actaccagga tgagacgact gggcgctgcg aggcgtgccg cgtgtgcgag gcgggctcgg    2700
gcctcgtgtt ctcctgccag gacaagcaga acaccgtgtg cgaggagtgc cccgacggca    2760
```

| | |
|---|---|
| cgtattccga cgaggccaac cacgtggacc cgtgcctgcc ctgcaccgtg tgcgaggaca | 2820 |
| ccgagcgcca gctccgcgag tgcacacgct gggccgacgc cgagtgcgag gagatccctg | 2880 |
| gccgttggat tacacggtcc acaccccag agggctcgga cagcacagcc cccagcaccc | 2940 |
| aggagcctga ggcacctcca gaacaagacc tcatagccag cacggtggca ggtgtggtga | 3000 |
| ccacagtgat gggcagctcc cagcccgtgg tgacccgagg caccaccgac aacctcatcc | 3060 |
| ctgtctattg ctccatcctg gctgctgtgg ttgtgggtct tgtggcctac atagccttca | 3120 |
| agaggtaact cgagtgtgcc ttctagttgc cagccatctg ttgtttgccc ctcccccgtg | 3180 |
| ccttccttga ccctggaagg tgccactccc actgtccttt cctaataaaa tgaggaaatt | 3240 |
| gcatcgcatt gtctgagtag gtgtcattct attctggggg gtggggtggg gcaggacagc | 3300 |
| aaggggggagg attgggaaga caatagcagg catgctgggg atgcggtggg ctctatggcg | 3360 |
| cggccgcacc gattttgatt ctcaaacaaa tgtgtcacaa agtaaggatt ctgatgtgta | 3420 |
| tatcacagac aaaactgtgc tagacatgag gtctatggac ttcaagagca acagtgctgt | 3480 |
| ggcctggagc aacaaatctg actttgcatg tgcaaacgcc ttcaacaaca gcattattcc | 3540 |
| agaagacacc ttcttcccca gcccaggtaa gggcagcttt ggtgccttcg caggctgttt | 3600 |
| ccttgcttca ggaatggcca ggttctgccc agagctctgg tcaatgatgt ctaaaactcc | 3660 |
| tctgattggt ggtctcggcc ttatccattg ccaccaaaac cctcttttta ctaagaaaca | 3720 |
| gtgagccttg ttctggcagt ccagagaatg acacgggaaa aaagcagatg aagagaaggt | 3780 |
| ggcaggagag ggcacgtggc ccagcctcag tctctccaac tgagttcctg cctgcctgcc | 3840 |
| tttgctcaga ctgtttgccc cttactgctc ttctaggcct cattctaagc cccttctcca | 3900 |
| agttgcctct ccttatttct ccctgtctgc caaaaaatct ttcccagctc actaagtcag | 3960 |
| tctcacgcag tcactcatta acccaccaat cactgattgt gccggacat gaatgcacca | 4020 |
| ggtgttgaag tggaggaatt aaaaagtcag atgaggggtg tgcccagagg aagcaccatt | 4080 |
| ctagttgggg gagcccatct gtcagctggg aaaagtccaa ataacttcag attggaatgt | 4140 |
| gttttaactc agggttgaga aaacagctac cttcaggaca aaagtcaggg aagggctctc | 4200 |
| tgaagaaatg ctacttgaag ataccagccc taccaagggc agggagagga ccctatagag | 4260 |
| gcctgggaca ggagctcaat gagaaaggag aagagcagca ggcatgagtt gaatgaagga | 4320 |
| ggcagggccg ggtcacaggg ccttctaggc catgagaggg tagacaggct agc | 4373 |

<210> SEQ ID NO 9
<211> LENGTH: 4787
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9

| | |
|---|---|
| ccgcctaatg agcgggcttt ttttggctt gttgtccaca accgttaaac cttaaaagct | 60 |
| ttaaaagcct tatatattct ttttttttctt ataaaactta aaaccttaga ggctatttaa | 120 |
| gttgctgatt tatattaatt ttattgttca aacatgagag cttagtacgt gaaacatgag | 180 |
| agcttagtac gttagccatg agagcttagt acgttagcca tgagggttta gttcgttaaa | 240 |
| catgagagct tagtacgtta acatgagag cttagtacgt actatcaaca ggttgaactg | 300 |
| ctgatccacg ttgtggtaga attggtaaag agagtcgtgt aaaatatcga gttcgcacat | 360 |
| cttgttgtct gattattgat ttttggcgaa accatttgat catatgacaa gatgtgtatc | 420 |

```
taccttaact taatgatttt gataaaaatc attaggtacc tggttgctga ctaattgaga    480
tgcatgcttt gcatacttct gcctgctggg gagcctgggg actttccaca ccccatggac    540
attaaaaaca caaatcccta cggaaatact gaagaatgag tctcagcact aaggaaaagc    600
ctccagcagc tcctgctttc tgagggtgaa ggatagacgc tgtggctctg catgactcac    660
tagcactcta tcacggccat attctggcag ggtcagtggc tccaactaac atttgtttgg    720
tactttacag tttattaaat agatgtttat atggagaagc tctcatttct ttctcagaag    780
agcctggcta ggaaggtgga tgaggcacca tattcatttt gcaggtgaaa ttcctgagat    840
gtaaggagct gctgtgactt gctcaaggcc ttatatcgag taaacggtag tgctggggct    900
tagacgcagg tgttctgatt tatagttcaa aacctctatc aatgagagag caatctcctg    960
gtaatgtgat agatttccca acttaatgcc aacataccat aaacctccca ttctgctaat   1020
gcccagccta agttggggag accactccag attccaagat gtacagtttg ctttgctggg   1080
ccttttttccc atgcctgcct ttactctgcc agagttatat tgctggggtt ttgaagaaga   1140
tcctattaaa taaaagaata agcagtatta ttaagtagcc ctgcatttca ggtttccttg   1200
agtggcaggc caggcctggc cgtgaacgtt cactgaaatc atggcctctt ggccaagatt   1260
gatagcttgt gcctgtccct gagtcccagt ccatcacgag cagctggttt ctaagatgct   1320
atttcccgta taaagcatga gaccgtgact tgccagcccc acagagcccc gcccttgtcc   1380
atcactggca tctggactcc agcctgggtt ggggcaaaga gggaaatgag atcatgtcct   1440
aaccctgatc ctcttgtccc acagatatcc agaaccctga ccctgccgtg taccagctga   1500
gagactctaa atccagtgac aagtctgtct gcctattcga attcggctcc ggagccacta   1560
acttctccct gttgaaacag gctggcgatg ttgaagaaaa ccccggtcct atggccaccg   1620
gctctagaac aagcctgctg ctcgcttttg gcctgctctg cctgccatgt ctccaagagg   1680
gatctgccgg cattacacag gcccctacat ctcagattct ggccgctggc agacggatga   1740
cactgagatg cacccaggac atgagacaca acgccatgta ctggtatcgg caggacctcg   1800
gcctgggact gagactgatc cactactcta ataccgccgg caccaccggc aaaggcgaag   1860
tgcctgatgg ctactccgtg tccagagcca ataccgacga cttcccactg acactggcct   1920
ctgctgtgcc tagccagacc tccgtgtact ctgtgccag cagcctgtcc tttggcaccg   1980
aggcctttt cggccaaggc accagactga ccgtggtgga agatctgaac aaagtgttcc   2040
ctccagaggt ggccgtgttc gagccttctg aggccgagat cagccacaca cagaaagcca   2100
cactcgtgtg tctggctacc ggcttcttcc ccgatcacgt ggaactgtct tggtgggtca   2160
acggcaaaga ggtgcacagc ggcgtcagca cagatcccca gcctctgaaa gaacagcccg   2220
ctctgaacga cagccgctac tgcctgtcta gcagactgag agtgtccgcc accttctggc   2280
agaaccccag aaaccacttc agatgccagg tccagttcta cggcctgagc gagaacgatg   2340
agtggaccca agagagagcc aagcctgtga cacagatcgt gtctgccgaa gcctgggca   2400
gagccgattg tggctttacc agcgtgtcat accagcaggg cgtgctgtct gccaccatcc   2460
tgtatgagat cctgctcggc aaggccacac tgtacgctgt gctggtgtct gctctggtgc   2520
tgatggctat ggtcaagcgg aaggacttcc gggccaagcg gggcagcggc gccaccaact   2580
tcagcctgct gaagcaggcc ggcgacgtgg aggagaaccc cggccctatg ccacaggca   2640
gcagaacatc tctgctgctg gccttcggac tgctgtgtct gccttggctg caagaggctt   2700
ccgcccagca gaaagaggtg gaacagaata gcggccctct gagcgttcca gaaggcgcta   2760
```

```
tcgccagcct gaactgcacc tacagcgata gaggcagcca gagcttcttc tggtacagac    2820
agtacagcgg caagagcccc gagctgatca tgttcatcta cagcaacggc gacaaagagg    2880
acggccggtt tacagcccag ctgaacaagg ccagccaata cgtgtccctg ctgatcagag    2940
atagccagcc tagcgacagc gccacctatc tgtgcgccgt gaattttggc ggcggaaagc    3000
tgatctttgg ccagggcaca gagctgagcg tgaagcccaa cattcagaac cccgatcctg    3060
ccgtgtacca gctgagagac agcaagagca gcgacaagag cgtgtgcctg ttcaccgact    3120
tcgacagcca gaccaacgtg tcccagagca aggacagcga cgtgtacatc accgacaaga    3180
ccgtgctgga catgcggagc atggacttca gagcaacag cgccgtggcc tggtccaaca    3240
agagcgattt cgcctgcgcc aacgccttca acaacagcat tatccccgag gacacattct    3300
tcccaagtcc tgagagcagc tgcgacgtga agctggtgga aaagagcttc gagacagaca    3360
ccaacctgaa cttccagaac ctgtccgtga tcggcttccg catcctgctg ctgaaagtgg    3420
ccggcttcaa cctgctgatg accctgagac tgtggtccag ctgactcgag tgtgccttct    3480
agttgccagc catctgttgt ttgcccctcc cccgtgcctt ccttgaccct ggaaggtgcc    3540
actcccactg tccttcctta ataaaatgag gaaattgcat cgcattgtct gagtaggtgt    3600
cattctattc tggggggtgg ggtggggcag gacagcaagg gggaggattg ggaagacaat    3660
agcaggcatg ctggggatgc ggtgggctct atggcgcggc cgcaccgatt ttgattctca    3720
aacaaatgtg tcacaaagta aggattctga tgtgtatatc acagacaaaa ctgtgctaga    3780
catgaggtct atggacttca agagcaacag tgctgtggcc tggagcaaca atctgactt    3840 tgcatgtgca aacgccttca acaacagcat tattccagaa gacaccttct tccccagccc    3900
aggtaagggc agctttggtg ccttcgcagg ctgtttcctt gcttcaggaa tggccaggtt    3960
ctgcccagag ctctggtcaa tgatgtctaa aactcctctg attggtggtc tcggccttat    4020
ccattgccac caaaaccctc tttttactaa gaaacagtga gccttgttct ggcagtccag    4080
agaatgacac gggaaaaaag cagatgaaga gaaggtggca ggagagggca cgtggcccag    4140
cctcagtctc tccaactgag ttcctgcctg cctgcctttg ctcagactgt tgcccctta    4200 ctgctcttct aggcctcatt ctaagcccct tctccaagtt gcctctcctt atttctccct    4260
gtctgccaaa aaatctttcc cagctcacta agtcagtctc acgcagtcac tcattaaccc    4320
accaatcact gattgtgccg gcacatgaat gcaccaggtg ttgaagtgga ggaattaaaa    4380
agtcagatga ggggtgtgcc cagaggaagc accattctag ttgggggagc ccatctgtca    4440
gctgggaaaa gtccaaataa cttcagattg gaatgtgttt taactcaggg ttgagaaaac    4500
agctaccttc aggacaaaag tcagggaagg gctctctgaa gaaatgctac ttgaagatac    4560
cagccctacc aagggcaggg agaggaccct atagaggcct gggacaggag ctcaatgaga    4620
aaggagaaga gcagcaggca tgagttgaat gaaggaggca gggccgggtc acagggcctt    4680
ctaggccatg agagggtaga cagggatccg gtgtggaaag tccccaggct ccccagcagg    4740
cagaagtatg caaagcatgc atctcaatta gtcagcaacc agctagc                 4787
```

<210> SEQ ID NO 10
<211> LENGTH: 4197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
ccgcctaatg agcgggcttt ttttttggctt gttgtccaca accgttaaac cttaaaagct    60
ttaaaagcct tatatattct ttttttttctt ataaaactta aaaccttaga ggctatttaa   120
gttgctgatt tatattaatt ttattgttca aacatgagag cttagtacgt gaaacatgag   180
agcttagtac gttagccatg agagcttagt acgttagcca tgagggttta gttcgttaaa   240
catgagagct tagtacgtta aacatgagag cttagtacgt actatcaaca ggttgaactg   300
ctgatccacg ttgtggtaga attggtaaag agagtcgtgt aaaatatcga gttcgcacat   360
cttgttgtct gattattgat ttttggcgaa accatttgat catatgacaa gatgtgtatc   420
taccttaact taatgatttt gataaaaatc attaggtacc tggttgctga ctaattgaga   480
tgcatgcttt gcatacttct gcctgctggg gagcctgggg actttccaca ccccatggac   540
attaaaaaca caaatcctac ggaaatact gaagaatgag tctcagcact aaggaaaagc   600
ctccagcagc tcctgctttc tgagggtgaa ggatagacgc tgtggctctg catgactcac   660
tagcactcta tcacggccat attctggcag ggtcagtggc tccaactaac atttgtttgg   720
tactttacag tttattaaat agatgtttat atggagaagc tctcatttct ttctcagaag   780
agcctggcta ggaaggtgga tgaggcacca tattcatttt gcaggtgaaa ttcctgagat   840
gtaaggagct gctgtgactt gctcaaggcc ttatatcgag taaacggtag tgctggggct   900
tagacgcagg tgttctgatt tatagttcaa aacctctatc aatgagagag caatctcctg   960
gtaatgtgat agatttccca acttaatgcc aacataccat aaacctccca ttctgctaat  1020
gcccagccta agttggggag accactccag attccaagat gtacagtttg ctttgctggg  1080
ccttttttccc atgcctgcct ttactctgcc agagttatat tgctggggtt ttgaagaaga  1140
tcctattaaa taaaagaata agcagtatta ttaagtagcc ctgcatttca ggtttccttg  1200
agtggcaggc caggcctggc cgtgaacgtt cactgaaatc atggcctctt ggccaagatt  1260
gatagcttgt gcctgtccct gagtcccagt ccatcacgag cagctggttt ctaagatgct  1320
atttcccgta taaagcatga gaccgtgact tgccagcccc acagagcccc gcccttgtcc  1380
atcactggca tctggactcc agcctgggtt ggggcaaaga gggaaatgag atcatgtcct  1440
aaccctgatc ctcttgtccc acagatatcc agaaccctga ccctgccgtg taccagctga  1500
gagactctaa atccagtgac aagtctgtct gcctattcga attcggctcc ggagccacta  1560
acttctccct gttgaaacag gctggcgatg ttgaagaaaa ccccggtcct atggccaccg  1620
gctctagaac aagcctgctg ctcgcttttg gcctgctctg cctgccatgt ctccaagagg  1680
gatctgccgg cattacacag gcccctacat ctcagattct ggccgctggc agacggatga  1740
cactgagatg cacccaggac atgagacaca acgccatgta ctggtatcgg caggacctcg  1800
gcctgggact gagactgatc cactactcta ataccgccgg caccaccggc aaaggcgaag  1860
tgcctgatgg ctactccgtg tccagagcca ataccgacga cttcccactg acactggcct  1920
ctgctgtgcc tagccagacc tccgtgtact tctgtgccag cagcctgtcc tttggcaccg  1980
aggcttttt cggccaaggc accagactga ccgtggtgga agatctgaac aaagtgttcc  2040
ctccagaggt ggccgtgttc gagccttctg aggccgagat cagccacaca cagaaagcca  2100
cactcgtgtg tctggctacc ggcttcttcc ccgatcacgt ggaactgtct tggtgggtca  2160
acggcaaaga ggtgcacagc ggcgtcagca cagatcccca gcctctgaaa gaacagcccg  2220
ctctgaacga cagccgctac tgcctgtcta gcagactgag agtgtccgcc accttctggc  2280
agaacccag aaaccacttc agatgccagg tccagttcta cggcctgagc gagaacgatg  2340
agtggaccca gaagagagcc aagcctgtga cacagatcgt gtctgccgaa gcctggggca  2400
```

```
gagccgattg tggctttacc agcgtgtcat accagcaggg cgtgctgtct gccaccatcc    2460
tgtatgagat cctgctcggc aaggccacac tgtacgctgt gctggtgtct gctctggtgc    2520
tgatggctat ggtcaagcgg aaggacttcc gggccaagcg gggcagcggc gccaccaact    2580
tcagcctgct gaagcaggcc ggcgacgtgg aggagaaccc cggccctatg ccacaggca    2640 gcagaacatc tctgctgctg gccttcggac tgctgtgtct gccttggctg caagaggctt    2700
ccgcccagca gaaagaggtg aacagaata gcggccctct gagcgttcca gaaggcgcta    2760
tcgccagcct gaactgcacc tacagcgata gaggcagcca gagcttcttc tggtacagac    2820
agtacagcgg caagagcccc gagctgatca tgttcatcta cagcaacggc gacaaagagg    2880
acggccggtt tacagcccag ctgaacaagg ccagccaata cgtgtccctg ctgatcagag    2940
atagccagcc tagcgacagc gccacctatc tgtgcgccgt gaattttggc ggcggaaagc    3000
tgatctttgg ccagggcaca gagctgagcg tgaagcccaa cattcagaac ccgatcctg    3060 ctgtgtatca gctgcgcgac agcaagagca gcgacaagag cgtgtgtttg ttcaccgatt    3120
ttgattctca aacaaatgtg tcacaaagta aggattctga tgtgtatatc acagacaaaa    3180
ctgtgctaga catgaggtct atggacttca agagcaacag tgctgtggcc tggagcaaca    3240
aatctgactt tgcatgtgca aacgccttca acaacagcat tattccagaa gacaccttct    3300
tccccagccc aggtaagggc agctttggtg ccttcgcagg ctgtttcctt gcttcaggaa    3360
tggccaggtt ctgcccagag ctctggtcaa tgatgtctaa aactcctctg attggtggtc    3420
tcggccttat ccattgccac caaaaccctc tttttactaa gaaacagtga gccttgttct    3480
ggcagtccag agaatgacac gggaaaaaag cagatgaaga aaggtggca ggagagggca    3540 cgtggcccag cctcagtctc tccaactgag ttcctgcctg cctgcctttg ctcagactgt    3600
ttgcccctta ctgctcttct aggcctcatt ctaagcccct tctccaagtt gcctctcctt    3660
atttctccct gtctgccaaa aaatctttcc cagctcacta agtcagtctc acgcagtcac    3720
tcattaaccc accaatcact gattgtgccg gcacatgaat gcaccaggtg ttgaagtgga    3780
ggaattaaaa agtcagatga ggggtgtgcc cagaggaagc accattctag ttggggagc    3840 ccatctgtca gctgggaaaa gtccaaataa cttcagattg aatgtgttt taactcaggg    3900 ttgagaaaac agctaccttc aggacaaaag tcagggaagg gctctctgaa gaaatgctac    3960
ttgaagatac cagccctacc aagggcaggg agaggaccct atagaggcct gggacaggag    4020
ctcaatgaga aaggagaaga gcagcaggca tgagttgaat gaaggaggca gggccgggtc    4080
acagggcctt ctaggccatg agagggtaga cagggatccg gtgtggaaag tccccaggct    4140
ccccagcagg cagaagtatg caaagcatgc atctcaatta gtcagcaacc agctagc    4197
```

<210> SEQ ID NO 11
<211> LENGTH: 4799
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 11

```
ccgcctaatg agcgggcttt ttttggctt gttgtccaca accgttaaac cttaaaagct     60
ttaaaagcct tatatattct ttttttcctt ataaaactta aaaccttaga ggctatttaa    120
gttgctgatt tatattaatt ttattgttca aacatgagag cttagtacgt gaaacatgag    180
agcttagtac gttagccatg agagcttagt acgttagcca tgagggttta gttcgttaaa    240
```

```
catgagagct tagtacgtta aacatgagag cttagtacgt actatcaaca ggttgaactg    300
ctgatccacg ttgtggtaga attggtaaag agagtcgtgt aaaatatcga gttcgcacat    360
cttgttgtct gattattgat ttttggcgaa accatttgat catatgacaa gatgtgtatc    420
taccttaact taatgatttt gataaaaatc attaggtacc tggttgctga ctaattgaga    480
tgcatgcttt gcatacttct gcctgctggg gagcctgggg actttccaca ccccatggac    540
attaaaaaca caaatcctac ggaaatact gaagaatgag tctcagcact aaggaaaagc    600
ctccagcagc tcctgctttc tgagggtgaa ggatagacgc tgtggctctg catgactcac    660
tagcactcta tcacggccat attctggcag ggtcagtggc tccaactaac atttgtttgg    720
tactttacag tttattaaat agatgtttat atggagaagc tctcatttct ttctcagaag    780
agcctggcta ggaaggtgga tgaggcacca tattcatttt gcaggtgaaa ttcctgagat    840
gtaaggagct gctgtgactt gctcaaggcc ttatatcgag taaacggtag tgctggggct    900
tagacgcagg tgttctgatt tatagttcaa aacctctatc aatgagagag caatctcctg    960
gtaatgtgat agatttccca acttaatgcc aacataccat aaacctccca ttctgctaat   1020
gcccagccta agttggggag accactccag attccaagat gtacagtttg ctttgctggg   1080
ccttttttccc atgcctgcct ttactctgcc agagttatat tgctggggtt ttgaagaaga   1140
tcctattaaa taaagaaata agcagtatta ttaagtagcc ctgcatttca ggtttccttg   1200
agtggcaggc caggcctggc cgtgaacgtt cactgaaatc atggcctctt ggccaagatt   1260
gatagcttgt gcctgtccct gagtcccagt ccatcacgag cagctggttt ctaagatgct   1320
atttcccgta taaagcatga gaccgtgact tgccagcccc acagagcccc gcccttgtcc   1380
atcactggca tctggactcc agcctgggtt ggggcaaaga gggaaatgag atcatgtcct   1440
aaccctgatc ctcttgtccc acagatatcc agaaccctga ccctgccgtg taccagctga   1500
gagactctaa atccagtgac aagtctgtct gcctattcga attcggctcc ggagccacta   1560
acttctccct gttgaaacag gctggcgatg ttgaagaaaa ccccggtcct atggccaccg   1620
gctctagaac aagcctgctg ctcgcttttg gcctgctctg cctgccatgt ctccaagagg   1680
gatctgccgg tgtcactcag acccccaaaat tccaggtcct gaagacagga cagagcatga   1740
cactgcagtg tgcccaggat atgaaccatg aatacatgtc ctggtatcga caagacccag   1800
gcatggggct gaggctgatt cattactcag ttggtgctgg tatcactgac caaggagaag   1860
tccccaatgg ctacaatgtc tccagatcaa ccacagagga tttcccgctc aggctgctgt   1920
cggctgctcc ctcccagaca tctgtgtact ctctgtgccag cagttacgtc gggaacaccg   1980
gggagctgtt ttttggagaa ggctctaggc tgaccgtact ggaggacctg aacaaagtgt   2040
tccctccaga ggtggccgtg ttcgagcctt ctgaggccga gatcagccac acacagaaag   2100
ccacactcgt gtgtctggct accggcttct ccccgatca cgtggaactg tcttggtggg   2160
tcaacggcaa agaggtgcac agcggcgtca gcacagatcc ccagcctctg aaagaacagc   2220
ccgctctgaa cgacagccgc tactgcctgt ctagcagact gagagtgtcc gccaccttct   2280
ggcagaaccc cagaaaccac ttcagatgcc aggtccagtt ctacggcctg agcgagaacg   2340
atgagtggac ccagaagaga gccaagcctg tgacacagat cgtgtctgcc gaagcctggg   2400
gcagagccga ttgtggcttt accagcgtgt cataccagca gggcgtgctg tctgccacca   2460
tcctgtatga gatcctgctc ggcaaggcca cactgtacgc tgtgctggtg tctgctctgg   2520
tgctgatggc tatggtcaag cggaaggact tccgggccaa gcggggcagc ggcgccacca   2580
```

```
acttcagcct gctgaagcag gccggcgacg tggaggagaa ccccggccct atggccacag    2640
gcagcagaac atctctgctg ctggcctccg gactgctgtg tctgccttgg ctgcaagagg    2700
cttccgccaa acaggaggtg acgcagattc ctgcagctct gagtgtccca aaggagaaa    2760 acttggttct caactgcagt ttcactgata gcgctattta aacctccag tggtttaggc    2820 aggaccctgg gaaaggtctc acatctctgt tgcttattca gtcaagtcag agagagcaaa    2880
caagtggaag acttaatgcc tcgctggata aatcatcagg acgtagtact ttatacattg    2940
cagcttctca gcctggtgac tcagccacct acctctgtgc tgtgaggccc acatcaggag    3000
gaagctacat acctacattt ggaagaggaa ccagccttat tgttcatccg tatattcaga    3060
accccgatcc tgccgtgtac cagctgagag acagcaagag cagcgacaag agcgtgtgcc    3120
tgttcaccga cttcgacagc cagaccaacg tgcccagag caaggacagc gacgtgtaca    3180
tcaccgacaa gaccgtgctg gacatgcgga gcatggactt caagagcaac agcgccgtgg    3240
cctggtccaa caagagcgat ttcgcctgcg ccaacgcctt caacaacagc attatccccg    3300
aggacacatt cttcccaagt cctgagagca gctgcgacgt gaagctggtg aaaagagct    3360 tcgagacaga caccaacctg aacttccaga acctgtccgt gatcggcttc cgcatcctgc    3420
tgctgaaagt ggccggcttc aacctgctga tgaccctgag actgtggtcc agctgactcg    3480
agtgtgcctt ctagttgcca gccatctgtt gtttgcccct ccccgtgcc ttccttgacc    3540 ctggaaggtg ccactcccac tgtcctttcc taataaatg aggaaattgc atcgcattgt    3600
ctgagtaggt gtcattctat tctgggggt ggggtggggc aggacagcaa gggggaggat    3660
tgggaagaca atagcaggca tgctggggat gcggtgggct ctatggcgcg gccgcaccga    3720
ttttgattct caaacaaatg tgtcacaaag taaggattct gatgtgtata tcacagacaa    3780
aactgtgcta gacatgaggt ctatggactt caagagcaac agtgctgtgg cctggagcaa    3840
caaatctgac tttgcatgtg caaacgcctt caacaacagc attattccag aagacacctt    3900
cttccccagc ccaggtaagg gcagctttgg tgccttcgca ggctgtttcc ttgcttcagg    3960
aatggccagg ttctgcccag agctctggtc aatgatgtct aaaactcctc tgattggtgg    4020
tctcggcctt atccattgcc accaaaaccc tcttttttact aagaaacagt gagccttgtt    4080
ctggcagtcc agagaatgac acgggaaaaa agcagatgaa gagaaggtgg caggagaggg    4140
cacgtggccc agcctcagtc tctccaactg agttcctgcc tgcctgcctt tgctcagact    4200
gtttgcccct tactgctctt ctaggcctca ttctaagccc cttctccaag ttgcctctcc    4260
ttatttctcc ctgtctgcca aaaaatcttt cccagctcac taagtcagtc tcacgcagtc    4320
actcattaac ccaccaatca ctgattgtgc cggcacatga atgcaccagg tgttgaagtg    4380
gaggaattaa aaagtcagat gagggtgtg cccagaggaa gcaccattct agttgggga    4440 gcccatctgt cagctgggaa aagtccaaat aacttcagat tggaatgtgt tttaactcag    4500
ggttgagaaa acagctacct tcaggacaaa agtcagggaa gggctctctg aagaaatgct    4560
acttgaagat accagcccta ccaagggcag ggagaggacc ctatagaggc ctgggacagg    4620
agctcaatga gaaaggagaa gagcagcagg catgagttga atgaaggagg cagggccggg    4680
tcacagggcc ttctaggcca tgagagggta gacagggatc cggtgtggaa agtccccagg    4740 ctcccccagca ggcagaagta tgcaaagcat gcatctcaat tagtcagcaa ccagctagc    4799
```

<210> SEQ ID NO 12
<211> LENGTH: 3575
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
acattaaaaa cacaaaatcc tacggaaata ctgaagaatg agtctcagca ctaaggaaaa      60
gcctccagca gctcctgctt tctgagggtg aaggatagac gctgtggctc tgcatgactc     120
actagcactc tatcacggcc atattctggc agggtcagtg gctccaacta acatttgttt     180
ggtactttac agtttattaa atagatgttt atatggagaa gctctcattt ctttctcaga     240
agagcctggc taggaaggtg gatgaggcac catattcatt ttgcaggtga aattcctgag     300
atgtaaggag ctgctgtgac ttgctcaagg ccttatatcg agtaaacggt agtgctgggg     360
cttagacgca ggtgttctga tttatagttc aaaacctcta tcaatgagag agcaatctcc     420
tggtaatgtg atagatttcc caacttaatg ccaacatacc ataaacctcc cattctgcta     480
atgcccagcc taagttgggg agaccactcc agattccaag atgtacagtt tgctttgctg     540
ggccttttc ccatgcctgc ctttactctg ccagagttat attgctgggg ttttgaagaa     600
gatcctatta aataaaagaa taagcagtat tattaagtag ccctgcattt caggtttcct     660
tgagtggcag gccaggcctg gccgtgaacg ttcactgaaa tcatggcctc ttggccaaga     720
ttgatagctt gtgcctgtcc ctgagtccca gtccatcacg agcagctggt ttctaagatg     780
ctatttcccg tataaagcat gagaccgtga cttgccagcc ccacagagcc ccgcccttgt     840
ccatcactgg catctggact ccagcctggg ttggggcaaa gagggaaatg agatcatgtc     900
ctaaccctga tcctcttgtc ccacagatat ccagaaccct gacctgccg tgtaccagct     960
gagagactct aaatccagtg acaagtctgt ctgcctattc gaattcggct ccggagccac    1020
taacttctcc ctgttgaaac aggctggcga tgttgaagaa aacccggtc ctatggccac    1080
cggctctaga acaagcctgc tgctcgcttt tggcctgctc tgcctgccat gtctccaaga    1140
gggatctgcc gaaacgggag ttacgcagac accaagacac ctggtcatgg gaatgacaaa    1200
taagaagtct ttgaaatgtg aacaacatct gggtcataac gctatgtatt ggtacaagca    1260
aagtgctaag aagccactgg agctcatgtt tgtctacagt cttgaagaac gggttgaaaa    1320
caacagtgtg ccaagtcgct tctcacctga atgccccaac agctctcact tattccttca    1380
cctacacacc ctgcagccag aagactcggc cctgtatctc tgcgccagca gccagtcgag    1440
gggggctcag cagtacttcg gccgggcaca caggctcacg gtcacagagg acctgaacaa    1500
agtgttccct ccagaggtgg ccgtgttcga gccttctgag gccgagatca gccacacaca    1560
gaaagccaca ctcgtgtgtc tggctaccgg cttcttcccc gatcacgtgg aactgtcttg    1620
gtgggtcaac ggcaaagagg tgcacagcgg cgtcagcaca gatcccagc ctctgaaaga    1680
acagcccgct ctgaacgaca ccgctactg cctgtctagc agactgagag tgtccgccac    1740
cttctggcag aaccccagaa accacttcag atgccaggtc cagttctacg gcctgagcga    1800
gaacgatgag tggacccaga agagagccaa gcctgtgaca cagatcgtgt ctgccgaagc    1860
ctggggcaga gccgattgtg gctttaccag cgtgtcatac cagcagggcg tgctgtctgc    1920
caccatcctg tatgagatcc tgctcggcaa ggccacactg tacgctgtgc tggtgtctgc    1980
tctggtgctg atggctatgg tcaagcggaa ggacttccgg gccaagcggg gcagcggcgc    2040
caccaacttc agcctgctga gcaggccgg cgacgtggag gagaacccg gccctatggc    2100
cacaggcagc agaacatctc tgctgctggc cttcggactg ctgtgtctgc cttggctgca    2160
agaggcttcc gcccagaagg aggtggagca ggatcctgga ccactcagtg ttccagaggg    2220
```

-continued

```
agccattgtt tctctcaact gcacttacag caacagtgct tttcaatact tcatgtggta    2280
cagacagtat tccagaaaag gccctgagtt gctgatgtac acatactcca gtggtaacaa    2340
agaagatgga aggtttacag cacaggtcga taaatccagc aagtatatct ccttgttcat    2400
cagagactca cagcccagtg attcagccac ctacctctgt gcaatgagtg aggactacaa    2460
gctcagcttt ggagccggaa ccacagtaac tgtaagagca aatattcaga accccgatcc    2520
tgctgtgtat cagctgcgcg acagcaagag cagcgacaag agcgtgtgtt tgttcaccga    2580
ttttgattct caaacaaatg tgtcacaaag taaggattct gatgtgtata tcacagacaa    2640
aactgtgcta gacatgaggt ctatggactt caagagcaac agtgctgtgg cctggagcaa    2700
caaatctgac tttgcatgtg caaacgcctt caacaacagc attattccag aagacacctt    2760
cttccccagc ccaggtaagg gcagctttgg tgccttcgca ggctgtttcc ttgcttcagg    2820
aatggccagg ttctgcccag agctctggtc aatgatgtct aaaactcctc tgattggtgg    2880
tctcggcctt atccattgcc accaaaaccc tcttttact aagaaacagt gagccttgtt    2940
ctggcagtcc agagaatgac acgggaaaaa agcagatgaa gagaaggtgg caggagaggg    3000
cacgtggccc agcctcagtc tctccaactg agttcctgcc tgcctgcctt tgctcagact    3060
gtttgcccct tactgctctt ctaggcctca ttctaagccc cttctccaag ttgcctctcc    3120
ttatttctcc ctgtctgcca aaaaatcttt cccagctcac taagtcagtc tcacgcagtc    3180
actcattaac ccaccaatca ctgattgtgc cggcacatga atgcaccagg tgttgaagtg    3240
gaggaattaa aaagtcagat gagggtgtg cccagaggaa gcaccattct agttggggga    3300
gcccatctgt cagctgggaa aagtccaaat aacttcagat tggaatgtgt tttaactcag    3360
ggttgagaaa acagctacct tcaggacaaa agtcagggaa gggctctctg aagaaatgct    3420
acttgaagat accagcccta ccaagggcag ggagaggacc ctatagaggc ctgggacagg    3480
agctcaatga gaaaggagaa gagcagcagg catgagttga atgaaggagg cagggccggg    3540
tcacagggcc ttctaggcca tgagagggta gacag                                3575
```

<210> SEQ ID NO 13
<211> LENGTH: 4197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
ccgcctaatg agcgggcttt ttttggctt gttgtccaca accgttaaac cttaaaagct      60
ttaaaagcct tatatattct ttttttctt ataaaactta aaccttaga ggctatttaa     120 gttgctgatt tatattaatt ttattgttca acatgagag cttagtacgt gaaacatgag     180
agcttagtac gttagccatg agagcttagt acgttagcca tgagggttta gttcgttaaa     240
catgagagct tagtacgtta acatgagag cttagtacgt actatcaaca ggttgaactg     300
ctgatccacg ttgtggtaga attggtaaag agagtcgtgt aaaatatcga gttcgcacat     360
cttgttgtct gattattgat ttttggcgaa accatttgat catatgacaa gatgtgtatc     420
taccttaact taatgatttt gataaaaatc attaggtacc tggttgctga ctaattgaga     480
tgcatgcttt gcatacttct gcctgctggg gagcctgggg actttccaca ccccatggac     540
attaaaaaca caaatccta cggaaatact gaagaatgag tctcagcact aaggaaaagc     600
ctccagcagc tcctgctttc tgagggtgaa ggatagacgc tgtggctctg catgactcac     660
```

```
tagcactcta tcacggccat attctggcag ggtcagtggc tccaactaac atttgtttgg    720
tactttacag tttattaaat agatgtttat atggagaagc tctcatttct ttctcagaag    780
agcctggcta ggaaggtgga tgaggcacca tattcatttt gcaggtgaaa ttcctgagat    840
gtaaggagct gctgtgactt gctcaaggcc ttatatcgag taaacggtag tgctggggct    900
tagacgcagg tgttctgatt tatagttcaa aacctctatc aatgagagag caatctcctg    960
gtaatgtgat agatttccca acttaatgcc aacataccat aaacctccca ttctgctaat   1020
gcccagccta agttggggag accactccag attccaagat gtacagtttg ctttgctggg   1080 ccttttttccc atgcctgcct ttactctgcc agagttatat tgctggggtt ttgaagaaga   1140
tcctattaaa taaagaata agcagtatta ttaagtagcc ctgcatttca ggtttccttg    1200
agtggcaggc caggcctggc cgtgaacgtt cactgaaatc atggcctctt ggccaagatt   1260
gatagcttgt gcctgtccct gagtcccagt ccatcacgag cagctggttt ctaagatgct   1320
atttcccgta taaagcatga gaccgtgact tgccagcccc acagagcccc gcccttgtcc   1380
atcactggca tctggactcc agcctgggtt ggggcaaaga gggaaatgag atcatgtcct   1440
aaccctgatc ctcttgtccc acagatatcc agaaccctga ccctgccgtg taccagctga   1500
gagactctaa atccagtgac aagtctgtct gcctattcga attcggctcc ggagccacta   1560
acttctccct gttgaaacag gctggcgatg ttgaagaaaa ccccggtcct atggccaccg   1620
gctctagaac aagcctgctg ctcgcttttg gcctgctctg cctgccatgt ctccaagagg   1680
gatctgccga acgggagtt acgcagacac caagacacct ggtcatggga atgcaaata    1740 agaagtcttt gaaatgtgaa caacatctgg gtcataacgc tatgtattgg tacaagcaaa   1800
gtgctaagaa gccactggag ctcatgtttg tctacagtct tgaagaacgg gttgaaaaca   1860
acagtgtgcc aagtcgcttc tcacctgaat gccccaacag ctctcactta ttccttcacc   1920
tacacaccct gcagccagaa gactcggccc tgtatctctg cgccagcagc cagtcgaggg   1980
gggctcagca gtacttcggg ccgggcacca ggctcacggt cacagaggac ctgaacaaag   2040
tgttccctcc agaggtggcc gtgttcgagc cttctgaggc cgagatcagc cacacacaga   2100
aagccacact cgtgtgtctg gctaccggct tcttccccga tcacgtggaa ctgtcttggt   2160
gggtcaacgg caaagaggtg cacagcggcg tcagcacaga tcccagcct ctgaaagaac    2220 agcccgctct gaacgacagc cgctactgcc tgtctagcag actgagagtg tccgccacct   2280
tctggcagaa ccccagaaac cacttcagat gccaggtcca gttctacggc ctgagcgaga   2340
acgatgagtg gacccagaag agagccaagc ctgtgacaca gatcgtgtct gccgaagcct   2400
ggggcagagc cgattgtggc tttaccagcg tgtcatacca gcaggcgtg ctgtctgcca    2460 ccatcctgta tgagatcctg ctcggcaagg ccacactgta cgctgtgctg gtgtctgctc   2520
tggtgctgat ggctatggtc aagcggaagg acttccgggc caagcggggc agcggcgcca   2580
ccaacttcag cctgctgaag caggccgcg acgtggagga aaccccggc cctatggcca     2640 caggcagcag aacatctctg ctgctggcct tcggactgct gtgtctgcct tggctgcaag   2700
aggcttccgc ccagaaggag gtggagcagg atcctggacc actcagtgtt ccagagggag   2760
ccattgtttc tctcaactgc acttacagca acagtgcttt tcaatacttc atgtggtaca   2820
gacagtattc cagaaaaggc cctgagttgc tgatgtacac atactccagt ggtaacaaag   2880
aagatggaag gtttacagca caggtcgata atccagcaa gtatatctcc ttgttcatca    2940
gagactcaca gcccagtgat tcagccacct acctctgtgc aatgagtgag gactacaagc   3000
```

-continued

```
tcagctttgg agccggaacc acagtaactg taagagcaaa tattcagaac cccgatcctg      3060
ctgtgtatca gctgcgcgac agcaagagca gcgacaagag cgtgtgtttg ttcaccgatt      3120
ttgattctca aacaaatgtg tcacaaagta aggattctga tgtgtatatc acagacaaaa      3180
ctgtgctaga catgaggtct atggacttca agagcaacag tgctgtggcc tgagcaaca      3240 aatctgactt tgcatgtgca aacgccttca acaacagcat tattccagaa gacaccttct      3300
tccccagccc aggtaagggc agctttggtg ccttcgcagg ctgtttcctt gcttcaggaa      3360
tggccaggtt ctgcccagag ctctggtcaa tgatgtctaa aactcctctg attggtggtc      3420
tcggccttat ccattgccac caaaaccctc ttttttactaa gaaacagtga gccttgttct      3480
ggcagtccag agaatgacac gggaaaaaag cagatgaaga aaggtggca ggagagggca      3540 cgtggcccag cctcagtctc tccaactgag ttcctgcctg cctgcctttg ctcagactgt      3600
ttgcccctta ctgctcttct aggcctcatt ctaagcccct tctccaagtt gcctctcctt      3660
atttctccct gtctgccaaa aaatctttcc cagctcacta agtcagtctc acgcagtcac      3720
tcattaaccc accaatcact gattgtgccg gcacatgaat gcaccaggtg ttgaagtgga      3780
ggaattaaaa agtcagatga ggggtgtgcc cagaggaagc accattctag ttgggggagc      3840
ccatctgtca gctgggaaaa gtccaaataa cttcagattg aatgtgtttt taactcaggg      3900
ttgagaaaac agctaccttc aggacaaaag tcagggaagg gctctctgaa gaaatgctac      3960
ttgaagatac cagccctacc aagggcaggg agaggaccct atagaggcct gggacaggag      4020
ctcaatgaga aggagaaga gcagcaggca tgagttgaat gaaggaggca gggccgggtc      4080
acagggcctt ctaggccatg agagggtaga cagggatccg gtgtggaaag tccccaggct      4140
ccccagcagg cagaagtatg caaagcatgc atctcaatta gtcagcaacc agctagc       4197
```

<210> SEQ ID NO 14
<211> LENGTH: 5125
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
ggtaccacat taaaaacaca aaatcctacg gaaatactga agaatgagtc tcagcactaa       60
ggaaaagcct ccagcagctc ctgctttctg agggtgaagg atagacgctg tggctctgca      120
tgactcacta gcactctatc acggccatat tctggcaggg tcagtggctc caactaacat      180
ttgtttggta ctttacagtt tattaaatag atgtttatat ggagaagctc tcatttcttt      240
ctcagaagag cctggctagg aaggtggatg aggcaccata ttcattttgc aggtgaaatt      300
cctgagatgt aaggagctgc tgtgacttgc tcaaggcctt atatcgagta aacggtagtg      360
ctggggctta gacgcaggtg ttctgattta tagttcaaaa cctctatcaa tgagagagca      420
atctcctggt aatgtgatag atttcccaac ttaatgccaa cataccataa acctcccatt      480
ctgctaatgc ccagcctaag ttggggagac cactccagat tccaagatgt acagtttgct      540
ttgctgggcc ttttttccat gcctgccttt actctgccag agttatattg ctggggtttt      600
gaagaagatc ctattaaata aaagaataag cagtattatt aagtagccct gcatttcagg      660
tttccttgag tggcaggcca ggcctggccg tgaacgttca ctgaaatcat ggcctcttgg      720
ccaagattga tagcttgtgc ctgtccctga gtcccagtcc atcacgagca gctggtttct      780
aagatgctat ttcccgtata aagcatgaga ccgtgacttg ccagccccac agagccccgc      840
```

```
ccttgtccat cactggcatc tggactccag cctgggttgg ggcaaagagg gaaatgagat    900
catgtcctaa ccctgatcct cttgtcccac agatatccag aaccctgacc ctgccgtgta    960
ccagctgaga gactctaaat ccagtgacaa gtctgtctgc ctattcgaat tcggctccgg   1020
agccactaac ttctccctgt tgaaacaggc tggcgatgtt gaagaaaacc ccggtcctat   1080
ggccaccggc tctagaacaa gcctgctgct cgcttttggc ctgctctgcc tgccatgtct   1140
ccaagaggga tctgccgaaa cgggagttac gcagacacca agacacctgg tcatgggaat   1200
gacaaataag aagtctttga aatgtgaaca acatctgggt cataacgcta tgtattggta   1260
caagcaaagt gctaagaagc cactggagct catgtttgtc tacagtcttg aagaacgggt   1320
tgaaaacaac agtgtgccaa gtcgcttctc acctgaatgc cccaacagct ctcacttatt   1380
ccttcaccta cacaccctgc agccagaaga ctcggccctg tatctctgcg ccagcagcca   1440
gtcgaggggg gctcagcagt acttcgggcc gggcaccagg ctcacggtca cagaggacct   1500
gaaaaacgtg ttccctccaa aagtggccgt gttcgagcct tctgaggccg agatcagcca   1560
cacacagaaa gccacactcg tgtgtctggc taccggcttc taccccgatc acgtggaact   1620
gtcttggtgg gtcaacggca agaggtgca cagcggcgtc agcacagatc cccagcctct   1680
gaaagaacag cccgctctga cgacagccg ctactgcctg tctagcagac tgagagtgtc   1740
cgccaccttc tggcagaacc ccagaaacca cttcagatgc caggtccagt tctacggcct   1800
gagcgagaac gatgagtgga cccaggacag agccaagcct gtgacacaga tcgtgtctgc   1860
cgaagcctgg ggcagagccg attgtggctt taccagcgag tcataccagc agggcgtgct   1920
gtctgccacc atcctgtatg agatcctgct cggcaaggcc acactgtacg ctgtgctggt   1980
gtctgctctg gtgctgatgg ctatggtctc ccgggagcgc atccccgagg cccgggccaa   2040
gcggggcagc ggcgccacca acttcagcct gctgaagcag gccggcgacg tggaggagaa   2100
ccccggccct atggccacag gcagcagaac atctctgctg ctggccttcg gactgctgtg   2160
tctgccttgg ctgcaagagg cttccgccca gaaggaggtg gagcaggatc ctggaccact   2220
cagtgttcca gagggagcca ttgtttctct caactgcact tacagcaaca gtgcttttca   2280
atacttcatg tggtacagac agtattccag aaaaggccct gagttgctga tgtacacata   2340
ctccagtggt aacaaagaag atggaaggtt tacagcacag gtcgataaat ccagcaagta   2400
tatctccttg ttcatcagag actcacagcc cagtgattca gccacctacc tctgtgcaat   2460
gagtgaggac tacaagctca gctttggagc cggaaccaca gtaactgtaa gagcaaatat   2520
tcagaacccc gatcctgctg tgtatcagct gcgcgacagc aagagcagcg acaagagcgt   2580
gtgtttgttc accgattttg attctcaaac aaatgtgtca caaagtaagg attctgatgt   2640
gtatatcaca gacaaaactg tgctagacat gaggtctatg gacttcaaga gcaacagtgc   2700
tgtggcctgg agcaacaaat ctgactttgc atgtgcaaac gccttcaaca acagcattat   2760
tccagaagac accttcttcc ccagcccagg taagggcagc tttggtgcct cgcaggctg   2820
tttccttgct tcaggaatgg ccaggttctg cccagagctc tggtcaatga tgtctaaaac   2880
tcctctgatt ggtggtctcg gccttatcca ttgccaccaa aaccctcttt ttactaagaa   2940
acagtgagcc ttgttctggc agtccagaga atgacgggg aaaaaagcag atgaagagaa   3000
ggtggcagga gagggcacgt ggcccagcct cagtctctcc aactgagttc ctgcctgcct   3060
gcctttgctc agactgtttg ccccttactg ctcttctagg cctcattcta agccccttct   3120
ccaagttgcc tctccttatt tctccctgtc tgccaaaaaa tctttcccag ctcactaagt   3180
cagtctcacg cagtcactca ttaacccacc aatcactgat tgtgccggca catgaatgca   3240
```

```
ccaggtgttg aagtggagga attaaaaagt cagatgaggg gtgtgcccag aggaagcacc    3300
attctagttg ggggagccca tctgtcagct gggaaaagtc caaataactt cagattggaa    3360
tgtgttttaa ctcagggttg agaaaacagc taccttcagg acaaaagtca gggaagggct    3420
ctctgaagaa atgctacttg aagataccag ccctaccaag gcagggagag gaccctata     3480 gaggcctggg acaggagctc aatgagaaag gagaagagca gcaggcatga gttgaatgaa    3540
ggaggcaggg ccgggtcaca gggccttcta ggccatgaga gggtagacag gctagccgcg    3600
ttgctggcgt ttttccatag gctccgcccc cctgacgagc atcacaaaaa tcgacgctca    3660
agtcagaggt ggcgaaaccc gacaggacta taaagatacc aggcgtttcc ccctggaagc    3720
tccctcgtgc gctctcctgt tccgaccctg ccgcttaccg gatacctgtc cgcctttctc    3780
ccttcgggaa gcgtggcgct ttctcatagc tcacgctgta ggtatctcag ttcggtgtag    3840
gtcgttcgct ccaagctggg ctgtgtgcac gaaccccccg ttcagcccga ccgctgcgcc    3900
ttatccggta actatcgtct tgagtccaac ccggtaagac acgacttatc gccactggca    3960
gcagccactg gtaacaggat tagcagagcg aggtatgtag gcggtgctac agagttcttg    4020
aagtggtggc ctaactacgg ctacactaga agaacagtat ttggtatctg cgctctgctg    4080
aagccagtta ccttcggaaa aagagttggt agctcttgat ccggcaaaca aaccaccgct    4140
ggtagcggtg gttttttttgt ttgcaagcag cagattacgc gcagaaaaaa aggatctcaa    4200
gaagatcctt tgatctttag aaaaactcat cgagcatcaa atgaaactgc aatttattca    4260
tatcaggatt atcaatacca tatttttgaa aaagccgttt ctgtaatgaa ggagaaaact    4320
caccgaggca gttccatagg atggcaagat cctggtatcg gtctgcgatt ccgactcgtc    4380
caacatcaat acaacctatt aatttcccct cgtcaaaaat aaggttatca agtgagaaat    4440
caccatgagt gacgactgaa tccggtgaga atggcaaaag tttatgcatt tctttccaga    4500
cttgttcaac aggccagcca ttacgctcgt catcaaaatc actcgcatca accaaaccgt    4560
tattcattcg tgattgcgcc tgagccagac gaaatacgcg atcgctgtta aaaggacaat    4620
tacaaacagg aatcgaatgc aaccggcgca ggaacactgc cagcgcatca acaatatttt    4680
cacctgaatc aggatattct tctaatacct ggaatgctgt ttttccgggg atcgcagtgg    4740
tgagtaacca tgcatcatca ggagtacgga taaaatgctt gatggtcgga agaggcataa    4800
attccgtcag ccagtttagt ctgaccatct catctgtaac atcattggca acgctacctt    4860
tgccatgttt cagaaacaac tctggcgcat cgggcttccc atacaagcga tagattgtcg    4920
cacctgattg cccgacatta tcgcgagccc atttataccc atataaatca gcatccatgt    4980
tggaatttaa tcgcggcctc gacgtttccc gttgaatatg gctcataaca ccccttgtat    5040
tactgtttat gtaagcagac agttttattg ttcatgatga tatattttta tcttgtgcaa    5100
tgtaacatca gagattttga gacac                                          5125
```

<210> SEQ ID NO 15
<211> LENGTH: 5605
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
ggtaccacat taaaaacaca aaatcctacg gaaatactga agaatgagtc tcagcactaa       60
ggaaaagcct ccagcagctc ctgctttctg agggtgaagg atagacgctg tggctctgca     120
```

```
tgactcacta gcactctatc acggccatat tctggcaggg tcagtggctc caactaacat    180
ttgtttggta ctttacagtt tattaaatag atgtttatat ggagaagctc tcatttcttt    240
ctcagaagag cctggctagg aaggtggatg aggcaccata ttcattttgc aggtgaaatt    300
cctgagatgt aaggagctgc tgtgacttgc tcaaggcctt atatcgagta aacggtagtg    360
ctggggctta gacgcaggtg ttctgattta tagttcaaaa cctctatcaa tgagagagca    420
atctcctggt aatgtgatag atttcccaac ttaatgccaa cataccataa acctcccatt    480
ctgctaatgc ccagcctaag ttggggagac cactccagat tccaagatgt acagtttgct    540
ttgctgggcc ttttttccat gcctgccttt actctgccag agttatattg ctggggtttt    600
gaagaagatc ctattaaata aaagaataag cagtattatt aagtagccct gcatttcagg    660
tttccttgag tggcaggcca ggcctggccg tgaacgttca ctgaaatcat ggcctcttgg    720
ccaagattga tagcttgtgc ctgtccctga gtcccagtcc atcacgagca gctggtttct    780
aagatgctat ttcccgtata aagcatgaga ccgtgacttg ccagcccac agagcccgc     840 ccttgtccat cactggcatc tggactccag cctgggttgg ggcaaagagg gaaatgagat    900
catgtcctaa ccctgatcct cttgtcccac agatatccag aaccctgacc ctgccgtgta    960
ccagctgaga gactctaaat ccagtgacaa gtctgtctgc ctattcgaac agagaaacag   1020
gagaatatgg gccaaacagg atatctgtgg taagcagttc ctgccccggc tcagggccaa   1080
gaacagttgg aacagcagaa tatgggccaa acaggatatc tgtggtaagc agttcctgcc   1140
ccggctcagg gccaagaaca gatggtcccc agatgcggtc ccgccctcag cagtttctag   1200
agaaccatca gatgtttcca gggtgcccca aggacctgaa atgaccctgt gccttatttg   1260
aactaaccaa tcagttcgct tctcgcttct gttcgcgcgc ttctgctccc cgagctctat   1320
ataagcagag ctcgtttagt gaaccgtcag atcgcctgga gacgccatcc acgctgtttt   1380
gacttccata gaaggcggcc gcgccgccac catgggccag tccaagcacg gcctgaccaa   1440
ggagatgacc atgaagtacc gcatggaggg ctgcgtggac ggccacaagt tcgtgatcac   1500
cggcgagggc atcggctacc ccttcaaggg caagcaggcc atcaacctgt gcgtggtgga   1560
gggcggcccc ttgcccttcg ccgaggacat cttgtccgcc gccttcatgt acggcaaccg   1620
cgtgttcacc gagtaccccc aggacatcgt ggactacttc aagaactcct gccccgccgg   1680
atacacctgg gaccgctcct tcctgttcga ggacggcgcc gtgtgcatct gcaacgccga   1740
catcaccgtc agcgtggagg agaactgcat gtaccacgag tccaagttct acggcgtgaa   1800
cttccccgcc gacggccccg tgatgaagaa gatgaccgac aactgggagc cctcctgcga   1860
gaagatcatc cccgtgccca gcagggcat cttgaagggc gacgtcagca tgtacctgct    1920
gctgaaggac ggtggccgct tgcgctgcca gttcgacacc gtgtacaagg ccaagtccgt   1980
gccccgcaag atgcccgact ggcacttcat ccagcacaag ctgacccgcg aggaccgcag   2040
cgacgccaag aaccagaagt ggcacctgac cgagcacgcc atcgcctccg gctccgcctt   2100
gccccgggcc aagcggggca gcggcgccac caacttcagc ctgctgaagc aggccggcga   2160
cgtggaggag aaccccggcc ctatgggggc aggtgccacc ggccgcgcta tggacgggcc   2220
gcgcctgctg ctgttgctgc ttctgggggt gtcccttgga ggtgccaagg aggcatgccc   2280
cacaggcctg tacacacaca gcggtgagtg ctgcaaagcc tgcaacctgg gcgagggtgt   2340
ggcccagcct tgtggagcca accagaccgt gtgtgagccc tgcctggaca gcgtgacgtt   2400
ctccgacgtg gtgagcgcga ccgagccgtg caagccgtgc accgagtgcg tggggctcca   2460
```

```
gagcatgtcg gcgccgtgcg tggaggccga cgacgccgtg tgccgctgcg cctacggcta    2520
ctaccaggat gagacgactg ggcgctgcga ggcgtgccgc gtgtgcgagg cgggctcggg    2580
cctcgtgttc tcctgccagg acaagcagaa caccgtgtgc gaggagtgcc ccgacggcac    2640
gtattccgac gaggccaacc acgtggaccc gtgcctgccc tgcaccgtgt gcgaggacac    2700
cgagcgccag ctccgcgagt gcacacgctg ggccgacgcc gagtgcgagg agatccctgg    2760
ccgttggatt acacggtcca caccccagag gggctcggac agcacagccc ccagcaccca    2820
ggagcctgag gcacctccag aacaagacct catagccagc acggtggcag gtgtggtgac    2880
cacagtgatg ggcagctccc agcccgtggt gacccgaggc accaccgaca acctcatccc    2940
tgtctattgc tccatcctgg ctgctgtggt tgtgggtctt gtggcctaca tagccttcaa    3000
gaggggctcc ggagccacta acttctccct gttgaaacag gctggcgatg ttgaagaaaa    3060
ccccggtcct accgattttg attctcaaac aaatgtgtca caaagtaagg attctgatgt    3120
gtatatcaca gacaaaactg tgctagacat gaggtctatg gacttcaaga gcaacagtgc    3180
tgtggcctgg agcaacaaat ctgactttgc atgtgcaaac gccttcaaca acagcattat    3240
tccagaagac accttcttcc ccagcccagg taagggcagc tttggtgcct tcgcaggctg    3300
tttccttgct tcaggaatgg ccaggttctg cccagagctc tggtcaatga tgtctaaaac    3360
tcctctgatt ggtggtctcg gccttatcca ttgccaccaa aaccctcttt ttactaagaa    3420
acagtgagcc ttgttctggc agtccagaga atgcacggg aaaaaagcag atgaagagaa    3480
ggtggcagga gagggcacgt ggcccagcct cagtctctcc aactgagttc ctgcctgcct    3540
gcctttgctc agactgtttg ccccttactg ctcttctagg cctcattcta agccccttct    3600
ccaagttgcc tctccttatt tctccctgtc tgccaaaaaa tctttcccag ctcactaagt    3660
cagtctcacg cagtcactca ttaacccacc aatcactgat tgtgccggca catgaatgca    3720
ccaggtgttg aagtggagga attaaaaagt cagatgaggg gtgtgcccag aggaagcacc    3780
attctagttg ggggagccca tctgtcagct gggaaaagtc caaataactt cagattggaa    3840
tgtgttttaa ctcagggttg agaaaacagc taccttcagg acaaaagtca gggaagggct    3900
ctctgaagaa atgctacttg aagataccag ccctaccaag ggcagggaga ggaccctata    3960
gaggcctggg acaggagctc aatgagaaag gagaagagca gcaggcatga gttgaatgaa    4020
ggaggcagga ccgggtcaca gggccttcta ggccatgaga gggtagacag gctagccgcg    4080
ttgctggcgt ttttccatag gctccgcccc cctgacgagc atcacaaaaa tcgacgctca    4140
agtcagaggt ggcgaaaccc gacaggacta taaagatacc aggcgtttcc ccctggaagc    4200
tccctcgtgc gctctcctgt tccgaccctg ccgcttaccg gatacctgtc cgcctttctc    4260
ccttcgggaa gcgtggcgct ttctcatagc tcacgctgta ggtatctcag ttcggtgtag    4320
gtcgttcgct ccaagctggg ctgtgtgcac gaaccccccg ttcagcccga ccgctgcgcc    4380
ttatccggta actatcgtct tgagtccaac ccggtaagac acgacttatc gccactggca    4440
gcagccactg gtaacaggat tagcagagcg aggtatgtag gcggtgctac agagttcttg    4500
aagtggtggc ctaactacgg ctacactaga agaacagtat ttggtatctg cgctctgctg    4560
aagccagtta ccttcggaaa aagagttggt agctcttgat ccgcaaaca aaccaccgct    4620 ggtagcggtg gtttttttgt ttgcaagcag cagattacgc gcagaaaaaa aggatctcaa    4680
gaagatcctt tgatctttag aaaaactcat cgagcatcaa atgaaactgc aatttattca    4740
tatcaggatt atcaatacca tatttttgaa aaagccgttt ctgtaatgaa ggagaaaact    4800
caccgaggca gttccatagg atggcaagat cctggtatcg gtctgcgatt ccgactcgtc    4860
```

```
caacatcaat acaacctatt aatttcccct cgtcaaaaat aaggttatca agtgagaaat    4920
caccatgagt gacgactgaa tccggtgaga atggcaaaag tttatgcatt tctttccaga    4980
cttgttcaac aggccagcca ttacgctcgt catcaaaatc actcgcatca accaaaccgt    5040
tattcattcg tgattgcgcc tgagccagac gaaatacgcg atcgctgtta aaaggacaat    5100
tacaaacagg aatcgaatgc aaccggcgca ggaacactgc cagcgcatca acaatatttt    5160
cacctgaatc aggatattct tctaatacct ggaatgctgt ttttccgggg atcgcagtgg    5220
tgagtaacca tgcatcatca ggagtacgga taaaatgctt gatggtcgga agaggcataa    5280
attccgtcag ccagtttagt ctgaccatct catctgtaac atcattggca acgctacctt    5340
tgccatgttt cagaaacaac tctggcgcat cgggcttccc atacaagcga tagattgtcg    5400
cacctgattg cccgacatta tcgcgagccc atttataccc atataaatca gcatccatgt    5460
tggaatttaa tcgcggcctc gacgtttccc gttgaatatg gctcataaca ccccttgtat    5520
tactgtttat gtaagcagac agttttattg ttcatgatga tatatttta tcttgtgcaa    5580 tgtaacatca gagattttga gacac                                         5605
```

<210> SEQ ID NO 16
<211> LENGTH: 1541
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
gctagccgcg ttgctggcgt ttttccatag gctccgcccc cctgacgagc atcacaaaaa      60
tcgacgctca agtcagaggt ggcgaaaccc gacaggacta taaagatacc aggcgtttcc     120
ccctggaagc tccctcgtgc gctctcctgt tccgaccctg ccgcttaccg gatacctgtc     180
cgcctttctc ccttcgggaa gcgtggcgct ttctcatagc tcacgctgta ggtatctcag     240
ttcggtgtag gtcgttcgct ccaagctggg ctgtgtgcac gaaccccccg ttcagcccga     300
ccgctgcgcc ttatccggta actatcgtct tgagtccaac ccggtaagac acgacttatc     360
gccactggca gcagccactg gtaacaggat tagcagagcg aggtatgtag gcggtgctac     420
agagttcttg aagtggtggc ctaactacgg ctacactaga agaacagtat ttggtatctg     480
cgctctgctg aagccagtta ccttcggaaa aagagttggt agctcttgat ccggcaaaca     540
aaccaccgct ggtagcggtg gtttttttgt ttgcaagcag cagattacgc gcagaaaaaa     600
aggatctcaa gaagatcctt tgatctttag aaaaactcat cgagcatcaa atgaaactgc     660
aatttattca tatcaggatt atcaatacca tatttttgaa aaagccgttt ctgtaatgaa     720
ggagaaaact caccgaggca gttccatagg atggcaagat cctggtatcg gtctgcgatt     780
ccgactcgtc caacatcaat acaacctatt aatttcccct cgtcaaaaat aaggttatca     840
agtgagaaat caccatgagt gacgactgaa tccggtgaga atggcaaaag tttatgcatt     900
tctttccaga cttgttcaac aggccagcca ttacgctcgt catcaaaatc actcgcatca     960
accaaaccgt tattcattcg tgattgcgcc tgagccagac gaaatacgcg atcgctgtta    1020
aaaggacaat tacaaacagg aatcgaatgc aaccggcgca ggaacactgc cagcgcatca    1080
acaatatttt cacctgaatc aggatattct tctaatacct ggaatgctgt ttttccgggg    1140
atcgcagtgg tgagtaacca tgcatcatca ggagtacgga taaaatgctt gatggtcgga    1200
agaggcataa attccgtcag ccagtttagt ctgaccatct catctgtaac atcattggca    1260
```

```
acgctacctt tgccatgttt cagaaacaac tctggcgcat cgggcttccc atacaagcga      1320
tagattgtcg cacctgattg cccgacatta tcgcgagccc atttatacccc atataaatca     1380 gcatccatgt tggaatttaa tcgcggcctc gacgtttccc gttgaatatg gctcataaca     1440
ccccttgtat tactgtttat gtaagcagac agttttattg ttcatgatga tatattttta     1500
tcttgtgcaa tgtaacatca gagattttga gacacggtac c                         1541
```

<210> SEQ ID NO 17
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
acattaaaaa cacaaaatcc tacggaaata ctgaagaatg agtctcagca ctaaggaaaa       60
gcctccagca gctcctgctt tctgagggtg aaggatagac gctgtggctc tgcatgactc     120
actagcactc tatcacggcc atattctggc agggtcagtg gctccaacta acatttgttt     180
ggtactttac agtttattaa atagatgttt atatggagaa gctctcatt cttctcaga      240 agagcctggc taggaaggtg gatgaggcac catattcatt ttgcaggtga aattcctgag     300
atgtaaggag ctgctgtgac ttgctcaagg ccttatatcg agtaaacggt agtgctgggg     360
cttagacgca ggtgttctga tttatagttc aaaacctcta tcaatgagag agcaatctcc     420
tggtaatgtg atagatttcc caacttaatg ccaacatacc ataaacctcc cattctgcta     480
atgcccagcc taagttgggg agaccactcc agattccaag atgtacagtt tgctttgctg     540
ggcctttttc ccatgcctgc ctttactctg ccagagttat attgctgggg ttttgaagaa     600
gatcctatta aataaaagaa taagcagtat tattaagtag ccctgcattt caggtttcct     660
tgagtggcag gccaggcctg gccgtgaacg ttcactgaaa tcatggcctc ttggccaaga     720
ttgatagctt gtgcctgtcc ctgagtccca gtccatcacg agcagctggt ttctaagatg     780
ctatttcccg tataaagcat gagaccgtga cttgccagcc ccacagagcc ccgcccttgt     840
ccatcactgg catctggact ccagcctggg ttggggcaaa gagggaaatg agatcatgtc     900
ctaaccctga tcctcttgtc ccacagatat ccagaaccct gaccctgccg tgtaccagct     960
gagagactct aaatccagtg acaagtctgt ctgcctattc                          1000
```

<210> SEQ ID NO 18
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
accgattttg attctcaaac aaatgtgtca caaagtaagg attctgatgt gtatatcaca       60
gacaaaactg tgctagacat gaggtctatg gacttcaaga gcaacagtgc tgtggcctgg     120
agcaacaaat ctgactttgc atgtgcaaac gccttcaaca acagcattat tccagaagac     180
accttcttcc ccagcccagg taagggcagc tttggtgcct tcgcaggctg tttccttgct     240
tcaggaatgg ccaggttctg cccagagctc tggtcaatga tgtctaaaac tcctctgatt     300
ggtggtctcg gccttatcca ttgccaccaa aaccctcttt ttactaagaa acagtgagcc     360
```

```
ttgttctggc agtccagaga atgacacggg aaaaaagcag atgaagagaa ggtggcagga      420
gagggcacgt ggcccagcct cagtctctcc aactgagttc ctgcctgcct gcctttgctc      480
agactgtttg ccccttactg ctcttctagg cctcattcta agccccttct ccaagttgcc      540
tctccttatt tctccctgtc tgccaaaaaa tctttcccag ctcactaagt cagtctcacg      600
cagtcactca ttaacccacc aatcactgat tgtgccggca catgaatgca ccaggtgttg      660
aagtggagga attaaaaagt cagatgaggg gtgtgcccag aggaagcacc attctagttg      720
ggggagccca tctgtcagct gggaaaagtc caaataactt cagattggaa tgtgttttaa      780
ctcagggttg agaaaacagc taccttcagg acaaagtca gggaagggct ctctgaagaa       840
atgctacttg aagataccag ccctaccaag ggcagggaga ggaccctata gaggcctggg      900
acaggagctc aatgagaaag gagaagagca gcaggcatga gttgaatgaa ggaggcaggg      960
ccgggtcaca gggccttcta ggccatgaga gggtagacag                            1000
```

```
<210> SEQ ID NO 19
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 19
gagaaucaaa aucggugaau guuuuagagc uagaaauagc aaguuaaaau aaggcuaguc       60
cguuaucaac uugaaaaagu ggcaccgagu cggugcuuuu                            100

<210> SEQ ID NO 20
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 20
ggcucucgga gaaugacgag guuuuagagc uagaaauagc aaguuaaaau aaggcuaguc       60
cguuaucaac uugaaaaagu ggcaccgagu cggugcuuuu                            100

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gagaatcaaa atcggtgaat                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggctctcgga gaatgacgag                                                   20
```

```
<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agggtcattt caggtcctt                                               19
```

PRIMARY CELL GENE EDITING

CROSS REFERENCE TO RELATED APPLICATIONS

This application is a Continuation of U.S. patent application Ser. No. 16/552,714, filed on Aug. 27, 2019, now allowed, which is a Continuation of International Application No. PCT/US2018/058230, filed on Oct. 30, 2018, which claims the benefit of U.S. Provisional Application No. 62/579,113, filed on Oct. 30, 2017, and U.S. Provisional Application No. 62/579,114, filed on Oct. 30, 2017, each of which is hereby incorporated by reference in their entirety for all purposes.

SEQUENCE LISTING

The instant application contains a Sequence Listing which has been submitted via EFS-Web and is hereby incorporated herein by reference in its entirety. Said ASCII copy, created on Feb. 5, 2020, is named 087520 0126 ST25.txt, and is 57,503 bytes in size.

BACKGROUND

Gene targeting is a method by which the genome can be directly edited, providing a path for engineering cell products, repairing mutations that cause genetic diseases, or creating mutations to study genes. Gene targeting relies on homologous recombination after delivery of a homology repair template DNA bearing the desired altered sequence, along with a site-specific nuclease targeting the locus of interest.

Gene targeting has been used in primary human T cells to create T cells with novel specificities. In these instances, AAV has been used to deliver the homology repair template DNA. The DNA contains coding sequence for chimeric antigen receptors (CARs) or T-cell receptors (TCRs) specific for a new epitope. When these sequences are targeted to the TCRα (commonly) or TCRβ locus, the investigator can achieve simultaneous knockout of the endogenous TCR (and removal of the corresponding specificity), and knock-in of the new protein (and corresponding specificity). This process is used at scale to produce CAR T cells and TCR T cells for therapeutic use. However, AAV production takes a great deal of time, is costly, difficult, and highly regulated, limiting its application.

Gene editing with naked plasmid DNA has been described previously, but only in the context of immortalized cell lines, citing issues with toxicity in primary cells. These issues may stem from investigators using mRNA to deliver the nuclease, which exhibits some toxicity, along with the DNA which further decreases cell viability. These issues may also stem from the fact that DNA delivery efficiency is dependent on DNA size, and vectors may not have been optimized appropriately. Furthermore, DNA impurities common to kit-based plasmid preparations used by most research labs are known to contribute to cellular toxicity, which may have impeded progress in using plasmid DNA as a homology repair template. Only recently have DNA purification and delivery techniques improved (e.g. emergence of plasmid vaccines, and optimized electroporation protocols and equipment such as Nucleofection).

Transposons have also been used to insert DNA into primary human T cells, but in a nonspecific fashion (more akin to retroviral delivery). In this case, naked DNA to be randomly inserted into the genome is delivered as naked plasmid DNA. However, high toxicity and low efficiency are limitations of this method. Gene editing in primary human T cells via homologous recombination has also been described previously (e.g., Schumann et al. Proc Natl Acad Sci USA. 2015 Aug. 18; 112(33):10437-42), however only in the context of very small edits or repairs, for example 20 nucleotides or less. Gene editing through electroporation of ribonucleoprotein (RNP) complexes via homologous recombination has also been described previously, for example in Kim et al., (Genome Res. 2014 June; 24(6):1012-9) and in International Pub. No. WO2016/123578, however only relatively small insertions (or replacements of genomic sequence) of 12 nucleotides were demonstrated in each using linear templates. Compositions and methods for larger edits are also not well described for primary cells other than T cells, such as hematopoietic stem cells and natural killer (NK) cells. Lacking in the field are efficient methods of making large edits in primary cells, thereby potentially limiting the therapeutic applications of gene editing.

Therefore, improved compositions and methods for mediating gene editing in cells, such as human primary cells and human primary T cells, are greatly needed in the field.

SUMMARY

Provided herein are modified cells comprising: a circular polynucleotide comprising an exogenous nucleotide sequence, the exogenous nucleotide sequence comprising: a) a nucleotide sequence encoding at least a portion of a gene; b) a nucleotide sequence identical to a first region of an endogenous genomic target locus; and c) a nucleotide sequence identical to a second region of the endogenous genomic target locus, the nucleotide sequences identical to the first and the second regions of the endogenous genomic target locus are oriented to facilitate homologous recombination at the endogenous genomic target locus, and wherein the modified cell is substantially free of viral mediated delivery components. In some embodiments, the modified cell further comprises an integrated nucleotide sequence, wherein the integrated nucleotide sequence comprises a sequence identical to the nucleotide sequence encoding the at least the portion of the gene, the integrated nucleotide sequence is integrated at the endogenous genomic target locus, and the integrated nucleotide sequence is orientated such that the at least a portion of the gene is capable of being expressed. In some embodiments, the modified cell further comprises a nuclease composition capable of cleaving a defined nucleotide sequence within the endogenous genomic target locus.

Also provided herein are modified cells comprising a T cell, the T cell comprising: a) a nucleotide sequence encoding a TCR-alpha polypeptide sequence; b) a nucleotide sequence encoding a TCR-beta polypeptide sequence; c) a nucleotide sequence encoding a first linker polypeptide sequence; d) a nucleotide sequence encoding a second linker polypeptide sequence; wherein the nucleotide sequence encoding the TCR-alpha polypeptide sequence, the nucleotide sequence encoding the TCR-beta polypeptide sequence, and the nucleotide sequences encoding the first and the second linker polypeptide sequences are integrated into an endogenous TCR-alpha locus, the nucleotide sequence encoding the TCR-alpha polypeptide sequence, the nucleotide sequence encoding the TCR-beta polypeptide sequence, and the nucleotide sequences encoding the first and the second linker polypeptide sequences are orientated such that each of the polypeptide sequences is capable of being expressed as a single polypeptide, wherein the second linker polypeptide sequence is positioned between the TCR-alpha polypeptide sequence and the TCR-beta polypeptide sequence, the first and the second linker polypeptide are cleavable linker polypeptides capable of being cleaved in the T cell such that the TCR-alpha polypeptide sequence and the TCR-beta polypeptide sequence each form a separate polypeptide, wherein the separate polypeptides are capable of associating together to form a functional TCR, wherein the modified cell is substantially free of viral mediated delivery components, and wherein an endogenous TCR-beta locus is disrupted.

Also provided herein are modified cells comprising a T cell, the T cell comprising: a) a nucleotide sequence encoding a TCR-alpha polypeptide sequence; b) a nucleotide sequence encoding a TCR-beta polypeptide sequence; c) a nucleotide sequence encoding a first linker polypeptide sequence; d) a nucleotide sequence encoding a second linker polypeptide sequence; wherein the nucleotide sequence encoding the TCR-alpha polypeptide sequence, the nucleotide sequence encoding the TCR-beta polypeptide sequence, and the nucleotide sequences encoding the first and the second linker polypeptide sequences are integrated into an endogenous TCR locus, the nucleotide sequence encoding the TCR-alpha polypeptide sequence, the nucleotide sequence encoding the TCR-beta polypeptide sequence, and the nucleotide sequences encoding the first and the second linker polypeptide sequences are orientated such that each of the polypeptide sequences is capable of being expressed as a single polypeptide, wherein the second linker polypeptide sequence is positioned between the TCR-alpha polypeptide sequence and the TCR-beta polypeptide sequence, and the first and the second linker polypeptide are cleavable linker polypeptides capable of being cleaved in the T cell such that the TCR-alpha polypeptide sequence and the TCR-beta polypeptide sequence each form a separate polypeptide, wherein the separate polypeptides are capable of associating together to form a functional TCR. In some embodiments, the modified cell further comprises a circular polynucleotide comprising an exogenous nucleotide sequence, the exogenous nucleotide sequence comprising: a) a nucleotide sequence encoding the nucleotide sequence encoding the TCR-alpha polypeptide sequence, the nucleotide sequence encoding the TCR-beta polypeptide sequence, and the nucleotide sequences encoding the first and the second linker polypeptide sequences; b) a nucleotide sequence identical to a first region of the endogenous TCR locus; and c) a nucleotide sequence identical to a second region of the endogenous TCR locus, and the nucleotide sequences identical to the first and the second regions of the endogenous TCR locus are oriented to facilitate homologous recombination at the endogenous TCR locus. In some embodiments, the modified cell is substantially free of viral mediated delivery components. In some embodiments, the modified cell further comprises a nuclease composition capable of cleaving a defined nucleotide sequence within the endogenous TCR locus.

In some embodiments, the modified cell further comprises a mutation that produces a non-functional gene encoded by a second defined nucleotide sequence. In some embodiments, the mutation that produces the non-functional gene comprises a mutation in a coding region of the gene selected from the group consisting of: a frameshift mutation resulting in a change in the frame of the protein translated, a nonsense mutation causing a substitution from an amino acid to a stop codon, and a missense mutation resulting in a substitution from one amino acid to another. In some embodiments, the mutation that produces the non-functional gene comprises a mutation in a non-coding region of the gene selected from the group consisting of: a mutation that alters expression of an mRNA product encoded by the gene, and a mutation that alters stability of an mRNA product encoded by the gene. In some embodiments, the modified cell further comprises a second nuclease composition capable of cleaving the second defined nucleotide sequence within the modified cell.

In some embodiments, the nuclease composition comprises a nuclease selected from the group consisting of a Clustered Regularly Interspaced Short Palindromic Repeats (CRISPR) family nuclease or derivative thereof, a Transcription activator-like effector nuclease (TALEN) or derivative thereof, a zinc-finger nuclease (ZFN) or derivative thereof, and a homing endonuclease (HE) or derivative thereof. In some embodiments, the CRISPR family nuclease is a Cas9 nuclease. In some embodiments, the nuclease composition comprises a preformed protein complex. In some embodiments, the nuclease composition comprises a nucleotide vector capable of expressing the nuclease within the modified cell. In some embodiments, the nuclease composition comprises a CRISPR RNA (crRNA) and a transactivating CRISPR RNA (tracrRNA). In some embodiments, the crRNA comprises a guide RNA (gRNA), wherein the gRNA is complementary to the defined nucleotide sequence. In some embodiments, the crRNA and the tracrRNA are on a single polynucleotide. In some embodiments, the crRNA and the tracrRNA are on separate polynucleotides.

In some embodiments, expression of the nucleotide sequence encoding at least a portion of a gene or the encoded polypeptide sequences is directed by an endogenous promoter within the endogenous genomic target locus or endogenous TCR locus. In some embodiments, expression of the nucleotide sequence encoding at least a portion of a gene or the encoded polypeptide sequences is directed by an exogenous promoter. In some embodiments, the exogenous promoter is selected from the group consisting of mammalian promoters, human promoters, viral promoters, long-terminal repeat (LTR) derived promoters from a retrovirus or lentivirus, fusions of two promoters, fusions of two portions of promoters, MMLV LTR promoters, HIV LTR promoters, MCMV LTR promoters, EF1α, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems.

In some embodiments, the nucleotide sequence encoding the at least a portion of the gene, the nucleotide sequence encoding the TCR-alpha polypeptide sequence, or the nucleotide sequence encoding the TCR-beta polypeptide sequence is greater than or equal to 100 bases in length. In some embodiments, the nucleotide sequence encoding the at least a portion of the gene, the nucleotide sequence encoding the TCR-alpha polypeptide sequence, or the nucleotide sequence encoding the TCR-beta polypeptide sequence is greater than or equal to 200 bases in length, greater than or equal to 400 bases in length, greater than or equal to 600 bases in length, greater than or equal to 800 bases in length, greater than or equal to 1500 bases in length, greater than or equal to 2000 bases in length, or greater than or equal to 4000 bases in length.

In some embodiments, the nucleotide sequences identical to the first region of the endogenous genomic target locus or the endogenous TCR locus are greater than or equal to 50 bases in length, greater than or equal to 100 bases in length, greater than or equal to 200 bases in length, greater than or equal to 300 bases in length, greater than or equal to 600 bases in length, greater than or equal to 1000 bases in length, or greater than or equal to 2000 bases in length.

In some embodiments, the nucleotide sequences identical to the second region of the endogenous genomic target locus or the endogenous TCR locus are greater than or equal to 50 bases in length, greater than or equal to 100 bases in length, greater than or equal to 200 bases in length, greater than or equal to 300 bases in length, greater than or equal to 600 bases in length, greater than or equal to 1000 bases in length, or greater than or equal to 2000 bases in length.

In some embodiments, the nucleotide sequences identical to the first region of the endogenous genomic target locus or the endogenous TCR locus and the nucleotide sequences identical to the second region of the endogenous genomic target locus or the endogenous TCR locus are each greater than or equal to 600 bases in length.

In some embodiments, the defined nucleotide sequence is disrupted following integration of the nucleotide sequences.

In some embodiments, expression of an endogenous gene operably associated with the endogenous genomic target locus or the endogenous TCR locus is disrupted.

In some embodiments, the modified cell further comprises additional reagents that are capable of increasing homologous recombination rates. In some embodiments, the additional reagents that are capable of increasing homologous recombination rates comprise activators of homologous recombination repair pathways, inhibitors non-homologous end joining (NHEJ) repair pathways, or combinations thereof.

In some embodiments, the modified cell further comprises additional reagents that are capable of increasing viability of the modified cell. In some embodiments, the additional reagents that are capable of increasing viability of the modified cell comprise inhibitors of nucleic acid sensing pathways. In some embodiments, the nucleic acid sensing pathways comprise the group selected from: TLR9 nucleic acid sensing pathways, AIM2 nucleic acid sensing pathways, IFI16 nucleic acid sensing pathways, cGAS nucleic acid sensing pathways, and cytosolic nucleic acid sensing pathways. In some embodiments, the inhibitors of nucleic acid sensing pathways comprise an oligonucleotide antagonist. In some embodiments, the oligonucleotide antagonist comprises the sequence TTAGGG or tandem repeats thereof.

In some embodiments, the circular polynucleotide comprises a plasmid or a nanoplasmid. In some embodiments, the plasmid has a vector backbone that is less than 500 bases, and wherein the vector backbone is a nucleotide sequence that is not the nucleotide sequence encoding the at least a portion of the gene, not the nucleotide sequence encoding the TCR-alpha polypeptide sequence, not the nucleotide sequence encoding the TCR-beta polypeptide sequence, not the nucleotide sequences encoding the first and the second linker polypeptide, not the nucleotide sequence identical to the first endogenous target genomic locus or endogenous TCR locus, and not the nucleotide sequence identical to the second endogenous target genomic locus or endogenous TCR locus.

In some embodiments, the circular polynucleotide is not a polymerase chain reaction (PCR) amplified polynucleotide.

In some embodiments, the endogenous genomic target locus or the endogenous TCR locus comprises a coding region. In some embodiments, the endogenous genomic target locus or the endogenous TCR locus comprises an intron.

In some embodiments, the endogenous genomic target locus or the endogenous TCR locus comprises the T cell receptor (TCR)-alpha locus. In some embodiments, the non-functional gene encoded by the second defined nucleotide sequence is a disrupted TCR-beta gene.

In some embodiments, the endogenous genomic target locus or the endogenous TCR locus comprises the TCR-beta locus. In some embodiments, the non-functional gene encoded by the second defined nucleotide sequence is a disrupted TCR-alpha gene.

In some embodiments, the endogenous genomic target comprises an immune checkpoint locus. In some embodiments, the immune checkpoint locus is selected from the group consisting of PD-1, CTLA-4, BTLA, TIM3, LAG3, and VISTA.

In some embodiments, the at least a portion of the gene comprises a linker sequence. In some embodiments, the linker sequence encodes a cleavable linker polypeptide sequence, wherein following expression the cleavable linker polypeptide is cleaved such that a polypeptide encoded only by the at least a portion of the gene is produced. In some embodiments, any one of the cleavable linker polypeptides comprises a furin cleavage site. In some embodiments, any one of the linker sequences comprise a 2A ribosome skipping element selected from the group consisting of: T2A, E2A, P2A, and F2A. In some embodiments, any one of the cleavable linker polypeptides comprise a Gly-Ser-Gly linker, optionally wherein the Gly-Ser-Gly linker is N-terminal of a 2A ribosome skipping element, and optionally wherein the Gly-Ser-Gly linker is in a furin cleavage site: Gly-Ser-Gly linker:2A ribosome skipping element orientation from N-terminus to C-terminus.

In some embodiments, the linker sequence, the nucleotide sequences encoding the first linker polypeptide sequence, or the nucleotide sequences encoding the second linker polypeptide sequence comprises an internal ribosome entry site (IRES).

In some embodiments, the linker sequence, the nucleotide sequences encoding the first linker polypeptide sequence, or the nucleotide sequences encoding the second linker polypeptide sequence comprises an exogenous promoter.

In some embodiments, wherein the linker sequence, the nucleotide sequences encoding the first linker polypeptide sequence, or the nucleotide sequences encoding the second linker polypeptide sequence comprises a splice acceptor sequence.

In some embodiments, the at least a portion of the gene, the nucleotide sequence encoding the TCR-alpha polypeptide sequence, the nucleotide sequence encoding the TCR-beta polypeptide sequence, or the nucleotide sequence encoding the at least a portion of the TCR gene comprises a nucleotide sequence encoding a signal peptide, wherein the signal peptide is operably linked to a polypeptide encoded by the at least a portion of the gene, the TCR-alpha polypeptide sequence, the TCR-beta polypeptide sequence, or a polypeptide encoded by the at least a portion of the TCR gene. In some embodiments, the signal peptide is an exogenous signal peptide, optionally wherein the exogenous signal peptide is a Human Growth Hormone signal peptide.

In some embodiments, the first linker polypeptide sequence and the second linker polypeptide sequence comprise the same linker polypeptide sequence. In some embodiments, the nucleotide sequences encoding the first linker polypeptide sequence and the nucleotide sequence encoding the second linker polypeptide sequence that encode the same linker polypeptide sequence comprise codon diverged nucleotide sequences, and wherein the nucleotide sequences encoding the first linker polypeptide sequence and the nucleotide sequence encoding the second linker polypeptide are codon diverged relative to each other.

In some embodiments, the at least a portion of the gene encodes a coding region. In some embodiments, the coding region is selected from the group consisting of: a factor that modulates the immune system, a cytokine, a factor that modulates T cell function, a factor that promotes T-cell survival, a factor that promotes T-cell function, and an immune checkpoint inhibitor.

In some embodiments, the at least a portion of the gene encodes a non-coding region. In some embodiments, the non-coding region is selected from the group consisting of: an shRNA, an siRNA, an miRNA, a factor that modulates the immune system, a cytokine, a factor that modulates T cell function, a factor that promotes T-cell survival, and a factor that promotes T-cell function. In some embodiments, the at least a portion of the gene comprises at least a portion of a TCR gene. In some embodiments, the at least a portion of the TCR gene comprises: a) a nucleotide sequence encoding a TCR-alpha polypeptide sequence; b) a nucleotide sequence encoding a TCR-beta polypeptide sequence; and c) a nucleotide sequence encoding a second linker sequence.

In some embodiments, the nucleotide sequence encoding the TCR-alpha polypeptide sequence, the nucleotide sequence encoding the TCR-beta polypeptide sequence, or the at least a portion of the TCR gene is selected from the group consisting of: at least a portion of a murinized TCR, a humanized TCR, a domain swapped TCR, a point-mutated TCR, an engineered TCR with an engineered cysteine capable of forming a disulfide linkage, a codon optimized TCR optimized for expression in humans, a sequence optimized TCR optimized for codon usage and removal of RNA instability elements, a variable region sequence of the TCR gene, a chimeric antigen receptor (CAR), and a single-chain TCR.

In some embodiments, the TCR-alpha polypeptide sequence, the TCR-beta polypeptide sequence, or a polypeptide encoded by the at least a portion of the TCR gene is engineered to demonstrate a greater association with a second exogenous TCR polypeptide sequence relative to an endogenous TCR polypeptide sequence, optionally wherein the TCR-alpha polypeptide sequence and the TCR-beta polypeptide sequence are engineered to demonstrate a greater association with each other relative to an endogenous TCR polypeptide sequence.

In some embodiments, the encoded polypeptide sequences are in a linker:TCR-alpha: second linker: TCR-beta orientation from N-terminus to C-terminus. In some embodiments, the encoded polypeptide sequences are in a linker:TCR-beta:second linker:TCR-alpha orientation from N-terminus to C-terminus.

In some embodiments, the at least a portion of the gene, the nucleotide sequence encoding the TCR-alpha polypeptide sequence, the nucleotide sequence encoding the TCR-beta polypeptide sequence, or the nucleotide sequence encoding the at least a portion of the TCR gene comprises a codon diverged nucleotide sequence, and wherein the codon diverged nucleotide sequence is codon diverged relative to an endogenous nucleotide sequence.

In some embodiments, the modified cell comprises an immune cell. In some embodiments, the immune cell comprises a T cell. In some embodiments, the T cell is selected from the group consisting of: a cytotoxic T lymphocyte (CTL), a CD8+ T cell, a CD4+ T cell, a primary T cell, a tumor infiltrating T cell, an engineered T cell, a regulatory T cell (Treg), a helper T cell, a Th1 cell, a Th2 cell, a Th17 cell, an alpha-beta T cell, and a gamma-delta T cell. In some embodiments, wherein the immune cell comprises a natural killer cell. In some embodiments, the immune cell is selected from the group consisting of: a B cell, a monocyte, a macrophage, a dendritic cell, and a natural killer T cell.

In some embodiments, the modified cell comprises a stem cell. In some embodiments, the stem cell comprises a hematopoietic stem cell. In some embodiments, the stem cell comprises an embryonic stem cell.

In some embodiments, the modified cell is a primary cell.

In some embodiments, the modified cell is an isolated cell, wherein the isolated cell is isolated from a subject. In some embodiments, the subject is known or suspected to have cancer.

In some embodiments, the modified cell comprises a human cell or human-derived cell.

In some embodiments, the modified cell is an ex vivo cultured cell. In some embodiments, the ex vivo cultured cell comprises a stimulated cell. In some embodiments, the stimulated cell comprises a cytokine stimulated T cell, optionally wherein the cytokine stimulated T cell comprises a CD3 stimulated T cell, a CD28 stimulated T cell, or a CD3 and CD28 stimulated T cell. In some embodiments, the cytokine stimulated T cell is cultured in the presence of IL7, IL15, or a combination thereof. In some embodiments, the cytokine stimulated T cell is cultured in the presence of IL2. In some embodiments, the cytokine stimulated T cell is cultured in media substantially free of IL2.

In some embodiments, the modified cell is free of an integrated virus, wherein the integrated virus is operably associated with the viral mediated delivery components. In some embodiments, MHC class I on surface of the modified cell is free of peptides derived from viral mediated delivery components or an integrated virus, wherein the integrated virus is operably associated with the viral mediated delivery components.

In some embodiments, the modified cell further comprises a second circular polynucleotide comprising a second exogenous nucleotide composition, the second exogenous nucleotide composition comprising: a) a nucleotide sequence encoding at least a portion of a second gene; b) a nucleotide sequence identical to a first region of a second endogenous genomic target locus; and c) a nucleotide sequence identical to a second region of the second endogenous genomic target locus, and the nucleotide sequences identical to the first and the second regions of the second endogenous genomic target locus are oriented to facilitate homologous recombination at the second endogenous genomic target locus. In some embodiments, the modified cell further comprises a second integrated nucleotide sequence, wherein the second integrated nucleotide sequence comprises a sequence identical to the nucleotide sequence encoding the at least the portion of the second gene, the second integrated nucleotide sequence is integrated at the second endogenous genomic target locus, and the second integrated nucleotide sequence is orientated such that the at least a portion of the second gene is capable of being expressed.

Also provided for herein is a population of cells comprising any one of the modified cells of described herein, wherein greater than 10%, greater than 20%, greater than 30%, greater than 40%, greater than 50%, greater than 60%, or greater than 70% of the population comprise the integrated nucleotide sequence. In some embodiments, the modified cells have not undergone sorting, selection, or isolation following integration of the integrated nucleotide sequence.

Also provided for herein is a population of cells comprising: an integrated nucleotide sequence, wherein the integrated nucleotide sequence comprises at least a portion of a gene, the integrated nucleotide sequence is integrated at an endogenous genomic target locus, and the integrated nucleotide sequence is orientated such that the at least a portion of the gene is capable of being expressed, wherein the population of cells is substantially free of viral mediated delivery components, and wherein greater than 10%, greater than 20%, greater than 30%, greater than 40%, greater than 50%, greater than 60%, or greater than 70% of the T cells in the population comprise the integrated nucleotide sequence. In some embodiments, the T cells have not undergone sorting, selection, or isolation following integration of the integrated nucleotide sequence.

In some embodiments, the population of cells further comprises a nuclease composition capable of cleaving a defined nucleotide sequence within the endogenous TCR locus.

In some embodiments, the population of cells further comprises a circular polynucleotide comprising an exogenous nucleotide sequence, the exogenous nucleotide sequence comprising: a) a nucleotide sequence encoding the at least a portion of a gene; b) a nucleotide sequence identical to a first region of the endogenous locus; and c) a nucleotide sequence identical to a second region of the endogenous locus, and the nucleotide sequences identical to the first and the second regions of the endogenous locus are oriented to facilitate homologous recombination at the endogenous locus.

In some embodiments, the population of cells is at least $1\times10^6$ T cells, at least $2\times10^6$ T cells, at least $5\times10^6$ T cells, at least $1\times10^7$ T cells, or at least $5\times10^7$ T cells.

In some embodiments, the population of cells further comprises a mutation that produces a non-functional gene encoded by a second defined nucleotide sequence. In some embodiments, the mutation that produces the non-functional gene comprises a mutation in a coding region of the gene selected from the group consisting of: a frameshift mutation resulting in a change in the frame of the protein translated, a nonsense mutation causing a substitution from an amino acid to a stop codon, and a missense mutation resulting in a substitution from one amino acid to another. In some embodiments, the mutation that produces the non-functional gene comprises a mutation in a non-coding region of the gene selected from the group consisting of: a mutation that alters expression of an mRNA product encoded by the gene, and a mutation that alters stability of an mRNA product encoded by the gene.

In some embodiments, the nuclease composition comprises a nuclease selected from the group consisting of a Clustered Regularly Interspaced Short Palindromic Repeats (CRISPR) family nuclease, a Transcription activator-like effector nuclease (TALEN) or derivative thereof, a zinc-finger nuclease (ZFN) or derivative thereof, and a homing endonuclease (HE) or derivative thereof. In some embodiments, the CRISPR family nuclease is a Cas9 nuclease. In some embodiments, the nuclease composition comprises a preformed protein complex. In some embodiments, the nuclease composition comprises a nucleotide vector capable of expressing the nuclease within the population of cells. In some embodiments, the nuclease composition comprises a guide RNA that directs nuclease mediated cleavage at the defined nucleotide sequence. In some embodiments, the guide RNA comprises a CRISPR RNA (crRNA) and a trans-activating CRISPR RNA (tracrRNA). In some embodiments, the crRNA and the tracrRNA are on a single polynucleotide. In some embodiments, the crRNA and the tracrRNA are on separate polynucleotides.

In some embodiments, the population of cells further comprises a second nuclease composition capable of cleaving the second defined nucleotide sequence within the population of cells.

In some embodiments, expression of the encoded polypeptide sequences is directed by an endogenous promoter within the endogenous genomic target locus. In some embodiments, expression of the encoded polypeptide sequences is directed by an exogenous promoter. In some embodiments, the exogenous promoter is selected from the group consisting of mammalian promoters, human promoters, viral promoters, long-terminal repeat (LTR) derived promoters from a retrovirus or lentivirus, fusions of two promoters, fusions of two portions of promoters, MMLV LTR promoters, HIV LTR promoters, MCMV LTR promoters, EF1a, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems.

In some embodiments, the nucleotide sequence encoding the at least a portion of the gene is greater than or equal to 100 bases in length. In some embodiments, the nucleotide sequence encoding the at least a portion of the gene is greater than or equal to 200 bases in length, greater than or equal to 400 bases in length, greater than or equal to 600 bases in length, greater than or equal to 800 bases in length, greater than or equal to 1500 bases in length, greater than or equal to 2000 bases in length, or greater than or equal to 4000 bases in length.

In some embodiments, nucleotide sequences identical to the first region of the endogenous genomic target locus are greater than or equal to 50 bases in length, greater than or equal to 100 bases in length, greater than or equal to 200 bases in length, greater than or equal to 300 bases in length, greater than or equal to 600 bases in length, greater than or equal to 1000 bases in length, or greater than or equal to 2000 bases in length.

In some embodiments, the nucleotide sequences identical to the second region of the endogenous genomic target locus are greater than or equal to 50 bases in length, greater than or equal to 100 bases in length, greater than or equal to 200 bases in length, greater than or equal to 300 bases in length, greater than or equal to 600 bases in length, greater than or equal to 1000 bases in length, or greater than or equal to 2000 bases in length.

In some embodiments, the nucleotide sequences identical to the first region of the endogenous genomic target locus and the nucleotide sequences identical to the second region of the endogenous genomic target locus are each greater than or equal to 600 bases in length.

In some embodiments, the defined nucleotide sequence is disrupted following integration of the nucleotide sequences.

In some embodiments, expression of an endogenous gene operably associated with the endogenous genomic target locus or the endogenous TCR locus is disrupted.

In some embodiments, the population of cells further comprises additional reagents that are capable of increasing homologous recombination rates.

In some embodiments, the population of cells further comprises additional reagents that are capable of increasing viability of the population of cells.

In some embodiments, the circular polynucleotide comprises a plasmid or a nanoplasmid. In some embodiments, the plasmid has a vector backbone that is less than 500 bases, and wherein the vector backbone is a nucleotide sequence that is not the nucleotide sequence encoding the at least a portion of the gene, not the nucleotide sequence encoding the TCR-alpha polypeptide sequence, not the nucleotide sequence encoding the TCR-beta polypeptide sequence, not the nucleotide sequences encoding the first and the second linker polypeptide, not the nucleotide sequence identical to the first endogenous target genomic locus or endogenous TCR locus, and not the nucleotide sequence identical to the second endogenous target genomic locus or endogenous TCR locus.

In some embodiments, the circular polynucleotide is not a polymerase chain reaction (PCR) amplified polynucleotide.

In some embodiments, the endogenous genomic target locus comprises a coding region. In some embodiments, the endogenous genomic target locus comprises an intron.

In some embodiments, the endogenous genomic target locus comprises the T cell receptor (TCR)-alpha locus. In some embodiments, the non-functional gene encoded by the second defined nucleotide sequence is a disrupted TCR-beta gene.

In some embodiments, the endogenous genomic target locus comprises the TCR-beta locus. In some embodiments, the non-functional gene encoded by the second defined nucleotide sequence is a disrupted TCR-alpha gene.

In some embodiments, the endogenous genomic target comprises an immune checkpoint locus. In some embodiments, the immune checkpoint locus is selected from the group consisting of PD-1, CTLA-4, BTLA, TIM3, LAG3, and VISTA.

In some embodiments, the at least a portion of the gene comprises a linker sequence. In some embodiments, the linker sequence encodes a cleavable linker polypeptide sequence, wherein following expression the cleavable linker polypeptide is cleaved such that a polypeptide encoded only by the at least a portion of the gene is produced. In some embodiments, the cleavable linker polypeptide comprises a 2A ribosome skipping element selected from the group consisting of: T2A, E2A, P2A, and F2A. In some embodiments, the cleavable linker polypeptides comprise a furin cleavage site. In some embodiments, the cleavable linker polypeptides comprise a Gly-Ser-Gly linker, optionally wherein the Gly-Ser-Gly linker is N-terminal of a 2A ribosome skipping element, and optionally wherein the Gly-Ser-Gly linker is in a furin cleavage site:Gly-Ser-Gly linker:2A ribosome skipping element orientation from N-terminus to C-terminus.

In some embodiments, the linker sequence comprises an internal ribosome entry site (IRES).

In some embodiments, the linker sequence comprises an exogenous promoter sequence.

In some embodiments, the linker sequence comprises a splice acceptor sequence.

In some embodiments, the at least a portion of the gene comprises a first linker polypeptide sequence and a second linker polypeptide sequence. In some embodiments, the first linker polypeptide sequence and the second linker polypeptide sequence comprise the same linker polypeptide sequence. In some embodiments, the nucleotide sequences encoding the first linker polypeptide sequence and the nucleotide sequence encoding the second linker polypeptide sequence that encode the same linker polypeptide sequence comprise codon diverged nucleotide sequences, and wherein the nucleotide sequences encoding the first linker polypeptide sequence and the nucleotide sequence encoding the second linker polypeptide are codon diverged relative to each other.

T In some embodiments, the at least a portion of the gene encodes a coding region. In some embodiments, the coding region is selected from the group consisting of: a factor that modulates the immune system, a cytokine, a factor that modulates T cell function, a factor that promotes T-cell survival, a factor that promotes T-cell function, and an immune checkpoint inhibitor.

In some embodiments, the at least a portion of the gene encodes a non-coding region. In some embodiments, the non-coding region is selected from the group consisting of: an shRNA, an siRNA, an miRNA, a factor that modulates the immune system, a cytokine, a factor that modulates T cell function, a factor that promotes T-cell survival, and a factor that promotes T-cell function.

In some embodiments, the at least a portion of the gene comprises at least a portion of a TCR gene. In some embodiments, the at least a portion of the TCR gene comprises: a) a nucleotide sequence encoding a TCR-alpha polypeptide sequence; b) a nucleotide sequence encoding a TCR-beta polypeptide sequence; and c) a nucleotide sequence encoding a second linker sequence. In some embodiments, the nucleotide sequence encoding the TCR-alpha polypeptide sequence, the nucleotide sequence encoding the TCR-beta polypeptide sequence, or the at least a portion of the TCR gene is selected from the group consisting of: at least a portion of a murinized TCR, a humanized TCR, a domain swapped TCR, a point-mutated TCR, an engineered TCR with an engineered cysteine capable of forming a disulfide linkage, a codon optimized TCR optimized for expression in humans, a sequence optimized TCR optimized for codon usage and removal of RNA instability elements, a variable region sequence of the TCR gene, a chimeric antigen receptor (CAR), and a single-chain TCR. In some embodiments, the TCR-alpha polypeptide sequence, the TCR-beta polypeptide sequence, or a polypeptide encoded by the at least a portion of the TCR gene is engineered to demonstrate a greater association with a second exogenous TCR polypeptide sequence relative to an endogenous TCR polypeptide sequence, optionally wherein the TCR-alpha polypeptide sequence and the TCR-beta polypeptide sequence are engineered to demonstrate a greater association with each other relative to an endogenous TCR polypeptide sequence. In some embodiments, the encoded polypeptide sequences are in a linker:TCR-alpha:second linker:TCR-beta orientation. In some embodiments, the encoded polypeptide sequences are in a linker:TCR-beta:second linker:TCR-alpha orientation. In some embodiments, the nucleotide sequence encoding the TCR-alpha polypeptide sequence, the nucleotide sequence encoding the TCR-beta polypeptide sequence, or the nucleotide sequence encoding the at least a portion of the TCR gene comprises a codon diverged nucleotide sequence, and wherein the codon diverged nucleotide sequence is codon diverged relative to an endogenous nucleotide sequence.

In some embodiments, the population of cells comprise human cells or human-derived cells.

In some embodiments, the population of cells comprises a population of immune cells. In some embodiments, the population of immune cells comprises a population of T cells. In some embodiments, the population of T cells is selected from the group consisting of: a cytotoxic T lymphocyte (CTL), a CD8+ T cell, a CD4+ T cell, a primary T cell, a tumor infiltrating T cell, an engineered T cell, a regulatory T cell (Treg), a helper T cell, a Th1 cell, a Th2 cell, a Th17 cell, an alpha-beta T cell, and a gamma-delta T cell. In some embodiments, the population of immune cells comprises a population of natural killer cells. In some embodiments, the population of cells comprises a population selected from the group consisting of: B cells, monocytes, macrophages, dendritic cells, and natural killer T cells.

In some embodiments, the population of cells comprises a population of stem cells. In some embodiments, the population of stem cells comprises a population of hematopoietic stem cells. In some embodiments, the population of stem cells comprises a population of embryonic stem cells.

In some embodiments, the population of cells is a primary cell.

In some embodiments, the population of cells is an isolated population of cells, wherein the isolated population of cells is isolated from a subject. In some embodiments, the subject is known or suspected to have cancer.

In some embodiments, the population of cells comprises ex vivo cultured cells. In some embodiments, the ex vivo cultured cells comprise stimulated cells. In some embodiments, the stimulated cells comprise cytokine stimulated T cells, optionally wherein the cytokine stimulated T cells comprises CD3 stimulated T cells, CD28 stimulated T cells, or CD3 and CD28 stimulated T cells. In some embodiments, the cytokine stimulated T cells are cultured in the presence of IL7, IL15, or a combination thereof. In some embodiments, the cytokine stimulated T cells are cultured in the presence of IL2. In some embodiments, the cytokine stimulated T cells are cultured in media substantially free of IL2.

In some embodiments, the population of cells further comprises a second integrated nucleotide sequence, wherein the second integrated nucleotide sequence comprises a sequence identical to the nucleotide sequence encoding at least the portion of a second gene, the second integrated nucleotide sequence is integrated at a second endogenous genomic target locus, and the second integrated nucleotide sequence is orientated such that the at least a portion of the second gene is capable of being expressed. In some embodiments, the population of cells further comprises a second circular polynucleotide comprising a second exogenous nucleotide composition, the second exogenous nucleotide composition comprising: a) the nucleotide sequence encoding the at least a portion of the second gene; b) the nucleotide sequence identical to a first region of the second endogenous genomic target locus; and c) a nucleotide sequence identical to a second region of the second endogenous genomic target locus, wherein the nucleotide sequences identical to the first and the second regions of the second endogenous genomic target locus are oriented to facilitate homologous recombination at the second endogenous genomic target locus.

Also provided for herein is a method of treatment for a subject in need thereof, wherein the treatment comprises administering a therapeutically effective dose of any of the modified cells or any of the population of cells described herein. In some embodiments, the modified cells or population of cells are derived from the subject. In some embodiments, the modified cells or population of cells are allogeneic with reference to the subject.

Also provided for herein is a method for genetically modifying a cell, the method comprising the steps of: 1) providing a nucleotide composition comprising a single polynucleotide, the single polynucleotide comprising: a) a nucleotide sequence encoding at least a portion of a gene; b) a nucleotide sequence identical to a first region of an endogenous genomic target locus; and c) a nucleotide sequence identical to a second region of the endogenous genomic target locus, the nucleotide sequences identical to the first and the second regions of the endogenous genomic target locus are oriented to facilitate homologous recombination at the endogenous genomic target locus, the nucleotide sequence encoding the at least a portion of the gene is orientated such that the at least a portion of the gene is capable of being expressed following integration of the composition into the endogenous genomic target locus; and 2) providing a nuclease composition capable of cleaving a defined nucleotide sequence within the endogenous genomic target locus; 3) contacting the cell with the nucleotide composition and the nuclease composition, 4) delivering the nucleotide composition and the nuclease composition into the cell by means other than infecting the cell with a virus. In some embodiments, the method further comprises providing a second nuclease composition capable of cleaving a second defined nucleotide sequence within the cell, wherein the second nuclease composition contacted with the cell in the contacting step and is delivered into the cell in the delivering step. In some embodiments, the cleavage results in a mutation that produces a non-functional gene encoded by the second defined nucleotide sequence. In some embodiments, mutation that produces the non-functional gene comprises a mutation in a coding region of the gene selected from the group consisting of a frameshift mutation resulting in a change in the frame of the protein translated, a nonsense mutation causing a substitution from an amino acid to a stop codon, and a missense mutation resulting in a substitution from one amino acid to another. In some embodiments, the mutation that produces the non-functional gene comprises a mutation in a non-coding region of the gene selected from the group consisting of a mutation that alters expression of a mRNA product encoded by the gene, and a mutation that alters stability of a mRNA product encoded by the gene. In some embodiments, the method further comprises: providing a second nucleotide composition, the second composition comprising: a) a nucleotide sequence encoding at least a portion of a second gene; b) a nucleotide sequence identical to a first region of a second endogenous genomic target locus; and c) a nucleotide sequence identical to a second region of the second endogenous genomic target locus, wherein all of the nucleotide sequences are on a single polynucleotide, the nucleotide sequences identical to the first and the second regions of the second endogenous genomic target locus are oriented to facilitate homologous recombination at the second endogenous genomic target locus, the nucleotide sequence encoding the at least a portion of the gene is orientated such that the at least a portion of the second gene is capable of being expressed following integration of the composition into the second endogenous genomic target locus, and the second nucleotide composition is contacted with the cell in the contacting step and is delivered into the cell in the delivering step.

In some embodiments, the nuclease composition comprises a nuclease selected from the group consisting of a Clustered Regularly Interspaced Short Palindromic Repeats (CRISPR) family nuclease, a Transcription activator-like effector nuclease (TALEN) or derivative thereof, a zinc-finger nuclease (ZFN) or derivative thereof, and a homing endonuclease (HE) or derivative thereof. In some embodiments, the CRISPR family nuclease is a Cas9 nuclease. In some embodiments, the nuclease composition comprises a preformed protein complex. In some embodiments, the nuclease composition comprises a nucleotide vector capable of expressing the nuclease within the cell. In some embodiments, the contacting step is less than 60 minutes, less than 45 minutes, less than 30 minutes, less than 20 minutes, less than 15 minutes, less than 10 minutes, less than 5 minutes, or less than 1 minute between contacting the cell with the nucleotide composition and the nuclease composition and the delivery step.

In some embodiments, the delivering step is selected from the group consisting of electroporation, transfection, cell membrane deformation by physical means, lipid nanoparticles (LNP), virus like particles (VLP), and sonication. In some embodiments, the delivering step comprises electroporation. In some embodiments, expression of the encoded polypeptide sequences is directed by an endogenous promoter within the endogenous genomic target locus. In some embodiments, expression of the encoded polypeptide sequences is directed by an exogenous promoter. In some embodiments, the exogenous promoter is selected from the group consisting of mammalian promoters, human promoters, viral promoters, long-terminal repeat (LTR) derived promoters from a retrovirus or lentivirus, fusions of two promoters, fusions of two portions of promoters, MMLV LTR promoters, HIV LTR promoters, MCMV LTR promoters, EF1a, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems.

In some embodiments, the at least a portion of the gene is greater than or equal to 100 bases in length. In some embodiments, the at least a portion of the gene is greater than or equal to 200 bases in length, greater than or equal to 400 bases in length, greater than or equal to 600 bases in length, greater than or equal to 800 bases in length, greater than or equal to 1500 bases in length, greater than or equal to 2000 bases in length, or greater than or equal to 4000 bases in length.

In some embodiments, the nucleotide sequences identical to the first region or the second region of the endogenous genomic target locus are 50 bases in length, 100 bases in length, 200 bases in length, 400 bases in length, 600 bases in length, 800 bases in length, 1500 bases in length, 2000 bases in length, or 4000 bases in length.

In some embodiments, the defined nucleotide sequence is disrupted following integration.

In some embodiments, expression of an endogenous gene operably associated with the endogenous genomic target locus is disrupted.

In some embodiments, the method further comprises additional reagents that are capable of increasing homologous recombination rates or viability.

In some embodiments, the single polynucleotide is selected from the group consisting of a circular plasmid, a linear DNA fragment, a minicircle, and a ssDNA. In some embodiments, circular plasmid has a vector backbone that is less than 500 bases, wherein the vector backbone comprises a nucleotide sequence that is not the nucleotide sequence encoding the at least a portion of the gene, the nucleotide sequence identical to the first endogenous genomic target locus, nor the nucleotide sequence identical to the second endogenous genomic target locus. In some embodiments, the single polynucleotide is not a polymerase chain reaction (PCR) amplified polynucleotide. In some embodiments, the single polynucleotide is substantially free of contaminants.

In some embodiments, the single polynucleotide is substantially free of components that reduce cell-viability.

In some embodiments, the endogenous genomic target locus comprises a coding region. In some embodiments, wherein the endogenous genomic target locus comprises an intron.

In some embodiments, the endogenous genomic target locus is the T cell receptor (TCR)-alpha locus. In some embodiments, the endogenous genomic target locus is the TCR-beta locus. In some embodiments, endogenous genomic target locus is an immune checkpoint locus. In some embodiments, the immune checkpoint locus is selected from the group consisting of PD-1, CTLA-4, BTLA, TIM3, LAG3, and VISTA.

In some embodiments, the at least a portion of the gene comprises a linker sequence. In some embodiments, the linker sequence encodes a cleavable linker polypeptide sequence, wherein following expression the cleavable linker polypeptide is cleaved such that a polypeptide encoded only by the at least a portion of the gene is produced. In some embodiments, the cleavable linker polypeptide sequence comprises a 2A ribosome skipping element selected from the group consisting of T2A, E2A, P2A, and F2A.

In some embodiments, the cleavable linker polypeptide sequence comprises a furin cleavage site sequence. In some embodiments, the linker sequence comprises an internal ribosome entry site (IRES). In some embodiments, the linker sequence comprises an exogenous promoter. In some embodiments, the linker sequence further comprises a splice acceptor sequence.

In some embodiments, the at least a portion of the gene encodes a coding region. In some embodiments, the coding region is selected from the group consisting of: a factor that modulates the immune system, a cytokine, a factor that modulates T cell function, a factor that promotes T-cell survival, a factor that promotes T-cell function, and an immune checkpoint inhibitor.

In some embodiments, the at least a portion of the gene encodes a non-coding region. In some embodiments, the non-coding region is selected from the group consisting of: an shRNA, an siRNA, an miRNA, a factor that modulates the immune system, a cytokine, a factor that modulates T cell function, a factor that promotes T-cell survival, and a factor that promotes T-cell function.

In some embodiments, the at least a portion of the gene comprises at least a portion of a TCR gene. In some embodiments, the at least a portion of the TCR gene is selected from the group consisting of at least a portion of a murinized TCR, a humanized TCR, a domain swapped TCR, a point-mutated TCR, an engineered TCR with an engineered cysteine capable of forming a disulfide linkage, a codon optimized TCR optimized for expression in humans, a sequence optimized TCR optimized for codon usage and removal of RNA instability elements, a variable region sequence of the TCR gene, a chimeric antigen receptor (CAR), and a single-chain TCR. In some embodiments, the at least a portion of the TCR gene comprises: a) a nucleotide sequence encoding a TCR-alpha polypeptide sequence; b) a nucleotide sequence encoding a TCR-beta polypeptide sequence; and c) a nucleotide sequence encoding a second linker sequence. In some embodiments, the TCR-alpha polypeptide sequence is selected from the group consisting of a murinized TCR-alpha, a humanized TCR-alpha, a domain swapped TCR-alpha, a point-mutated TCR-alpha, an engineered TCR-alpha with an engineered cysteine capable of forming a disulfide linkage, a codon optimized TCR-alpha optimized for expression in humans, a chimeric antigen receptor (CAR), and a sequence optimized TCR-alpha optimized for codon usage and removal of RNA instability elements. In some embodiments, the TCR-beta polypeptide sequence is selected from the group consisting of a murinized TCR-beta, a humanized TCR-beta, a domain swapped TCR-beta, a point-mutated TCR-beta, an engineered TCR-beta with an engineered cysteine capable of forming a disulfide linkage, a codon optimized TCR-beta optimized for expression in humans, a chimeric antigen receptor (CAR), and a sequence optimized TCR-beta optimized for codon usage and removal of RNA instability elements. In some embodiments, the encoded polypeptide sequences are in a linker:TCR-alpha:second linker:TCR-beta orientation. In some embodiments, the encoded polypeptide sequences are in a linker:TCR-beta:second linker:TCR-alpha orientation. In some embodiments, the second linker sequence comprises a cleavable linker polypeptide sequence. In some embodiments, the cleavable linker polypeptide sequence comprises a 2A ribosome skipping element selected from the group consisting of T2A, E2A, P2A, and F2A. In some embodiments, the cleavable linker polypeptide sequence comprises a furin cleavage site sequence. In some embodiments, the second linker sequence comprises an internal ribosome entry site (IRES). In some embodiments, the second linker sequence comprises an exogenous promoter.

In some embodiments, the at least a portion of the gene is selected from the group consisting of a shRNA, a siRNA, a miRNA, a factor that modulates the immune system, a cytokine, a factor that modulates T cell function, a factor that promotes T-cell survival, a factor that promotes T-cell function, and an immune checkpoint inhibitor.

In some embodiments, the at least a portion of the second gene comprises at least a portion of a TCR gene.

In some embodiments, the modified cell comprises an immune cell. In some embodiments, the immune cell comprises a T cell. In some embodiments, the T cell is selected from the group consisting of: a cytotoxic T lymphocyte (CTL), a CD8+ T cell, a CD4+ T cell, a primary T cell, a tumor infiltrating T cell, an engineered T cell, a regulatory T cell (Treg), a helper T cell, a Th1 cell, a Th2 cell, a Th17 cell, an alpha-beta T cell, and a gamma-delta T cell. In some embodiments, wherein the immune cell comprises a natural killer cell. In some embodiments, the immune cell is selected from the group consisting of: a B cell, a monocyte, a macrophage, a dendritic cell, and a natural killer T cell.

In some embodiments, the modified cell comprises a stem cell. In some embodiments, the stem cell comprises a hematopoietic stem cell. In some embodiments, the stem cell comprises an embryonic stem cell.

In some embodiments, the modified cell is a primary cell.

In some embodiments, the modified cell is an isolated cell, wherein the isolated cell is isolated from a subject. In some embodiments, the subject is known or suspected to have cancer.

In some embodiments, the modified cell comprises a human cell or human-derived cell.

In some embodiments, the modified cell is an ex vivo cultured cell. In some embodiments, the ex vivo cultured cell comprises a stimulated cell. In some embodiments, the stimulated cell comprises a cytokine stimulated T cell, optionally wherein the cytokine stimulated T cell comprises a CD3 stimulated T cell, a CD28 stimulated T cell, or a CD3 and CD28 stimulated T cell. In some embodiments, the cytokine stimulated T cell is cultured in the presence of IL7, IL15, or a combination thereof. In some embodiments, the cytokine stimulated T cell is cultured in the presence of IL2. In some embodiments, the cytokine stimulated T cell is cultured in media substantially free of IL2.

In some embodiments, the modified cell is free of an integrated virus, wherein the integrated virus is operably associated with the viral mediated delivery components. In some embodiments, MHC class I on surface of the modified cell is free of peptides derived from viral mediated delivery components or an integrated virus, wherein the integrated virus is operably associated with the viral mediated delivery components.

Also provided for herein is a modified cell produced by any of the methods described herein, wherein the modified cell comprises an integrated nucleotide sequence, wherein the integrated nucleotide sequence comprises a sequence identical to the nucleotide sequence encoding the at least the portion of the gene, the integrated nucleotide sequence is integrated at the endogenous genomic target locus, and the integrated nucleotide sequence is orientated such that the at least a portion of the gene is capable of being expressed.

A population of cells produced by any of the methods described herein, wherein greater than 10%, greater than 20%, greater than 30%, greater than 40%, greater than 50%, greater than 60%, or greater than 70% of the cells in the population comprise an integrated nucleotide sequence, wherein the integrated nucleotide sequence comprises a sequence identical to the nucleotide sequence encoding the at least the portion of the gene, the integrated nucleotide sequence is integrated at the endogenous genomic target locus, and the integrated nucleotide sequence is orientated such that the at least a portion of the gene is capable of being expressed.

In some embodiments, the cells have not undergone sorting, selection, or isolation following integration of the integrated nucleotide sequence. In some embodiments, viability of the population of cells following the delivery step is at least 10%, at least 20%, at least 40%, at least 60%, or at least 80%. In some embodiments, the viability is assessed 4 days after the delivery step. In some embodiments, the viability is assessed by AOPI staining.

Also provided for herein is a method treatment for a subject in need thereof, wherein the treatment comprises administering a therapeutically effective dose of any of the cells or population of cells of produced by any of the methods described herein. In some embodiments, the cells or population of cells are derived from the subject. In some embodiments, the cells or population of cells are allogeneic with reference to the subject.

Also provided for herein is a method for genetically modifying a cell, the method comprising the steps of: 1) providing a nucleotide composition, comprising: a) a nucleotide sequence encoding at least a portion of a gene; b) a nucleotide sequence identical to a first region of an endogenous genomic target locus; and c) a nucleotide sequence identical to a second region of the endogenous genomic target locus, wherein the at least a portion of the gene is 100 bases in length, all of the nucleotide sequences are on a single polynucleotide, the nucleotide sequences identical to the first and the second regions of the endogenous genomic target locus are oriented to facilitate homologous recombination at the endogenous genomic target locus, the nucleotide sequence encoding the at least a portion of the gene is orientated such that the at least a portion of the gene is capable of being expressed following integration of the composition into the endogenous genomic target locus; and 2) providing a CRISPR/Cas9 nuclease composition capable of cleaving a defined nucleotide sequence within the endogenous genomic target locus; 3) contacting the T cell with the nucleotide composition and the CRISPR/Cas9 nuclease composition, and 4) delivering the nucleotide composition and the CRISPR/Cas9 nuclease composition into the T cell by electroporation.

Also provided for herein is a method of generating a modified T cell with a defined T cell receptor, the method comprising the steps of: 1) providing a nucleotide composition, comprising: a) a nucleotide sequence encoding at least a portion of a TCR-alpha polypeptide sequence; b) a nucleotide sequence encoding at least a portion of a TCR-beta polypeptide sequence; c) a nucleotide sequence encoding a first linker polypeptide sequence; d) a nucleotide sequence encoding a second linker polypeptide sequence; e) a nucleotide sequence identical to a first region of an endogenous TCR locus; and f) a nucleotide sequence identical to a second region of the endogenous TCR locus, wherein all of the nucleotide sequences are on a single polynucleotide, the nucleotide sequences identical to the first and the second regions of the endogenous TCR locus are oriented to facilitate homologous recombination at the endogenous TCR locus, the nucleotide sequence encoding the at least a portion of the TCR-alpha polypeptide sequence, the nucleotide sequence encoding the at least a portion of the TCR-beta polypeptide sequence, and the nucleotide sequences encoding the first and the second linker polypeptide sequences are orientated such that each of the polypeptide sequences is capable of being expressed as a single polypeptide following integration of the composition into the endogenous TCR locus, the first linker polypeptide sequence is positioned before the at least a portion of the TCR-alpha polypeptide sequence, the at least a portion of the TCR-beta polypeptide sequence, and the second linker polypeptide sequence, the second linker polypeptide sequence is positioned between the TCR-alpha polypeptide sequence and the TCR-beta polypeptide sequence, and the TCR-alpha polypeptide sequence and the TCR-beta polypeptide sequence each form a separate polypeptide, wherein the separate polypeptides are capable of associating together to form a functional TCR; 2) providing a nuclease composition capable of cleaving a defined nucleotide sequence within the endogenous TCR locus; 3) contacting the T cell with the nucleotide composition and the nuclease composition, and 4) delivering the nucleotide composition and the nuclease composition into the T cell.

In some embodiments, the method further comprises providing a second nuclease composition capable of cleaving a second defined nucleotide sequence within the T cell, wherein the second nuclease composition is contacted with the T cell in the contacting step and is delivered into the T cell in the delivering step. In some embodiments, the cleavage results in a mutation that produces a non-functional gene encoded by the second defined nucleotide sequence. In some embodiments, the mutation that produces the non-functional gene comprises a mutation in a coding region of the gene selected from the group consisting of a frameshift mutation resulting in a change in the frame of the protein translated, a nonsense mutation causing a substitution from an amino acid to a stop codon, and a missense mutation resulting in a substitution from one amino acid to another. In some embodiments, the mutation that produces the non-functional gene comprises a mutation in a non-coding region of the gene selected from the group consisting of a mutation that alters expression of a mRNA product encoded by the gene, and a mutation that alters stability of a mRNA product encoded by the gene.

In some embodiments, the method further comprises: providing a second nucleotide composition, the second composition comprising: a) a nucleotide sequence encoding at least a portion of a gene; b) a nucleotide sequence identical to a first region of an endogenous genomic target locus; and c) a nucleotide sequence identical to a second region of the endogenous genomic target locus, wherein all of the nucleotide sequences are on a single polynucleotide, the nucleotide sequences identical to the first and the second regions of the endogenous genomic target locus are oriented to facilitate homologous recombination at the endogenous genomic target locus, the nucleotide sequence encoding the at least a portion of the gene is orientated such that the at least a portion of the gene is capable of being expressed following integration of the composition into the endogenous genomic target locus, and the second nucleotide composition is contacted with the T cell in the contacting step and is delivered into the T cell in the delivering step.

In some embodiments, the nuclease composition comprises a nuclease selected from the group consisting of a Clustered Regularly Interspaced Short Palindromic Repeats (CRISPR) family nuclease, a Transcription activator-like effector nuclease (TALEN) or derivative thereof, a zinc-finger nuclease (ZFN) or derivative thereof, and a homing endonuclease (HE) or derivative thereof. In some embodiments, the CRISPR family nuclease is a Cas9 nuclease. In some embodiments, the nuclease composition comprises a preformed protein complex. In some embodiments, the nuclease composition comprises a nucleotide vector capable of expressing the nuclease within the T cell. In some embodiments, the contacting step is less than 60 minutes, less than 45 minutes, less than 30 minutes, less than 20 minutes, less than 15 minutes, less than 10 minutes, or less than 5 minutes between contacting the T cell with the nucleotide composition and the nuclease composition and the delivery step.

In some embodiments, the delivering step is selected from the group consisting of electroporation, transfection, cell membrane deformation by physical means, lipid nanoparticles (LNP), virus like particles (VLP), and sonication. In some embodiments, the delivering step comprises electroporation.

In some embodiments, expression of the encoded polypeptide sequences is directed by an endogenous promoter within the endogenous genomic target locus. In some embodiments, expression of the encoded polypeptide sequences is directed by an exogenous promoter. In some embodiments, the exogenous promoter is selected from the group consisting of mammalian promoters, human promoters, viral promoters, long-terminal repeat (LTR) derived promoters from a retrovirus or lentivirus, fusions of two promoters, fusions of two portions of promoters, MMLV LTR promoters, HIV LTR promoters, MCMV LTR promoters, EF1a, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter systems.

In some embodiments, the nucleotide sequence encoding the at least a portion of the TCR-alpha polypeptide sequence or the nucleotide sequence encoding the at least a portion of the TCR-beta polypeptide sequence is greater than or equal to 100 bases in length. In some embodiments, the nucleotide sequence encoding the at least a portion of the TCR-alpha polypeptide sequence or the nucleotide sequence encoding the at least a portion of the TCR-beta polypeptide sequence is greater than or equal to 200 bases in length, greater than or equal to 400 bases in length, greater than or equal to 600 bases in length, greater than or equal to 800 bases in length, greater than or equal to 1500 bases in length, greater than or equal to 2000 bases in length, or greater than or equal to 4000 bases in length.

In some embodiments, the nucleotide sequences identical to the first region or the second region of the endogenous TCR locus are 50 bases in length, 100 bases in length, 200 bases in length, 400 bases in length, 600 bases in length, 800 bases in length, 1500 bases in length, 2000 bases in length, or 4000 bases in length.

In some embodiments, the defined nucleotide sequence is disrupted following integration.

In some embodiments, expression of an endogenous gene operably associated with the endogenous TCR locus is disrupted.

In some embodiments, the method further comprises additional reagents that are capable of increasing homologous recombination rates or viability.

In some embodiments, the single polynucleotide is selected from the group consisting of a circular plasmid, a linear DNA fragment, a minicircle, and a ssDNA. In some embodiments, the circular plasmid has a vector backbone that is less than 500 bases, wherein the vector backbone is a nucleotide sequence that is not the nucleotide sequence encoding the at least a portion of the TCR-alpha polypeptide sequence, the nucleotide sequence encoding the at least a portion of the TCR-beta polypeptide sequence, nor the nucleotide sequences encoding the first and the second linker polypeptide sequences. In some embodiments, the single polynucleotide is not a polymerase chain reaction (PCR) amplified polynucleotide. In some embodiments, the single polynucleotide is substantially free of contaminants.

In some embodiments, the endogenous TCR locus comprises a coding region. In some embodiments, the endogenous TCR locus comprises an intron.

In some embodiments, the endogenous TCR locus comprises the TCR-alpha locus. In some embodiments, the endogenous TCR locus comprises the TCR-beta locus.

In some embodiments, the first linker sequence comprises a cleavable linker polypeptide sequence, wherein following expression the cleavable linker polypeptide is cleaved such that a polypeptide encoded only by the encoding the at least a portion of the TCR-alpha polypeptide sequence, the at least a portion of the TCR-beta polypeptide sequence and the second linker polypeptide sequence is produced. In some embodiments, the cleavable linker polypeptide sequence comprises a 2A ribosome skipping element selected from the group consisting of T2A, E2A, P2A, and F2A. In some embodiments, the cleavable linker polypeptide sequence comprises a furin cleavage site sequence. In some embodiments, the first linker polypeptide sequence comprises an IRES. In some embodiments, the first linker sequence comprises a splice acceptor sequence.

In some embodiments, the second linker sequence comprises a cleavable linker polypeptide sequence, wherein following expression the cleavable linker polypeptide is cleaved such that the TCR-alpha polypeptide sequence and the TCR-beta polypeptide sequence each form a separate polypeptide, wherein the separate polypeptides are capable of associating together to form a functional TCR. In some embodiments, cleavable linker polypeptide sequence comprises a 2A ribosome skipping element selected from the group consisting of T2A, E2A, P2A, and F2A. In some embodiments, the cleavable linker polypeptide sequence comprises a furin cleavage site sequence.

In some embodiments, the second linker sequence comprises an internal ribosome entry site (IRES). In some embodiments, the second linker sequence comprises an exogenous promoter.

In some embodiments, the TCR-alpha polypeptide sequence is selected from the group consisting of a murinized TCR-alpha, a humanized TCR-alpha, a domain swapped TCR-alpha, a point-mutated TCR-alpha, an engineered TCR-alpha with an engineered cysteine capable of forming a disulfide linkage, a codon optimized TCR-alpha optimized for expression in humans, a chimeric antigen receptor (CAR), and a sequence optimized TCR-alpha optimized for codon usage and removal of RNA instability elements.

In some embodiments, the TCR-beta polypeptide sequence is selected from the group consisting of a murinized TCR-beta, a humanized TCR-beta, a domain swapped TCR-beta, a point-mutated TCR-beta, an engineered TCR-beta with an engineered cysteine capable of forming a disulfide linkage, a codon optimized TCR-beta optimized for expression in humans, a chimeric antigen receptor (CAR), and a sequence optimized TCR-beta optimized for codon usage and removal of RNA instability elements.

In some embodiments, the encoded polypeptide sequences are in a first linker: TCR-alpha:second linker: TCR-beta orientation. In some embodiments, the encoded polypeptide sequences are in a linker: TCR-beta: second linker:TCR-alpha orientation.

In some embodiments, the second defined nucleotide sequence is within an endogenous TCR-beta locus if the defined nucleotide sequence is within an endogenous TCR-alpha locus.

In some embodiments, the second defined nucleotide sequence is within an endogenous TCR-alpha locus if the defined nucleotide sequence is within an endogenous TCR-beta locus. In some embodiments, the second defined nucleotide sequence is within an immune checkpoint locus.

In some embodiments, the at least a portion of the gene is selected from the group consisting of a shRNA, a siRNA, a miRNA, a cytokine, a factor that promotes T-cell survival, a factor that promotes T-cell function, and an immune checkpoint inhibitor.

Also provided for herein is a nucleotide composition for use in directing homologous recombination at an endogenous genomic target locus, comprising a circular polynucleotide comprising: a) a nucleotide sequence encoding at least a portion of a gene; b) a nucleotide sequence identical to a first region of an endogenous genomic target locus; and c) a nucleotide sequence identical to a second region of the endogenous genomic target locus, wherein all of the nucleotide sequences are on a single polynucleotide, the nucleotide sequences identical to the first and the second regions of the endogenous genomic target locus are oriented to facilitate homologous recombination at the endogenous genomic target locus, the nucleotide sequence encoding the at least a portion of the gene is orientated such that the at least a portion of the gene is capable of being expressed following integration of the composition into the endogenous genomic target locus. In some embodiments, the nucleotide sequence encoding the at least a portion of the gene is greater than or equal to 100 bases in length. In some embodiments, the nucleotide sequence encoding the at least a portion of the gene is greater than or equal to 200 bases in length, greater than or equal to 400 bases in length, greater than or equal to 600 bases in length, greater than or equal to 800 bases in length, greater than or equal to 1500 bases in length, greater than or equal to 2000 bases in length, or greater than or equal to 4000 bases in length.

In some embodiments, the nucleotide sequences identical to the first region of the endogenous genomic target locus is greater than or equal to 50 bases in length, greater than or equal to 100 bases in length, greater than or equal to 200 bases in length, greater than or equal to 300 bases in length, greater than or equal to 600 bases in length, greater than or equal to 1000 bases in length, or greater than or equal to 2000 bases in length.

In some embodiments, the nucleotide sequences identical to the second region of the endogenous genomic target locus is greater than or equal to 50 bases in length, greater than or equal to 100 bases in length, greater than or equal to 200 bases in length, greater than or equal to 300 bases in length, greater than or equal to 600 bases in length, greater than or equal to 1000 bases in length, or greater than or equal to 2000 bases in length.

In some embodiments, the nucleotide sequences identical to the first region of the endogenous genomic target locus and the nucleotide sequences identical to the second region of the endogenous genomic target locus are each greater than or equal to 600 bases in length.

In some embodiments, the circular polynucleotide comprises a plasmid or a nanoplasmid. In some embodiments, the plasmid has a vector backbone that is less than 500 bases, and wherein the vector backbone is a nucleotide sequence that is not the nucleotide sequence encoding the at least a portion of the gene and not the nucleotide sequence identical to the first endogenous target genomic locus.

In some embodiments, the circular polynucleotide is not a polymerase chain reaction (PCR) amplified polynucleotide.

In some embodiments, the endogenous genomic target locus comprises a coding region. In some embodiments, the endogenous genomic target locus comprises an intron.

In some embodiments, the endogenous genomic target locus or the endogenous TCR locus comprises the T cell receptor (TCR)-alpha locus. In some embodiments, the endogenous genomic target locus or the endogenous TCR locus comprises the TCR-beta locus.

In some embodiments, the endogenous genomic target comprises an immune checkpoint locus. In some embodiments, the immune checkpoint locus is selected from the group consisting of PD-1, CTLA-4, BTLA, TIM3, LAG3, and VISTA.

In some embodiments, the at least a portion of the gene comprises a linker sequence. In some embodiments, the linker sequence encodes a cleavable linker polypeptide sequence, wherein following expression the cleavable linker polypeptide is cleaved such that a polypeptide encoded only by the at least a portion of the gene is produced. In some embodiments, any one of the cleavable linker polypeptides comprises a furin cleavage site. In some embodiments, any one of the linker sequences comprise a 2A ribosome skipping element selected from the group consisting of: T2A, E2A, P2A, and F2A. In some embodiments, any one of the cleavable linker polypeptides comprise a Gly-Ser-Gly linker, optionally wherein the Gly-Ser-Gly linker is N-terminal of a 2A ribosome skipping element, and optionally wherein the Gly-Ser-Gly linker is in a furin cleavage site: Gly-Ser-Gly linker:2A ribosome skipping element orientation from N-terminus to C-terminus. In some embodiments, the linker sequence, the nucleotide sequences encoding the first linker polypeptide sequence, or the nucleotide sequences encoding the second linker polypeptide sequence comprises an internal ribosome entry site (IRES). In some embodiments, the linker sequence, the nucleotide sequences encoding the first linker polypeptide sequence, or the nucleotide sequences encoding the second linker polypeptide sequence comprises an exogenous promoter.

In some embodiments, the nucleotide sequences encoding the first linker polypeptide sequence, or the nucleotide sequences encoding the second linker polypeptide sequence comprises a splice acceptor sequence.

In some embodiments, the at least a portion of the gene comprises a nucleotide sequence encoding a signal peptide, wherein the signal peptide is operably linked to a polypeptide encoded by the at least a portion of the gene, the TCR-alpha polypeptide sequence, the TCR-beta polypeptide sequence, or a polypeptide encoded by the at least a portion of the TCR gene. In some embodiments, the signal peptide is an exogenous signal peptide, optionally wherein the exogenous signal peptide is a Human Growth Hormone signal peptide.

In some embodiments, the first linker polypeptide sequence and the second linker polypeptide sequence comprise the same linker polypeptide sequence. In some embodiments, the nucleotide sequences encoding the first linker polypeptide sequence and the nucleotide sequence encoding the second linker polypeptide sequence that encode the same linker polypeptide sequence comprise codon diverged nucleotide sequences, and wherein the nucleotide sequences encoding the first linker polypeptide sequence and the nucleotide sequence encoding the second linker polypeptide are codon diverged relative to each other.

In some embodiments, the at least a portion of the gene encodes a coding region. In some embodiments, the coding region is selected from the group consisting of: a factor that modulates the immune system, a cytokine, a factor that modulates T cell function, a factor that promotes T-cell survival, a factor that promotes T-cell function, and an immune checkpoint inhibitor.

In some embodiments, the at least a portion of the gene encodes a non-coding region. In some embodiments, the non-coding region is selected from the group consisting of: an shRNA, an siRNA, an miRNA, a factor that modulates the immune system, a cytokine, a factor that modulates T cell function, a factor that promotes T-cell survival, and a factor that promotes T-cell function.

T In some embodiments, the at least a portion of the gene comprises at least a portion of a TCR gene. In some embodiments, the at least a portion of the TCR gene comprises: a) a nucleotide sequence encoding a TCR-alpha polypeptide sequence; b) a nucleotide sequence encoding a TCR-beta polypeptide sequence; and c) a nucleotide sequence encoding a second linker sequence.

In some embodiments, the nucleotide sequence encoding the TCR-alpha polypeptide sequence, the nucleotide sequence encoding the TCR-beta polypeptide sequence, or the at least a portion of the TCR gene is selected from the group consisting of: at least a portion of a murinized TCR, a humanized TCR, a domain swapped TCR, a point-mutated TCR, an engineered TCR with an engineered cysteine capable of forming a disulfide linkage, a codon optimized TCR optimized for expression in humans, a sequence optimized TCR optimized for codon usage and removal of RNA instability elements, a variable region sequence of the TCR gene, a chimeric antigen receptor (CAR), and a single-chain TCR.

In some embodiments, the TCR-alpha polypeptide sequence, the TCR-beta polypeptide sequence, or a polypeptide encoded by the at least a portion of the TCR gene is engineered to demonstrate a greater association with a second exogenous TCR polypeptide sequence relative to an endogenous TCR polypeptide sequence, optionally wherein the TCR-alpha polypeptide sequence and the TCR-beta polypeptide sequence are engineered to demonstrate a greater association with each other relative to an endogenous TCR polypeptide sequence.

In some embodiments, the encoded polypeptide sequences are in a linker:TCR-alpha: second linker: TCR-beta orientation from N-terminus to C-terminus. In some embodiments, the encoded polypeptide sequences are in a linker:TCR-beta:second linker:TCR-alpha orientation from N-terminus to C-terminus.

In some embodiments, the at least a portion of the gene, the nucleotide sequence encoding the TCR-alpha polypeptide sequence, the nucleotide sequence encoding the TCR-beta polypeptide sequence, or the nucleotide sequence encoding the at least a portion of the TCR gene comprises a codon diverged nucleotide sequence, and wherein the codon diverged nucleotide sequence is codon diverged relative to an endogenous nucleotide sequence.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 5A illustrates the target TCRα locus (endogenous TRAC, top panel) and its CRISPR Cas9 target site (horizontal stripe, cleavage site designated by arrow), and the circular plasmid HR template (bottom panel) with the polynucleotide encoding the neoTCR, which is located between left and right homology arms ("LHA" and "RHA" respectively) prior to integration. FIG. 5B illustrates the integrated neoTCR in the TCRα locus (top panel), the transcribed and spliced neoTCR mRNA (middle panel), and translation and processing of the expressed neoTCR (bottom panel).

FIG. 8A shows expression of the MART-1 neoTCR using MART-1 specific dextramer staining. FIG. 8B shows a summary of editing results for the MART-1 neoTCR using MART-1 specific dextramer staining at Day 10.

FIG. 13A shows a standard PCR product (top) and a semi-protect PCR product (bottom). FIG. 13B shows editing efficiencies using a circular plasmid, a standard PCR product, and a semi-protected PCR product for an HR template.

FIG. 18A shows editing efficiency (as % of CD8+) of the neoTCRs MART-1, Neo12, and NY-ESO as detected by specific dextramer staining in either healthy donor or patient derived T cells. FIG. 18B shows editing efficiency (as % of CD8+) of the neoTCR neo12 in healthy donor-derived T cells.

FIG. 20A shows histograms of MFI for the endogenous TCR (left histogram) and Neo12 neoTCR TCR (right histogram) stained using the same antibody (CD3).

FIG. 20B shows surface expression levels analysis of the neoTCRs MART-1, Neo12, and NY-ESO compared to an endogenous TCR. *TCR expression levels per cell are based on literature.

FIG. 25A shows a representative histogram plot demonstrating proliferation with percent dividing cells calculated in FIG. 25B.

FIGS. 26A-26D show assessment of engineered T cells in an antigen-specific cytokine production assay for the cytokines IFNγ (FIG. 26A), IL-2 (FIG. 26B), TNFα (FIG. 26C), and IL-6 (FIG. 26D).

FIGS. 27A-27D show assessment of edited T cells using donor-derived T cells.

FIG. 27A shows editing efficiencies of T cells derived from healthy donors and patient donors.

FIG. 27B shows an antigen-specific T cell-mediated killing assay for T cells derived from healthy donors and patient donors. FIG. 27C shows an antigen-specific proliferation assay for T cells derived from healthy donors and patient donors. FIG. 27D shows an antigen-specific cytokine production assay for T cells derived from healthy donors and patient donors.

FIGS. 28A-28C show assessment of edited T cells using donor-derived T cells.

FIG. 28A shows editing efficiencies of donor T cells expressing either a Neo12 neoTCR or a MART-1 neoTCR. FIG. 28B shows an antigen-specific T cell-mediated killing assay for donor T cells expressing either a Neo12 neoTCR or a MART-1 neoTCR. FIG. 28C shows an antigen-specific proliferation assay for donor T cells expressing either a Neo12 neoTCR or a MART-1 neoTCR.

FIGS. 30A-30C show Isoplexis analysis for an edited T cell expressing either a Neo12 neoTCR (FIG. 30A) or a MART-1 neoTCR (FIG. 30B). FIG. 30C shows contribution of the engineered T cells to a cytokine response (left panel) and the percentage of T cells producing each cytokine (right panel).

DETAILED DESCRIPTION OF THE INVENTION

Definitions

Figure 1:
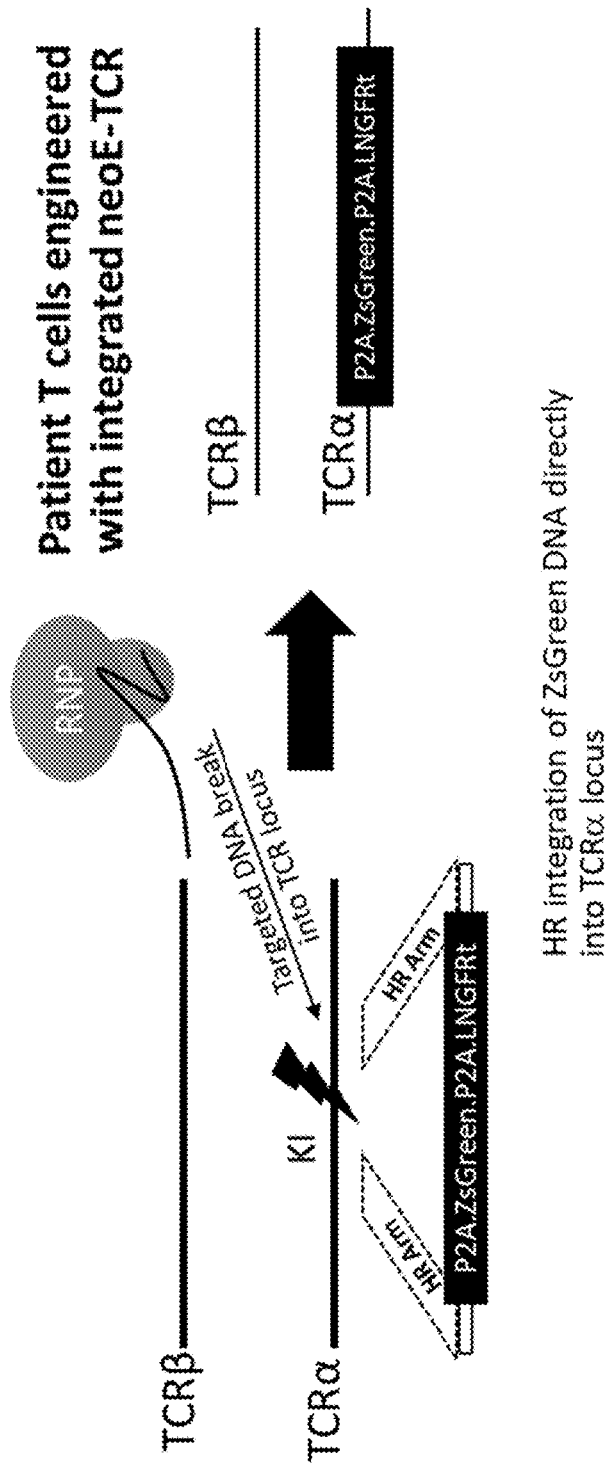
FIG. 1 presents a schematic representing the general editing strategy used for ZsGreen reporter integration into an TRAC locus. The general TCRα locus targeting strategy used a homologous repair template containing a promoterless ZsGreen and truncated LNGRF coding sequence flanked by 1 kb left and right homology arms ("HR Arms") and separated by P2A sequences, as well as a 5' P2A sequence separating the ZsGreen and LNGRF cassette from TCRα locus sequences, encoded in a circular Nanoplasmid.

As used herein, "antigen" includes any antigen including patient-specific neoantigens. An antigen includes any substance that can induce an immune response.

As used herein, "antigen-specific T cells" refer to cells that are distinguished from one another by their T cell receptors (TCRs), which give them their antigen specificity.

As used herein, "antigen complex," "antigen-MHC," "antigen-MHC complex," "recombinant antigen-MHC complex," "peptide MHC," "p/MHC," and "pHLA" are used interchangeably to refer to a recombinant major histocompatibility complex with a peptide in the antigen binding groove. As used herein, the term MHC includes, but is not limited to, human MHCs termed human leukocyte antigens (HLAs).

The term "effective amount" or "therapeutically effective amount" refers to an amount that is effective to ameliorate a symptom of a disease, e.g. an amount that is effective to inhibit the growth of a tumor.

The term "ameliorating" refers to any therapeutically beneficial result in the treatment of a disease state, e.g., a cancerous disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al.).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (<www.ncbi.nlm.nih.gov/>).

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in Tables 1-4 are, in some embodiments, considered conservative substitutions for one another.

TABLE 1

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 2

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 3

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, Proteins: Structures and Molecular Properties 2nd ed. (1993) W. H. Freeman & Co., New York, N.Y. A protein generated by making one or more conservative substitutions of amino acid residues in a parent protein is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The term "substantially free of" is understood to mean less than a statistically significant amount of component (e.g., a contaminant or a viral component) present in a relevant total composition, including the component being at an undetectable level in the relevant total composition (i.e., "free of"). Less than a statistically significant amount can refer to a level of detection that does not qualify as having statistical confidence that a component is present in a relevant composition, such as a p-value greater than 0.1, 0.05, or 0.01. A composition can be substantially free of a component if the composition contains less than 10%, 9%, 8%, 7%, 6%, 5%, 4%, 3%, 2%, 1%, 0.5%, 0.1%, 0.05%, 0.01%, 0.001%, or 0.0001% of the component by mass/volume percentage concentration.

It must be noted that, as used in the specification and the appended claims, the singular forms "a," "an" and "the" include plural referents unless the context clearly dictates otherwise.

Modified Cells

Provided herein are modified cells, e.g., including primary human cells modified to add and/or remove genetic elements without the use of a viral delivery system.

In one aspect, the modified cells comprise: a circular polynucleotide comprising an exogenous nucleotide sequence, the exogenous nucleotide sequence comprising: a) a nucleotide sequence encoding at least a portion of a gene; b) a nucleotide sequence identical to a first region of an endogenous genomic target locus; and c) a nucleotide sequence identical to a second region of the endogenous genomic target locus, the nucleotide sequences identical to the first and the second regions of the endogenous genomic target locus are oriented to facilitate homologous recombination at the endogenous genomic target locus, and wherein the modified cell is substantially free of viral-mediated delivery components. The modified cell can further comprise an integrated nucleotide sequence, wherein the integrated nucleotide sequence comprises a sequence identical to the nucleotide sequence encoding the at least the portion of the gene, the integrated nucleotide sequence is integrated at the endogenous genomic target locus, and the integrated nucleotide sequence is orientated such that the at least a portion of the gene is capable of being expressed.

In another aspect, a modified cell is provided, the modified cell comprising: a T cell, the T cell comprising: a) a nucleotide sequence encoding a TCR-alpha polypeptide sequence; b) a nucleotide sequence encoding a TCR-beta polypeptide sequence; c) a nucleotide sequence encoding a first linker polypeptide sequence; d) a nucleotide sequence encoding a second linker polypeptide sequence; wherein the nucleotide sequence encoding the TCR-alpha polypeptide sequence, the nucleotide sequence encoding the TCR-beta polypeptide sequence, and the nucleotide sequences encoding the first and the second linker polypeptide sequences are integrated into an endogenous TCR-alpha locus, the nucleotide sequence encoding the TCR-alpha polypeptide sequence, the nucleotide sequence encoding the TCR-beta polypeptide sequence, and the nucleotide sequences encoding the first and the second linker polypeptide sequences are orientated such that each of the polypeptide sequences is capable of being expressed as a single polypeptide, wherein the second linker polypeptide sequence is positioned between the TCR-alpha polypeptide sequence and the TCR-beta polypeptide sequence, the first and the second linker polypeptide are cleavable linker polypeptides capable of being cleaved in the T cell such that the TCR-alpha polypeptide sequence and the TCR-beta polypeptide sequence each form a separate polypeptide, wherein the separate polypeptides are capable of associating together to form a functional TCR, wherein the modified cell is substantially free of viral mediated delivery components, and wherein an endogenous TCR-beta locus is disrupted. The modified T cell can further comprise a circular polynucleotide comprising an exogenous nucleotide sequence, the exogenous nucleotide sequence comprising: a) a nucleotide sequence encoding the nucleotide sequence encoding the TCR-alpha polypeptide sequence, the nucleotide sequence encoding the TCR-beta polypeptide sequence, and the nucleotide sequences encoding the first and the second linker polypeptide sequences; b) a nucleotide sequence identical to a first region of the endogenous TCR locus; and c) a nucleotide sequence identical to a second region of the endogenous TCR locus, and the nucleotide sequences identical to the first and the second regions of the endogenous TCR locus are oriented to facilitate homologous recombination at the endogenous TCR locus.

In another aspect, modified T cells are provided comprising: a) a nucleotide sequence encoding a TCR-alpha polypeptide sequence; b) a nucleotide sequence encoding a TCR-beta polypeptide sequence; c) a nucleotide sequence encoding a first linker polypeptide sequence; d) a nucleotide sequence encoding a second linker polypeptide sequence; wherein the nucleotide sequence encoding the TCR-alpha polypeptide sequence, the nucleotide sequence encoding the TCR-beta polypeptide sequence, and the nucleotide sequences encoding the first and the second linker polypeptide sequences are integrated into an endogenous TCR locus, the nucleotide sequence encoding the TCR-alpha polypeptide sequence, the nucleotide sequence encoding the TCR-beta polypeptide sequence, and the nucleotide sequences encoding the first and the second linker polypeptide sequences are orientated such that each of the polypeptide sequences is capable of being expressed as a single polypeptide, wherein the second linker polypeptide sequence is positioned between the TCR-alpha polypeptide sequence and the TCR-beta polypeptide sequence, and the first and the second linker polypeptide are cleavable linker polypeptides capable of being cleaved in the modified T cell such that the TCR-alpha polypeptide sequence and the TCR-beta polypeptide sequence each form a separate polypeptide, wherein the separate polypeptides are capable of associating together to form a functional TCR. The modified T cell can further comprise a circular polynucleotide comprising an exogenous nucleotide sequence, the exogenous nucleotide sequence comprising: a) a nucleotide sequence encoding the nucleotide sequence encoding the TCR-alpha polypeptide sequence, the nucleotide sequence encoding the TCR-beta polypeptide sequence, and the nucleotide sequences encoding the first and the second linker polypeptide sequences; b) a nucleotide sequence identical to a first region of the endogenous TCR locus; and c) a nucleotide sequence identical to a second region of the endogenous TCR locus, and the nucleotide sequences identical to the first and the second regions of the endogenous TCR locus are oriented to facilitate homologous recombination at the endogenous TCR locus. The modified T cell can be substantially free of viral-mediated delivery components.

Cell Modifications and Genomic Editing

In general, modified cells are modified such that they are genomically edited or are capable of being genomically edited. For example, a modified cell can be genomically edited to express an exogenous gene using nuclease-mediated gene editing systems. As such, the modified cell can comprise a nuclease composition that cleaves a defined nucleotide sequence within an endogenous genomic target locus, including an endogenous TCR locus. A cell can be considered modified if an exogenous polynucleotide (e.g., an exogenous gene or portion thereof) is integrated into the genome of the modified cell. A cell can be considered modified if it contains one or more of the components generally used in nuclease-mediated gene editing, i.e., containing components that can promote genomic editing (e.g., nucleases, homology repair templates, CRISPR system nucleotides, etc.). A cell can be considered modified if it contains one or more non-templated mutations (e.g., mutations separate from an integrated exogenous polynucleotide), such as one or more non-templated mutations that disrupt an endogenous target locus. The various modifications are not mutually exclusive, i.e., a modified cell can have an integrated exogenous polynucleotide (e.g., an exogenous gene or portion thereof), as well as one or more of the components generally used in nuclease-mediated gene editing, such as those components that promote the integration of exogenous polynucleotides.

In an illustrative example, a modified T cell can have an integrated polynucleotide encoding an exogenous TCR sequence, a CRISPR/Cas9 RNP that targets an endogenous TCR locus, and a homology repair template (HRT) that encodes an exogenous TCR sequence. In another illustrative example, a modified cell can have a CRISPR/Cas9 RNP that targets an endogenous TCR locus and a homology repair template (HRT) that encodes an exogenous TCR sequence.

In another illustrative example, a modified cell can have an integrated polynucleotide encoding an exogenous sequence (e.g., at least a portion of a gene), a CRISPR/Cas9 RNP that targets an endogenous locus, and a homology repair template (HRT) that encodes an exogenous sequence. In another illustrative example, a modified cell can have a CRISPR/Cas9 RNP that targets an endogenous locus and a homology repair template (HRT) that encodes an exogenous sequence.

In another illustrative example, a modified hematopoietic stem cell (HSC) can have an integrated polynucleotide encoding an exogenous sequence (e.g., at least a portion of a gene), a CRISPR/Cas9 RNP that targets an endogenous locus, and a homology repair template (HRT) that encodes an exogenous sequence. In another illustrative example, a modified HSC can have a CRISPR/Cas9 RNP that targets an endogenous locus and a homology repair template (HRT) that encodes an exogenous sequence.

In another illustrative example, a modified natural killer (NK) cell can have an integrated polynucleotide encoding an exogenous sequence (e.g., at least a portion of a gene), a CRISPR/Cas9 RNP that targets an endogenous locus, and a homology repair template (HRT) that encodes an exogenous sequence. In another illustrative example, a modified NK cell can have a CRISPR/Cas9 RNP that targets an endogenous locus and a homology repair template (HRT) that encodes an exogenous sequence.

Disruption of an Endogenous Gene

Modified cells can be modified such that a non-functional gene is produced or is capable of being produced.

Mutations that result in a non-functional gene produced by a nuclease composition can be a result of templated genomic editing, e.g., homologous recombination DNA repair mechanisms. Modified cells are that are genomically edited to express an exogenous polynucleotide (e.g., a gene) at a genomic target locus can also disrupt expression of an endogenous gene operably associated with the endogenous genomic target locus. For example, an endogenous gene encoded by the genomic target locus can be functionally deleted (e.g., removal/replacement of the endogenous gene or portion thereof by the integrated exogenous gene) or functionally disrupted (e.g., integration of the exogenous gene within the endogenous gene or portion thereof such that transcription and/or translation of the endogenous gene is disrupted). In an illustrative example, an exogenous gene encoding a TCR can be integrated in an endogenous TCR locus, such as a TCR alpha constant region encoding exon, such that expression of the endogenous TCR gene is disrupted. Disrupted expression can be reduced expression of mRNA encoding the endogenous gene compared to a non-modified cell or can be reduced translation of the endogenous gene compared to a non-modified cell. Disrupted expression can be elimination of detectable expression of mRNA encoding the endogenous gene compared to a non-modified cell or can be elimination of detectable translation of the endogenous gene compared to a non-modified cell.

Modified cells can have modifications that include non-templated mutations (e.g., mutations separate from an integrated exogenous polynucleotide) that produce a non-functional gene encoded by a defined nucleotide sequence (i.e., a genomic target locus). Mutations that result in a non-functional gene produced by a nuclease composition can be a result of non-templated genomic deletions, e.g., nuclease cleavage induced non-homologous end joining (NHEJ) DNA repair mechanisms resulting in genomic insertion or deletions (also referred to as indels). Mutations that can produce a non-functional gene include a mutation in a coding region of the gene (e.g., a frameshift mutation resulting in a change in the frame of the protein translated, a nonsense mutation causing a substitution from an amino acid to a stop codon, or a missense mutation resulting in a substitution from one amino acid to another) or a mutation in a non-coding region (e.g., a mutation that alters expression of an mRNA product encoded by the gene, or a mutation that alters stability of an mRNA product encoded by the gene). Modifications can include nuclease compositions capable of producing non-templated mutations in modified cells (e.g., a nuclease composition capable of cleaving a defined nucleotide sequence).

Multiple Modifications

Modified cells can have more than one modification, e.g., modifications at more than one genomic locus in the modified cell. For example, modified cells can have more than one integrated exogenous polynucleotide at more than one genomic locus, such as the modified cell further comprising a second integrated nucleotide sequence, wherein the second integrated nucleotide sequence comprises a sequence identical to the nucleotide sequence encoding the at least the portion of a second gene, the second integrated nucleotide sequence is integrated at the second endogenous genomic target locus, and the second integrated nucleotide sequence is orientated such that the at least a portion of the second gene is capable of being expressed. The modified cell can have components that promote integration of a second exogenous polynucleotide, such as a second circular polynucleotide comprising a second exogenous nucleotide composition, the second exogenous nucleotide composition comprising: a) a nucleotide sequence encoding at least a portion of a second gene; b) a nucleotide sequence identical to a first region of a second endogenous genomic target locus; and c) a nucleotide sequence identical to a second region of the second endogenous genomic target locus, and the nucleotide sequences identical to the first and the second regions of the second endogenous genomic target locus are oriented to facilitate homologous recombination at the second endogenous genomic target locus, and/or a second nuclease composition capable of cleaving a second defined nucleotide sequence within the modified cell. In general, a modified cell is not limited to only one or two integrated nucleotide sequences and can include any number of integrated nucleotide sequences, such as 1-10, 1-2, 1-3, 2-3, 3, 4, 5, 6, 7, 8, 9, 10 or more integrated nucleotide sequences.

Likewise, a modified cell can have components that can result in 1-10, 1-2, 1-3, 2-3, 3, 4, 5, 6, 7, 8, 9, 10 or more integrated nucleotide sequences, such as homologous repair templates, nucleases, etc. In an illustrative example, a "multiplexed" CRISPR-mediated gene editing approach can be used to integrate multiple genes or portions thereof through introducing multiple homologous repair templates simultaneously with multiple CRISPR RNP complexes that direct cleavage at multiple genomic locations. The multiple sequences can also be integrated sequentially.

Modified cells can have modifications that include multiple non-templated mutations (e.g., mutations separate from an integrated exogenous polynucleotide), such as multiple non-templated mutations that produce a non-functional gene encoded by a defined nucleotide sequence (i.e., a genomic target locus). Modifications can include nuclease compositions capable of producing multiple non-templated mutations in modified cells. For example, a modified cell can have two or three separate non-templated mutations that result in two or three non-functional genes, respectively. In general, a modified cell can have any number of non-templated mutations, e.g., 4, 5, 6, 7, 8, 9, 10 or more separate non-templated mutations, respectively. In an illustrative example, a "multiplexed" CRISPR-mediated gene editing approach can be used to disrupt multiple genes through simultaneously introducing multiple CRISPR RNP complexes that direct cleavage at multiple genomic locations resulting in multiple non-templated mutations.

A modified cell can have more than one mutation that results in more than one non-functional gene. For example, a modified cell can have two or three separate mutations that result in two or three non-functional genes, respectively. In general, a modified cell can have any number of mutations that result in any number of non-functional genes, e.g., 4, 5, 6, 7, 8, 9, 10 or more separate mutations that result in 4, 5, 6, 7, 8, 9, 10 or more non-functional genes, respectively. In an illustrative example, a "multiplexed" CRISPR-mediated gene editing approach can be used to disrupt multiple genes through simultaneously introducing multiple CRISPR RNP complexes that direct cleavage at multiple genomic locations resulting in multiple mutations. The multiple genes can also be disrupted sequentially. Mutations that result in a non-functional gene produced by a nuclease composition can be a result of templated genomic editing, e.g., homologous recombination DNA repair mechanisms. Mutations that result in a non-functional gene produced by a nuclease composition can be a result of non-templated genomic deletions, e.g., nuclease cleavage induced non-homologous end joining (NHEJ) DNA repair mechanisms resulting in genomic insertion or deletions (also referred to as indels).

Multiple modifications can include a combination of any of the modifications described, such as one or more integrated nucleotide sequences in combination with one or more non-templated mutations. In an illustrative example, a "multiplexed" CRISPR-mediated gene editing approach can be used to both integrate one or more genes or portions thereof through homology directed repair (i.e., introduce multiple homologous repair templates simultaneously with multiple CRISPR RNP complexes that direct cleavage at multiple genomic locations) while simultaneously disrupting multiple genes (i.e., simultaneously introducing multiple CRISPR RNP complexes that direct cleavage at multiple genomic locations resulting in multiple non-templated mutations, e.g., multiple indels). The integrations and disruptions can be performed sequentially.

As an illustrative example of a modified cell with multiple modifications, a modified T cell with a TCR expression cassette integrated in a TCRα locus and a disrupted TCRβ locus such that the TCRβ locus is non-functional gene. As another illustrative example, illustrative example of a modified cell with multiple modifications, a modified T cell with a TCR expression cassette integrated in a TCRβ locus and a disrupted TCRα locus such that the TCRα locus is non-functional gene.

Target Locus

The modified cells are genomically edited, or capable of being genomically edited, at an endogenous genomic target locus, i.e., at a specific genomic location within the modified cell, such as a specific gene of interest or a specific nucleotide sequence of interest. An endogenous genomic target locus can be a coding region of a gene. An endogenous genomic target locus can be a non-coding region of a gene, such as an intron. An endogenous genomic target locus can be a non-coding genomic region other than a genomic region typically associated with a typical gene, such as one or more regions encoding non-coding functional RNAs, repetitive DNA elements, retroviral elements, pseudogenes, and the like.

Cell Populations

In a particular aspect, a population of cells (e.g., a population of T cells), is provided. The population of cells can comprise any of the modified cells described herein. The modified cell can be within a heterogeneous population of cells and/or a heterogeneous population of different cell types. The population of cells can be heterogeneous with respect to the percentage of cells that are genomically edited. A population of cells can have greater than 10%, greater than 20%, greater than 30%, greater than 40%, greater than 50%, greater than 60%, greater than 70%, greater than 80%, or greater than 90% of the population comprise an integrated nucleotide sequence. In a certain aspect, a populations of cells comprises an integrated nucleotide sequence, wherein the integrated nucleotide sequence comprises at least a portion of a gene, the integrated nucleotide sequence is integrated at an endogenous genomic target locus, and the integrated nucleotide sequence is orientated such that the at least a portion of the gene is capable of being expressed, wherein the population of cells is substantially free of viral-mediated delivery components, and wherein greater than 10%, greater than 20%, greater than 30%, greater than 40%, greater than 50%, greater than 60%, greater than 70%, greater than 80%, or greater than 90% of the cells in the population comprise the integrated nucleotide sequence.

A population of cells can have greater than 91%, greater than 92%, greater than 93%, greater than 94%, greater than 95%, greater than 96%, or greater than 97%, greater than 98%, greater than 99%, greater than 99.5%, or greater than 99.9% of the population comprise an integrated nucleotide sequence. A population of cells can have greater than 20% of the population comprise an integrated nucleotide sequence. A population of cells can have greater than 30% of the population comprise an integrated nucleotide sequence. A population of cells can have greater than 60% of the population comprise an integrated nucleotide sequence. A population of cells can have greater than 70% of the population comprise an integrated nucleotide sequence.

A population of cells can have between 10% and 70%, between 20% and 70%, between 30% and 70%, between 40% and 70%, between 50% and 70%, between 60% and 70%, between 10% and 80%, between 10% and 60%, between 10% and 50%, between 10% and 40%, between 10% and 30%, between 10% and 20%, between 20% and 80%, between 30% and 80%, between 40% and 80%, between 50% and 80%, between 60% and 80%, between 70% and 80% of the population comprise an integrated nucleotide sequence. A population of cells can have between 10% and 100%, between 20% and 100%, between 30% and 100%, between 40% and 100%, between 50% and 100%, between 60% and 100%, between 70% and 100%, between 80% and 100%, between 90% and 100%, between 95% and 100%, between 96% and 100%, between 97% and 100%, between 980% and 100%, between 99% and 100%, between 99.5% and 100% of the population comprise an integrated nucleotide sequence. A population of cells can have between 10% and 70% comprise an integrated nucleotide sequence. A population of cells can have between 20% and 70% comprise an integrated nucleotide sequence. A population of cells can have between 30% and 70% comprise an integrated nucleotide sequence. A population of cells can have between 10% and 80% comprise an integrated nucleotide sequence. A population of cells can have between 20% and 80% comprise an integrated nucleotide sequence. A population of cells can have between 30% and 80% comprise an integrated nucleotide sequence.

The population of cells can be heterogeneous with respect to the percentage of cells that have a single modification, e.g., an integrated nucleotide sequence. The population of cells can be heterogeneous with respect to the percentage of cells that have either a first modification, a second modification, or both a first and a second modification, e.g., as an illustrative example, heterogeneous with respect to the percentage of cells that have either an integrated nucleotide sequence, a mutation that produces a non-functional gene encoded by a second defined nucleotide sequence, or both an integrated nucleotide sequence and a mutation that produces a non-functional gene encoded by a second defined nucleotide sequence.

A population of cells can have greater than 10%, greater than 20%, greater than 30%, greater than 40%, greater than 50%, greater than 60%, greater than 70%, greater than 80%, or greater than 90% of the population comprise an integrated nucleotide sequence and a mutation that produces a non-functional gene encoded by a second defined nucleotide sequence. A population of cells can have greater than 91%, greater than 92%, greater than 93%, greater than 94%, greater than 95%, greater than 96%, or greater than 97%, greater than 98%, greater than 99%, greater than 99.5%, or greater than 99.9% of the population comprise an integrated nucleotide sequence and a mutation that produces a non-functional gene encoded by a second defined nucleotide sequence. A population of cells can have greater than 20% of the population comprise an integrated nucleotide sequence and a mutation that produces a non-functional gene encoded by a second defined nucleotide sequence. A population of cells can have greater than 30% of the population comprise an integrated nucleotide sequence and a mutation that produces a non-functional gene encoded by a second defined nucleotide sequence. A population of cells can have greater than 60% of the population comprise an integrated nucleotide sequence and a mutation that produces a non-functional gene encoded by a second defined nucleotide sequence. A population of cells can have greater than 70% of the population comprise an integrated nucleotide sequence and a mutation that produces a non-functional gene encoded by a second defined nucleotide sequence. A population of cells can have between 10% and 70%, between 20% and 70%, between 30% and 70%, between 40% and 70%, between 50% and 70%, between 60% and 70%, between 10% and 80%, between 10% and 60%, between 10% and 50%, between 10% and 40%, between 10% and 30%, between 10% and 20%, between 20% and 80%, between 30% and 80%, between 40% and 80%, between 50% and 80%, between 60% and 80%, between 70% and 80% of the population comprise an integrated nucleotide sequence and a mutation that produces a non-functional gene encoded by a second defined nucleotide sequence. A population of cells can have between 10% and 100%, between 20% and 100%, between 30% and 100%, between 40% and 100%, between 50% and 100%, between 60% and 100%, between 70% and 100%, between 80% and 100%, between 90% and 100%, between 95% and 100%, between 96% and 100%, between 97% and 100%, between 980% and 100%, between 99% and 100%, between 99.5% and 100% of the population comprise an integrated nucleotide sequence and a mutation that produces a non-functional gene encoded by a second defined nucleotide sequence. A population of cells can have between 10% and 70% comprise an integrated nucleotide sequence and a mutation that produces a non-functional gene encoded by a second defined nucleotide sequence. A population of cells can have between 20% and 70% comprise an integrated nucleotide sequence and a mutation that produces a non-functional gene encoded by a second defined nucleotide sequence. A population of cells can have between 30% and 70% comprise an integrated nucleotide sequence and a mutation that produces a non-functional gene encoded by a second defined nucleotide sequence. A population of cells can have between 10% and 80% comprise an integrated nucleotide sequence and a mutation that produces a non-functional gene encoded by a second defined nucleotide sequence. A population of cells can have between 20% and 80% comprise an integrated nucleotide sequence and a mutation that produces a non-functional gene encoded by a second defined nucleotide sequence. A population of cells can have between 30% and 80% comprise an integrated nucleotide sequence and a mutation that produces a non-functional gene encoded by a second defined nucleotide sequence.

A population of cells can have greater than 10%, greater than 20%, greater than 30%, greater than 40%, greater than 50%, greater than 60%, greater than 70%, greater than 80%, or greater than 90% of the population comprise an integrated nucleotide sequence or a mutation that produces a non-functional gene encoded by a second defined nucleotide sequence. A population of cells can have between 10% and 70%, between 20% and 70%, between 30% and 70%, between 40% and 70%, between 50% and 70%, between 60% and 70%, between 10% and 80%, between 10% and 60%, between 10% and 50%, between 10% and 40%, between 10% and 30%, between 10% and 20%, between 20% and 80%, between 30% and 80%, between 40% and 80%, between 50% and 80%, between 60% and 80%, between 70% and 80% of the population comprise an integrated nucleotide sequence or a mutation that produces a non-functional gene encoded by a second defined nucleotide sequence. A population of cells can have greater than 91%, greater than 92%, greater than 93%, greater than 94%, greater than 95%, greater than 96%, or greater than 97%, greater than 98%, greater than 99%, greater than 99.5%, or greater than 99.9% of the population comprise an integrated nucleotide sequence or a mutation that produces a non-functional gene encoded by a second defined nucleotide sequence. A population of cells can have greater than 20% of the population comprise an integrated nucleotide sequence or a mutation that produces a non-functional gene encoded by a second defined nucleotide sequence. A population of cells can have greater than 30% of the population comprise an integrated nucleotide sequence or a mutation that produces a non-functional gene encoded by a second defined nucleotide sequence. A population of cells can have greater than 60% of the population comprise an integrated nucleotide sequence or a mutation that produces a non-functional gene encoded by a second defined nucleotide sequence. A population of cells can have greater than 70% of the population comprise an integrated nucleotide sequence or a mutation that produces a non-functional gene encoded by a second defined nucleotide sequence.

A population of cells can have greater than 10%, greater than 20%, greater than 30%, greater than 40%, greater than 50%, greater than 60%, greater than 70%, greater than 80%, greater than 90%, greater than 95%, greater than 98%, or greater than 99% of modified cells that comprise an integrated nucleotide sequence also comprise a mutation that produces a non-functional gene encoded by a second defined nucleotide sequence. A population of cells can have between 10% and 70%, between 20% and 70%, between 30% and 70%, between 40% and 70%, between 50% and 70%, between 60% and 70%, between 10% and 80%, between 10% and 60%, between 10% and 50%, between 10% and 40%, between 10% and 30%, between 10% and 20%, between 20% and 80%, between 30% and 80%, between 40% and 80%, between 50% and 80%, between 60% and 80%, between 70% and 80%, 10% and 90%, between 20% and 90%, between 30% and 90%, between 40% and 90%, between 50% and 90%, between 60% and 90%, between 70% and 90%, between 80% and 90%, between 10% and 95%, between 20% and 95%, between 30% and 95%, between 40% and 95%, between 50% and 95%, between 60% and 95%, between 70% and 95%, between 80% and 95%, between 10% and 98%, between 20% and 98%, between 30% and 98%, between 40% and 98%, between 50% and 98%, between 60% and 98%, between 70% and 98%, between 80% and 98%, between 10% and 99%, between 20% and 99%, between 30% and 99%, between 40% and 99%, between 50% and 99%, between 60% and 99%, between 70% and 99%, between 80% and 99%, between 90% and 99%, between 95% and 99%, between 90% and 95%, and between 95% and 98% of modified cells that comprise an integrated nucleotide sequence also comprise a mutation that produces a non-functional gene encoded by a second defined nucleotide sequence.

A population of cells can have greater than 10%, greater than 20%, greater than 30%, greater than 40%, greater than 50%, greater than 60%, greater than 70%, greater than 80%, greater than 90%, greater than 95%, greater than 98%, or greater than 99% of modified cells that comprise a mutation that produces a non-functional gene encoded by a second defined nucleotide sequence also comprise an integrated nucleotide sequence. A population of cells can have between 10% and 70%, between 20% and 70%, between 30% and 70%, between 40% and 70%, between 50% and 70%, between 60% and 70%, between 10% and 80%, between 10% and 60%, between 10% and 50%, between 10% and 40%, between 10% and 30%, between 10% and 20%, between 20% and 80%, between 30% and 80%, between 40% and 80%, between 50% and 80%, between 60% and 80%, between 70% and 80%, 10% and 90%, between 20% and 90%, between 30% and 90%, between 40% and 90%, between 50% and 90%, between 60% and 90%, between 70% and 90%, between 80% and 90%, between 10% and 95%, between 20% and 95%, between 30% and 95%, between 40% and 95%, between 50% and 95%, between 60% and 95%, between 70% and 95%, between 80% and 95%, between 10% and 98%, between 20% and 98%, between 30% and 98%, between 40% and 98%, between 50% and 98%, between 60% and 98%, between 70% and 98%, between 80% and 98%, between 10% and 99%, between 20% and 99%, between 30% and 99%, between 40% and 99%, between 50% and 99%, between 60% and 99%, between 70% and 99%, between 80% and 99%, between 90% and 99%, between 95% and 99%, between 90% and 95%, and between 95% and 98% of modified cells that comprise a mutation that produces a non-functional gene encoded by a second defined nucleotide sequence also comprise an integrated nucleotide sequence.

Modified cells can be enriched within a population of cells following modification (e.g., following genomic editing) to enrich for a specific modification (e.g., integration of an exogenous gene). The population can be enriched using methods including, but not limited to, fluorescent activated cell sorting (FACS) (e.g., the exogenous gene expresses or co-expresses a fluorescent marker, or the population is stained using antibodies for expression of an exogenous gene or loss of an endogenous gene), drug selection (e.g., the exogenous gene expresses or co-expresses a drug selection gene), or affinity purification (e.g., the exogenous gene expresses or co-expresses an affinity tag).

In a particular aspect, the homogenous populations described herein can be achieved without enrichment for modified cells, i.e., no enrichment step is performed following modification of cells, such as following nuclease-mediated (e.g., CRISPR-mediated) genome editing.

A population of cells, in particular a population of cells immediately following modification wherein the population has not been enriched, can be at least 10 cells, at least 100 cells, at least 1000 cells, at least 10000 cells, $1\times10^6$ cells, at least $2\times10^6$ cells, at least $5\times10^6$ cells, at least $1\times10^7$ cells, at least $5\times10^7$ cells, at least $1\times10^8$ cells, at least $5\times10^8$ cells, at least $1\times10^9$ cells, or at least $5\times10^9$ cells. The population of cells, in particular a population of cells immediately following modification wherein the population has not been enriched, can be at least $1\times10^7$ cells. The population of cells, in particular a population of cells immediately following modification wherein the population has not been enriched, at least $5\times10^7$ cells.

Gene Editings Systems

As described above, in general, modified cells are modified such that they are genomically edited, or are capable of being genomically edited, using nuclease-mediated editing.

In general, nucleases promote editing through first directing cleavage at a specific nucleic acid sequence (i.e., a "defined nucleotide sequence" cleaved by a nuclease), e.g., a genome sequence, and subsequent editing results from non-templated based DNA repair, e.g., nuclease cleavage induced non-homologous end joining DNA repair mechanisms, or results from template-based repair, e.g., homologous recombination DNA repair mechanisms.

A variety of nucleases that can be engineered to promote sequence specific cleavage are known to those skilled in the art and include, but are not limited to, Clustered Regularly Interspaced Short Palindromic Repeats (CRISPR) family nuclease, a Transcription activator-like effector nuclease (TALEN) or derivative thereof, a zinc-finger nuclease (ZFN) or derivative thereof, and a homing endonuclease (HE) or derivative thereof. In particular, CRISPR-mediated gene editing systems can be used, such as the CRISPR/Cas9 editing system. Nuclease-mediated editing, and specifically CRISPR-mediated editing, is discussed in more detail in Adli M (*The CRISPR tool kit for genome editing and beyond*. Nat Commun. 2018 May 15; 9(1):1911), herein incorporated by reference for all that it teaches.

CRISPR-Mediated Gene Editing

In general, a CRISPR-mediated gene editing system comprises a CRISPR-associated (Cas) nuclease and a RNA(s) that directs cleavage to a particular target sequence. An exemplary CRISPR-mediated gene editing system is the CRISPR/Cas9 systems comprised of a Cas9 nuclease and a RNA(s) that has a CRISPR RNA (crRNA) domain and a trans-activating CRISPR (tracrRNA) domain. The crRNA typically has two RNA domains: a guide RNA sequence (gRNA) that directs specificity through base-pair hybridization to a target sequence ("a defined nucleotide sequence"), e.g., a genomic sequence; and an RNA domain that hybridizes to a tracrRNA. A tracrRNA can interact with and thereby promote recruitment of a nuclease (e.g., Cas9) to a genomic locus. The crRNA and tracrRNA polynucleotides can be separate polynucleotides. The crRNA and tracrRNA polynucleotides can be a single polynucleotide, also referred to as a single guide RNA (sgRNA). While the Cas9 system is illustrated here, other CRISPR systems can be used, such as the Cpf1 system. Nucleases can include derivatives thereof, such as Cas9 functional mutants, e.g., a Cas9 "nickase" mutant that in general mediates cleavage of only a single strand of a defined nucleotide sequence as opposed to a complete double-stranded break typically produced by Cas9 enzymes.

In general, the components of a CRISPR system interact with each other to form a Ribonucleoprotein (RNP) complex to mediate sequence specific cleavage. In some CRISPR systems, each component can be separately produced and used to form the RNP complex. In some CRISPR systems, each component can be separately produced in vitro and contacted (i.e., "complexed") with each other in vitro to form the RNP complex. The in vitro produced RNP can then be introduced (i.e., "delivered") into a cell's cytosol and/or nucleus, e.g., a T cell's cytosol and/or nucleus. The in vitro produced RNP complexes can be delivered to a cell by a variety of means including, but not limited to, electroporation, lipid-mediated transfection, cell membrane deformation by physical means, lipid nanoparticles (LNP), virus like particles (VLP), and sonication. In a particular example, in vitro produced RNP complexes can be delivered to a cell using a Nucleofactor/Nucleofection® electroporation-based delivery system (Lonza®). Other electroporation systems include, but are not limited to, MaxCyte electroporation systems, Miltenyi CliniMACS electroporation systems, Neon electroporation systems, and BTX electroporation systems. CRISPR nucleases, e.g., Cas9, can be produced in vitro (i.e., synthesized and purified) using a variety of protein production techniques known to those skilled in the art. CRISPR system RNAs, e.g., an sgRNA, can be produced in vitro (i.e., synthesized and purified) using a variety of RNA production techniques known to those skilled in the art, such as in vitro transcription or chemical synthesis.

An in vitro produced RNP complexes can be complexed at different ratios of nuclease to gRNA. For example, an in vitro produced RNP complexes can be formed with sgRNAs complexed with Cas9 protein at a Cas9:sgRNA molar ratio of between 1:1-1:9, such as a Cas9:sgRNA molar ratio of 1:1, 1:2, 1:3, 1:4, 1:5, 1:6, 1:7, 1:8, or 1:9. An in vitro produced RNP complexes can be formed with sgRNAs complexed with Cas9 protein at a Cas9:sgRNA molar ratio of about 1:1, about 1:2, about 1:3, about 1:4, about 1:5, about 1:6, about 1:7, about 1:8, or about 1:9.

An in vitro produced RNP complex can be also be used at different amounts in a CRISPR-mediated editing system. For example, depending on the number of cells desired to be edited, the total RNP amount added can be adjusted, such as a reduction in the amount of RNP complex added when editing a large number (e.g., $5 \times 10^7$) of cells in a reaction.

In some CRISPR systems, each component (e.g., Cas9 and an sgRNA) can be separately encoded by a polynucleotide and each polynucleotide introduced into a cell. In some CRISPR systems, each component can be encoded by a single polynucleotide (i.e., a multi-promoter or multicistronic vector, see description of exemplary multicistronic systems below) and introduced into a cell. Following expression of each polynucleotide encoded CRISPR component within a cell (e.g., translation of a nuclease and transcription of CRISPR RNAs), an RNP complex can form within the cell and can then direct site-specific cleavage.

Some RNPs can be engineered to have moieties that promote delivery of the RNP into the nucleus. For example, a Cas9 nuclease can have a nuclear localization signal (NLS) domain such that if a Cas9 RNP complex is delivered into a cell's cytosol or following translation of Cas9 and subsequent RNP formation, the NLS can promote further trafficking of a Cas9 RNP into the nucleus.

The modified cells described herein can be modified using non-viral methods, e.g., the nuclease and CRISPR mediated gene editing systems described herein can be delivered to a cell using non-viral methods. While viral-mediated delivery (e.g., adenoviral, retroviral, and lentiviral based delivery methods) has been used to deliver nuclease and CRISPR mediated gene editing systems, viral-mediated systems can suffer from the viral systems also introducing components that lead to immunogenicity. For example, viral-mediated delivery components can include viral or virus-derived nucleotide sequences that are capable of integration into a genome. Thus, the modified cells described herein can be substantially free of viral mediated delivery components. The term "substantially free of viral-mediated delivery components" is understood to mean less than a statistically significant amount of one or more viral mediated delivery components present in a relevant total composition (e.g., a cell or populations of cells), including viral mediated delivery components being at an undetectable level in the relevant total composition (i.e., "the modified cells described herein can be free of viral-mediated delivery components"). Less than a statistically significant amount can refer to a level of detection that does not qualify as having statistical confidence that a viral mediated delivery component is present in a relevant composition, such as a p-value greater than 0.1, 0.05, or 0.01. Viral-mediated delivery components can include viral proteins, such as viral structural proteins (e.g., capsid, envelope, and/or membrane-fusion proteins). In general, all peptides that are derived from integrated viral sequences or from introduced viral proteins can potentially be presented by MHC molecules on the cell surface, particularly MHC class I alleles, and can subsequently lead to immunogenicity. In therapeutic contexts, such as adoptive cell therapies, immunogenicity can negatively impact therapeutic efficacy. Thus, non-viral delivery methods can be advantageous in modifying and editing cells to be used in adoptive cell therapies, such as adoptive T cell therapies. Therefore, in a particular aspect, MHC class I on the surface of a modified cell can be free of peptides derived from viral mediated delivery components or an integrated virus, wherein the integrated virus is operably associated with the viral mediated delivery components.

In some CRISPR systems, more than one CRISPR composition can be provided such that each separately target the same gene or general genomic locus at more than one defined nucleotide sequence. For example, two separate CRISPR compositions can be provided to direct cleavage at two different defined nucleotide sequences within a certain distance of each other, such as less than or equal to 10 base-pairs, less than or equal to 20 base-pairs, less than or equal to 30 base-pairs, less than or equal to 40 base-pairs, less than or equal to 50 base-pairs, less than or equal to 100 base-pairs, less than or equal to 200 base-pairs, less than or equal to 300 base-pairs, less than or equal to 400 base-pairs, less than or equal to 500 base-pairs, less than or equal to 1,000 base-pairs, less than or equal to 2,000 base-pairs, less than or equal to 5,000 base-pairs, or less than or equal to 10,000 base-pairs of each other. In some CRISPR systems, more than one CRISPR composition can be provided such that each separately target opposite strands of the same gene or general genomic locus. For example, two separate CRISPR "nickase" compositions can be provided to direct cleavage at the same gene or general genomic locus at opposite strands.

Homology Directed Repair (HDR) in Gene Editing

Without wishing to be bound by theory, in general, the nuclease-mediated gene editing systems used to introduce an exogenous gene take advantage of a cell's natural DNA repair mechanisms, particularly homologous recombination (HR) repair pathways. Briefly, following an insult to genomic DNA (typically a double-stranded break), a cell can resolve the insult by using another DNA source that has identical, or substantially identical, sequences at both its 5' and 3' ends as a template during DNA synthesis to repair the lesion. In a natural context, HDR can use the other chromosome present in a cell as a template. In gene editing systems, exogenous polynucleotides are introduced into the cell to be used as a homologous recombination template (HRT or HR template). In general, any additional exogenous sequence not originally found in the chromosome with the lesion that is included between the 5' and 3' complimentary ends within the HRT (e.g., a gene or a portion of a gene) can be incorporated (i.e., "integrated") into the given genomic locus during templated HDR. Thus, a typical HR template for a given genomic locus has a nucleotide sequence identical to a first region of an endogenous genomic target locus, a nucleotide sequence identical to a second region of the endogenous genomic target locus, and a nucleotide sequence encoding at least a portion of a gene (e.g., an exogenous gene of interest).

In some examples, a HR template can be linear. Examples of linear HR templates include, but are not limited to, a linearized plasmid vector, a ssDNA, a synthesized DNA, and a PCR amplified DNA In particular examples, a HR template can be circular, such as a plasmid or nanoplasmid. Without wishing to be bound by theory, a circular HR template can have particular advantages over similar linear templates, such as increased stability, reduced synthesis errors (e.g., during PCR amplification), and ease of manufacturing. As demonstrated herein, a circular HR template can have improved editing efficiency relative to similar linear templates, e.g., a linear template of similar size. A circular template can include a supercoiled template.

Without wishing to be bound by theory, in general, the larger the HR template used, the less efficient the homologous recombination (HR) repair pathway typically is overall. Thus, it can be advantageous to limit the size of a HR template, such as by removing extraneous nucleotide sequences from HR templates, particularly from circular templates. For example, a vector backbone (i.e., all nucleotides sequences other than a gene or portion thereof) can be used that is less than 500 bases in length, such as a vector with all extraneous sequences removed except for an antibiotic resistance marker and an Origin of Replication.

In an illustrative example of a circular HR template, Nanoplasmids™ (Nature Technology) are used. Nanoplasmid™ is a trademark of Nature Technology Corp. Antibiotic-free RNA-OUT selection vectors and cell lines are described in greater detail in World Patent Application WO2008153733 and in equivalent US, European, and Australian patents: US 2010/0303859; EP2333091; and AU 2008262478, respectively, hereby incorporated by reference in their entirety for all that they teach. Nanoplasmid™ vectors and cell lines are additionally described in greater detail in the following world patents under the Patent Cooperation Treaty: PCT/US 13/000,259; PCT/US 13/00067; and PCT/US 13/00068, hereby incorporated by reference in their entirety for all that they teach.

Without wishing to be bound by theory, in general, impurities in the HR template can lead to a decrease in editing efficiency of the modified cell and/or viability of the modified cells. Thus, the HR template used can be substantially free of impurities (e.g., any component other than a HR template's DNA) or free of contaminants based on limits of detection. Impurities can include, but are not limited to, purification process-related impurities (e.g., salts or solvents from buffers, etc.), DNA and other nucleic acids other than the HR template, and residual contaminants from a residual host cell (e.g., a bacterial cell, such as *E. coli*) used to produce a HR template, such as endotoxin, residual host cell protein, residual host cell RNA, residual host cell gDNA, and residual host cell lipids or carbohydrates.

Homogeneity of a HR template (e.g., purity of a HR template free from DNA and other nucleic acids other than the HR template) can be assessed by agarose gel electrophoresis and can typically be considered substantially free of DNA and other nucleic acids other than the HR template when the purity is at least 75%, at least 80%, at least 85%, at least 90%, at least 98%, at least 95%, at least 96%, at least 97%, at least 98%, or at least 99% pure as assessed by agarose gel electrophoresis. HR templates can be considered substantially free of DNA and other nucleic acids other than the HR template when the purity is at least 99.5%, at least 99.6%, at least 99.7%, at least 99.8%, or at least 99.9% pure as assessed by agarose gel electrophoresis.

Endotoxin contamination of a HR template can be assessed by a Limulous amoebocyte lysate (LAL) assay and can typically be considered substantially free of endotoxin when less than 1000 EU/mg, less than 900 EU/mg, less than 800 EU/mg, less than 700 EU/mg, or less than 600 EU/mg is detected. An HR template be considered substantially free of endotoxin when less than 450 EU/mg, less than 400 EU/mg, less than 350 EU/mg, less than 300 EU/mg, less than 250 EU/mg, less than 200 EU/mg, less than 150 EU/mg, less than 100 EU/mg, or less than 50 EU/mg is detected. An HR template be considered substantially free of endotoxin when less than 500 EU/mg is detected.

Residual host cell protein can be assessed by Micro BCA. An HR template be considered substantially free of residual host cell protein when less than 5%, less than 4%, less than 3%, less than 2%, less than 1%, less than 0.5%, or less than 0.1% of the composition comprises residual host cell protein. An HR template be considered substantially free of residual host cell protein when less than 2% of the composition comprises residual host cell protein.

Residual host cell RNA can be assessed by agarose gel electrophoresis and stain with SYBR Gold. An HR template be considered substantially free of residual host cell RNA when less than 10%, less than 7.5%, less than 5%, less than 2.5%, less than 1%, less than 0.5%, or less than 0.1% of the composition comprises residual host cell RNA. An HR template be considered substantially free of residual host cell RNA when less than 5% of the composition comprises residual host cell RNA.

Residual host cell genomic DNA can be assessed by qPCR. An HR template be considered substantially free of residual host cell genomic DNA when less than 10%, less than 7.5%, less than 5%, less than 2.5%, less than 1%, less than 0.5%, or less than 0.1% of the composition comprises residual host cell genomic DNA. An HR template be considered substantially free of residual host cell genomic DNA when less than 5% of the composition comprises residual host cell genomic DNA.

Process-related impurities (e.g. salts or solvents from buffers, etc.) can be assessed by methods known in the art.

Residual host cell lipids or carbohydrates can be assessed by methods known in the art.

HR templates can be assessed by spectrometry. An HR template be considered substantially free of contaminants when a A260/A280 ratio of 1.8, 1.8+/−0.001, 1.8+/−0.01, or 1.8+/−0.1 is assessed by spectrometry.

Other assays known in the art can be used to assess HR template purity. HR templates can be at least 95%, at least 96%, at least 97%, at least 98%, or at least 99% pure as assessed by assays known in the art. HR templates can be at least 99.5%, at least 99.6%, at least 99.7%, at least 99.8%, or at least 99.9% pure as assessed by assays known in the art. HR templates can be between 95% and 100%, between 96% and 100%, between 97% and 100%, between 98% and 100%, between 99% and 100%, between 99.5% and 100%, or between 99.9% and 100%, pure as assessed by assays known in the art.

HR templates can be purified by methods known to those skilled in the art including, but not limited to, silica column-based purification, phenol chloroform extraction, chromatography purification (e.g., HPLC), polyacrylamide gel electrophoresis (PAGE) purification, and combinations thereof.

Following HDR, a target sequence ("a defined nucleotide sequence") can be removed such that an endogenous genomic target locus is no longer capable of being cleaved. For example, an exogenous nucleotide sequences encoded on a HR template can lack the target sequence a given nuclease cleaves.

HR Arms

The identical, or substantially identical, sequences found at the 5' and 3' ends of the HR template (i.e., the nucleotide sequences identical to the first and the second regions of the endogenous genomic target locus), with respect to the exogenous sequence to be introduced, are generally referred to as arms (HR arms). HR arms can be identical to regions of the endogenous genomic target locus (i.e., 100% identical). HR arms in some examples can be substantially identical to regions of the endogenous genomic target locus (e.g., at least 95%, at least 96%, at least 97%, at least 98%, at least 99%, at least 99.5%, at least 99.6%, at least 99.7%, at least 99.8%, or at least 99.9% identical to regions of the endogenous genomic target locus). While substantially identical HR arms can be used, it can be advantageous for HR arms to be identical as the efficiency of the HDR pathway may be impacted by HR arms having less than 100% identity.

Although HR arms can, in general, be of any length, practical considerations, such as the impact of HR arm length and overall template size on overall editing efficiency, can also be taken into account. The nucleotide sequences identical to, or substantially identical to, the first region of the endogenous genomic target locus (i.e., the 5' HR arm) can be greater than or equal to 50 bases in length, greater than or equal to 100 bases in length, greater than or equal to 200 bases in length, greater than or equal to 300 bases in length, greater than or equal to 400 bases in length, greater than or equal to 500 bases in length, greater than or equal to 600 bases in length, greater than or equal to 700 bases in length, greater than or equal to 800 bases in length, greater than or equal to 900 bases in length, greater than or equal to 1000 bases in length, greater than or equal to 1100 bases in length, greater than or equal to 1200 bases in length, greater than or equal to 1300 bases in length, greater than or equal to 1400 bases in length, greater than or equal to 1500 bases in length, greater than or equal to 1600 bases in length, greater than or equal to 1700 bases in length, greater than or equal to 1800 bases in length, greater than or equal to 1900 bases in length, greater than or equal to 2000 bases in length. The nucleotide sequences identical to, or substantially identical to, the first region of the endogenous genomic target locus (i.e., the 5' HR arm) can be greater than or equal to 300 bases in length. The nucleotide sequences identical to, or substantially identical to, the first region of the endogenous genomic target locus (i.e., the 5' HR arm) can be greater than or equal to 600 bases in length. The nucleotide sequences identical to, or substantially identical to, the first region of the endogenous genomic target locus (i.e., the 5' HR arm) can be greater than or equal to 1000 bases in length. The nucleotide sequences identical to, or substantially identical to, the first region of the endogenous genomic target locus (i.e., the 5' HR arm) can be greater than or equal to 2000 bases in length.

The nucleotide sequences identical to, or substantially identical to, the second region of the endogenous genomic target locus (i.e., the 3' HR arm) can be greater than or equal to 50 bases in length, greater than or equal to 100 bases in length, greater than or equal to 200 bases in length, greater than or equal to 300 bases in length, greater than or equal to 400 bases in length, greater than or equal to 500 bases in length, greater than or equal to 600 bases in length, greater than or equal to 700 bases in length, greater than or equal to 800 bases in length, greater than or equal to 900 bases in length, greater than or equal to 1000 bases in length, greater than or equal to 1100 bases in length, greater than or equal to 1200 bases in length, greater than or equal to 1300 bases in length, greater than or equal to 1400 bases in length, greater than or equal to 1500 bases in length, greater than or equal to 1600 bases in length, greater than or equal to 1700 bases in length, greater than or equal to 1800 bases in length, greater than or equal to 1900 bases in length, greater than or equal to 2000 bases in length. The nucleotide sequences identical to, or substantially identical to, the second region of the endogenous genomic target locus (i.e., the 3' HR arm) can be greater than or equal to 300 bases in length. The nucleotide sequences identical to, or substantially identical to, the second region of the endogenous genomic target locus (i.e., the 3' HR arm) can be greater than or equal to 600 bases in length. The nucleotide sequences identical to, or substantially identical to, the second region of the endogenous genomic target locus (i.e., the 3' HR arm) can be greater than or equal to 1000 bases in length. The nucleotide sequences identical to, or substantially identical to, the second region of the endogenous genomic target locus (i.e., the 3' HR arm) can be greater than or equal to 2000 bases in length.

Each of the nucleotide sequences identical to, or substantially identical to, the first and the second regions of the endogenous genomic target locus can be the same size or different sizes. For example, the nucleotide sequences identical to, or substantially identical to, the first region of the endogenous genomic target locus and the nucleotide sequences identical to, or substantially identical to, the second region of the endogenous genomic target locus can each be greater than or equal to 600 bases in length.

The nucleotide sequences identical to, or substantially identical to, the first or the second region of the endogenous genomic target locus can be identical, or substantially identical to, regions of an endogenous genomic target locus immediately adjacent to a cleavage site (i.e., a defined nucleotide sequence). The nucleotide sequences identical to, or substantially identical to, the first and the second region of the endogenous genomic target locus can each be identical to, or substantially identical to, regions of an endogenous genomic target locus immediately adjacent to a cleavage site (i.e., a defined nucleotide sequence). The nucleotide sequences identical to, or substantially identical to, the first or the second region of the endogenous genomic target locus can be identical, or substantially identical to, regions of an endogenous genomic target locus within a certain distance of a cleavage site (i.e., a defined nucleotide sequence), such as 1 base-pair, less than or equal to 2 base-pairs, less than or equal to 3 base-pairs, less than or equal to 4 base-pairs, less than or equal to 5 base-pairs, less than or equal to 6 base-pairs, less than or equal to 7 base-pairs, less than or equal to 8 base-pairs, less than or equal to 9 base-pairs, less than or equal to 10 base-pairs, less than or equal to 15 base-pairs, less than or equal to 20 base-pairs, less than or equal to 50 base-pairs, or less than or equal to 100 base-pairs of each other. The nucleotide sequences identical to, or substantially identical to, the first or the second region of the endogenous genomic target locus can be identical, or substantially identical to, regions of an endogenous genomic target locus within 1, 2, 3, 4, 5, 6, 7, 8, 9, 10, 11, 12, 13, 14, 15, 16, 17, 18, 19, or 20 base-pairs of a cleavage site.

Exogenous Sequences

A nucleotide sequence encoding at least a portion of a gene (e.g., an exogenous gene of interest) can, in general, be any exogenous nucleotide sequence of interest. For example, an exogenous nucleotide sequence of interest can be a short sequence, e.g., of 3-100 nucleotides in length. An exogenous nucleotide sequence of interest can be a single nucleotide. In addition, an exogenous nucleotide sequence of interest can be a long sequence, e.g., of 500-3000 nucleotides in length. An exogenous nucleotide sequence of interest can be coding or non-coding for a polypeptide sequence. In addition, an exogenous nucleotide sequence of interest can be inserted in a cell such that it forms a chimeric gene upon insertion. For example, an exogenous receptor portion can be inserted in frame in an endogenous receptor coding sequence to produce a chimeric receptor coding sequence that, post-editing, includes the exogenous receptor portion operably linked to an endogenous intracellular portion (e.g., for signal transduction).

In some examples, a gene or portion thereof can be a protein-coding nucleotide sequence (i.e., a nucleotide sequence encoding a polypeptide sequence). In general, any protein coding nucleotide can be used. In some examples, a protein coding nucleotide sequence encodes a protein useful in autologous cell therapies (e.g., autologous T cell therapies). In some examples, a protein coding nucleotide sequence can include, but is not limited to, a factor that modulates the immune system, a cytokine, a factor that modulates T cell function, a factor that promotes T-cell survival, a factor that promotes T-cell function, or an immune checkpoint inhibitor. A protein coding nucleotide sequence, particularly a secreted protein or membrane-bound proteins, can include a nucleotide sequence encoding a signal peptide. The signal peptide can be endogenous to the protein encoded by the protein coding nucleotide sequence. The signal peptide can be exogenous to the protein encoded by the protein coding nucleotide sequence, such as a Human Growth Hormone signal peptide.

In some examples, a gene or portion thereof can be a non-protein coding nucleotide sequence. In general, any non-protein coding nucleotide can be used. In some cases, a non-protein coding nucleotide sequence can be a nucleotide sequence useful in autologous cell therapies (e.g., autologous T cell therapies). In some cases, a non-protein coding nucleotide sequence can include, but is not limited to, an shRNA, an siRNA, an miRNA, and an lncRNA.

Although a nucleotide sequence encoding at least a portion of a gene (e.g., an exogenous gene of interest) can, in general, be any size, practical considerations, such as the impact of gene size on overall template size and on subsequent overall editing efficiency, can be taken into account. Thus, in a particular aspect, provided herein are modified cells that are genomically edited, or are capable of being genomically edited, to express an exogenous gene greater than or equal to 100 bases in length at HR efficiency rates greater than those previously described (e.g., a greater percentage of a population having an integrated polynucleotide sequence), particularly when using non-viral delivery methods. The improved HR efficiency rates similarly apply to genes greater than 100 bases in length, such as introducing exogenous sequences greater than or equal to 200 bases in length, greater than or equal to 400 bases in length, greater than or equal to 500 bases in length, greater than or equal to 600 bases in length, greater than or equal to 750 bases in length, greater than or equal to 1000 bases in length greater than or equal to 1500 bases in length, greater than or equal to 2000 bases in length, greater than or equal to 3000 bases in length, or greater than or equal to 4000 bases in length. The at least a portion of a gene can be greater than or equal to 800 bases in length. The at least a portion of a gene can be greater than or equal to 1600 bases in length.

Exogenous sequences can be between 100-200 bases in length, between 100-300 bases in length, between 100-400 bases in length, between 100-500 bases in length, between 100-600 bases in length, between 100-700 bases in length, between 100-800 bases in length, between 100-900 bases in length, or between 100-1000 bases in length. Exogenous sequences can be between 100-2000 bases in length, between 100-3000 bases in length, between 100-4000 bases in length, between 100-5000 bases in length, between 100-6000 bases in length, between 100-7000 bases in length, between 100-8000 bases in length, between 100-9000 bases in length, or between 100-10,000 bases in length. Exogenous sequences can be between 1000-2000 bases in length, between 1000-3000 bases in length, between 1000-4000 bases in length, between 1000-5000 bases in length, between 1000-6000 bases in length, between 1000-7000 bases in length, between 1000-8000 bases in length, between 1000-9000 bases in length, or between 1000-10,000 bases in length.

Exogenous sequences can be greater than or equal to 10 bases in length, greater than or equal to 20 bases in length, greater than or equal to 30 bases in length, greater than or equal to 40 bases in length, greater than or equal to 50 bases in length, greater than or equal to 60 bases in length, greater than or equal to 70 bases in length, greater than or equal to 80 bases in length greater than or equal to 90 bases in length, or greater than or equal to 95 bases in length. Exogenous sequences can be between 1-100 bases in length, between 1-90 bases in length, between 1-80 bases in length, between 1-70 bases in length, between 1-60 bases in length, between 1-50 bases in length, between 1-40 bases in length, or between 1-30 bases in length. Exogenous sequences can be between 1-20 bases in length, between 2-20 bases in length, between 3-20 bases in length, between 5-20 bases in length, between 10-20 bases in length, or between 15-20 bases in length. Exogenous sequences can be between 1-10 bases in length, between 2-10 bases in length, between 3-10 bases in length, between 5-10 bases in length, between 1-5 bases in length, or between 1-15 bases in length. Exogenous sequences can be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 115, 120, 125, 150, 175, 200, 225, or 250 bases in length. Exogenous sequences can be 1, 2, 3, 4, 5, 6, 7, 8, 9, 10, 11, 12, 13, or 14 bases in length.

In examples were multiple exogenous sequences are introduced, the multiple exogenous sequences can be different sizes, e.g., a first exogenous sequence can be greater than or equal to 100 bases and a second exogenous sequence can be greater than or equal to 100 bases, or a first exogenous sequence can be greater than or equal to 100 bases and a second exogenous sequence can be less than 100 bases (e.g., between 1-100 bases in length).

The at least a portion of a gene can be expressed following integration into endogenous genomic target locus.

In some examples, the HR template does not encode a promoter sequence. Expression of the nucleotide sequence encoding at least a portion of a gene can be directed by an endogenous promoter within the endogenous genomic target locus, i.e., the at least a portion of a gene is integrated into an endogenous genomic target locus such that an endogenous promoter is operably linked to the at least a portion of a gene. In an illustrative example, an exogenous sequence encoding a TCR can be integrated into a TCR genomic locus, such as a TCR alpha constant region encoding exon, such that the endogenous TCR alpha promoter is operably linked to the TCR.

In some examples, the HR template encodes an exogenous promoter sequence that is operably linked to at least a portion of a gene. Examples of exogenous promoters include, but are not limited to, mammalian promoters, human promoters, viral promoters, long-terminal repeat (LTR) derived promoters from a retrovirus or lentivirus, fusions of two promoters, fusions of two portions of promoters, MMLV LTR promoters, HIV LTR promoters, MCMV LTR promoters, EF1a, MND, CMV, SV40, PGK1, Ubc, beta-actin, CAG, small molecule inducible promoters, tetracycline inducible promoters, small molecule conditional promoters, Cre-LoxP conditional promoter systems, Flp-FRT conditional promoter systems, and tamoxifen conditional promoter system. Exogenous promoters can be constitutive. Exogenous promoters can be inducible, such as inducible by a small molecule (e.g., tetracycline and derivatives). Exogenous promoters can be conditional, such as promoters that are active following genomic rearrangements (e.g., Cre-LoxP and FLP-Frt systems). Exogenous promoters can be cell-type dependent, i.e., only direct expression in particular cell populations. Exogenous promoters can be mammalian, including human. Exogenous promoters can be viral.

Exogenous sequences can have a linker sequence. For example, an exogenous sequence can have a linker sequence that links at least a portion of a gene to an endogenous sequence following integration into an endogenous genomic target locus. A linker can encode a cleavable linker polypeptide sequence, wherein following expression the cleavable linker polypeptide is cleaved such that a polypeptide encoded only by the at least a portion of the gene is produced as a separate polypeptide. Examples of cleavable peptides include a Furin cleavage site and a TEV cleavage site. In some examples, a cleavable linker includes a polypeptide sequence that further promotes cleavage, such a flexible linker (e.g., a Gly-Ser-Gly sequence). In another example, a linker can encode a 2A ribosome skipping element e.g., T2A, E2A, P2A, and F2A, such that a polypeptide encoded only by the at least a portion of the gene is produced as a separate polypeptide during translation. In another example, a linker can encode an Internal Ribosome Entry Site (IRES), such that a polypeptide encoded only by the at least a portion of the gene is produced as a separate polypeptide during translation. A linker can encode a splice acceptor, such as a viral splice acceptor.

The HR template can encode an exogenous polynucleotide that is codon diverged from an endogenous nucleotide sequence. For example, a codon diverged sequence can be codon optimized to promote increased expression of an encoded protein. A codon diverged sequence can be codon diverged to remove sequence elements that may lead to genomic instability, such as sequence elements that promote recombination (e.g., Recombination Signal Sequences).

Multicistronic and Multi-promoter Systems

Exogenous sequences can be multicistronic, i.e., more than one separate polypeptide can be produced from a single mRNA transcript. Exogenous sequences can be multicistronic through the use of various linkers, e.g., a nucleotide sequence encoding at least a portion of a first gene can be linked to a nucleotide sequence encoding at least a portion of a second gene, such as in a first gene:linker:second gene in a 5' to 3' orientation. For example, a linker can encode a cleavable linker polypeptide sequence, wherein following expression the cleavable linker polypeptide is cleaved such that separate polypeptides encoded by the first and second genes are produced. Examples of cleavable peptides include a Furin cleavage site and a TEV cleavage site. In some examples, a cleavable linker includes a polypeptide sequence that further promotes cleavage, such a flexible linker (e.g., a Gly-Ser-Gly sequence). In another example, a linker can encode a 2A ribosome skipping element e.g., T2A, E2A, P2A, and F2A, such that separate polypeptides encoded by the first and second genes are produced during translation. In another example, a linker can encode an Internal Ribosome Entry Site (IRES), such that separate polypeptides encoded by the first and second genes are produced during translation. A linker can encode a splice acceptor, such as a viral splice acceptor. In general, a multicistronic system can use any number or combination of linkers, such as those described above, to express any number of genes or portions thereof (e.g., an exogenous sequence can encode a first, a second, and a third gene, each separated by linkers such that separate polypeptides encoded by the first, second, and third genes are produced. In multicistronic systems that use multiples of the same linkers, the linkers can encode the same polypeptide sequence but have codon diverged nucleotide sequences.

Exogenous sequences can have multiple open reading frames (ORFs), i.e., more than one separate mRNA transcript can be produced from the exogenous sequence. Exogenous sequences can have multiple ORFs through the use of multiple promoters, e.g., a first promoter can be operably linked to a nucleotide sequence encoding at least a portion of a first gene, and a second promoter can be operably linked to a nucleotide sequence encoding at least a portion of a second gene. "Linkers," as used herein can refer to either the multicistronic linkers described above, the additional promoters that are operably linked to additional ORFs described above, or to polypeptides that link a first polypeptide sequence and a second polypeptide sequence.

A second gene can be any of the exogenous sequences described herein (see Exogenous Sequences section).

Additional Reagents

In some examples, modified cells (or cells to be modified) can be contacted with (e.g., cultured with) reagents that promote HDR repair (i.e., increase homology recombination rates and/or efficiency), including promoting HDR repair relative to other DNA repair pathways, such as NHEJ. Reagents that promote HDR repair include, but are not limited to, activators of homologous recombination repair pathways, inhibitors non-homologous end joining (NHEJ) repair pathways, or combinations thereof.

In general, the cell modification and editing techniques described herein can be toxic to (i.e., reduce viability of) the modified cells. Thus, in some cases, it can be advantageous for overall editing efficiencies, particularly HR editing efficiencies, to provide reagents that are capable of increasing viability of the modified cell. Reagents that are capable of increasing viability can include inhibitors of nucleic acid sensing pathways, such as inhibitors of TLR9 nucleic acid sensing pathways, AIM2 nucleic acid sensing pathways, IFI16 nucleic acid sensing pathways, cGAS nucleic acid sensing pathways, and cytosolic nucleic acid sensing pathways. Without wishing to be bound by theory, these inhibitors of nucleic acid sensing pathways can reduce cellular responses (e.g., innate immune signaling pathways) that respond to the various introduced (i.e., delivered) nucleic acids (e.g., HR templates and sgRNAs), and reduction of the cellular responses can improve viability. In an illustrative example, a reagent capable of increasing viability can be an oligonucleotide antagonist, such as the antagonist A151 possessing the tandem repeat TTAGGG. Reagents that are capable of increasing viability can include factors other than those provided in cell culture, such as modifying T cells to express viability factors (e.g., a factor that promotes cell survival), for example those described in more detail in Portt, el al. (*Biochim Biophys Acta.* 2011 January; 1813(1): 238-59), herein incorporated by reference for all that it teaches.

Modified T Cells

In a particular aspect, modified cells are modified T cells. In general, the modified T cells can be modified such that they are genomically edited, or are capable of being genomically edited, at any endogenous genomic target locus. The endogenous genomic target locus can be an endogenous TCR locus. An endogenous TCR locus can be a TCR-alpha locus or a TCR-beta locus. The endogenous genomic target locus can be an immune checkpoint locus, such as a PD-1, CTLA-4, BTLA, TIM3, LAG3, and VISTA locus.

In general, the modified T cells can be modified such that they are genomically edited, or are capable of being genomically edited, to express any exogenous gene of interest. For example, an exogenous gene of interest ("at least a portion of a gene") can include at least a portion of a TCR gene, such as a TCR-alpha or TCR-beta gene, or portion thereof. A TCR gene can include both a TCR-alpha gene and a TCR-beta gene. A TCR-alpha gene and a TCR-beta gene can be linked by a linker (see linkers described above in multicistronic systems). A TCR gene can include a TCR-gamma or TCR-delta gene, or portion thereof. A TCR gene can include both a TCR-gamma and a TCR-delta gene. A TCR gene can include, but is not limited to, a murinized TCR, a humanized TCR, a domain swapped TCR, a point-mutated TCR, an engineered TCR with an engineered cysteine capable of forming a disulfide linkage, a codon optimized TCR optimized for expression in humans, a sequence optimized TCR optimized for codon usage and removal of RNA instability elements, a variable region sequence of the TCR gene, a chimeric antigen receptor (CAR), or a single-chain TCR. A TCR gene can include at least a portion of: a murinized TCR, a humanized TCR, a domain swapped TCR, a point-mutated TCR, an engineered TCR with an engineered cysteine capable of forming a disulfide linkage, a codon optimized TCR optimized for expression in humans, a sequence optimized TCR optimized for codon usage and removal of RNA instability elements, a variable region sequence of the TCR gene, a chimeric antigen receptor (CAR), or a single-chain TCR. A TCR gene can include a TCR gene engineered to demonstrate a greater association with a second exogenous TCR polypeptide sequence relative to an endogenous TCR polypeptide sequence, such as a TCR-alpha polypeptide sequence and a TCR-beta polypeptide sequence engineered to demonstrate a greater association with each other relative to an endogenous TCR polypeptide sequence.

In a particular aspect, a modified T cell has: a) a nucleotide sequence encoding a TCR-alpha polypeptide sequence; b) a nucleotide sequence encoding a TCR-beta polypeptide sequence; c) a nucleotide sequence encoding a first linker polypeptide sequence; d) a nucleotide sequence encoding a second linker polypeptide sequence. In one example, the encoded polypeptide sequences are in a linker:TCR-alpha:second linker:TCR-beta orientation from N-terminus to C-terminus. In one example, the encoded polypeptide sequences are in a linker:TCR-beta:second linker:TCR-alpha orientation from N-terminus to C-terminus.

A TCR gene can be a TCR (e.g., a linked TCR-alpha and TCR-beta construct) that recognizes a disease specific epitope presented on an MHC. A TCR gene can be a TCR (e.g., both a TCR-alpha and a TCR-beta chain) that recognizes a cancer specific epitope presented on an MHC allele, such as a TCR that recognizes a cancer specific neoepitope (neoantigen) presented on an MHC allele. TCR recognition, in general, refers to a TCR binding an antigen-MHC complex with sufficient affinity such that the TCR binding, or combination of multiple TCRs binding (i.e., TCR clustering), can lead to an immune response. Methods and compositions for identifying TCRs that recognize neoepitopes, specifically patient specific neoepitopes, are described in greater detail in WO2018165475, herein incorporated by reference in its entirety. In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety.

In general, a modified T cell can be any T cell. A modified T cell can be a human T cell. A modified T cell can be a human-derived T cell, such as an immortalized T cell or an ex vivo developed T cell (e.g., a thymic organ culture developed cell). A modified T cell can be a cytotoxic T lymphocyte (CTL), a CD8+ T cell, a CD4+ T cell, a primary T cell, a tumor infiltrating T cell, or an engineered T cell. A modified T cell can be a regulatory T cell (Treg), a helper T cell (e.g., a Th1 cell, a Th2 cell, or a Th17 cell), an alpha-beta T cell, or a gamma-delta T cell. A modified T cell can be a naïve T cell, a stem cell memory T cell, central memory T cells, a transitional memory T cell, an effector memory T cell, or an effector T cell. A modified T cell can be a primary T cell.

A modified T cell, such as a primary T cell, can be isolated from a subject, such as a subject known or suspected to have cancer. T cell isolation methods are known to those skilled in the art and include, but are not limited to, sorting techniques based on cell-surface marker expression, such as FACS sorting, positive isolation techniques (e.g., CD4 and/or CD8 MACS®), and negative isolation (e.g., CD3 MACS®), magnetic isolation, and combinations thereof. Sources used to isolate T cells include, but are not limited to, blood, PBMCs, blood collected by apheresis (e.g., a leukopak), and tumor tissues.

A modified T cell can be a cultured T cell, such as an ex vivo cultured T cell. A modified T cell can be an ex vivo cultured primary T cell, such as a primary T cell isolated from a subject. Cultured T cell cans be cultured with one or more cytokines. Cultured T cells can be cultured with IL2, IL7, IL15, or combinations thereof. For example, a cultured T cell can be cultured with IL2. In another example, a cultured T cell can be cultured with IL7 and IL15. In another example, a cultured T cell can be cultured with IL2, IL7, and IL15. In another example, a cultured T cell can be cultured with IL7 and IL15 in the absence of (substantially free of) IL2. In another example, a cultured T cell can be cultured with IL21 alone for in combination with IL2, IL7, and/or IL15 (e.g., in combination with IL2, in combination with IL7, in combination with IL15, or in combination with IL7 and IL15). Cultured T cell cans be stimulated, e.g., cultured with one or more stimulatory molecules (e.g., a receptor agonist). Stimulatory molecules include, but are not limited to, CD3 and CD28. In an example, a cultured T cell can be stimulated with CD3 (a CD3 stimulated T cell). In another example, a cultured T cell can be stimulated with CD28 (a CD28 stimulated T cell). In another example, a cultured T cell can be stimulated with both CD3 and CD28 (a CD3 and CD28 stimulated T cell). Stimulatory molecules can be immobilized on a surface, such as the surface of a plate (plate-bound) or the surface of a bead (bead-bound).

In an illustrative example, a modified T cell can be a primary T cell genomically edited to express a TCR that recognizes a specific epitope (i.e., antigen), such as a tumor antigen, a neoantigen, a tumor neoantigen, a viral antigen, a phospho-antigen, a bacterial antigen, a microbial antigen, or combinations thereof.

In an illustrative example, a modified T cell can be a primary T cell genomically edited to express a TCR that recognizes a cancer specific epitope, such as a TCR that recognizes a cancer specific neoepitope (neoantigen), presented on an MHC allele. As used herein the term "neoantigen" is an antigen that has at least one alteration that makes it distinct from the corresponding wild-type, parental antigen, e.g., via mutation in a tumor cell or post-translational modification specific to a tumor cell. A neoantigen can include a polypeptide sequence or a nucleotide sequence. A mutation can include a frameshift or non-frameshift indel, missense or nonsense substitution, splice site alteration, genomic rearrangement or gene fusion, or any genomic or expression alteration giving rise to a neoORF. A mutation can also include a splice variant. Post-translational modifications specific to a tumor cell can include aberrant phosphorylation. Post-translational modifications specific to a tumor cell can also include a proteasome-generated spliced antigen (see Liepe et al., A large fraction of HLA class I ligands are proteasome-generated spliced peptides: Science. 2016 Oct. 21; 354(6310):354-358.) A neoantigen can be selected by analyzing tumor, viral, or bacterial sequencing data from a subject to identify one or more somatic mutations, such as analyzing sequencing data using an in silico predictive algorithm. Predictive algorithms can be an MHC binding algorithm to predict binding between the neoantigen and a MHC allele of a subject.

In another illustrative example, a modified T cell can be a primary T cell isolated from a subject and genomically edited to express a TCR that recognizes a cancer specific epitope, such as a TCR that recognizes a cancer specific neoepitope (neoantigen), presented on an MHC allele of the subject.

In another illustrative example, a modified T cell can be a primary T cell isolated from a subject and genomically edited to express a TCR that recognizes a cancer specific epitope, such as a TCR that recognizes a cancer specific neoepitope (neoantigen), predicted to be present on an MHC allele of the subject. MHC presentation prediction methods are known to those skilled in the art and include, but are not limited to, identifying neoantigens through combining sequencing data with mass-spectrometry and MHC presentation prediction (e.g., US Publication No. 2017/0199961, herein incorporated by reference for all that it teaches), and combining sequencing data with MHC binding affinity prediction (e.g., issued U.S. Pat. No. 9,115,402, herein incorporated by reference for all that it teaches).

In another illustrative example, a modified T cell can be a primary T cell that is allogenic with reference to a subject and genomically edited to express a TCR that recognizes a cancer specific epitope, such as a TCR that recognizes a cancer specific neoepitope (neoantigen), presented on an MHC allele of the subject. The allogenic T cell can be HLA typed and matched to a subject (HLA matched), such as in examples where a reduction in immunogenicity as a result of administering a modified T cell is desired. Human leukocyte antigen (HLA) typing can be determined from a tumor or blood sample of the patient. HLAs commonly found in the human population can also be included in neoantigen prediction algorithms, such as HLA-A*02, 24, 01; HLA-B*35, 44, 51; DRB1*11, 13, 07 in caucasians, HLA-A*02, 03, 30; HLA-B*35, 15, 44; DRB1*13, 11, 03 in afro-brazialians, and HLA-A*24, 02, 26; HLA-B*40, 51, 52; DRB1*04, 15, 09 in Asians. Specific pairing of HLA alleles can also be used. Common alleles found in the human population are further described in Bardi et al. (Rev Bras Hematol Hemoter. 2012; 34(1): 25-30), herein incorporated by reference for all it teaches. HLA information can be utilized together with identified putative neoantigen peptide sequences in a predictive algorithm for MHC binding, as described in greater detail in Fritsch et al., 2014, Cancer Immunol Res., 2:522-529, the entire contents of which are herein incorporated by reference.

Modified Primary Cells

In a particular aspect, modified cells are modified primary cells. In general, the modified primary cells can be modified such that they are genomically edited, or are capable of being genomically edited, at any endogenous genomic target locus. In general, the modified primary cells can be modified such that they are genomically edited, or are capable of being genomically edited, to express any exogenous gene of interest.

In general, a modified primary cell can be any primary cell. Exemplary primary cells include stem cells, human stem cells, embryonic stem cells, and immune cells (e.g., hematopoietic cells). Examples of immune cells include, but are not limited to, B cells, T cells, monocytes, macrophages, dendritic cells, and natural killer (NK) cells. An immune cell can be a NK cell. An immune cell can be a NK-T cell. Immune cells can include cells of the adaptive immune system and/or the innate immune system. Stems cells, including human stem cells, can be hematopoietic stem cells.

A modified primary cell can be a human primary cell. A modified primary cell can be a tumor infiltrating primary cell or an engineered primary cell. A modified primary cell can be a primary T cell. A modified primary cell can be a hematopoietic stem cell (HSC). A modified primary cell can be a natural killer cell. A modified primary cell can be any somatic cell.

A modified primary cell can be isolated from a subject, such as a subject known or suspected to have cancer. Primary cell isolation methods are known to those skilled in the art and include, but are not limited to, sorting techniques based on cell-surface marker expression, such as FACS sorting, positive isolation techniques, and negative isolation, magnetic isolation, and combinations thereof.

A modified primary cell can be a cultured primary cell, such as an ex vivo cultured primary cell. A modified primary cell can be an ex vivo cultured primary cell, such as a primary cell isolated from a subject. Cultured primary cell can be cultured with one or more cytokines.

Homology Repair Directed Cell Editing Methods

In one aspect, methods for genetically modifying a cell are provided.

A method for genetically modifying a cell can include providing any of the HR templates described herein, providing any of the nuclease compositions described herein, contacting any of the cells described herein (e.g., a T cell, a primary cell, an HSC, or an NK cell) with the HR template and the nuclease composition, and delivering the HR template and nuclease composition into the cell, particularly by delivery means other than viral-mediated delivery. The contacting step can be less than 60 minutes, less than 45 minutes, less than 30 minutes, less than 20 minutes, less than 15 minutes, less than 10 minutes, or less than 5 minutes, or less than 1 minute between contacting the cell with the HR template and the nuclease composition and the delivery step. Delivery means can include any of the methods described for delivery CRISPR-mediated systems described herein, such as the methods for delivering RNP complexes described herein. As described above, multiple HR templates and/or nuclease compositions can be delivered into a cell, such as delivering multiple HR templates and/or nuclease compositions into a cell simultaneously.

Without wishing to be bound by theory, in general (and as discussed in the context of HR template purity), impurities and contaminants introduced during the editing process can lead to a decrease in editing efficiency of the modified cell and/or viability of the modified cells. For example, residual media from culturing cells can introduce impurities and contaminants in the editing process. Thus, a method for genetically modifying a cell can include steps taken to minimize or eliminate residual media.

In an illustrative example, a method for genetically modifying a human primary T cell (e.g., a T cell isolated from a human subject) can include providing an HR template encoding a full TCR (both a TCR-alpha and TCR-beta), a CRISPR RNP complex capable of targeting a TCR locus (e.g., a TCR-alpha constant locus), and delivering the HR template and RNP complex into the T cell using electroporation.

Methods are also provided for that can produce populations of modified cells, such as any of the modified populations of cells described herein.

Method of Treatment

In one aspect, methods for treatment are also provided. For example, methods of treatment of subjects with cancer are provided. In another example, genes can be corrected (e.g., replaced, also known a gene therapy or gene replacement therapy), such as replacing a non-functional gene with a functional gene (e.g., HSCs for hemaglobinopathies). Said methods of the invention include administering a therapeutically effective amount of modified cells, such as genomically edited cells (e.g., genomically edited T cells). The modified cells can be formulated in pharmaceutical compositions. These compositions can comprise, in addition to one or more of the modified cells, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intravenous.

The modified cells can be derived (e.g., isolated) from the subject being administered the treatment (autologous).

The modified cells can be allogenic with reference to the subject being administered the treatment. Allogenic modified cells can be HLA-matched to the subject being administered the treatment, as described above.

Modified cells can be administered alone or in combination with other treatments, either simultaneously or sequentially dependent upon the condition to be treated.

Nucleotide Compositions

Described herein are polypeptide and nucleic acid sequences of genes useful for the invention, e.g., genes, vectors, exogenous sequences, expression constructs, HR templates. Polypeptide and nucleic acid sequences useful for the invention are at least 95%, at least 96%, at least 97%, at least 98%, at least 99%, or at least 99.5% identical to sequences described herein or referred to herein by a database accession number. Polypeptide and nucleic acid sequences useful for the invention can be 100% identical to sequences described herein or referred to herein by a database accession number.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al.). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (<www.ncbi.nlm.nih.gov/>).

In one aspect, nucleotide compositions for use in directing homologous recombination at an endogenous genomic target locus are provided, such as any of the HR templates described herein.

In one example, nucleotide compositions for use in directing homologous recombination at an endogenous genomic target locus (i.e., an HR template) comprise: a) a nucleotide sequence encoding at least a portion of a gene; b) a nucleotide sequence identical to a first region of an endogenous genomic target locus; and c) a nucleotide sequence identical to a second region of the endogenous genomic target locus, wherein the at least a portion of the gene is 100 bases in length, all of the nucleotide sequences are on a single polynucleotide, the nucleotide sequences identical to the first and the second regions of the endogenous genomic target locus are oriented to facilitate homologous recombination at the endogenous genomic target locus, and the nucleotide sequence encoding the at least a portion of the gene is orientated such that the at least a portion of the gene is capable of being expressed following integration of the composition into the endogenous genomic target locus. The nucleotide composition can be circular.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers and sequences used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton,

*Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B (1992).

Example 1: Methods and Materials for T Cell Editing Using CRISPR

Methods and materials used to incorporate genes of interest (i.e., "at a portion of a gene") into an endogenous genomic target locus and to analyze the same are described below.

T Cells

PBMCs were isolated from blood (e.g., a leukopak collected by apheresis) following a standard Ficoll isolation method. Isolated PBMCs were frozen in aliquots following standard protocols. As part of the standard protocol, frozen human peripheral blood mononuclear cells (PBMCs) were thawed and cultured with media (TexMACS, 3% human AB serum, with cytokines) as part of the standard gene editing protocol. In variations of the protocol, frozen PBMCs were purchased (AllCells). The following day, CD8 and CD4 positive T cells were enriched by positive selection using magnetic beads (Miltenyi) following the manufacturer's protocol as part of the standard gene editing protocol. In variations of the protocol, cells were enriched using CD3 negative selection or CD62L positive selection, as indicated below. Enriched cells were stimulated with TransAct (CD3/CD28 reagent, Miltenyi) used at manufacturers recommendation at a ratio of 1:17.5 for 48-72 hours prior to the electroporation procedure (see below) and cultured with media (TexMACS, 3% human serum containing 12.5 ng/mL IL-7 and IL-15 each) and as part of the standard gene editing protocol.

Where isolation of patient/donor PBMCs is indicated, a leukopak of cells was collected by patient apheresis. The leukopak was then frozen and subsequently thawed as needed as part of the standard gene editing protocol, or in variations of the protocol maintained at 2-8° C. (fresh) as indicated. The following day, CD8 and CD4 positive T cells were enriched by positive selection using the Prodigy platform (Miltenyi). Enriched cells were cultured as above.

Homologous Recombination (HR) Templates

Nanoplasmids™ (Nature Technology) were used as noted (HR templates denoted as "NTC"). Nanoplasmid™ is a trademark of Nature Technology Corp. Antibiotic-free RNA-OUT selection vectors and cell lines are covered by World Patent Application WO2008153733 and by equivalent US, European, and Australian patents: US 2010/0303859; EP2333091; and AU 2008262478, respectively, hereby incorporated by reference in their entirety for all that they teach. Nanoplasmid™ vectors and cell lines are additionally covered by the following world patents under the Patent Cooperation Treaty: PCT/US 13/000259; PCT/US 13/00067; and PCT/US 13/00068, hereby incorporated by reference in their entirety for all that they teach.

Standard plasmids containing a PBR322 Origin of Replication derived from a pUC57 vector and a Kanamycin (Kan) antibiotic resistance marker were also used as noted (HR templates denoted as "pUCu"). Extraneous sequences were removed except for the antibiotic resistance marker and the Origin of Replication.

Where indicated, purified HR template was either purchased (Nature Technology) or purified "in-house" using standard DNA purification techniques following manufacturer's protocols (Maxi kit, Macherey Nagel).

The HR templates used are described in Table 4. Unless noted otherwise, the sequences provided include the complete HR templates with homology arms, gene cassette, and plasmid backbone.

TABLE 4

| Homologous Repair Template Sequences |
|---|
| NTC9385R-TRAC(1k)_P2A.ZsGreen.f-P2A.LNGFRt.BGHpA (SEQ ID NO: 8) |
| CCGCCTAATGAGCGGGCTTTTTTTTGGCTTGTTGTCCACAACCGTTAAACCTTA |
| AAAGCTTTAAAAGCCTTATATATTCTTTTTTTTCTTATAAAACTTAAAACCTTAG |
| AGGCTATTTAAGTTGCTGATTTATATTAATTTTATTGTTCAAACATGAGAGCTT |
| AGTACGTGAAACATGAGAGCTTAGTACGTTAGCCATGAGAGCTTAGTACGTTA |
| GCCATGAGGGTTTAGTTCGTTAAACATGAGAGCTTAGTACGTTAAACATGAGA |
| GCTTAGTACGTACTATCAACAGGTTGAACTGCTGATCCACGTTGTGGTAGAATT |
| GGTAAAGAGAGTCGTGTAAAATATCGAGTTCGCACATCTTGTTGTCTGATTATT |
| GATTTTTGGCGAAACCATTTGATCATATGACAAGATGTGTATCTACCTTAACTT |
| AATGATTTTGATAAAAATCATTAGGTACCACATTAAAAACACAAAATCCTACG |
| GAAATACTGAAGAATGAGTCTCAGCACTAAGGAAAAGCCTCCAGCAGCTCCTG |
| CTTTCTGAGGGTGAAGGATAGACGCTGTGGCTCTGCATGACTCACTAGCACTCT |
| ATCACGGCCATATTCTGGCAGGGTCAGTGGCTCCAACTAACATTTGTTTGGTAC |
| TTTACAGTTTATTAAATAGATGTTTATATGGAGAAGCTCTCATTTCTTTCTCAGA |

TABLE 4-continued

Homologous Repair Template Sequences

AGAGCCTGGCTAGGAAGGTGGATGAGGCACCATATTCATTTTGCAGGTGAAAT

TCCTGAGATGTAAGGAGCTGCTGTGACTTGCTCAAGGCCTTATATCGAGTAAAC

GGTAGTGCTGGGGCTTAGACGCAGGTGTTCTGATTTATAGTTCAAAACCTCTAT

CAATGAGAGAGCAATCTCCTGGTAATGTGATAGATTTCCCAACTTAATGCCAA

CATACCATAAACCTCCCATTCTGCTAATGCCCAGCCTAAGTTGGGGAGACCACT

CCAGATTCCAAGATGTACAGTTTGCTTTGCTGGGCCTTTTTCCCATGCCTGCCTT

TACTCTGCCAGAGTTATATTGCTGGGGTTTTGAAGAAGATCCTATTAAATAAAA

GAATAAGCAGTATTATTAAGTAGCCCTGCATTTCAGGTTTCCTTGAGTGGCAGG

CCAGGCCTGGCCGTGAACGTTCACTGAAATCATGGCCTCTTGGCCAAGATTGA

TAGCTTGTGCCTGTCCCTGAGTCCCAGTCCATCACGAGCAGCTGGTTTCTAAGA

TGCTATTTCCCGTATAAAGCATGAGACCGTGACTTGCCAGCCCCACAGAGCCC

CGCCCTTGTCCATCACTGGCATCTGGACTCCAGCCTGGGTTGGGGCAAAGAGG

GAAATGAGATCATGTCCTAACCCTGATCCTCTTGTCCCACAGATATCCAGAACC

CTGACCCTGCCGTGTACCAGCTGAGAGACTCTAAATCCAGTGACAAGTCTGTCT

GCCTATTCGAATTCGGCTCCGGAGCCACTAACTTCTCCCTGTTGAAACAGGCTG

GCGATGTTGAAGAAAACCCCGGTCCTATGGCCCAGTCCAAGCACGGCCTGACC

AAGGAGATGACCATGAAGTACCGCATGGAGGGCTGCGTGGACGGCCACAAGT

TCGTGATCACCGGCGAGGGCATCGGCTACCCCTTCAAGGGCAAGCAGGCCATC

AACCTGTGCGTGGTGGAGGGCGGCCCCTTGCCCTTCGCCGAGGACATCTTGTCC

GCCGCCTTCATGTACGGCAACCGCGTGTTCACCGAGTACCCCCAGGACATCGT

GGACTACTTCAAGAACTCCTGCCCCGCCGGATACACCTGGGACCGCTCCTTCCT

GTTCGAGGACGGCGCCGTGTGCATCTGCAACGCCGACATCACCGTCAGCGTGG

AGGAGAACTGCATGTACCACGAGTCCAAGTTCTACGGCGTGAACTTCCCCGCC

GACGGCCCCGTGATGAAGAAGATGACCGACAACTGGGAGCCCTCCTGCGAGA

AGATCATCCCCGTGCCCAAGCAGGGCATCTTGAAGGGCGACGTCAGCATGTAC

CTGCTGCTGAAGGACGGTGGCCGCTTGCGCTGCCAGTTCGACACCGTGTACAA

GGCCAAGTCCGTGCCCCGCAAGATGCCCGACTGGCACTTCATCCAGCACAAGC

TGACCCGCGAGGACCGCAGCGACGCCAAGAACCAGAAGTGGCACCTGACCGA

GCACGCCATCGCCTCCGGCTCCGCCTTGCCCCGGGCCAAGCGGGGCAGCGGCG

CCACCAACTTCAGCCTGCTGAAGCAGGCCGGCGACGTGGAGGAGAACCCCGGC

CCTATGGGGGCAGGTGCCACCGGCCGCGCTATGGACGGGCCGCGCCTGCTGCT

GTTGCTGCTTCTGGGGGTGTCCCTTGGAGGTGCCAAGGAGGCATGCCCCACAG

GCCTGTACACACACAGCGGTGAGTGCTGCAAAGCCTGCAACCTGGGCGAGGGT

GTGGCCCAGCCTTGTGGAGCCAACCAGACCGTGTGTGAGCCCTGCCTGGACAG

CGTGACGTTCTCCGACGTGGTGAGCGCGACCGAGCCGTGCAAGCCGTGCACCG

AGTGCGTGGGGCTCCAGAGCATGTCGGCGCCGTGCGTGGAGGCCGACGACGCC

GTGTGCCGCTGCGCCTACGGCTACTACCAGGATGAGACGACTGGGCGCTGCGA

GGCGTGCCGCGTGTGCGAGGCGGGCTCGGGCCTCGTGTTCTCCTGCCAGGACA

AGCAGAACACCGTGTGCGAGGAGTGCCCCGACGGCACGTATTCCGACGAGGCC

TABLE 4-continued

Homologous Repair Template Sequences

AACCACGTGGACCCGTGCCTGCCCTGCACCGTGTGCGAGGACACCGAGCGCCA

GCTCCGCGAGTGCACACGCTGGGCCGACGCCGAGTGCGAGGAGATCCCTGGCC

GTTGGATTACACGGTCCACACCCCCAGAGGGCTCGGACAGCACAGCCCCCAGC

ACCCAGGAGCCTGAGGCACCTCCAGAACAAGACCTCATAGCCAGCACGGTGGC

AGGTGTGGTGACCACAGTGATGGGCAGCTCCCAGCCCGTGGTGACCCGAGGCA

CCACCGACAACCTCATCCCTGTCTATTGCTCCATCCTGGCTGCTGTGGTTGTGG

GTCTTGTGGCCTACATAGCCTTCAAGAGGTAACTCGAGTGTGCCTTCTAGTTGC

CAGCCATCTGTTGTTTGCCCCTCCCCCGTGCCTTCCTTGACCCTGGAAGGTGCC

ACTCCCACTGTCCTTTCCTAATAAAATGAGGAAATTGCATCGCATTGTCTGAGT

AGGTGTCATTCTATTCTGGGGGGTGGGGTGGGGCAGGACAGCAAGGGGGAGG

ATTGGGAAGACAATAGCAGGCATGCTGGGGATGCGGTGGGCTCTATGGCGCGG

CCGCACCGATTTTGATTCTCAAACAAATGTGTCACAAAGTAAGGATTCTGATGT

GTATATCACAGACAAAACTGTGCTAGACATGAGGTCTATGGACTTCAAGAGCA

ACAGTGCTGTGGCCTGGAGCAACAAATCTGACTTTGCATGTGCAAACGCCTTC

AACAACAGCATTATTCCAGAAGACACCTTCTTCCCCAGCCCAGGTAAGGGCAG

CTTTGGTGCCTTCGCAGGCTGTTTCCTTGCTTCAGGAATGGCCAGGTTCTGCCC

AGAGCTCTGGTCAATGATGTCTAAAACTCCTCTGATTGGTGGTCTCGGCCTTAT

CCATTGCCACCAAAACCCTCTTTTTACTAAGAAACAGTGAGCCTTGTTCTGGCA

GTCCAGAGAATGACACGGGAAAAAAGCAGATGAAGAGAAGGTGGCAGGAGA

GGGCACGTGGCCCAGCCTCAGTCTCTCCAACTGAGTTCCTGCCTGCCTGCCTTT

GCTCAGACTGTTTGCCCCTTACTGCTCTTCTAGGCCTCATTCTAAGCCCCTTCTC

CAAGTTGCCTCTCCTTATTTCTCCCTGTCTGCCAAAAAATCTTTCCCAGCTCACT

AAGTCAGTCTCACGCAGTCACTCATTAACCCACCAATCACTGATTGTGCCGGCA

CATGAATGCACCAGGTGTTGAAGTGGAGGAATTAAAAAGTCAGATGAGGGGT

GTGCCCAGAGGAAGCACCATTCTAGTTGGGGGAGCCCATCTGTCAGCTGGGAA

AAGTCCAAATAACTTCAGATTGGAATGTGTTTTAACTCAGGGTTGAGAAAACA

GCTACCTTCAGGACAAAAGTCAGGGAAGGGCTCTCTGAAGAAATGCTACTTGA

AGATACCAGCCCTACCAAGGGCAGGGAGAGGACCCTATAGAGGCCTGGGACA

GGAGCTCAATGAGAAAGGAGAAGAGCAGCAGGCATGAGTTGAATGAAGGAGG

CAGGGCCGGGTCACAGGGCCTTCTAGGCCATGAGAGGGTAGACAGGCTAGC

NTC9385R-TRAC(1k)DTS_P2A.F5.TRBopt.f-P2A.TRAopt.BGHpA (SEQ ID NO: 9)

CCGCCTAATGAGCGGGCTTTTTTTGGCTTGTTGTCCACAACCGTTAAACCTTA

AAAGCTTTAAAAGCCTTATATATTCTTTTTTTTCTTATAAAACTTAAAACCTTAG

AGGCTATTTAAGTTGCTGATTTATATTAATTTTATTGTTCAAACATGAGAGCTT

AGTACGTGAAACATGAGAGCTTAGTACGTTAGCCATGAGAGCTTAGTACGTTA

GCCATGAGGGTTTAGTTCGTTAAACATGAGAGCTTAGTACGTTAAACATGAGA

GCTTAGTACGTACTATCAACAGGTTGAACTGCTGATCCACGTTGTGGTAGAATT

GGTAAAGAGAGTCGTGTAAAATATCGAGTTCGCACATCTTGTTGTCTGATTATT

GATTTTTGGCGAAACCATTTGATCATATGACAAGATGTGTATCTACCTTAACTT

TABLE 4-continued

Homologous Repair Template Sequences

AATGATTTTGATAAAAATCATTAGGTACCTGGTTGCTGACTAATTGAGATGCAT

GCTTTGCATACTTCTGCCTGCTGGGGAGCCTGGGGACTTTCCACACCCCATGGA

CATTAAAAACACAAAATCCTACGGAAATACTGAAGAATGAGTCTCAGCACTAA

GGAAAAGCCTCCAGCAGCTCCTGCTTTCTGAGGGTGAAGGATAGACGCTGTGG

CTCTGCATGACTCACTAGCACTCTATCACGGCCATATTCTGGCAGGGTCAGTGG

CTCCAACTAACATTTGTTTGGTACTTTACAGTTTATTAAATAGATGTTTATATGG

AGAAGCTCTCATTTCTTTCTCAGAAGAGCCTGGCTAGGAAGGTGGATGAGGCA

CCATATTCATTTTGCAGGTGAAATTCCTGAGATGTAAGGAGCTGCTGTGACTTG

CTCAAGGCCTTATATCGAGTAAACGGTAGTGCTGGGGCTTAGACGCAGGTGTT

CTGATTTATAGTTCAAAACCTCTATCAATGAGAGAGCAATCTCCTGGTAATGTG

ATAGATTTCCCAACTTAATGCCAACATACCATAAACCTCCCATTCTGCTAATGC

CCAGCCTAAGTTGGGGAGACCACTCCAGATTCCAAGATGTACAGTTTGCTTTGC

TGGGCCTTTTTCCCATGCCTGCCTTTACTCTGCCAGAGTTATATTGCTGGGGTTT

TGAAGAAGATCCTATTAAATAAAAGAATAAGCAGTATTATTAAGTAGCCCTGC

ATTTCAGGTTTCCTTGAGTGGCAGGCCAGGCCTGGCCGTGAACGTTCACTGAA

ATCATGGCCTCTTGGCCAAGATTGATAGCTTGTGCCTGTCCCTGAGTCCCAGTC

CATCACGAGCAGCTGGTTTCTAAGATGCTATTTCCCGTATAAAGCATGAGACC

GTGACTTGCCAGCCCCACAGAGCCCCGCCCTTGTCCATCACTGGCATCTGGACT

CCAGCCTGGGTTGGGGCAAAGAGGGAAATGAGATCATGTCCTAACCCTGATCC

TCTTGTCCCACAGATATCCAGAACCCTGACCCTGCCGTGTACCAGCTGAGAGA

CTCTAAATCCAGTGACAAGTCTGTCTGCCTATTCGAATTCGGCTCCGGAGCCAC

TAACTTCTCCCTGTTGAAACAGGCTGGCGATGTTGAAGAAAACCCCGGTCCTAT

GGCCACCGGCTCTAGAACAAGCCTGCTGCTCGCTTTTGGCCTGCTCTGCCTGCC

ATGTCTCCAAGAGGGATCTGCCGGCATTACACAGGCCCCTACATCTCAGATTCT

GGCCGCTGGCAGACGGATGACACTGAGATGCACCCAGGACATGAGACACAAC

GCCATGTACTGGTATCGGCAGGACCTCGGCCTGGGACTGAGACTGATCCACTA

CTCTAATACCGCCGGCACCACCGGCAAAGGCGAAGTGCCTGATGGCTACTCCG

TGTCCAGAGCCAATACCGACGACTTCCCACTGACACTGGCCTCTGCTGTGCCTA

GCCAGACCTCCGTGTACTTCTGTGCCAGCAGCCTGTCCTTTGGCACCGAGGCCT

TTTTCGGCCAAGGCACCAGACTGACCGTGGTGGAAGATCTGAACAAAGTGTTC

CCTCCAGAGGTGGCCGTGTTCGAGCCTTCTGAGGCCGAGATCAGCCACACACA

GAAAGCCACACTCGTGTGTCTGGCTACCGGCTTCTTCCCCGATCACGTGGAACT

GTCTTGGTGGGTCAACGGCAAAGAGGTGCACAGCGGCGTCAGCACAGATCCCC

AGCCTCTGAAAGAACAGCCCGCTCTGAACGACAGCCGCTACTGCCTGTCTAGC

AGACTGAGAGTGTCCGCCACCTTCTGGCAGAACCCCAGAAACCACTTCAGATG

CCAGGTCCAGTTCTACGGCCTGAGCGAGAACGATGAGTGGACCCAGAAGAGA

GCCAAGCCTGTGACACAGATCGTGTCTGCCGAAGCCTGGGGCAGAGCCGATTG

TGGCTTTACCAGCGTGTCATACCAGCAGGGCGTGCTGTCTGCCACCATCCTGTA

TGAGATCCTGCTCGGCAAGGCCACACTGTACGCTGTGCTGGTGTCTGCTCTGGT

TABLE 4-continued

Homologous Repair Template Sequences

GCTGATGGCTATGGTCAAGCGGAAGGACTTCCGGGCCAAGCGGGGCAGCGGC

GCCACCAACTTCAGCCTGCTGAAGCAGGCCGGCGACGTGGAGGAGAACCCCG

GCCCTATGGCCACAGGCAGCAGAACATCTCTGCTGCTGGCCTTCGGACTGCTGT

GTCTGCCTTGGCTGCAAGAGGCTTCCGCCCAGCAGAAAGAGGTGGAACAGAAT

AGCGGCCCTCTGAGCGTTCCAGAAGGCGCTATCGCCAGCCTGAACTGCACCTA

CAGCGATAGAGGCAGCCAGAGCTTCTTCTGGTACAGACAGTACAGCGGCAAGA

GCCCCGAGCTGATCATGTTCATCTACAGCAACGGCGACAAAGAGGACGGCCGG

TTTACAGCCCAGCTGAACAAGGCCAGCCAATACGTGTCCCTGCTGATCAGAGA

TAGCCAGCCTAGCGACAGCGCCACCTATCTGTGCGCCGTGAATTTTGGCGGCG

GAAAGCTGATCTTTGGCCAGGGCACAGAGCTGAGCGTGAAGCCCAACATTCAG

AACCCCGATCCTGCCGTGTACCAGCTGAGAGACAGCAAGAGCAGCGACAAGA

GCGTGTGCCTGTTCACCGACTTCGACAGCCAGACCAACGTGTCCCAGAGCAAG

GACAGCGACGTGTACATCACCGACAAGACCGTGCTGGACATGCGGAGCATGG

ACTTCAAGAGCAACAGCGCCGTGGCCTGGTCCAACAAGAGCGATTTCGCCTGC

GCCAACGCCTTCAACAACAGCATTATCCCCGAGGACACATTCTTCCCAAGTCCT

GAGAGCAGCTGCGACGTGAAGCTGGTGGAAAAGAGCTTCGAGACAGACACCA

ACCTGAACTTCCAGAACCTGTCCGTGATCGGCTTCCGCATCCTGCTGCTGAAAG

TGGCCGGCTTCAACCTGCTGATGACCCTGAGACTGTGGTCCAGCTGACTCGAGT

GTGCCTTCTAGTTGCCAGCCATCTGTTGTTTGCCCCTCCCCCGTGCCTTCCTTGA

CCCTGGAAGGTGCCACTCCCACTGTCCTTTCCTAATAAAATGAGGAAATTGCAT

CGCATTGTCTGAGTAGGTGTCATTCTATTCTGGGGGGTGGGGTGGGGCAGGAC

AGCAAGGGGGAGGATTGGGAAGACAATAGCAGGCATGCTGGGGATGCGGTGG

GCTCTATGGCGCGGCCGCACCGATTTTGATTCTCAAACAAATGTGTCACAAAGT

AAGGATTCTGATGTGTATATCACAGACAAAACTGTGCTAGACATGAGGTCTAT

GGACTTCAAGAGCAACAGTGCTGTGGCCTGGAGCAACAAATCTGACTTTGCAT

GTGCAAACGCCTTCAACAACAGCATTATTCCAGAAGACACCTTCTTCCCCAGCC

CAGGTAAGGGCAGCTTTGGTGCCTTCGCAGGCTGTTTCCTTGCTTCAGGAATGG

CCAGGTTCTGCCCAGAGCTCTGGTCAATGATGTCTAAAACTCCTCTGATTGGTG

GTCTCGGCCTTATCCATTGCCACCAAAACCCTCTTTTTACTAAGAAACAGTGAG

CCTTGTTCTGGCAGTCCAGAGAATGACACGGGAAAAAAGCAGATGAAGAGAA

GGTGGCAGGAGAGGGCACGTGGCCCAGCCTCAGTCTCTCCAACTGAGTTCCTG

CCTGCCTGCCTTTGCTCAGACTGTTTGCCCCTTACTGCTCTTCTAGGCCTCATTC

TAAGCCCCTTCTCCAAGTTGCCTCTCCTTATTTCTCCCTGTCTGCCAAAAAATCT

TTCCCAGCTCACTAAGTCAGTCTCACGCAGTCACTCATTAACCCACCAATCACT

GATTGTGCCGGCACATGAATGCACCAGGTGTTGAAGTGGAGGAATTAAAAAGT

CAGATGAGGGGTGTGCCCAGAGGAAGCACCATTCTAGTTGGGGGAGCCCATCT

GTCAGCTGGGAAAAGTCCAAATAACTTCAGATTGGAATGTGTTTTAACTCAGG

GTTGAGAAAACAGCTACCTTCAGGACAAAAGTCAGGGAAGGGCTCTCTGAAG

AAATGCTACTTGAAGATACCAGCCCTACCAAGGGCAGGGAGAGGACCCTATAG

TABLE 4-continued

Homologous Repair Template Sequences

AGGCCTGGGACAGGAGCTCAATGAGAAAGGAGAAGAGCAGCAGGCATGAGTT
GAATGAAGGAGGCAGGGCCGGGTCACAGGGCCTTCTAGGCCATGAGAGGGTA
GACAGGGATCCGGTGTGGAAAGTCCCCAGGCTCCCCAGCAGGCAGAAGTATGC
AAAGCATGCATCTCAATTAGTCAGCAACCAGCTAGC

NTC9385R-TRAC(1k)DTS_P2A.F5.TRBopt.f-P2A.TRA(Va)opt (SEQ ID NO: 10)

CCGCCTAATGAGCGGGCTTTTTTTTGGCTTGTTGTCCACAACCGTTAAACCTTA
AAAGCTTTAAAAGCCTTATATATTCTTTTTTTTCTTATAAAACTTAAAACCTTAG
AGGCTATTTAAGTTGCTGATTTATATTAATTTTATTGTTCAAACATGAGAGCTT
AGTACGTGAAACATGAGAGCTTAGTACGTTAGCCATGAGAGCTTAGTACGTTA
GCCATGAGGGTTTAGTTCGTTAAACATGAGAGCTTAGTACGTTAAACATGAGA
GCTTAGTACGTACTATCAACAGGTTGAACTGCTGATCCACGTTGTGGTAGAATT
GGTAAAGAGAGTCGTGTAAAATATCGAGTTCGCACATCTTGTTGTCTGATTATT
GATTTTTGGCGAAACCATTTGATCATATGACAAGATGTGTATCTACCTTAACTT
AATGATTTTGATAAAAATCATTAGGTACCTGGTTGCTGACTAATTGAGATGCAT
GCTTTGCATACTTCTGCCTGCTGGGGAGCCTGGGGACTTTCCACACCCCATGGA
CATTAAAAACACAAAATCCTACGGAAATACTGAAGAATGAGTCTCAGCACTAA
GGAAAAGCCTCCAGCAGCTCCTGCTTTCTGAGGGTGAAGGATAGACGCTGTGG
CTCTGCATGACTCACTAGCACTCTATCACGGCCATATTCTGGCAGGGTCAGTGG
CTCCAACTAACATTTGTTTGGTACTTTACAGTTTATTAAATAGATGTTTATATGG
AGAAGCTCTCATTTCTTTCTCAGAAGAGCCTGGCTAGGAAGGTGGATGAGGCA
CCATATTCATTTTGCAGGTGAAATTCCTGAGATGTAAGGAGCTGCTGTGACTTG
CTCAAGGCCTTATATCGAGTAAACGGTAGTGCTGGGGCTTAGACGCAGGTGTT
CTGATTTATAGTTCAAAACCTCTATCAATGAGAGAGCAATCTCCTGGTAATGTG
ATAGATTTCCCAACTTAATGCCAACATACCATAAACCTCCCATTCTGCTAATGC
CCAGCCTAAGTTGGGGAGACCACTCCAGATTCCAAGATGTACAGTTTGCTTTGC
TGGGCCTTTTTCCCATGCCTGCCTTTACTCTGCCAGAGTTATATTGCTGGGGTTT
TGAAGAAGATCCTATTAAATAAAAGAATAAGCAGTATTATTAAGTAGCCCTGC
ATTTCAGGTTTCCTTGAGTGGCAGGCCAGGCCTGGCCGTGAACGTTCACTGAA
ATCATGGCCTCTTGGCCAAGATTGATAGCTTGTGCCTGTCCCTGAGTCCCAGTC
CATCACGAGCAGCTGGTTTCTAAGATGCTATTTCCCGTATAAAGCATGAGACC
GTGACTTGCCAGCCCCACAGAGCCCCGCCCTTGTCCATCACTGGCATCTGGACT
CCAGCCTGGGTTGGGGCAAAGAGGGAAATGAGATCATGTCCTAACCCTGATCC
TCTTGTCCCACAGATATCCAGAACCCTGACCCTGCCGTGTACCAGCTGAGAGA
CTCTAAATCCAGTGACAAGTCTGTCTGCCTATTCGAATTCGGCTCCGGAGCCAC
TAACTTCTCCCTGTTGAAACAGGCTGGCGATGTTGAAGAAAACCCCGGTCCTAT
GGCCACCGGCTCTAGAACAAGCCTGCTGCTCGCTTTTGGCCTGCTCTGCCTGCC
ATGTCTCCAAGAGGGATCTGCCGGCATTACACAGGCCCCTACATCTCAGATTCT
GGCCGCTGGCAGACGGATGACACTGAGATGCACCCAGGACATGAGACACAAC
GCCATGTACTGGTATCGGCAGGACCTCGGCCTGGGACTGAGACTGATCCACTA

TABLE 4-continued

Homologous Repair Template Sequences

CTCTAATACCGCCGGCACCACCGGCAAAGGCGAAGTGCCTGATGGCTACTCCG

TGTCCAGAGCCAATACCGACGACTTCCCACTGACACTGGCCTCTGCTGTGCCTA

GCCAGACCTCCGTGTACTTCTGTGCCAGCAGCCTGTCCTTTGGCACCGAGGCCT

TTTTCGGCCAAGGCACCAGACTGACCGTGGTGGAAGATCTGAACAAAGTGTTC

CCTCCAGAGGTGGCCGTGTTCGAGCCTTCTGAGGCCGAGATCAGCCACACACA

GAAAGCCACACTCGTGTGTCTGGCTACCGGCTTCTTCCCCGATCACGTGGAACT

GTCTTGGTGGGTCAACGGCAAAGAGGTGCACAGCGGCGTCAGCACAGATCCCC

AGCCTCTGAAAGAACAGCCCGCTCTGAACGACAGCCGCTACTGCCTGTCTAGC

AGACTGAGAGTGTCCGCCACCTTCTGGCAGAACCCCAGAAACCACTTCAGATG

CCAGGTCCAGTTCTACGGCCTGAGCGAGAACGATGAGTGGACCCAGAAGAGA

GCCAAGCCTGTGACACAGATCGTGTCTGCCGAAGCCTGGGGCAGAGCCGATTG

TGGCTTTACCAGCGTGTCATACCAGCAGGGCGTGCTGTCTGCCACCATCCTGTA

TGAGATCCTGCTCGGCAAGGCCACACTGTACGCTGTGCTGGTGTCTGCTCTGGT

GCTGATGGCTATGGTCAAGCGGAAGGACTTCCGGGCCAAGCGGGGCAGCGGC

GCCACCAACTTCAGCCTGCTGAAGCAGGCCGGCGACGTGGAGGAGAACCCCG

GCCCTATGGCCACAGGCAGCAGAACATCTCTGCTGCTGGCCTTCGGACTGCTGT

GTCTGCCTTGGCTGCAAGAGGCTTCCGCCCAGCAGAAAGAGGTGGAACAGAAT

AGCGGCCCTCTGAGCGTTCCAGAAGGCGCTATCGCCAGCCTGAACTGCACCTA

CAGCGATAGAGGCAGCCAGAGCTTCTTCTGGTACAGACAGTACAGCGGCAAGA

GCCCCGAGCTGATCATGTTCATCTACAGCAACGGCGACAAAGAGGACGGCCGG

TTTACAGCCCAGCTGAACAAGGCCAGCCAATACGTGTCCCTGCTGATCAGAGA

TAGCCAGCCTAGCGACAGCGCCACCTATCTGTGCGCCGTGAATTTTGGCGGCG

GAAAGCTGATCTTTGGCCAGGGCACAGAGCTGAGCGTGAAGCCCAACATTCAG

AACCCCGATCCTGCTGTGTATCAGCTGCGCGACAGCAAGAGCAGCGACAAGAG

CGTGTGTTTGTTCACCGATTTTGATTCTCAAACAAATGTGTCACAAAGTAAGGA

TTCTGATGTGTATATCACAGACAAAACTGTGCTAGACATGAGGTCTATGGACTT

CAAGAGCAACAGTGCTGTGGCCTGGAGCAACAAATCTGACTTTGCATGTGCAA

ACGCCTTCAACAACAGCATTATTCCAGAAGACACCTTCTTCCCCAGCCCAGGTA

AGGGCAGCTTTGGTGCCTTCGCAGGCTGTTTCCTTGCTTCAGGAATGGCCAGGT

TCTGCCCAGAGCTCTGGTCAATGATGTCTAAAACTCCTCTGATTGGTGGTCTCG

GCCTTATCCATTGCCACCAAAACCCTCTTTTTACTAAGAAACAGTGAGCCTTGT

TCTGGCAGTCCAGAGAATGACACGGGAAAAAAGCAGATGAAGAGAAGGTGGC

AGGAGAGGGCACGTGGCCCAGCCTCAGTCTCTCCAACTGAGTTCCTGCCTGCC

TGCCTTTGCTCAGACTGTTTGCCCCTTACTGCTCTTCTAGGCCTCATTCTAAGCC

CCTTCTCCAAGTTGCCTCTCCTTATTTCTCCCTGTCTGCCAAAAAATCTTTCCCA

GCTCACTAAGTCAGTCTCACGCAGTCACTCATTAACCCACCAATCACTGATTGT

GCCGGCACATGAATGCACCAGGTGTTGAAGTGGAGGAATTAAAAAGTCAGATG

AGGGGTGTGCCCAGAGGAAGCACCATTCTAGTTGGGGGAGCCCATCTGTCAGC

TGGGAAAAGTCCAAATAACTTCAGATTGGAATGTGTTTTAACTCAGGGTTGAG

TABLE 4-continued

Homologous Repair Template Sequences

AAAACAGCTACCTTCAGGACAAAAGTCAGGGAAGGGCTCTCTGAAGAAATGCT

ACTTGAAGATACCAGCCCTACCAAGGGCAGGGAGAGGACCCTATAGAGGCCT

GGGACAGGAGCTCAATGAGAAAGGAGAAGAGCAGCAGGCATGAGTTGAATGA

AGGAGGCAGGGCCGGGTCACAGGGCCTTCTAGGCCATGAGAGGGTAGACAGG

GATCCGGTGTGGAAAGTCCCCAGGCTCCCCAGCAGGCAGAAGTATGCAAAGCA

TGCATCTCAATTAGTCAGCAACCAGCTAGC

NTC9385R-TRAC(1k)DTS_P2A.1G4.TRBopt.f-P2A.TRAopt.BGHpA (SEQ ID NO: 11)

CCGCCTAATGAGCGGGCTTTTTTTTGGCTTGTTGTCCACAACCGTTAAACCTTA

AAAGCTTTAAAAGCCTTATATATTCTTTTTTTTCTTATAAAACTTAAAACCTTAG

AGGCTATTTAAGTTGCTGATTTATATTAATTTTATTGTTCAAACATGAGAGCTT

AGTACGTGAAACATGAGAGCTTAGTACGTTAGCCATGAGAGCTTAGTACGTTA

GCCATGAGGGTTTAGTTCGTTAAACATGAGAGCTTAGTACGTTAAACATGAGA

GCTTAGTACGTACTATCAACAGGTTGAACTGCTGATCCACGTTGTGGTAGAATT

GGTAAAGAGAGTCGTGTAAAATATCGAGTTCGCACATCTTGTTGTCTGATTATT

GATTTTTGGCGAAACCATTTGATCATATGACAAGATGTGTATCTACCTTAACTT

AATGATTTTGATAAAAATCATTAGGTACCTGGTTGCTGACTAATTGAGATGCAT

GCTTTGCATACTTCTGCCTGCTGGGGAGCCTGGGGACTTTCCACACCCCATGGA

CATTAAAAACACAAAATCCTACGGAAATACTGAAGAATGAGTCTCAGCACTAA

GGAAAAGCCTCCAGCAGCTCCTGCTTTCTGAGGGTGAAGGATAGACGCTGTGG

CTCTGCATGACTCACTAGCACTCTATCACGGCCATATTCTGGCAGGGTCAGTGG

CTC AACTAACATTTGTTTGGTACTTTACAGTTTATTAAATAGATGTTTATATGG

AGAAGCTCTCATTTCTTTCTCAGAAGAGCCTGGCTAGGAAGGTGGATGAGGCA

CCATATTCATTTTGCAGGTGAAATTCCTGAGATGTAAGGAGCTGCTGTGACTTG

CTCAAGGCCTTATATCGAGTAAACGGTAGTGCTGGGGCTTAGACGCAGGTGTT

CTGATTTATAGTTCAAAACCTCTATCAATGAGAGAGCAATCTCCTGGTAATGTG

ATAGATTTCCCAACTTAATGCCAACATACCATAAACCTCCCATTCTGCTAATGC

CCAGCCTAAGTTGGGGAGACCACTCCAGATTCCAAGATGTACAGTTTGCTTTGC

TGGGCCTTTTTCCCATGCCTGCCTTTACTCTGCCAGAGTTATATTGCTGGGGTTT

TGAAGAAGATCCTATTAAATAAAAGAATAAGCAGTATTATTAAGTAGCCCTGC

ATTTCAGGTTTCCTTGAGTGGCAGGCCAGGCCTGGCCGTGAACGTTCACTGAA

ATCATGGCCTCTTGGCCAAGATTGATAGCTTGTGCCTGTCCCTGAGTCCCAGTC

CATCACGAGCAGCTGGTTTCTAAGATGCTATTTCCCGTATAAAGCATGAGACC

GTGACTTGCCAGCCCCACAGAGCCCCGCCCTTGTCCATCACTGGCATCTGGACT

CCAGCCTGGGTTGGGGCAAAGAGGGAAATGAGATCATGTCCTAACCCTGATCC

TCTTGTCCCACAGATATCCAGAACCCTGACCCTGCCGTGTACCAGCTGAGAGA

CTCTAAATCCAGTGACAAGTCTGTCTGCCTATTCGAATTCGGCTCCGGAGCCAC

TAACTTCTCCCTGTTGAAACAGGCTGGCGATGTTGAAGAAAACCCCGGTCCTAT

GGCCACCGGCTCTAGAACAAGCCTGCTGCTCGCTTTTGGCCTGCTCTGCCTGCC

ATGTCTCCAAGAGGGATCTGCCGGTGTCACTCAGACCCCAAAATTCCAGGTCC

TABLE 4-continued

Homologous Repair Template Sequences

TGAAGACAGGACAGAGCATGACACTGCAGTGTGCCCAGGATATGAACCATGA

ATACATGTCCTGGTATCGACAAGACCCAGGCATGGGGCTGAGGCTGATTCATT

ACTCAGTTGGTGCTGGTATCACTGACCAAGGAGAAGTCCCCAATGGCTACAAT

GTCTCCAGATCAACCACAGAGGATTTCCCGCTCAGGCTGCTGTCGGCTGCTCCC

TCCCAGACATCTGTGTACTTCTGTGCCAGCAGTTACGTCGGGAACACCGGGGA

GCTGTTTTTTGGAGAAGGCTCTAGGCTGACCGTACTGGAGGACCTGAACAAAG

TGTTCCCTCCAGAGGTGGCCGTGTTCGAGCCTTCTGAGGCCGAGATCAGCCAC

ACACAGAAAGCCACACTCGTGTGTCTGGCTACCGGCTTCTTCCCCGATCACGTG

GAACTGTCTTGGTGGGTCAACGGCAAAGAGGTGCACAGCGGCGTCAGCACAG

ATCCCCAGCCTCTGAAAGAACAGCCCGCTCTGAACGACAGCCGCTACTGCCTG

TCTAGCAGACTGAGAGTGTCCGCCACCTTCTGGCAGAACCCCAGAAACCACTT

CAGATGCCAGGTCCAGTTCTACGGCCTGAGCGAGAACGATGAGTGGACCCAGA

AGAGAGCCAAGCCTGTGACACAGATCGTGTCTGCCGAAGCCTGGGGCAGAGCC

GATTGTGGCTTTACCAGCGTGTCATACCAGCAGGGCGTGCTGTCTGCCACCATC

CTGTATGAGATCCTGCTCGGCAAGGCCACACTGTACGCTGTGCTGGTGTCTGCT

CTGGTGCTGATGGCTATGGTCAAGCGGAAGGACTTCCGGGCCAAGCGGGGCAG

CGGCGCCACCAACTTCAGCCTGCTGAAGCAGGCCGGCGACGTGGAGGAGAAC

CCCGGCCCTATGGCCACAGGCAGCAGAACATCTCTGCTGCTGGCCTTCGGACT

GCTGTGTCTGCCTTGGCTGCAAGAGGCTTCCGCCAAACAGGAGGTGACGCAGA

TTCCTGCAGCTCTGAGTGTCCCAGAAGGAGAAAACTTGGTTCTCAACTGCAGTT

TCACTGATAGCGCTATTTACAACCTCCAGTGGTTTAGGCAGGACCCTGGGAAA

GGTCTCACATCTCTGTTGCTTATTCAGTCAAGTCAGAGAGAGCAAACAAGTGG

AAGACTTAATGCCTCGCTGGATAAATCATCAGGACGTAGTACTTTATACATTGC

AGCTTCTCAGCCTGGTGACTCAGCCACCTACCTCTGTGCTGTGAGGCCCACATC

AGGAGGAAGCTACATACCTACATTTGGAAGAGGAACCAGCCTTATTGTTCATC

CGTATATTCAGAACCCCGATCCTGCCGTGTACCAGCTGAGAGACAGCAAGAGC

AGCGACAAGAGCGTGTGCCTGTTCACCGACTTCGACAGCCAGACCAACGTGTC

CCAGAGCAAGGACAGCGACGTGTACATCACCGACAAGACCGTGCTGGACATG

CGGAGCATGGACTTCAAGAGCAACAGCGCCGTGGCCTGGTCCAACAAGAGCG

ATTTCGCCTGCGCCAACGCCTTCAACAACAGCATTATCCCCGAGGACACATTCT

TCCCAAGTCCTGAGAGCAGCTGCGACGTGAAGCTGGTGGAAAAGAGCTTCGAG

ACAGACACCAACCTGAACTTCCAGAACCTGTCCGTGATCGGCTTCCGCATCCTG

CTGCTGAAAGTGGCCGGCTTCAACCTGCTGATGACCCTGAGACTGTGGTCCAG

CTGACTCGAGTGTGCCTTCTAGTTGCCAGCCATCTGTTGTTTGCCCCTCCCCCGT

GCCTTCCTTGACCCTGGAAGGTGCCACTCCCACTGTCCTTTCCTAATAAAATGA

GGAAATTGCATCGCATTGTCTGAGTAGGTGTCATTCTATTCTGGGGGGTGGGGT

GGGGCAGGACAGCAAGGGGGAGGATTGGGAAGACAATAGCAGGCATGCTGGG

GATGCGGTGGGCTCTATGGCGCGGCCGCACCGATTTTGATTCTCAAACAAATG

TGTCACAAAGTAAGGATTCTGATGTGTATATCACAGACAAAACTGTGCTAGAC

TABLE 4-continued

Homologous Repair Template Sequences

ATGAGGTCTATGGACTTCAAGAGCAACAGTGCTGTGGCCTGGAGCAACAAATC

TGACTTTGCATGTGCAAACGCCTTCAACAACAGCATTATTCCAGAAGACACCTT

CTTCCCCAGCCCAGGTAAGGGCAGCTTTGGTGCCTTCGCAGGCTGTTTCCTTGC

TTCAGGAATGGCCAGGTTCTGCCCAGAGCTCTGGTCAATGATGTCTAAAACTCC

TCTGATTGGTGGTCTCGGCCTTATCCATTGCCACCAAAACCCTCTTTTTACTAA

GAAACAGTGAGCCTTGTTCTGGCAGTCCAGAGAATGACACGGGAAAAAAGCA

GATGAAGAGAAGGTGGCAGGAGAGGGCACGTGGCCCAGCCTCAGTCTCTCCA

ACTGAGTTCCTGCCTGCCTGCCTTTGCTCAGACTGTTTGCCCCTTACTGCTCTTC

TAGGCCTCATTCTAAGCCCCTTCTCCAAGTTGCCTCTCCTTATTTCTCCCTGTCT

GCCAAAAAATCTTTCCCAGCTCACTAAGTCAGTCTCACGCAGTCACTCATTAAC

CCACCAATCACTGATTGTGCCGGCACATGAATGCACCAGGTGTTGAAGTGGAG

GAATTAAAAAGTCAGATGAGGGGTGTGCCCAGAGGAAGCACCATTCTAGTTGG

GGGAGCCCATCTGTCAGCTGGGAAAAGTCCAAATAACTTCAGATTGGAATGTG

TTTTAACTCAGGGTTGAGAAAACAGCTACCTTCAGGACAAAAGTCAGGGAAGG

GCTCTCTGAAGAAATGCTACTTGAAGATACCAGCCCTACCAAGGGCAGGGAGA

GGACCCTATAGAGGCCTGGGACAGGAGCTCAATGAGAAAGGAGAAGAGCAGC

AGGCATGAGTTGAATGAAGGAGGCAGGGCCGGGTCACAGGGCCTTCTAGGCC

ATGAGAGGGTAGACAGGGATCCGGTGTGGAAAGTCCCCAGGCTCCCCAGCAG

GCAGAAGTATGCAAAGCATGCATCTCAATTAGTCAGCAACCAGCTAGC

Linear_TRAC(1k)P2A.neo12.TRBopt.f-P2A.TRA(Va)opt (SEQ ID NO: 12)

ACATTAAAAACACAAAATCCTACGGAAATACTGAAGAATGAGTCTCAGCACTA

AGGAAAAGCCTCCAGCAGCTCCTGCTTTCTGAGGGTGAAGGATAGACGCTGTG

GCTCTGCATGACTCACTAGCACTCTATCACGGCCATATTCTGGCAGGGTCAGTG

GCTCCAACTAACATTTGTTTGGTACTTTACAGTTTATTAAATAGATGTTTATATG

GAGAAGCTCTCATTTCTTTCTCAGAAGAGCCTGGCTAGGAAGGTGGATGAGGC

ACCATATTCATTTTGCAGGTGAAATTCCTGAGATGTAAGGAGCTGCTGTGACTT

GCTCAAGGCCTTATATCGAGTAAACGGTAGTGCTGGGGCTTAGACGCAGGTGT

TCTGATTTATAGTTCAAAACCTCTATCAATGAGAGAGCAATCTCCTGGTAATGT

GATAGATTTCCCAACTTAATGCCAACATACCATAAACCTCCCATTCTGCTAATG

CCCAGCCTAAGTTGGGGAGACCACTCCAGATTCCAAGATGTACAGTTTGCTTTG

CTGGGCCTTTTTCCCATGCCTGCCTTTACTCTGCCAGAGTTATATTGCTGGGGTT

TTGAAGAAGATCCTATTAAATAAAAGAATAAGCAGTATTATTAAGTAGCCCTG

CATTTCAGGTTTCCTTGAGTGGCAGGCCAGGCCTGGCCGTGAACGTTCACTGAA

ATCATGGCCTCTTGGCCAAGATTGATAGCTTGTGCCTGTCCCTGAGTCCCAGTC

CATCACGAGCAGCTGGTTTCTAAGATGCTATTTCCCGTATAAAGCATGAGACC

GTGACTTGCCAGCCCCACAGAGCCCCGCCCTTGTCCATCACTGGCATCTGGACT

CCAGCCTGGGTTGGGGCAAAGAGGGAAATGAGATCATGTCCTAACCCTGATCC

TCTTGTCCCACAGATATCCAGAACCCTGACCCTGCCGTGTACCAGCTGAGAGA

CTCTAAATCCAGTGACAAGTCTGTCTGCCTATTCGAATTCGGCTCCGGAGCCAC

TABLE 4-continued

Homologous Repair Template Sequences

TAACTTCTCCCTGTTGAAACAGGCTGGCGATGTTGAAGAAAACCCCGGTCCTAT
GGCCACCGGCTCTAGAACAAGCCTGCTGCTCGCTTTTGGCCTGCTCTGCCTGCC
ATGTCTCCAAGAGGGATCTGCCGAAACGGGAGTTACGCAGACACCAAGACACC
TGGTCATGGGAATGACAAATAAGAAGTCTTTGAAATGTGAACAACATCTGGGT
CATAACGCTATGTATTGGTACAAGCAAAGTGCTAAGAAGCCACTGGAGCTCAT
GTTTGTCTACAGTCTTGAAGAACGGGTTGAAAACAACAGTGTGCCAAGTCGCT
TCTCACCTGAATGCCCCAACAGCTCTCACTTATTCCTTCACCTACACACCCTGC
AGCCAGAAGACTCGGCCCTGTATCTCTGCGCCAGCAGCCAGTCGAGGGGGGCT
CAGCAGTACTTCGGGCCGGGCACCAGGCTCACGGTCACAGAGGACCTGAACAA
AGTGTTCCCTCCAGAGGTGGCCGTGTTCGAGCCTTCTGAGGCCGAGATCAGCC
ACACACAGAAAGCCACACTCGTGTGTCTGGCTACCGGCTTCTTCCCCGATCACG
TGGAACTGTCTTGGTGGGTCAACGGCAAAGAGGTGCACAGCGGCGTCAGCACA
GATCCCCAGCCTCTGAAAGAACAGCCCGCTCTGAACGACAGCCGCTACTGCCT
GTCTAGCAGACTGAGAGTGTCCGCCACCTTCTGGCAGAACCCCAGAAACCACT
TCAGATGCCAGGTCCAGTTCTACGGCCTGAGCGAGAACGATGAGTGGACCCAG
AAGAGAGCCAAGCCTGTGACACAGATCGTGTCTGCCGAAGCCTGGGGCAGAG
CCGATTGTGGCTTTACCAGCGTGTCATACCAGCAGGGCGTGCTGTCTGCCACCA
TCCTGTATGAGATCCTGCTCGGCAAGGCCACACTGTACGCTGTGCTGGTGTCTG
CTCTGGTGCTGATGGCTATGGTCAAGCGGAAGGACTTCCGGGCCAAGCGGGGC
AGCGGCGCCACCAACTTCAGCCTGCTGAAGCAGGCCGGCGACGTGGAGGAGA
ACCCCGGCCCTATGGCCACAGGCAGCAGAACATCTCTGCTGCTGGCCTTCGGA
CTGCTGTGTCTGCCTTGGCTGCAAGAGGCTTCCGCCCAGAAGGAGGTGGAGCA
GGATCCTGGACCACTCAGTGTTCCAGAGGGAGCCATTGTTTCTCTCAACTGCAC
TTACAGCAACAGTGCTTTTCAATACTTCATGTGGTACAGACAGTATTCCAGAAA
AGGCCCTGAGTTGCTGATGTACACATACTCCAGTGGTAACAAAGAAGATGGAA
GGTTTACAGCACAGGTCGATAAATCCAGCAAGTATATCTCCTTGTTCATCAGAG
ACTCACAGCCCAGTGATTCAGCCACCTACCTCTGTGCAATGAGTGAGGACTAC
AAGCTCAGCTTTGGAGCCGGAACCACAGTAACTGTAAGAGCAAATATTCAGAA
CCCCGATCCTGCTGTGTATCAGCTGCGCGACAGCAAGAGCAGCGACAAGAGCG
TGTGTTTGTTCACCGATTTTGATTCTCAAACAAATGTGTCACAAAGTAAGGATT
CTGATGTGTATATCACAGACAAAACTGTGCTAGACATGAGGTCTATGGACTTC
AAGAGCAACAGTGCTGTGGCCTGGAGCAACAAATCTGACTTTGCATGTGCAAA
CGCCTTCAACAACAGCATTATTCCAGAAGACACCTTCTTCCCCAGCCCAGGTAA
GGGCAGCTTTGGTGCCTTCGCAGGCTGTTTCCTTGCTTCAGGAATGGCCAGGTT
CTGCCCAGAGCTCTGGTCAATGATGTCTAAAACTCCTCTGATTGGTGGTCTCGG
CCTTATCCATTGCCACCAAAACCCTCTTTTTACTAAGAAACAGTGAGCCTTGTT
CTGGCAGTCCAGAGAATGACACGGGAAAAAAGCAGATGAAGAGAAGGTGGCA
GGAGAGGGCACGTGGCCCAGCCTCAGTCTCTCCAACTGAGTTCCTGCCTGCCT
GCCTTTGCTCAGACTGTTTGCCCCTTACTGCTCTTCTAGGCCTCATTCTAAGCCC

TABLE 4-continued

Homologous Repair Template Sequences

CTTCTCCAAGTTGCCTCTCCTTATTTCTCCCTGTCTGCCAAAAAATCTTTCCCAG

CTCACTAAGTCAGTCTCACGCAGTCACTCATTAACCCACCAATCACTGATTGTG

CCGGCACATGAATGCACCAGGTGTTGAAGTGGAGGAATTAAAAAGTCAGATGA

GGGGTGTGCCCAGAGGAAGCACCATTCTAGTTGGGGGAGCCCATCTGTCAGCT

GGGAAAAGTCCAAATAACTTCAGATTGGAATGTGTTTTAACTCAGGGTTGAGA

AAACAGCTACCTTCAGGACAAAAGTCAGGGAAGGGCTCTCTGAAGAAATGCTA

CTTGAAGATACCAGCCCTACCAAGGGCAGGGAGAGGACCCTATAGAGGCCTG

GGACAGGAGCTCAATGAGAAAGGAGAAGAGCAGCAGGCATGAGTTGAATGAA

GGAGGCAGGGCCGGGTCACAGGGCCTTCTAGGCCATGAGAGGGTAGACAG

NTC9385R-TRAC(1k)DTS_P2A.neo12.TRBopt.f-P2A.TRA(Va)opt (SEQ ID NO: 13)

CCGCCTAATGAGCGGGCTTTTTTTTGGCTTGTTGTCCACAACCGTTAAACCTTA

AAAGCTTTAAAAGCCTTATATATTCTTTTTTTTCTTATAAAACTTAAAACCTTAG

AGGCTATTTAAGTTGCTGATTTATATTAATTTTATTGTTCAAACATGAGAGCTT

AGTACGTGAAACATGAGAGCTTAGTACGTTAGCCATGAGAGCTTAGTACGTTA

GCCATGAGGGTTTAGTTCGTTAAACATGAGAGCTTAGTACGTTAAACATGAGA

GCTTAGTACGTACTATCAACAGGTTGAACTGCTGATCCACGTTGTGGTAGAATT

GGTAAAGAGAGTCGTGTAAAATATCGAGTTCGCACATCTTGTTGTCTGATTATT

GATTTTTGGCGAAACCATTTGATCATATGACAAGATGTGTATCTACCTTAACTT

AATGATTTTGATAAAAATCATTAGGTACCTGGTTGCTGACTAATTGAGATGCAT

GCTTTGCATACTTCTGCCTGCTGGGGAGCCTGGGGACTTTCCACACCCCATGGA

CATTAAAAACACAAAATCCTACGGAAATACTGAAGAATGAGTCTCAGCACTAA

GGAAAAGCCTCCAGCAGCTCCTGCTTTCTGAGGGTGAAGGATAGACGCTGTGG

CTCTGCATGACTCACTAGCACTCTATCACGGCCATATTCTGGCAGGGTCAGTGG

CTCCAACTAACATTTGTTTGGTACTTTACAGTTTATTAAATAGATGTTTATATGG

AGAAGCTCTCATTTCTTTCTCAGAAGAGCCTGGCTAGGAAGGTGGATGAGGCA

CCATATTCATTTTGCAGGTGAAATTCCTGAGATGTAAGGAGCTGCTGTGACTTG

CTCAAGGCCTTATATCGAGTAAACGGTAGTGCTGGGGCTTAGACGCAGGTGTT

CTGATTTATAGTTCAAAACCTCTATCAATGAGAGAGCAATCTCCTGGTAATGTG

ATAGATTTCCCAACTTAATGCCAACATACCATAAACCTCCCATTCTGCTAATGC

CCAGCCTAAGTTGGGGAGACCACTCCAGATTCCAAGATGTACAGTTTGCTTTGC

TGGGCCTTTTTCCCATGCCTGCCTTTACTCTGCCAGAGTTATATTGCTGGGGTTT

TGAAGAAGATCCTATTAAATAAAAGAATAAGCAGTATTATTAAGTAGCCCTGC

ATTTCAGGTTTCCTTGAGTGGCAGGCCAGGCCTGGCCGTGAACGTTCACTGAA

ATCATGGCCTCTTGGCCAAGATTGATAGCTTGTGCCTGTCCCTGAGTCCCAGTC

CATCACGAGCAGCTGGTTTCTAAGATGCTATTTCCCGTATAAAGCATGAGACC

GTGACTTGCCAGCCCCACAGAGCCCCGCCCTTGTCCATCACTGGCATCTGGACT

CCAGCCTGGGTTGGGGCAAAGAGGGAAATGAGATCATGTCCTAACCCTGATCC

TCTTGTCCCACAGATATCCAGAACCCTGACCCTGCCGTGTACCAGCTGAGAGA

CTCTAAATCCAGTGACAAGTCTGTCTGCCTATTCGAATTCGGCTCCGGAGCCAC

TABLE 4-continued

Homologous Repair Template Sequences

TAACTTCTCCCTGTTGAAACAGGCTGGCGATGTTGAAGAAAACCCCGGTCCTAT
GGCCACCGGCTCTAGAACAAGCCTGCTGCTCGCTTTTGGCCTGCTCTGCCTGCC
ATGTCTCCAAGAGGGATCTGCCGAAACGGGAGTTACGCAGACACCAAGACACC
TGGTCATGGGAATGACAAATAAGAAGTCTTTGAAATGTGAACAACATCTGGGT
CATAACGCTATGTATTGGTACAAGCAAAGTGCTAAGAAGCCACTGGAGCTCAT
GTTTGTCTACAGTCTTGAAGAACGGGTTGAAAACAACAGTGTGCCAAGTCGCT
TCTCACCTGAATGCCCCAACAGCTCTCACTTATTCCTTCACCTACACACCCTGC
AGCCAGAAGACTCGGCCCTGTATCTCTGCGCCAGCAGCCAGTCGAGGGGGGCT
CAGCAGTACTTCGGGCCGGGCACCAGGCTCACGGTCACAGAGGACCTGAACAA
AGTGTTCCCTCCAGAGGTGGCCGTGTTCGAGCCTTCTGAGGCCGAGATCAGCC
ACACACAGAAAGCCACACTCGTGTGTCTGGCTACCGGCTTCTTCCCCGATCACG
TGGAACTGTCTTGGTGGGTCAACGGCAAAGAGGTGCACAGCGGCGTCAGCACA
GATCCCCAGCCTCTGAAAGAACAGCCCGCTCTGAACGACAGCCGCTACTGCCT
GTCTAGCAGACTGAGAGTGTCCGCCACCTTCTGGCAGAACCCCAGAAACCACT
TCAGATGCCAGGTCCAGTTCTACGGCCTGAGCGAGAACGATGAGTGGACCCAG
AAGAGAGCCAAGCCTGTGACACAGATCGTGTCTGCCGAAGCCTGGGGCAGAG
CCGATTGTGGCTTTACCAGCGTGTCATACCAGCAGGGCGTGCTGTCTGCCACCA
TCCTGTATGAGATCCTGCTCGGCAAGGCCACACTGTACGCTGTGCTGGTGTCTG
CTCTGGTGCTGATGGCTATGGTCAAGCGGAAGGACTTCCGGGCCAAGCGGGGC
AGCGGCGCCACCAACTTCAGCCTGCTGAAGCAGGCCGGCGACGTGGAGGAGA
ACCCCGGCCCTATGGCCACAGGCAGCAGAACATCTCTGCTGCTGGCCTTCGGA
CTGCTGTGTCTGCCTTGGCTGCAAGAGGCTTCCGCCCAGAAGGAGGTGGAGCA
GGATCCTGGACCACTCAGTGTTCCAGAGGGAGCCATTGTTTCTCTCAACTGCAC
TTACAGCAACAGTGCTTTTCAATACTTCATGTGGTACAGACAGTATTCCAGAAA
AGGCCCTGAGTTGCTGATGTACACATACTCCAGTGGTAACAAAGAAGATGGAA
GGTTTACAGCACAGGTCGATAAATCCAGCAAGTATATCTCCTTGTTCATCAGAG
ACTCACAGCCCAGTGATTCAGCCACCTACCTCTGTGCAATGAGTGAGGACTAC
AAGCTCAGCTTTGGAGCCGGAACCACAGTAACTGTAAGAGCAAATATTCAGAA
CCCCGATCCTGCTGTGTATCAGCTGCGCGACAGCAAGAGCAGCGACAAGAGCG
TGTGTTTGTTCACCGATTTTGATTCTCAAACAAATGTGTCACAAAGTAAGGATT
CTGATGTGTATATCACAGACAAAACTGTGCTAGACATGAGGTCTATGGACTTC
AAGAGCAACAGTGCTGTGGCCTGGAGCAACAAATCTGACTTTGCATGTGCAAA
CGCCTTCAACAACAGCATTATTCCAGAAGACACCTTCTTCCCCAGCCCAGGTAA
GGGCAGCTTTGGTGCCTTCGCAGGCTGTTTCCTTGCTTCAGGAATGGCCAGGTT
CTGCCCAGAGCTCTGGTCAATGATGTCTAAAACTCCTCTGATTGGTGGTCTCGG
CCTTATCCATTGCCACCAAAACCCTCTTTTTACTAAGAAACAGTGAGCCTTGTT
CTGGCAGTCCAGAGAATGACACGGGAAAAAAGCAGATGAAGAGAAGGTGGCA
GGAGAGGGCACGTGGCCCAGCCTCAGTCTCTCCAACTGAGTTCCTGCCTGCCT
GCCTTTGCTCAGACTGTTTGCCCCTTACTGCTCTTCTAGGCCTCATTCTAAGCCC

TABLE 4-continued

Homologous Repair Template Sequences

CTTCTCCAAGTTGCCTCTCCTTATTTCTCCCTGTCTGCCAAAAAATCTTTCCCAG

CTCACTAAGTCAGTCTCACGCAGTCACTCATTAACCCACCAATCACTGATTGTG

CCGGCACATGAATGCACCAGGTGTTGAAGTGGAGGAATTAAAAAGTCAGATGA

GGGGTGTGCCCAGAGGAAGCACCATTCTAGTTGGGGGAGCCCATCTGTCAGCT

GGGAAAAGTCCAAATAACTTCAGATTGGAATGTGTTTTAACTCAGGGTTGAGA

AAACAGCTACCTTCAGGACAAAAGTCAGGGAAGGGCTCTCTGAAGAAATGCTA

CTTGAAGATACCAGCCCTACCAAGGGCAGGGAGAGGACCCTATAGAGGCCTG

GGACAGGAGCTCAATGAGAAAGGAGAAGAGCAGCAGGCATGAGTTGAATGAA

GGAGGCAGGGCCGGGTCACAGGGCCTTCTAGGCCATGAGAGGGTAGACAGGG

ATCCGGTGTGGAAAGTCCCCAGGCTCCCCAGCAGGCAGAAGTATGCAAAGCAT

GCATCTCAATTAGTCAGCAACCAGCTAGC pUCu-Kan TRAC(1k)_P2A.Neo12.TRBC2opt.f-P2A.TRA(Va) (SEQ ID NO: 14)

GGTACCACATTAAAAACACAAAATCCTACGGAAATACTGAAGAATGAGTCTCA

GCACTAAGGAAAAGCCTCCAGCAGCTCCTGCTTTCTGAGGGTGAAGGATAGAC

GCTGTGGCTCTGCATGACTCACTAGCACTCTATCACGGCCATATTCTGGCAGGG

TCAGTGGCTCCAACTAACATTTGTTTGGTACTTTACAGTTTATTAAATAGATGTT

TATATGGAGAAGCTCTCATTTCTTTCTCAGAAGAGCCTGGCTAGGAAGGTGGAT

GAGGCACCATATTCATTTTGCAGGTGAAATTCCTGAGATGTAAGGAGCTGCTGT

GACTTGCTCAAGGCCTTATATCGAGTAAACGGTAGTGCTGGGGCTTAGACGCA

GGTGTTCTGATTTATAGTTCAAAACCTCTATCAATGAGAGAGCAATCTCCTGGT

AATGTGATAGATTTCCCAACTTAATGCCAACATACCATAAACCTCCCATTCTGC

TAATGCCCAGCCTAAGTTGGGGAGACCACTCCAGATTCCAAGATGTACAGTTT

GCTTTGCTGGGCCTTTTTCCCATGCCTGCCTTTACTCTGCCAGAGTTATATTGCT

GGGGTTTTGAAGAAGATCCTATTAAATAAAAGAATAAGCAGTATTATTAAGTA

GCCCTGCATTTCAGGTTTCCTTGAGTGGCAGGCCAGGCCTGGCCGTGAACGTTC

ACTGAAATCATGGCCTCTTGGCCAAGATTGATAGCTTGTGCCTGTCCCTGAGTC

CCAGTCCATCACGAGCAGCTGGTTTCTAAGATGCTATTTCCCGTATAAAGCATG

AGACCGTGACTTGCCAGCCCCACAGAGCCCCGCCCTTGTCCATCACTGGCATCT

GGACTCCAGCCTGGGTTGGGGCAAAGAGGGAAATGAGATCATGTCCTAACCCT

GATCCTCTTGTCCCACAGATATCCAGAACCCTGACCCTGCCGTGTACCAGCTGA

GAGACTCTAAATCCAGTGACAAGTCTGTCTGCCTATTCGAATTCGGCTCCGGAG

CCACTAACTTCTCCCTGTTGAAACAGGCTGGCGATGTTGAAGAAAACCCCGGT

CCTATGGCCACCGGCTCTAGAACAAGCCTGCTGCTCGCTTTTGGCCTGCTCTGC

CTGCCATGTCTCCAAGAGGGATCTGCCGAAACGGGAGTTACGCAGACACCAAG

ACACCTGGTCATGGGAATGACAAATAAGAAGTCTTTGAAATGTGAACAACATC

TGGGTCATAACGCTATGTATTGGTACAAGCAAAGTGCTAAGAAGCCACTGGAG

CTCATGTTTGTCTACAGTCTTGAAGAACGGGTTGAAAACAACAGTGTGCCAAG

TCGCTTCTCACCTGAATGCCCCAACAGCTCTCACTTATTCCTTCACCTACACAC

CCTGCAGCCAGAAGACTCGGCCCTGTATCTCTGCGCCAGCAGCCAGTCGAGGG

TABLE 4-continued

Homologous Repair Template Sequences

GGGCTCAGCAGTACTTCGGGCCGGGCACCAGGCTCACGGTCACAGAGGACCTG

AAAAACGTGTTCCCTCCAAAAGTGGCCGTGTTCGAGCCTTCTGAGGCCGAGAT

CAGCCACACACAGAAAGCCACACTCGTGTGTCTGGCTACCGGCTTCTACCCCG

ATCACGTGGAACTGTCTTGGTGGGTCAACGGCAAAGAGGTGCACAGCGGCGTC

AGCACAGATCCCCAGCCTCTGAAAGAACAGCCCGCTCTGAACGACAGCCGCTA

CTGCCTGTCTAGCAGACTGAGAGTGTCCGCCACCTTCTGGCAGAACCCCAGAA

ACCACTTCAGATGCCAGGTCCAGTTCTACGGCCTGAGCGAGAACGATGAGTGG

ACCCAGGACAGAGCCAAGCCTGTGACACAGATCGTGTCTGCCGAAGCCTGGGG

CAGAGCCGATTGTGGCTTTACCAGCGAGTCATACCAGCAGGGCGTGCTGTCTG

CCACCATCCTGTATGAGATCCTGCTCGGCAAGGCCACACTGTACGCTGTGCTGG

TGTCTGCTCTGGTGCTGATGGCTATGGTCTCCCGGGAGCGCATCCCCGAGGCCC

GGGCCAAGCGGGGCAGCGGCGCCACCAACTTCAGCCTGCTGAAGCAGGCCGG

CGACGTGGAGGAGAACCCCGGCCCTATGGCCACAGGCAGCAGAACATCTCTGC

TGCTGGCCTTCGGACTGCTGTGTCTGCCTTGGCTGCAAGAGGCTTCCGCCCAGA

AGGAGGTGGAGCAGGATCCTGGACCACTCAGTGTTCCAGAGGGAGCCATTGTT

TCTCTCAACTGCACTTACAGCAACAGTGCTTTTCAATACTTCATGTGGTACAGA

CAGTATTCCAGAAAAGGCCCTGAGTTGCTGATGTACACATACTCCAGTGGTAA

CAAAGAAGATGGAAGGTTTACAGCACAGGTCGATAAATCCAGCAAGTATATCT

CCTTGTTCATCAGAGACTCACAGCCCAGTGATTCAGCCACCTACCTCTGTGCAA

TGAGTGAGGACTACAAGCTCAGCTTTGGAGCCGGAACCACAGTAACTGTAAGA

GCAAATATTCAGAACCCCGATCCTGCTGTGTATCAGCTGCGCGACAGCAAGAG

CAGCGACAAGAGCGTGTGTTTGTTCACCGATTTTGATTCTCAAACAAATGTGTC

ACAAAGTAAGGATTCTGATGTGTATATCACAGACAAAACTGTGCTAGACATGA

GGTCTATGGACTTCAAGAGCAACAGTGCTGTGGCCTGGAGCAACAAATCTGAC

TTTGCATGTGCAAACGCCTTCAACAACAGCATTATTCCAGAAGACACCTTCTTC

CCCAGCCCAGGTAAGGGCAGCTTTGGTGCCTTCGCAGGCTGTTTCCTTGCTTCA

GGAATGGCCAGGTTCTGCCCAGAGCTCTGGTCAATGATGTCTAAAACTCCTCTG

ATTGGTGGTCTCGGCCTTATCCATTGCCACCAAAACCCTCTTTTTACTAAGAAA

CAGTGAGCCTTGTTCTGGCAGTCCAGAGAATGACACGGGAAAAAAGCAGATG

AAGAGAAGGTGGCAGGAGAGGGCACGTGGCCCAGCCTCAGTCTCTCCAACTG

AGTTCCTGCCTGCCTGCCTTTGCTCAGACTGTTTGCCCCTTACTGCTCTTCTAGG

CCTCATTCTAAGCCCCTTCTCCAAGTTGCCTCTCCTTATTTCTCCCTGTCTGCCA

AAAAATCTTTCCCAGCTCACTAAGTCAGTCTCACGCAGTCACTCATTAACCCAC

CAATCACTGATTGTGCCGGCACATGAATGCACCAGGTGTTGAAGTGGAGGAAT

TAAAAAGTCAGATGAGGGGTGTGCCCAGAGGAAGCACCATTCTAGTTGGGGGA

GCCCATCTGTCAGCTGGGAAAAGTCCAAATAACTTCAGATTGGAATGTGTTTTA

ACTCAGGGTTGAGAAAACAGCTACCTTCAGGACAAAAGTCAGGGAAGGGCTCT

CTGAAGAAATGCTACTTGAAGATACCAGCCCTACCAAGGGCAGGGAGAGGAC

CCTATAGAGGCCTGGGACAGGAGCTCAATGAGAAAGGAGAAGAGCAGCAGGC

TABLE 4-continued

Homologous Repair Template Sequences

ATGAGTTGAATGAAGGAGGCAGGGCCGGGTCACAGGGCCTTCTAGGCCATGA
GAGGGTAGACAGGCTAGCCGCGTTGCTGGCGTTTTTCCATAGGCTCCGCCCCCC
TGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGAACAGT
ATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAA
GCAGCAGATTACGCGCAGAAAAAAAGGATCTCAAGAAGATCCTTTGATCTTTA
GAAAAACTCATCGAGCATCAAATGAAACTGCAATTTATTCATATCAGGATTAT
CAATACCATATTTTTGAAAAAGCCGTTTCTGTAATGAAGGAGAAAACTCACCG
AGGCAGTTCCATAGGATGGCAAGATCCTGGTATCGGTCTGCGATTCCGACTCG
TCCAACATCAATACAACCTATTAATTTCCCCTCGTCAAAAATAAGGTTATCAAG
TGAGAAATCACCATGAGTGACGACTGAATCCGGTGAGAATGGCAAAAGTTTAT
GCATTTCTTTCCAGACTTGTTCAACAGGCCAGCCATTACGCTCGTCATCAAAAT
CACTCGCATCAACCAAACCGTTATTCATTCGTGATTGCGCCTGAGCCAGACGA
AATACGCGATCGCTGTTAAAAGGACAATTACAAACAGGAATCGAATGCAACCG
GCGCAGGAACACTGCCAGCGCATCAACAATATTTTCACCTGAATCAGGATATT
CTTCTAATACCTGGAATGCTGTTTTTCCGGGGATCGCAGTGGTGAGTAACCATG
CATCATCAGGAGTACGGATAAAATGCTTGATGGTCGGAAGAGGCATAAATTCC
GTCAGCCAGTTTAGTCTGACCATCTCATCTGTAACATCATTGGCAACGCTACCT
TTGCCATGTTTCAGAAACAACTCTGGCGCATCGGGCTTCCCATACAAGCGATA
GATTGTCGCACCTGATTGCCCGACATTATCGCGAGCCCATTTATACCCATATAA
ATCAGCATCCATGTTGGAATTTAATCGCGGCCTCGACGTTTCCCGTTGAATATG
GCTCATAACACCCCTTGTATTACTGTTTATGTAAGCAGACAGTTTTATTGTTCAT
GATGATATATTTTTATCTTGTGCAATGTAACATCAGAGATTTTGAGACAC pUCu-Kan TRAC(1k)_MNDZsGreen.f-P2A.LNGFRt.P2A (SEQ ID NO: 15)

GGTACCACATTAAAAACACAAAATCCTACGGAAATACTGAAGAATGAGTCTCA
GCACTAAGGAAAAGCCTCCAGCAGCTCCTGCTTTCTGAGGGTGAAGGATAGAC
GCTGTGGCTCTGCATGACTCACTAGCACTCTATCACGGCCATATTCTGGCAGGG
TCAGTGGCTCCAACTAACATTTGTTTGGTACTTTACAGTTTATTAAATAGATGTT
TATATGGAGAAGCTCTCATTTCTTTCTCAGAAGAGCCTGGCTAGGAAGGTGGAT
GAGGCACCATATTCATTTTGCAGGTGAAATTCCTGAGATGTAAGGAGCTGCTGT
GACTTGCTCAAGGCCTTATATCGAGTAAACGGTAGTGCTGGGGCTTAGACGCA
GGTGTTCTGATTTATAGTTCAAAACCTCTATCAATGAGAGAGCAATCTCCTGGT

TABLE 4-continued

Homologous Repair Template Sequences

AATGTGATAGATTTCCCAACTTAATGCCAACATACCATAAACCTCCCATTCTGC

TAATGCCCAGCCTAAGTTGGGGAGACCACTCCAGATTCCAAGATGTACAGTTT

GCTTTGCTGGGCCTTTTTCCCATGCCTGCCTTTACTCTGCCAGAGTTATATTGCT

GGGGTTTTGAAGAAGATCCTATTAAATAAAAGAATAAGCAGTATTATTAAGTA

GCCCTGCATTTCAGGTTTCCTTGAGTGGCAGGCCAGGCCTGGCCGTGAACGTTC

ACTGAAATCATGGCCTCTTGGCCAAGATTGATAGCTTGTGCCTGTCCCTGAGTC

CCAGTCCATCACGAGCAGCTGGTTTCTAAGATGCTATTTCCCGTATAAAGCATG

AGACCGTGACTTGCCAGCCCCACAGAGCCCCGCCCTTGTCCATCACTGGCATCT

GGACTCCAGCCTGGGTTGGGGCAAAGAGGGAAATGAGATCATGTCCTAACCCT

GATCCTCTTGTCCCACAGATATCCAGAACCCTGACCCTGCCGTGTACCAGCTGA

GAGACTCTAAATCCAGTGACAAGTCTGTCTGCCTATTCGAACAGAGAAACAGG

AGAATATGGGCCAAACAGGATATCTGTGGTAAGCAGTTCCTGCCCCGGCTCAG

GGCCAAGAACAGTTGGAACAGCAGAATATGGGCCAAACAGGATATCTGTGGT

AAGCAGTTCCTGCCCCGGCTCAGGGCCAAGAACAGATGGTCCCCAGATGCGGT

CCCGCCCTCAGCAGTTTCTAGAGAACCATCAGATGTTTCCAGGGTGCCCCAAG

GACCTGAAATGACCCTGTGCCTTATTTGAACTAACCAATCAGTTCGCTTCTCGC

TTCTGTTCGCGCGCTTCTGCTCCCCGAGCTCTATATAAGCAGAGCTCGTTTAGT

GAACCGTCAGATCGCCTGGAGACGCCATCCACGCTGTTTTGACTTCCATAGAA

GGCGGCCGCGCCGCCACCATGGCCCAGTCCAAGCACGGCCTGACCAAGGAGAT

GACCATGAAGTACCGCATGGAGGGCTGCGTGGACGGCCACAAGTTCGTGATCA

CCGGCGAGGGCATCGGCTACCCCTTCAAGGGCAAGCAGGCCATCAACCTGTGC

GTGGTGGAGGGCGGCCCCTTGCCCTTCGCCGAGGACATCTTGTCCGCCGCCTTC

ATGTACGGCAACCGCGTGTTCACCGAGTACCCCCAGGACATCGTGGACTACTT

CAAGAACTCCTGCCCCGCCGGATACACCTGGGACCGCTCCTTCCTGTTCGAGG

ACGGCGCCGTGTGCATCTGCAACGCCGACATCACCGTCAGCGTGGAGGAGAAC

TGCATGTACCACGAGTCCAAGTTCTACGGCGTGAACTTCCCCGCCGACGGCCC

CGTGATGAAGAAGATGACCGACAACTGGGAGCCCTCCTGCGAGAAGATCATCC

CCGTGCCCAAGCAGGGCATCTTGAAGGGCGACGTCAGCATGTACCTGCTGCTG

AAGGACGGTGGCCGCTTGCGCTGCCAGTTCGACACCGTGTACAAGGCCAAGTC

CGTGCCCCGCAAGATGCCCGACTGGCACTTCATCCAGCACAAGCTGACCCGCG

AGGACCGCAGCGACGCCAAGAACCAGAAGTGGCACCTGACCGAGCACGCCAT

CGCCTCCGGCTCCGCCTTGCCCCGGGCCAAGCGGGGCAGCGGCGCCACCAACT

TCAGCCTGCTGAAGCAGGCCGGCGACGTGGAGGAGAACCCCGGCCCTATGGG

GGCAGGTGCCACCGGCCGCGCTATGGACGGGCCGCGCCTGCTGCTGTTGCTGC

TTCTGGGGGTGTCCCTTGGAGGTGCCAAGGAGGCATGCCCCACAGGCCTGTAC

ACACACAGCGGTGAGTGCTGCAAAGCCTGCAACCTGGGCGAGGGTGTGGCCCA

GCCTTGTGGAGCCAACCAGACCGTGTGTGAGCCCTGCCTGGACAGCGTGACGT

TCTCCGACGTGGTGAGCGCGACCGAGCCGTGCAAGCCGTGCACCGAGTGCGTG

GGGCTCCAGAGCATGTCGGCGCCGTGCGTGGAGGCCGACGACGCCGTGTGCCG

TABLE 4-continued

Homologous Repair Template Sequences

CTGCGCCTACGGCTACTACCAGGATGAGACGACTGGGCGCTGCGAGGCGTGCC

GCGTGTGCGAGGCGGGCTCGGGCCTCGTGTTCTCCTGCCAGGACAAGCAGAAC

ACCGTGTGCGAGGAGTGCCCCGACGGCACGTATTCCGACGAGGCCAACCACGT

GGACCCGTGCCTGCCCTGCACCGTGTGCGAGGACACCGAGCGCCAGCTCCGCG

AGTGCACACGCTGGGCCGACGCCGAGTGCGAGGAGATCCCTGGCCGTTGGATT

ACACGGTCCACACCCCCAGAGGGCTCGGACAGCACAGCCCCCAGCACCCAGG

AGCCTGAGGCACCTCCAGAACAAGACCTCATAGCCAGCACGGTGGCAGGTGTG

GTGACCACAGTGATGGGCAGCTCCCAGCCCGTGGTGACCCGAGGCACCACCGA

CAACCTCATCCCTGTCTATTGCTCCATCCTGGCTGCTGTGGTTGTGGGTCTTGTG

GCCTACATAGCCTTCAAGAGGGGCTCCGGAGCCACTAACTTCTCCCTGTTGAA

ACAGGCTGGCGATGTTGAAGAAAACCCCGGTCCTACCGATTTTGATTCTCAAA

CAAATGTGTCACAAAGTAAGGATTCTGATGTGTATATCACAGACAAAACTGTG

CTAGACATGAGGTCTATGGACTTCAAGAGCAACAGTGCTGTGGCCTGGAGCAA

CAAATCTGACTTTGCATGTGCAAACGCCTTCAACAACAGCATTATTCCAGAAG

ACACCTTCTTCCCCAGCCCAGGTAAGGGCAGCTTTGGTGCCTTCGCAGGCTGTT

TCCTTGCTTCAGGAATGGCCAGGTTCTGCCCAGAGCTCTGGTCAATGATGTCTA

AAACTCCTCTGATTGGTGGTCTCGGCCTTATCCATTGCCACCAAAACCCTCTTT

TTACTAAGAAACAGTGAGCCTTGTTCTGGCAGTCCAGAGAATGACACGGGAAA

AAAGCAGATGAAGAGAAGGTGGCAGGAGAGGGCACGTGGCCCAGCCTCAGTC

TCTCCAACTGAGTTCCTGCCTGCCTGCCTTTGCTCAGACTGTTTGCCCCTTACTG

CTCTTCTAGGCCTCATTCTAAGCCCCTTCTCCAAGTTGCCTCTCCTTATTTCTCC

CTGTCTGCCAAAAAATCTTTCCCAGCTCACTAAGTCAGTCTCACGCAGTCACTC

ATTAACCCACCAATCACTGATTGTGCCGGCACATGAATGCACCAGGTGTTGAA

GTGGAGGAATTAAAAAGTCAGATGAGGGGTGTGCCCAGAGGAAGCACCATTCT

AGTTGGGGGAGCCCATCTGTCAGCTGGGAAAAGTCCAAATAACTTCAGATTGG

AATGTGTTTTAACTCAGGGTTGAGAAAACAGCTACCTTCAGGACAAAAGTCAG

GGAAGGGCTCTCTGAAGAAATGCTACTTGAAGATACCAGCCCTACCAAGGGCA

GGGAGAGGACCCTATAGAGGCCTGGGACAGGAGCTCAATGAGAAAGGAGAAG

AGCAGCAGGCATGAGTTGAATGAAGGAGGCAGGGCCGGGTCACAGGGCCTTC

TAGGCCATGAGAGGGTAGACAGGCTAGCCGCGTTGCTGGCGTTTTTCCATAGG

CTCCGCCCCCTGACGAGCATCACAAAAATCGACGCTCAAGTCAGAGGTGGCG

AAACCCGACAGGACTATAAAGATACCAGGCGTTTCCCCCTGGAAGCTCCCTCG

TGCGCTCTCCTGTTCCGACCCTGCCGCTTACCGGATACCTGTCCGCCTTTCTCCC

TTCGGGAAGCGTGGCGCTTTCTCATAGCTCACGCTGTAGGTATCTCAGTTCGGT

GTAGGTCGTTCGCTCCAAGCTGGGCTGTGTGCACGAACCCCCCGTTCAGCCCG

ACCGCTGCGCCTTATCCGGTAACTATCGTCTTGAGTCCAACCCGGTAAGACACG

ACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAA

TABLE 4-continued

| Homologous Repair Template Sequences |
|---|
| GAGTTGGTAGCTCTTGATCCGGCAAACAAACCACCGCTGGTAGCGGTGGTTTTT |
| TTGTTTGCAAGCAGCAGATTACGCGCAGAAAAAAAGGATCTCAAGAAGATCCT |
| TTGATCTTTAGAAAAACTCATCGAGCATCAAATGAAACTGCAATTTATTCATAT |
| CAGGATTATCAATACCATATTTTTGAAAAAGCCGTTTCTGTAATGAAGGAGAA |
| AACTCACCGAGGCAGTTCCATAGGATGGCAAGATCCTGGTATCGGTCTGCGAT |
| TCCGACTCGTCCAACATCAATACAACCTATTAATTTCCCCTCGTCAAAAATAAG |
| GTTATCAAGTGAGAAATCACCATGAGTGACGACTGAATCCGGTGAGAATGGCA |
| AAAGTTTATGCATTTCTTTCCAGACTTGTTCAACAGGCCAGCCATTACGCTCGT |
| CATCAAAATCACTCGCATCAACCAAACCGTTATTCATTCGTGATTGCGCCTGAG |
| CCAGACGAAATACGCGATCGCTGTTAAAAGGACAATTACAAACAGGAATCGA |
| ATGCAACCGGCGCAGGAACACTGCCAGCGCATCAACAATATTTTCACCTGAAT |
| CAGGATATTCTTCTAATACCTGGAATGCTGTTTTTCCGGGGATCGCAGTGGTGA |
| GTAACCATGCATCATCAGGAGTACGGATAAAATGCTTGATGGTCGGAAGAGGC |
| ATAAATTCCGTCAGCCAGTTTAGTCTGACCATCTCATCTGTAACATCATTGGCA |
| ACGCTACCTTTGCCATGTTTCAGAAACAACTCTGGCGCATCGGGCTTCCCATAC |
| AAGCGATAGATTGTCGCACCTGATTGCCCGACATTATCGCGAGCCCATTTATAC |
| CCATATAAATCAGCATCCATGTTGGAATTTAATCGCGGCCTCGACGTTTCCCGT |
| TGAATATGGCTCATAACACCCCTTGTATTACTGTTTATGTAAGCAGACAGTTTT |
| ATTGTTCATGATGATATATTTTTATCTTGTGCAATGTAACATCAGAGATTTTGA |
| GACAC |
| pUCu Backbone only (SEQ ID NO: 16) |
| GCTAGCCGCGTTGCTGGCGTTTTTCCATAGGCTCCGCCCCCCTGACGAGCATCA |
| CAAAAATCGACGCTCAAGTCAGAGGTGGCGAAACCCGACAGGACTATAAAGA |
| TACCAGGCGTTTCCCCCTGGAAGCTCCCTCGTGCGCTCTCCTGTTCCGACCCTG |
| CCGCTTACCGGATACCTGTCCGCCTTTCTCCCTTCGGGAAGCGTGGCGCTTTCT |
| CATAGCTCACGCTGTAGGTATCTCAGTTCGGTGTAGGTCGTTCGCTCCAAGCTG |
| GGCTGTGTGCACGAACCCCCCGTTCAGCCCGACCGCTGCGCCTTATCCGGTAAC |
| TATCGTCTTGAGTCCAACCCGGTAAGACACGACTTATCGCCACTGGCAGCAGC |
| CACTGGTAACAGGATTAGCAGAGCGAGGTATGTAGGCGGTGCTACAGAGTTCT |
| TGAAGTGGTGGCCTAACTACGGCTACACTAGAAGAACAGTATTTGGTATCTGC |
| GCTCTGCTGAAGCCAGTTACCTTCGGAAAAAGAGTTGGTAGCTCTTGATCCGG |
| CAAACAAACCACCGCTGGTAGCGGTGGTTTTTTTGTTTGCAAGCAGCAGATTAC |
| GCGCAGAAAAAAAGGATCTCAAGAAGATCCTTTGATCTTTAGAAAAACTCATC |
| GAGCATCAAATGAAACTGCAATTTATTCATATCAGGATTATCAATACCATATTT |
| TTGAAAAAGCCGTTTCTGTAATGAAGGAGAAAACTCACCGAGGCAGTTCCATA |
| GGATGGCAAGATCCTGGTATCGGTCTGCGATTCCGACTCGTCCAACATCAATA |
| CAACCTATTAATTTCCCCTCGTCAAAAATAAGGTTATCAAGTGAGAAATCACC |
| ATGAGTGACGACTGAATCCGGTGAGAATGGCAAAAGTTTATGCATTTCTTTCCA |
| GACTTGTTCAACAGGCCAGCCATTACGCTCGTCATCAAAATCACTCGCATCAAC |

TABLE 4-continued

Homologous Repair Template Sequences

CAAACCGTTATTCATTCGTGATTGCGCCTGAGCCAGACGAAATACGCGATCGC

TGTTAAAAGGACAATTACAAACAGGAATCGAATGCAACCGGCGCAGGAACAC

TGCCAGCGCATCAACAATATTTTCACCTGAATCAGGATATTCTTCTAATACCTG

GAATGCTGTTTTTCCGGGGATCGCAGTGGTGAGTAACCATGCATCATCAGGAG

TACGGATAAAATGCTTGATGGTCGGAAGAGGCATAAATTCCGTCAGCCAGTTT

AGTCTGACCATCTCATCTGTAACATCATTGGCAACGCTACCTTTGCCATGTTTC

AGAAACAACTCTGGCGCATCGGGCTTCCCATACAAGCGATAGATTGTCGCACC

TGATTGCCCGACATTATCGCGAGCCCATTTATACCCATATAAATCAGCATCCAT

GTTGGAATTTAATCGCGGCCTCGACGTTTCCCGTTGAATATGGCTCATAACACC

CCTTGTATTACTGTTTATGTAAGCAGACAGTTTTATTGTTCATGATGATATATTT

TTATCTTGTGCAATGTAACATCAGAGATTTTGAGACACGGTACC

TRAC 5' Homology Arm (SEQ ID NO: 17)

ACATTAAAAACACAAAATCCTACGGAAATACTGAAGAATGAGTCTCAGCACTA

AGGAAAAGCCTCCAGCAGCTCCTGCTTTCTGAGGGTGAAGGATAGACGCTGTG

GCTCTGCATGACTCACTAGCACTCTATCACGGCCATATTCTGGCAGGGTCAGTG

GCTCCAACTAACATTTGTTTGGTACTTTACAGTTTATTAAATAGATGTTTATATG

GAGAAGCTCTCATTTCTTTCTCAGAAGAGCCTGGCTAGGAAGGTGGATGAGGC

ACCATATTCATTTTGCAGGTGAAATTCCTGAGATGTAAGGAGCTGCTGTGACTT

GCTCAAGGCCTTATATCGAGTAAACGGTAGTGCTGGGGCTTAGACGCAGGTGT

TCTGATTTATAGTTCAAAACCTCTATCAATGAGAGCAATCTCCTGGTAATGT

GATAGATTTCCCAACTTAATGCCAACATACCATAAACCTCCCATTCTGCTAATG

CCCAGCCTAAGTTGGGGAGACCACTCCAGATTCCAAGATGTACAGTTTGCTTTG

CTGGGCCTTTTTCCCATGCCTGCCTTTACTCTGCCAGAGTTATATTGCTGGGGTT

TTGAAGAAGATCCTATTAAATAAAAGAATAAGCAGTATTATTAAGTAGCCCTG

CATTTCAGGTTTCCTTGAGTGGCAGGCCAGGCCTGGCCGTGAACGTTCACTGAA

ATCATGGCCTCTTGGCCAAGATTGATAGCTTGTGCCTGTCCCTGAGTCCCAGTC

CATCACGAGCAGCTGGTTTCTAAGATGCTATTTCCCGTATAAAGCATGAGACC

GTGACTTGCCAGCCCCACAGAGCCCCGCCCTTGTCCATCACTGGCATCTGGACT

CCAGCCTGGGTTGGGGCAAAGAGGGAAATGAGATCATGTCCTAACCCTGATCC

TCTTGTCCCACAGATATCCAGAACCCTGACCCTGCCGTGTACCAGCTGAGAGA

CTCTAAATCCAGTGACAAGTCTGTCTGCCTATTC

TRAC 3' Homology Arm (SEQ ID NO: 18)

ACCGATTTTGATTCTCAAACAAATGTGTCACAAAGTAAGGATTCTGATGTGTAT

ATCACAGACAAAACTGTGCTAGACATGAGGTCTATGGACTTCAAGAGCAACAG

TGCTGTGGCCTGGAGCAACAAATCTGACTTTGCATGTGCAAACGCCTTCAACA

ACAGCATTATTCCAGAAGACACCTTCTTCCCCAGCCCAGGTAAGGGCAGCTTT

GGTGCCTTCGCAGGCTGTTTCCTTGCTTCAGGAATGGCCAGGTTCTGCCCAGAG

CTCTGGTCAATGATGTCTAAAACTCCTCTGATTGGTGGTCTCGGCCTTATCCATT

GCCACCAAAACCCTCTTTTTACTAAGAAACAGTGAGCCTTGTTCTGGCAGTCCA

TABLE 4-continued

Homologous Repair Template Sequences

GAGAATGACACGGGAAAAAAGCAGATGAAGAGAAGGTGGCAGGAGAGGGCA

CGTGGCCCAGCCTCAGTCTCTCCAACTGAGTTCCTGCCTGCCTGCCTTTGCTCA

GACTGTTTGCCCCTTACTGCTCTTCTAGGCCTCATTCTAAGCCCCTTCTCCAAGT

TGCCTCTCCTTATTTCTCCCTGTCTGCCAAAAAATCTTTCCCAGCTCACTAAGTC

AGTCTCACGCAGTCACTCATTAACCCACCAATCACTGATTGTGCCGGCACATGA

ATGCACCAGGTGTTGAAGTGGAGGAATTAAAAAGTCAGATGAGGGGTGTGCCC

AGAGGAAGCACCATTCTAGTTGGGGGAGCCCATCTGTCAGCTGGGAAAAGTCC

AAATAACTTCAGATTGGAATGTGTTTTAACTCAGGGTTGAGAAAACAGCTACC

TTCAGGACAAAAGTCAGGGAAGGGCTCTCTGAAGAAATGCTACTTGAAGATAC

CAGCCCTACCAAGGGCAGGGAGAGGACCCTATAGAGGCCTGGGACAGGAGCT

CAATGAGAAAGGAGAAGAGCAGCAGGCATGAGTTGAATGAAGGAGGCAGGGC

CGGGTCACAGGGCCTTCTAGGCCATGAGAGGGTAGACAG

Ribonucleoprotein (RNP) Complex

RNP complexes were generated using CRISPR spCas9 as the nuclease (Aldevron, sNLS-SpCas9-sNLS Nuclease). sgRNAs were chemically synthesized (Synthego) and diluted from a stock concentration of 600 µM to a working concentration of 120 µM in electroporation buffer. sgRNAs were complexed with Cas9 protein at a 1:6 Cas9:sgRNA molar ratio and incubated for at least 10 minutes at room temperature and then kept cold (4° C. or on ice) until use.

The sgRNAs were designed by incorporating a gRNA sequence directed to a target site of interest (i.e., a defined nucleotide sequence within the endogenous genomic target) into an sgRNA nucleotide framework containing both a crRNA and tracrRNA sequence on the same nucleotide. sgRNAs used herein are presented below with "(ps)" indicating a phosphorothioate linkage and "m" indicating a 2' 0-Methyl Base.

```
TRAC-1 sgRNA (SEQ ID NO: 19):
[mG](ps)[mA](ps)[mG](ps)AAUCAAAAUCGGUGAAUGUUUUAGAG

CUAGAAAUAGCAAGUUAAAAUAAGGCUAGUCCGUUAUCAACUUGAAAAAG

UGGCACCGAGUCGGUGC[mU](ps)[mU](ps)[mU](ps)U

TRBC-2 sgRNA (SEQ ID NO: 20):
[mG](ps)[mG](ps)[mC](ps)UCUCGGAGAAUGACGAGGUUUUAGAG

CUAGAAAUAGCAAGUUAAAAUAAGGCUAGUCCGUUAUCAACUUGAAAAAG

UGGCACCGAGUCGGUGC[mU](ps)[mU](ps)[mU](ps)U
```

Electroporation/Nucleofection

A general protocol describing the electroporation conditions that were used for gene editing of T cells is outlined below:

Equipment
Cas9 protein
CRISPR sgRNA for electroporation
Homologous Repair Template
Lonza P3 Primary Cell 4D-Nucleofector ® X Kit S (32 RCT) with:

-continued

- P3 Nucleofector Solution
- Supplement (or mixed with P3 solution)
- pmaxGFP control vector
- 16-well Nucleocuvette Strip
Isolated primary human T cells
48-well tissue culture plate
T cell Culture media (3% HS TexMACS with IL-7 and IL-15)
200 µL PCR strip tubes, sterile
Lonza nucleofection system with X unit
Cell counter Note:
100 µL nucleofection cuvettes (Cat# V4XP-3012 or V4XP-3024) may be used instead of the 20 µL cuvettes, in which case the number of cells, amount of transfected reagent, and plating volumes must all be scaled up. An alternative electroporation apparatus may also be used (substitute buffers and volumes accordingly).

Procedure:
1. Prepare a sample plate by adding 1 mL T cell culture media (TexMACS, 3% human serum containing 12.5 ng/mL IL-7 and IL-15 each) to each well of a 48-well plate (enough wells for each sample and controls [e.g. mock and GFP], plus 1 media only, plus ~10% extra). Note: In variations of the protocol, cells were cultured with media containing IL-2 in place of IL-7 and IL-15, as indicated below.
2. Once mixed thoroughly, aliquot 1 mL media into the wells. Place the plate in the 37° C. incubator.
3. Add nucleofector supplement to the nucleofector solution (4.5:1).
4. Assemble the RNP complexes in the 200 µL strip tubes, as described. Include a mock (nucleofection buffer only) and a nucleofection control (e.g. 0.5 µg GFP plasmid).
5. Add the appropriate amount of HR DNA to each tube (typically 0.2-0.4 µg/µL).
6. Remove a small volume of cells (e.g. 20 µL for the cellometer) for counting and transfer the rest to a suitable conical vial to spin down the cells.
7. Pellet cells for 10 minutes at RT at 90×g.
8. Count cells.
9. Remove the supernatant from pelleted cells.
10. Resuspend the cells in enough nucleofector buffer such that each 20 µL nucleocuvette will have between 0.5 and 1 million cells, taking into account the volume of the cell pellet (~15 µL for 10 M cells).
11. Distribute the cells into the 200 µL strip tubes containing the sample. Incubate cells from 0-45 minutes, typically less than 10 minutes.
12. Transfer the nucleofection reaction to the nucleocuvettes.
13. Click the cover into place.
14. Remove the plate containing the pre-warmed media from the incubator.
15. Program the 4D unit to use the EO-115 program and place the vessel into the 4D-X in the proper orientation (A1 top with the larger cutout) and press start.
16. Slowly transfer ~100 µL of warmed cell media from the respective wells of the plate into the wells of the nucleocuvette (500 for the 100 µL cuvette).
17. Transfer all ~120 µL from each nucleocuvette to the respective wells on the plate.
18. Incubate the cells for 5-11 days (i.e., harvest day 7-14) before subsequent analysis, e.g., for transgene expression, genomic targeting, or functional assays (e.g., T cell killing or cytokine production). (note: knockout phenotype typically seen in less than 24 hours, knockout phenotype typically seen in 24-48 hours, with phenotypes stabilizing after 72 hours)

Flow Cytometry Analysis

Cells were assessed for expression of genes of interest by flow cytometry. For ZsGreen constructs, fluorescence of the ZsGreen construct (GFP) was assessed. For TCR expression, cells were stained using TCR specific antibodies (anti-human TCRα/β antibody clone IP26 Brilliant Violet 510, Biolegend). For CD3 expression, cells were stained using CD3 specific antibodies (clone SK7, Biolegend). For NK cell studies, CD5 (clone UCHT2, Biolegend) and CD56 (clone 5.1H11, Biolegend) were used.

Unless otherwise noted, T cells were gated by FSC/SSC, singlets, live cells (near-IR stain), then the specific gating (e.g. CD8, dextramer, etc.).

Where indicated, fluorophore-MHC trimer dextran complexes (also referred to as "dextramers") were used to identify antigen-specific TCR recognition and are described in more detail in Bethune, et al. (BioTechniques 62:123-130 March 2017) and Bethune, et al. (eLife 5: 2016), each herein incorporated by reference for all they teach. Dextramers were prepared by using fluorescently-labeled streptavidin (Life Technologies, Carlsbad, Calif.). Peptides used for antigen-specific TCR recognition were: ELAGIGILTV (Mart-1 F5, SEQ ID NO: 5); YLTHRVDVI (Neo12, SEQ ID NO: 6); SLLMWITQV (NY-ESO 1G4, SEQ ID NO: 7).

Lentiviral Production and Transduction

NY-ESO (1G4) and MART-1 (F5) TCR constructs were subcloned into a pCCLc-MND-based lentiviral vector (Addgene #81071) in the format TCRa-F2A-TCRb-P2A-Myc271. Myc271 is a chimeric transduction marker comprising the transmembrane and truncated extracellular domains of CD271 (LNGFR) fused to an extracellular cMyc epitope tag. Lentiviruses encoding NY-ESO (1G4) and MART-1 were produced in HEK-293T cells by transient transfection of lentiviral based vectors and their packaging vectors (pMD2.G). 48 hours after transfection, the virus was collected, filtered through a 0.45 µm syringe filter, and used for infection.

Human CD3+ T cells were isolated from PBMC of a healthy donor, stimulated for 24 hours and then grown in presence of cytokines, as described above. After 48 hours, cells were seeded at 2×10^6 cells per well in 250 µL of media with polybrene to which 500 µL of media (mock condition) or specific viral supernatant (pCCLc-MND-F5TCR-Myc271 or pCCLc-MND-1G4TCR-Myc271) was added. The CD3+ T cells were centrifuged in the presence of virus at 800 g, 90 min, 30° C., with slow acceleration and no brake. Following centrifugation, 500 µL of media was removed and 500 µL of fresh media or 500 µl of virus was added. After 4 days, human T cells were assayed for TCR surface expression. To test for surface expression, cells were rinsed and stained with fluorescent antibodies and pHLA multimers in FACS buffer, and analyzed by flow cytometry.

Viability Analysis

The cell count and viability were measured using the Nucleocounter NC-200 (Chemometic). This instrument utilizes a cassette, Via-2, with a built-in pipette to aspirate the sample volume, and stain the sample with fluorescent dyes acridine orange (AO) and 4',6-diamidino-2-phenylindole (DAPI) immobilized within the cassette which stain the total and dead cell populations, respectively, as they travel through the fluidic channels, preceding the reading window of the cassette. Once the cassette is loaded into the instrument, a protocol designed for PBMC samples was used and reported the total cell count in cells/mL (derived from a count of the cells which have taken up AO stain) and calculates the live cell population (cells/mL) from the percentage viability which is extrapolated from the fraction of the population that is DAPI marker positive.

In variations of the viability assay protocol, viability was assessed using Acridine Orange/Propidium Iodide (AOPI) and a Cellometer (Nexcelom), as indicated below.

Genomic Targeting Analysis

The in-out PCR technique was used to confirm precise genomic integration of genes of interest into the TCRα locus via two pairs of primers: a primer pair targeting the upstream junction, and a downstream junction primer pair. The detection of two amplified sequences of the correct mass following in-out PCR of engineered T cells confirmed the correct insertion of the integrated neoTCR sequence cassette into the TCRα genomic locus.

Primers used for the in-out PCR technique were

```
                              (SEQ ID NO: 1)
Upstream Forward:    TGCTAATCCTCCGGCAAACC (SEQ ID NO: 2)
Upstream Reverse:    TTCTTCAACATCGCCAGCCT (SEQ ID NO: 3)
Downstream Forward:  CAGCCATCTGTTGTTTGCCC (SEQ ID NO: 4)
Downstream Reverse:  AGCTTTCTGGCGTCCTTAGAAT
```

Genomic DNA was isolated from engineered T cells and standard PCR techniques were used to amplify the genomic regions of interest and analyze PCR products by gel electrophoresis.

T Cell/Target Cell Co-Culturing for Functional Analysis

Engineered T cells (100,000) were co-cultured with target cells (25,000) expressing HLA-A2 (Effector to Target ratio of 4:1) pulsed with different concentrations of the specific peptide (10-fold serial dilutions from 0.01-1000 nM). In variations of the protocol, T cells (50,000) were co-cultured with target cells (25,000) expressing HLA-A2 at an Effector to Target ratio of 2:1, as indicated below. Lyophilized peptides (Bio-Synthesis Inc, GenScript) were reconstituted in DMSO to 10 mM and then further diluted in DMSO to a 1 mM working stock. Next, 10-fold serial dilutions of the peptides were performed using a 1 mM starting solution (1

µL 1 mM working stock in 9 µL DMSO) until 0.01 nM was reached. Target A2-K562 cells (1M total cell per peptide concentration, 1×10⁶ cells/mL) were pulsed with 1 µL of the serial peptide dilutions in a 15 mL conical tube and incubated for 1 hours at 37° C. After incubation, 9 mL of medium was added to each tube and then centrifuged for 5 min at 1000 rpm. The cell pellets were washed once with 10 mL of medium and then resuspended in 4 mL of medium for co-incubation experiments. No peptide was used for "no peptide" or "0 peptide" condition.

Target cells constitutively expressing matched and mismatched peptide-HLA (pHLA) were also used as controls to assess specificity, as indicated. K562 target cells were transduced with lentiviral vectors encoding an HLA peptides molecule containing Neo12, MART1, or NYESO1 peptide with ZsGreen as a transduction marker to K562 cells. Expressed HLA (MHC) peptides molecules are composed of a single polypeptide chain with a linear composition of antigenic peptide, β2-microglobulin, and HLA-A2 domains via flexible GS linkers and a disulfide trap modification, as described in greater detail in Bethune, et al. (*eLife* 5: 2016), herein incorporated by reference for all it teaches.

T cell Cytotoxicity Analysis

Following 48 hours of co-culturing T cells and target cells, cells were stained using the Live/Dead Cell staining kit (Live/Dead Near IR viability stain for flow, cat # NC0584313, ThermoFisher) for 20 minutes at 4 C in the dark. In cells with compromised membranes, the dye reacts with free amines both in the cell interior and on the cell surface, yielding intense fluorescent staining. In viable cells, the dye's reactivity is restricted to the cell-surface amines, resulting in less intense fluorescence. The difference in intensity is typically greater than 50-fold between live and dead cells, allowing for easy discrimination. After incubation cells were washed, fixed with the eBioscience IC Fixation Buffer (ThermoFisher, cat #00-8222-49) and analyzed by flow cytometry.

Proliferation Analysis

Engineered T cells were pre-labelled with Cell Proliferation Dye e450 (ThermoFisher, cat #65-0842-90) prior to co-culture. This fluorescent dye binds to any cellular proteins containing primary amines, and as cells divide, the dye is distributed equally between daughter cells that can be measured as successive halving of the fluorescence intensity of the dye. Co-culture assay was performed as described for the T cell cytotoxicity assay. After 72 hours of co-culturing T cells and target cells, cells were fixed with the eBioscience IC Fixation Buffer (ThermoFisher, cat #00-8222-49) and analyzed by flow cytometry.

Cytokine Production Analysis

Cytokine production was assessed in the supernatant of the co-culture using the cytokine bead assay (CBA, BEAD-BASED IMMUNOASSAY from BD BioSciences). CBA is a flow cytometry multiplexed bead-based immunoassays application that allows quantification of multiple proteins simultaneously by using antibody-coated beads to efficiently capture analytes. After 24 hours of co-culturing T cells and target cells, supernatants were collected and analyzed for IFNγ, IL-2 and TNFα secretion.

Example 2: Reporter Integration in TCRα Locus

Figure 2:
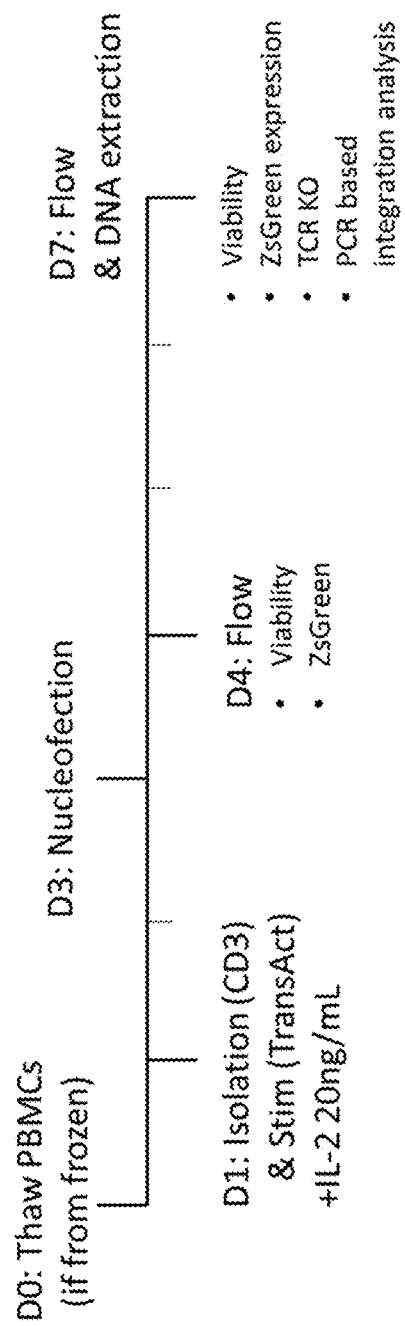
FIG. 2 presents the general editing timeline for ZsGreen integration.

A ZsGreen reporter construct was integrated into the TCRα locus. FIG. 1 presents a schematic representing the general editing strategy used. Briefly, the general TCRα locus targeting strategy used a homologous repair template containing a promoter-less ZsGreen and truncated LNGRF coding sequence flanked by 1 kb left and right homology arms ("HR Arms") and separated by P2A sequences, as well as a 5' P2A sequence separating the ZsGreen and LNGRF cassette from TCRα locus sequences, encoded in a circular Nanoplasmid (see SEQ ID NO: 8). FIG. 2 presents the general editing timeline for ZsGreen integration. Briefly, PBMCs were thawed and primary human T cells were isolated using CD3 negative selection and stimulated with anti-CD3/anti-CD28, as described above. A ribonucleoprotein (RNP) complex using an sgRNA targeting the endogenous TCRα locus (also referred to as the TRAC locus) was formed, as described above. Here, the sgRNA incorporated the TRAC gRNA targeting sequence (SEQ ID NO: 21)
GAGAATCAAAATCGGTGAAT.

The HR template, RNP complex, and T cells were mixed and electroporated, as described above. Following electroporation, cells were cultured with media containing IL-2 (20 ng/mL).

Figure 3:
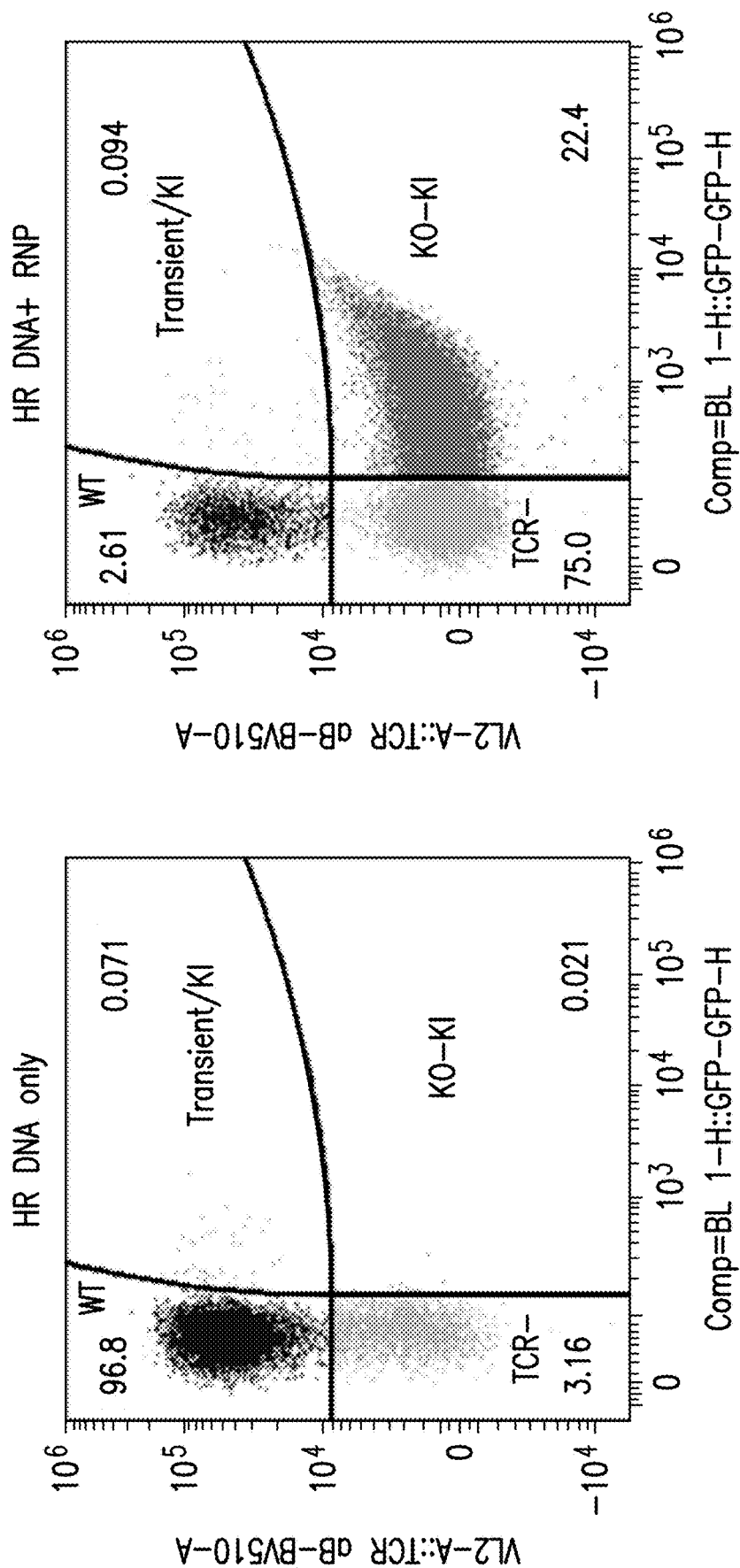
FIG. 3 shows editing efficiencies of T cells using ZsGreen reporter integrated into an TRAC locus.

Since the ZsGreen reporter has no promoter, only a precise in-frame fusion should generate a detectable signal. In addition, proper targeting of the TCRα locus should result in a concomitant knockout of TCRα and loss of surface expressed TCR complex. Indeed, as shown in FIG. 3, a high percentage (greater than 22%) of ZsGreen—positive/TCR-negative cells was detected in when both HR template and RNP was included (FIG. 3 right panel "KO-KI"). Notably, all ZsGreen-positive were also TCR-negative suggesting the ZsGreen reporter was properly integrating into the TCRα locus. As a control, absence of RNP did not result in ZsGreen-positive cells or TCR-negative cells above levels considered background (FIG. 3 left panel). Editing efficiency under the various conditions tested is quantified in Table 5.

TABLE 5

Editing Efficiency of T Cells Using ZsGreen Reporter

| | TCR+ GFP− | TCR+ GFP+ | TCR− GFP− | TCR− GFP+ |
|---|---|---|---|---|
| HR DNA + RNP | 2.61 | 0.094 | 75 | 22.4 |
| HR DNA only | 96.8 | 0.071 | 3.16 | 0.021 |
| Mock | 98.4 | 0.00948 | 1.6 | 0.00118 |
| RNP only | 18.4 | 0.023 | 81.6 | 0.065 |
| 1 µg DNA template ZsGreen | 73 | 25.6 | 1.8 | 0.36 |

Example 3: Neoantigen-Specific TCR Integration in TCRα Locus Strategy

Figure 4:
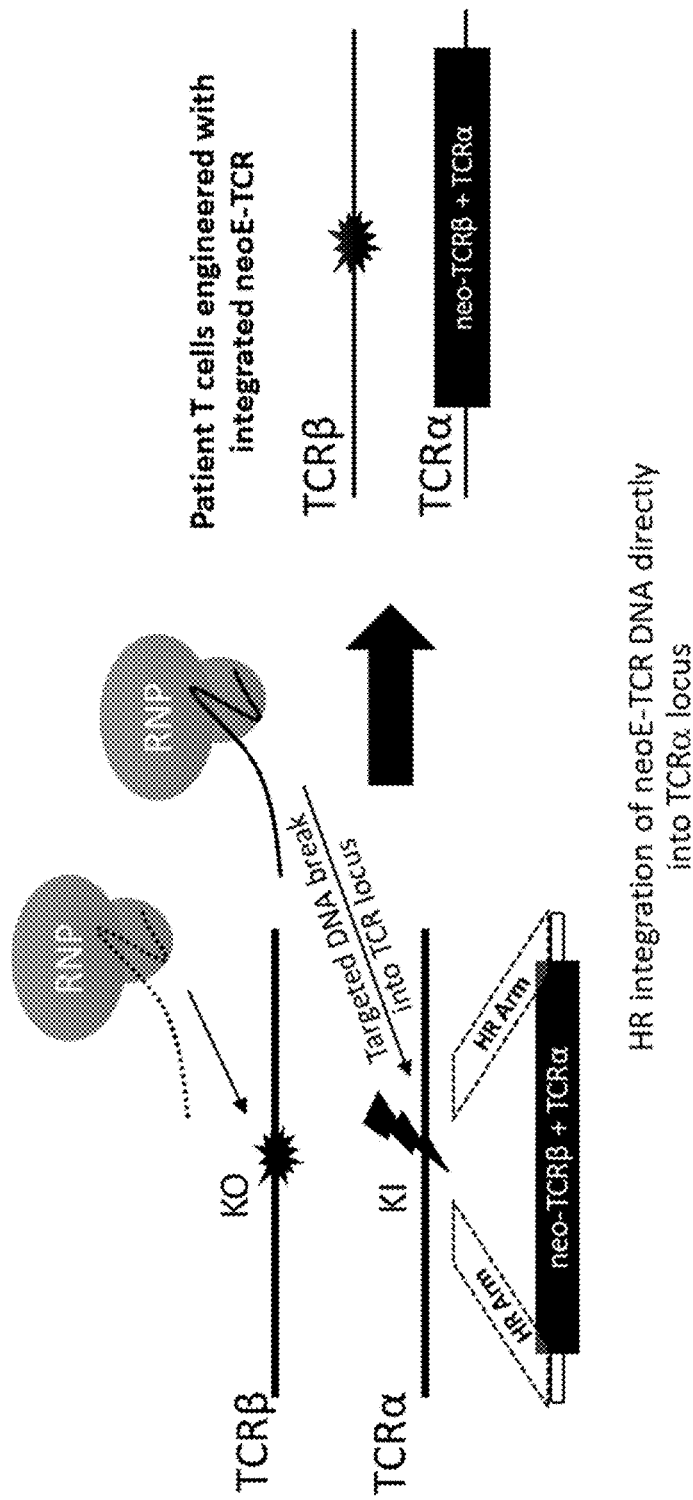
FIG. 4 presents a schematic representing the general targeting strategy used for integrating neoantigen-specific TCR constructs (neoTCRs) into the TCRα locus.

Neoantigen-specific TCR constructs (neoTCRs) were integrated into the TCRα locus. FIG. 4 presents a schematic representing the general targeting strategy used. Briefly, the general TCRα locus targeting strategy used a homologous repair template containing a neoTCR coding sequence flanked by 1 kb left and right HR Arms. In addition, the endogenous TCRβ locus is disrupted leading to expression of only TCR sequences encoded by the neoTCR construct. The general strategy was applied using circular HR templates that were Nanoplasmids or pUCu plasmids.

Figure 5A:
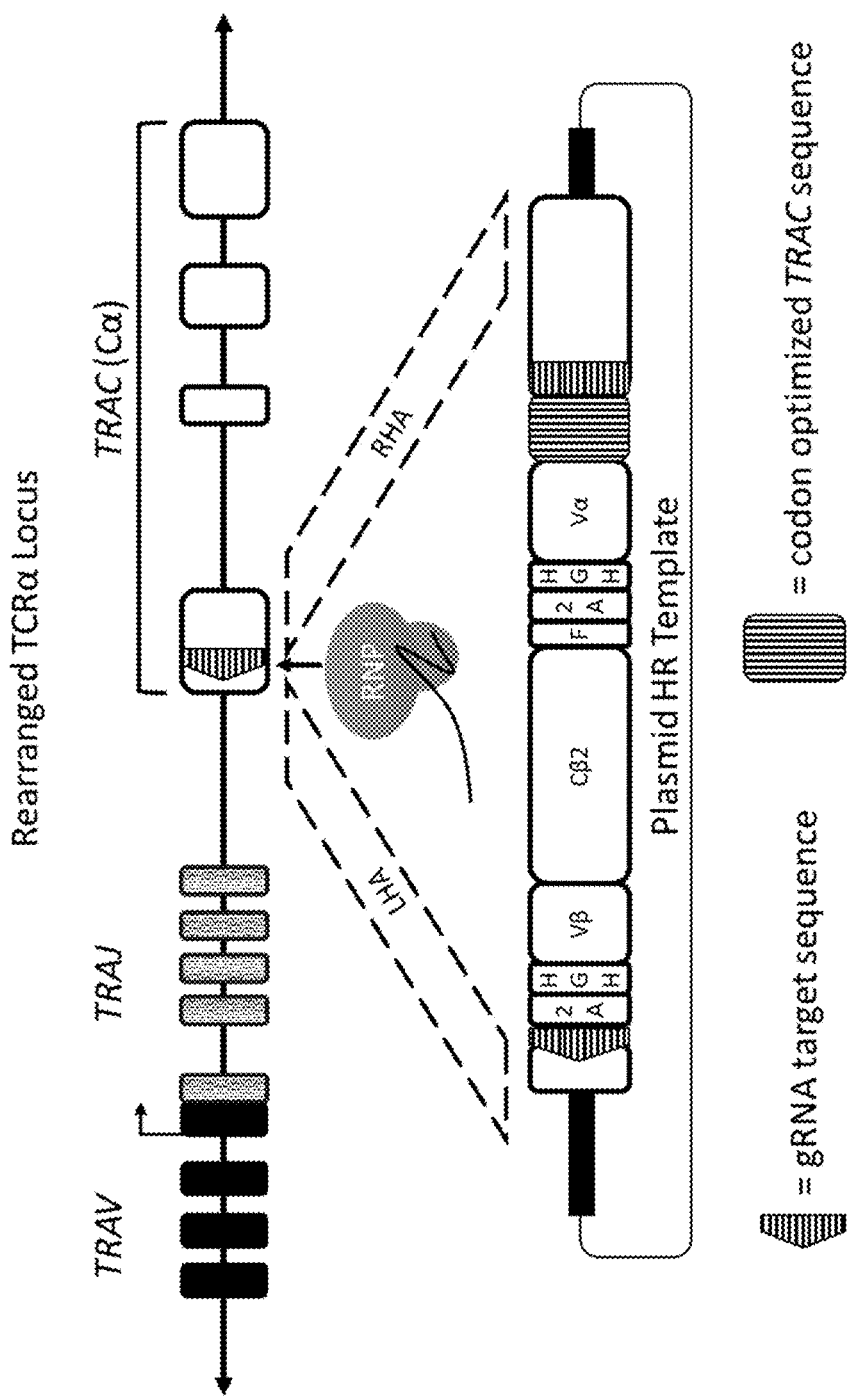
FIGS. 5A-5B illustrate the neoantigen-specific TCR construct design used for integrating neoantigen-specific TCR constructs (neoTCRs) into the TCRα locus.

The neoantigen-specific TCR construct design is diagrammed in FIGS. 5A and B. The target TCRα locus ("TRAC (Cα)") is shown along with the plasmid HR template, and the resulting edited sequence and downstream mRNA/protein products are shown. The target TCRα locus (endogenous TRAC) and its CRISPR Cas9 target site (horizontal stripe, cleavage site designated by arrow) are shown (FIG. 5A, top panel). The circular plasmid HR template with the polynucleotide encoding the neoTCR, which is located between left and right homology arms ("LHA" and "RHA" respectively), is shown (FIG. 5A, bottom panel). The region of the TRAC introduced by the HR template that was codon optimized is shown (vertical stripe). The TCRβ constant domain was derived from TRBC2, which is indicated as being functionally equivalent to TRBC1. Other elements in the neoTCR cassette include: 2A=P2A ribosome skipping element; F=furin cleavage site upstream of 2A that removes the 2A tag from the upstream TCRβ protein; HGH=human growth hormone signal sequence. The HR template of the neoTCR expression gene cassette includes two flanking homology arms to direct insertion into the TCRα genomic locus targeted by the CRISPR Cas9 nuclease RNP with the TCRα guide RNA. These homology arms (LHA and RHA) flank the neoE-specific TCR sequences of the neoTCR expression gene cassette.

Figure 5B:
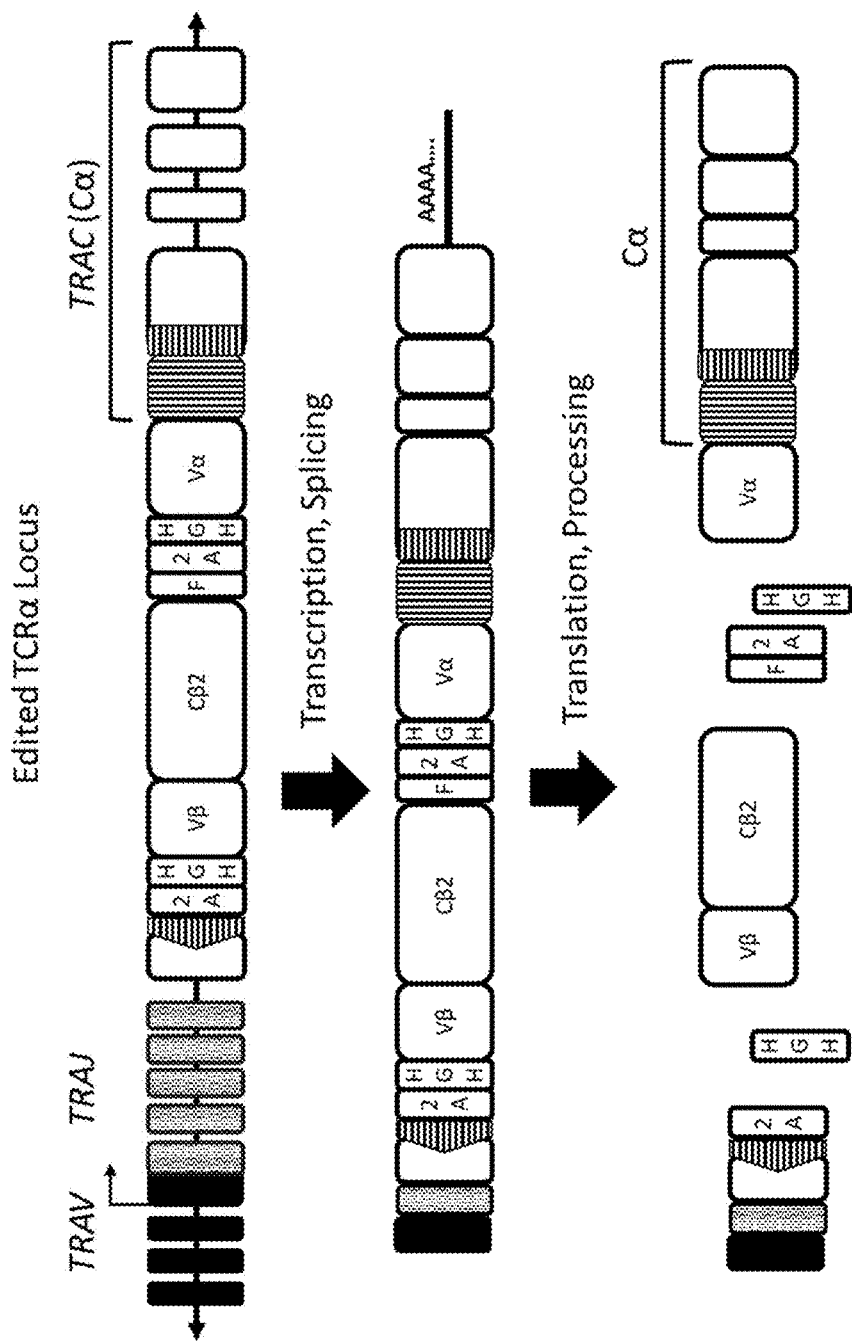

Once integrated into the genome (FIG. 5B, top panel), the neoTCR expression gene cassette is transcribed as a single messenger RNA from the endogenous TCRα promoter, which still includes a portion of the endogenous TCRα polypeptide from that individual T cell (FIG. 5B, middle panel). During ribosomal polypeptide translation of this single neoTCR messenger RNA, the PACT neoTCR sequences are unlinked from the endogenous, CRISPR-disrupted TCRα polypeptide by self-cleavage at a P2A ribosomal skip sequence derived from porcine teschovirus-1 (FIG. 5B, lower panel). The encoded neoTCRα and neoTCRβ polypeptides are also unlinked from each other through cleavage by the endogenous cellular human furin protease and a second self-cleaving P2A sequence motifs included in the neoTCR expression gene cassette (FIG. 5B, lower panel). The neoTCRα and neoTCRβ polypeptides are separately targeted by signal leader sequences (derived from the human growth hormone, HGH) to the endoplasmic reticulum for multimer assembly and trafficking of the neoTCR protein complexes to the T cell surface. The inclusion of the furin protease cleavage site facilitates removal of the 2A sequence from the upstream TCRβ chain to reduce potential interference with TCRβ function. Inclusion of a gly-ser-gly linker before each 2A (not shown) further enhances the separation of the three polypeptides.

Additionally, three repeated protein sequences are codon diverged within the HR template to promote genomic stability. The two P2A are codon diverged relative to each other, as well as the two HGH signal sequences relative to each other, within the TCR gene cassette to promote stability of the introduced neoTCR cassette sequences within the genome of the ex vivo engineered T cells. Similarly, the re-introduced 5' end of TRAC exon 1 (vertical stripe) reduces the likelihood of the entire cassette being lost over time through removal of intervening sequence of two direct repeats.

Figure 6:
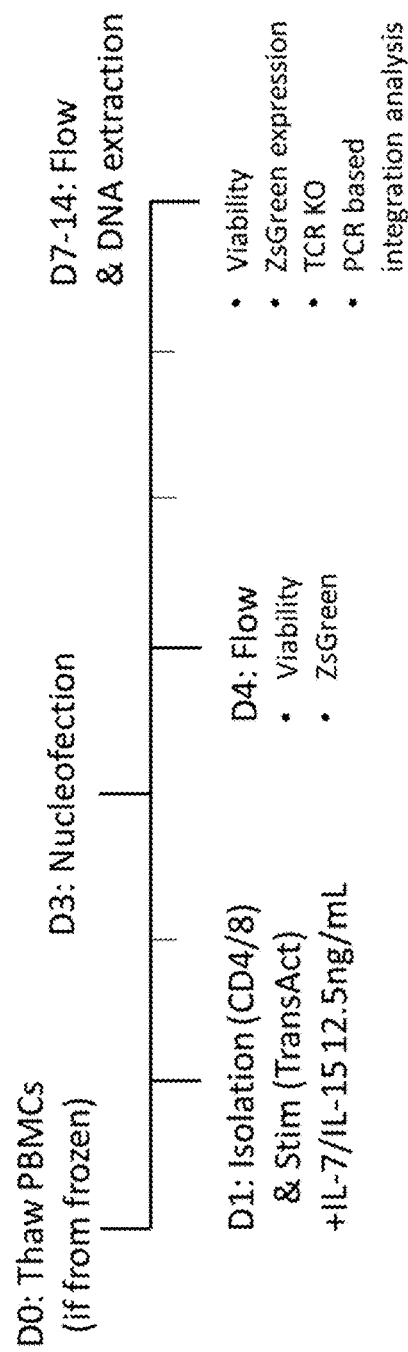
FIG. 6 presents the general editing timeline for editing T cells inserting a neoTCR construct.

FIG. 6 presents the general editing timeline for editing T cells inserting a neoTCR construct. Briefly, the primary human T cells (either fresh or frozen) were cultured following the standard editing procedure, as described above. A ribonucleoprotein (RNP) complex using a sgRNA targeting the endogenous TCRα locus (also referred to as the TRAC locus) with the TRAC gRNA targeting sequence

GAGAATCAAAATCGGTGAAT (SEQ ID NO: 21)

was formed, as described above. In addition, a RNP complex using a sgRNA targeting the endogenous TCRβ locus (also referred to as the TRBC locus) with the TRBC gRNA targeting sequence

GGCTCTCGGAGAATGACGAG (SEQ ID NO: 22)

was formed, as described above. The HR template, RNP complexes, and T cells were mixed and electroporated, as described above. The electroporated T cells (i.e., the modified cells), were then cultured in the presence of cytokines, as described above.

Example 4: NeoTCR Integration (MART-1)

A MART-1 neoTCR was integrated into the TCRα locus. T cells were edited following the standard electroporation-mediated editing procedure and inserting a MART-1 neoTCR construct encoded by the circular HR template NTC9385R-TRAC(1k)DTS_P2A.F5.TRBopt.f-P2A.TRAopt.BGHpA (SEQ ID NO: 9).

Figure 7:
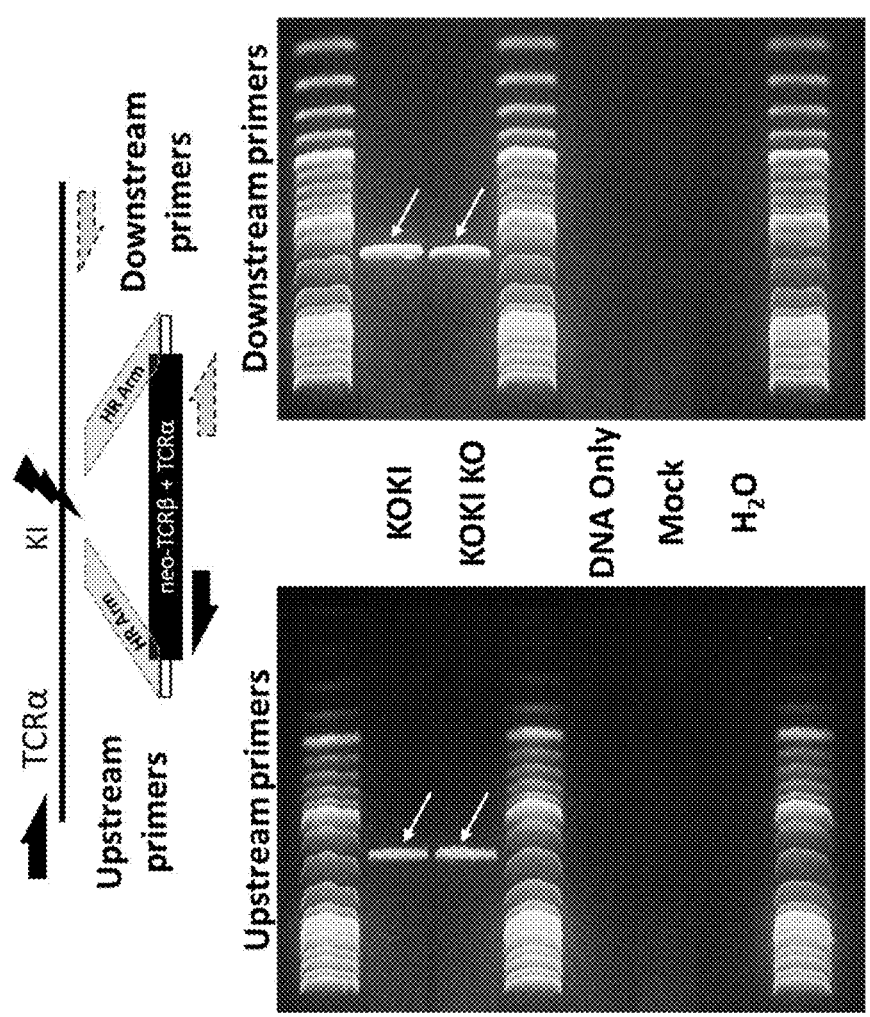
FIG. 7 shows the in-out PCR technique (general strategy, top panel) and the PCR amplification products visualized on an agarose gel (bottom panels) used to confirm precise genomic integration of a neoTCR construct into the TCRα locus.

The in-out PCR technique was used to confirm precise genomic integration of the neoTCR construct into the TCRα locus via two pairs of primers: a primer pair targeting the upstream junction, and a downstream junction primer pair (schematic presented in FIG. 7 top panel). Detection of two PCR amplified sequences of the correct mass following in-out PCR of engineered T cells was used to confirm the correct insertion of the integrated neoTCR sequence cassette into the TCRα genomic locus. As shown in FIG. 7, no integration was observed for cells treated with plasmid DNA HR template alone and no nuclease ("DNA only"). Amplified products for both upstream (FIG. 7 left panel) and downstream (FIG. 7 right panel) junctions were observed for cells engineered together with TCRα nuclease alone ("KOKI") or TCRα plus TCRβ nucleases together ("KOKI KO"). Thus, the results demonstrate the neoTCR construct was properly integrated and the endogenous TCRβ was disrupted, where appropriate.

Figure 8A:
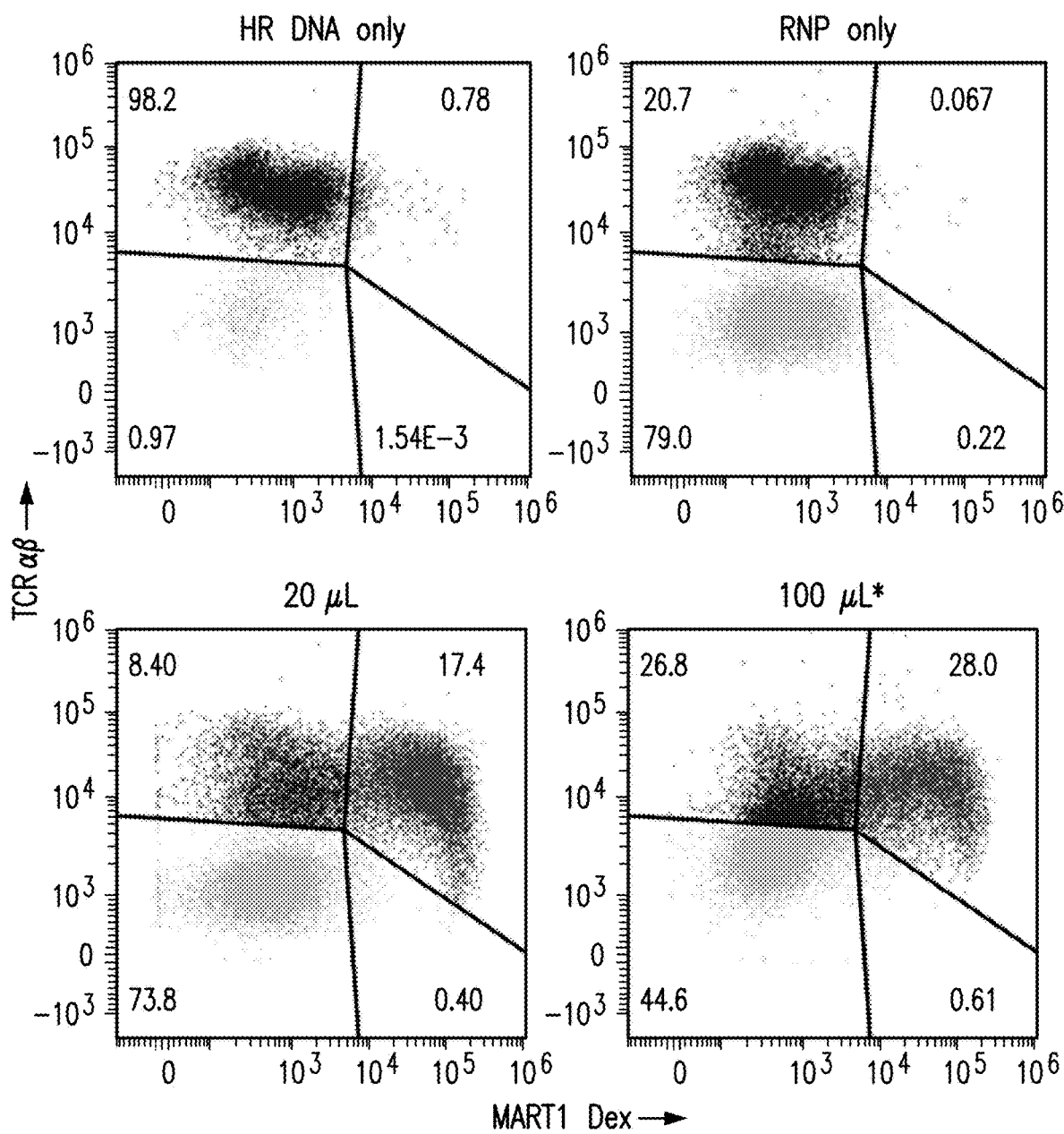
FIGS. 8A-8B show expression of the MART-1 neoTCR by flow cytometry.
Figure 8B:
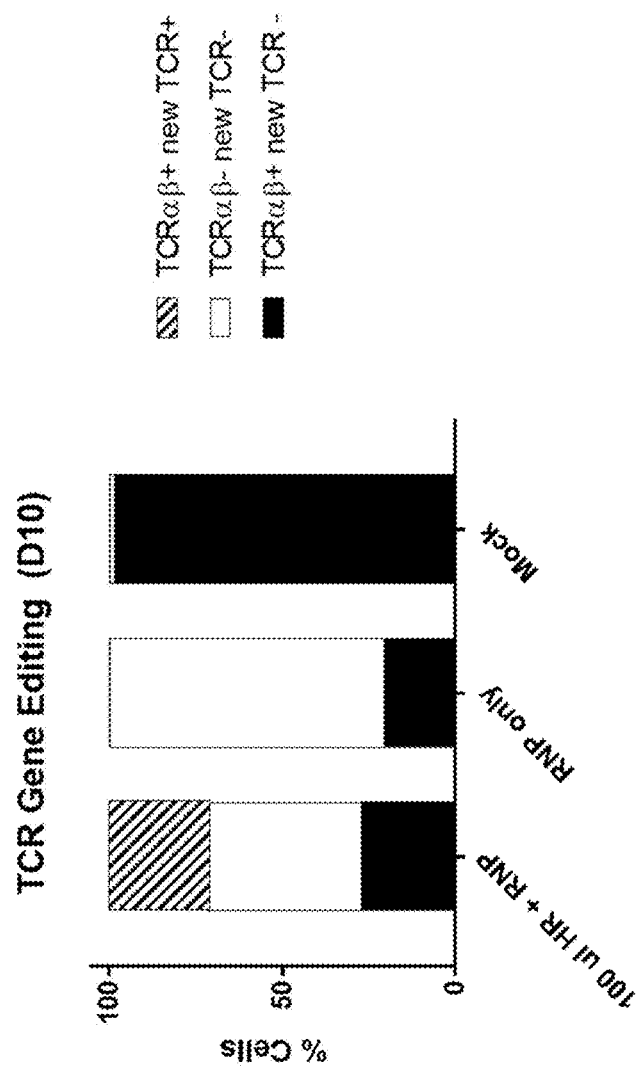

Engineered T cells were assessed for expression of the MART-1 neoTCR by flow cytometry. As shown in FIG. 8A, expression of the MART-1 neoTCR was detected by MART-1 specific dextramer staining in both small (20 μL, FIG. 8A bottom left panel) and large (100 μL, FIG. 8A bottom right panel) editing formats. Only background levels of signal was detected when only the HR template without the RNP (FIG. 8A top left panel) or when only RNP without the HR template (FIG. 8A top right panel) was used. Similar results were seen at various times point following the editing procedure. Results of gene editing at Day 4 following the editing procedure is quantitated in Table 6 below. Results of gene editing at Day 7 following the editing procedure is quantitated in Table 7 below. Results of gene editing at Day 10 following the editing procedure are shown in FIG. 8B, with integrated neoTCRs (striped) when both an HR template and RNP complex were provided. Thus, the results demonstrate the neoTCR construct was properly expressed following integration into the TCRα locus when both an HR template and RNP complex were provided.

TABLE 6

TCR Editing Day 4

| | TCR+ Dex− | TCR+ Dex+ | TCR− Dex+ | TCR− Dex− |
|---|---|---|---|---|
| 20 ul HR + RNP | 10.3 | 8.5 | 0.14 | 81.2 |
| 100 ul HR + RNP | 12.1 | 11.6 | 0.45 | 76.1 |
| RNP only* | | | | |
| 20 ul HR | 99 | 0.23 | 0 | 0.77 |
| Mock | 98.7 | 0.29 | 0 | 1.06 |

*Omitted from analysis

TABLE 7

TCR Editing Day 7

| | TCR+ Dex− | TCR+ Dex+ | TCR− Dex+ | TCR− Dex− |
|---|---|---|---|---|
| 20 ul HR + RNP | 8.4 | 17.4 | 0.4 | 73.8 |
| 100 ul HR + RNP | 26.8 | 28 | 0.61 | 44.6 |
| RNP only | 20.7 | 0.067 | 0.22 | 79 |
| 20 ul HR | 98.2 | 0.78 | 0.00154 | 0.97 |
| Mock | 98.6 | 0.37 | 0.00297 | 1.07 |

Figure 9:
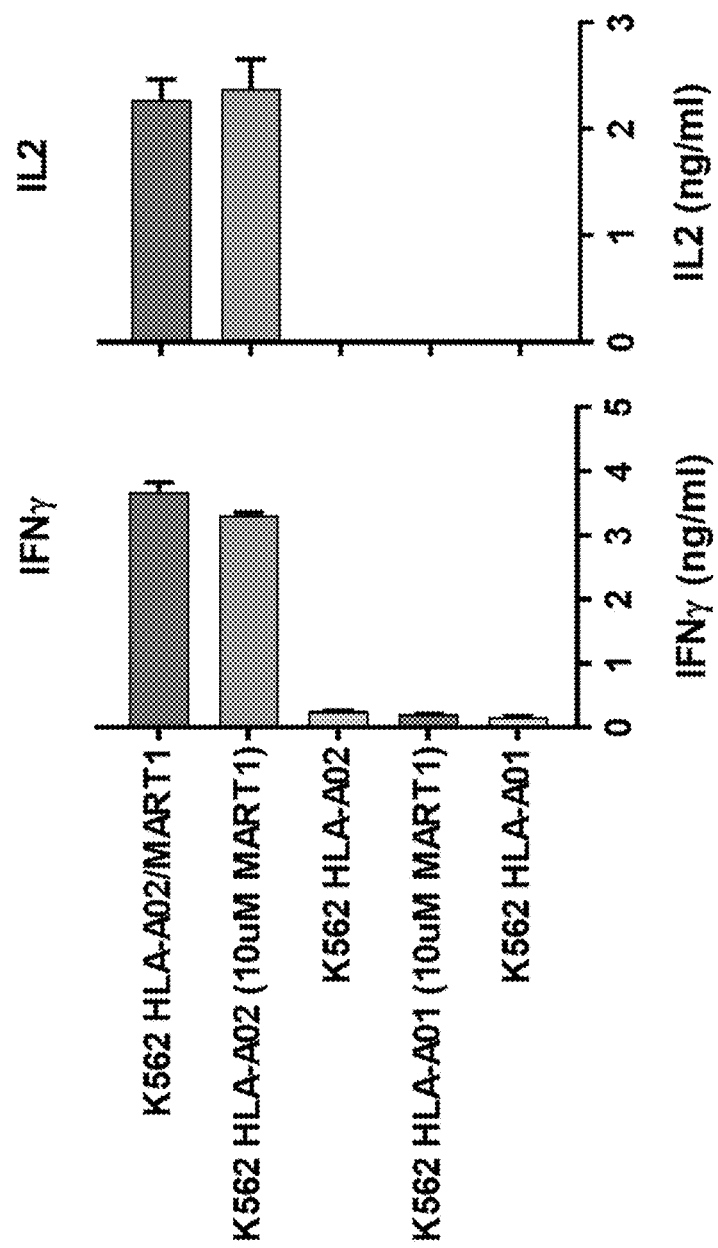
FIG. 9 shows assessment of engineered T cells in an antigen-specific cytokine production assay for IFNγ (left panel) and IL-2 (right panel).

Engineered T cells were assessed for antigen-specific cytokine production. As shown in FIG. 9, engineered T cells expressing the MART-1 neoTCR produced both IFNγ and IL-2 when co-incubated with HLA-A02 target cells (K562) either constitutively expressing (FIG. 9, "K562 HLA-A02/ MART1") or pulsed with (FIG. 9, "K562 HLA-A02 (10 μM MART1)") a MART-1 cognate antigenic peptide (E:T Ratio 2:1). Cytokine production was not observed at a meaningful level when co-incubated with HLA-A02 target cells not pulsed with a cognate peptide (FIG. 9, "K562 HLA-A02"), or when co-incubated with target cells expressing the non-cognate MHC HLA-A01 (FIG. 9, "K562 HLA-A01 (10 μM MART1)" and "K562 HLA-A01" respectively). Thus, engineered T cells expressing the MART-1 neoTCR demonstrated antigen-specific cytokine production.

Figure 10A:
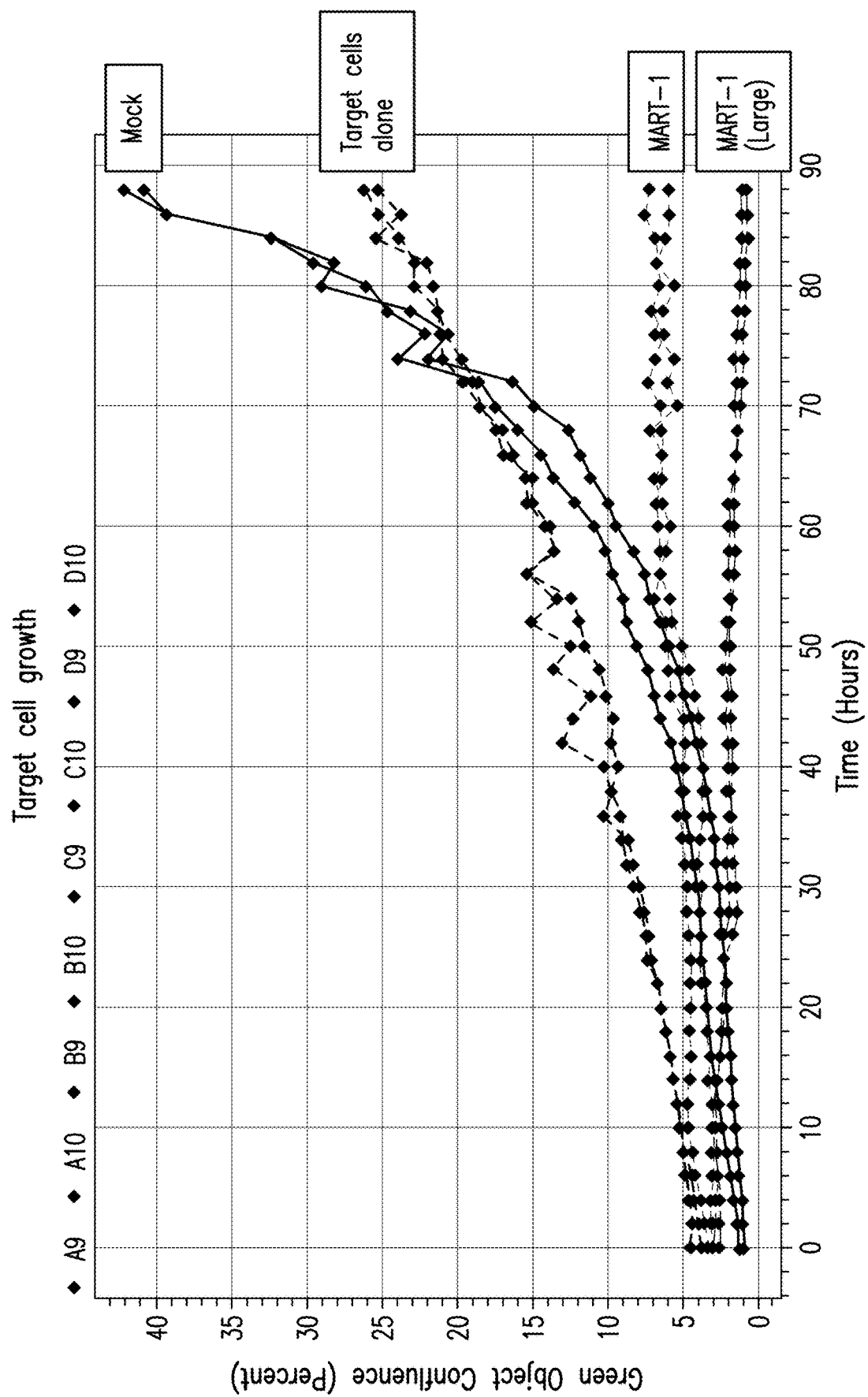
FIGS. 10A-10B show assessment of engineered T cells in an antigen-specific proliferation assay (FIG. 10A) and antigen-specific T cell-mediated killing assay (FIG. 10B).
Figure 10B:
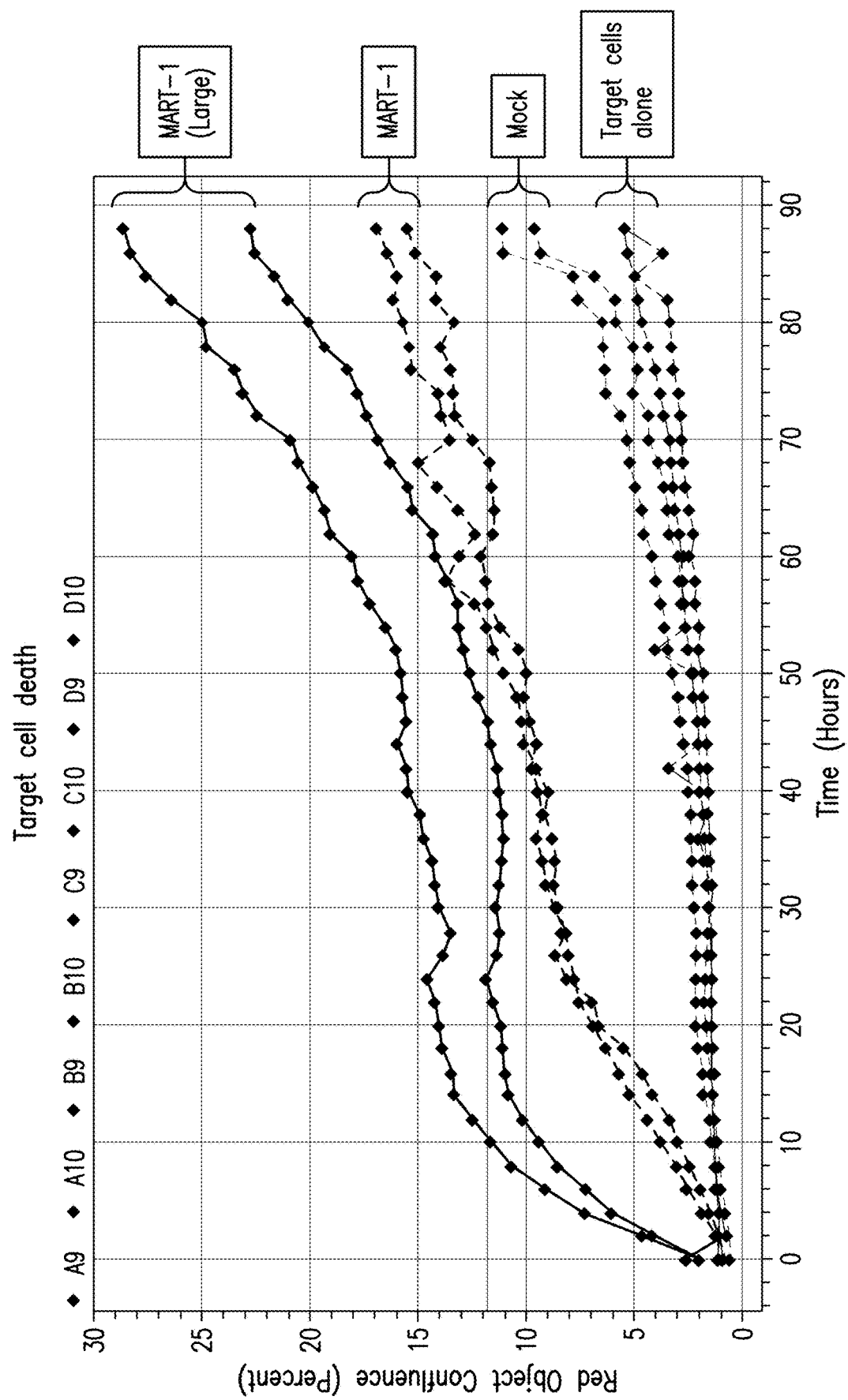

Engineered T cells were assessed for antigen-specific proliferation and antigen-specific T cell-mediated killing. As shown in FIG. 10A, transduced K562 target cells expressing peptide specific pHLAs demonstrated little or no proliferation when co-incubated with T cells expressing the MART-1 neoTCR engineered using either the small (FIG. 10A, "MART-1") or large (FIG. 10A, "MART-1 (Large)") editing formats (E:T Ratio 2:1). In contrast, target cells grew when incubated alone (FIG. 10A, "Target cells alone") or co-incubated with T cells that underwent a mock editing procedure but were not engineered to express a neoTCR (i.e., electroporated without an HR template or RNP) (FIG. 10A, "Mock"). As shown in FIG. 10B, target cells were killed when co-incubated with T cells expressing the MART-1 neoTCR engineered using either the small (FIG. 10B, "MART-1") or large (FIG. 10B, "MART-1 (Large)") editing formats (E:T Ratio 2:1). In contrast, minimal death of target cells was observed when incubated alone (FIG. 10B, "Target cells alone") or co-incubated with T cells that underwent a mock editing procedure but were not engineered to express a neoTCR (FIG. 10B, "Mock"). Thus, engineered T cells expressing the MART-1 neoTCR demonstrated antigen-specific killing of target cells.

Figure 11:
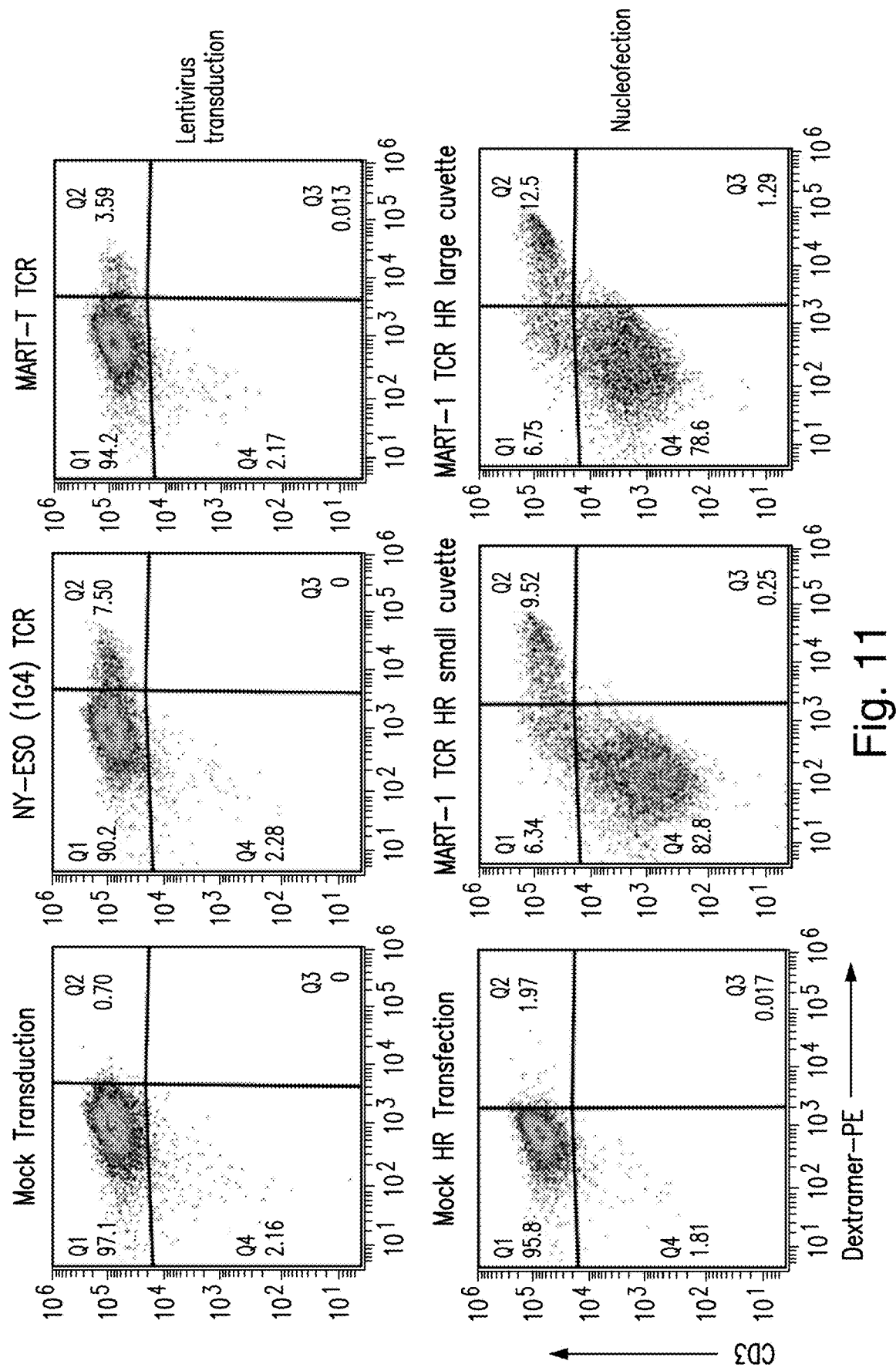
FIG. 11 shows engineered T cells expressing either the MART-1 or NY-ESO neoTCR were generated using a lentiviral transduction procedure (FIG. 11, top panels) or engineered T cells expressing the MART-1 neoTCR generated using electroporation-mediated HR editing using small or large formats (FIG. 11, bottom panels).

Example 5: Comparison of Editing Efficiency Via Electroporation and Transduction T cells were engineered to express a neoTCR at the TCRα locus following either the standard electroporation-mediated HR editing procedure or the lentiviral transduction procedure. A MART-1 neoTCR construct encoded by the circular HR template NTC9385R-TRAC(1k)DTS_P2A.F5. TR Bopt.f-P2A.TRAopt.BGHpA (SEQ ID NO: 9) was used for electroporation-mediated editing. As shown in FIG. 11, engineered T cells expressing either the MART-1 or NY-ESO neoTCR were generated using the lentiviral transduction procedure (FIG. 11, top panels) and engineered T cells expressing the MART-1 neoTCR were generated using electroporation-mediated HR editing using small or large formats (FIG. 11, bottom panels). Thus, electroporation-mediated HR editing generated a percentage of engineered T cells comparable to or greater than lentiviral transduction.

Figure 12:
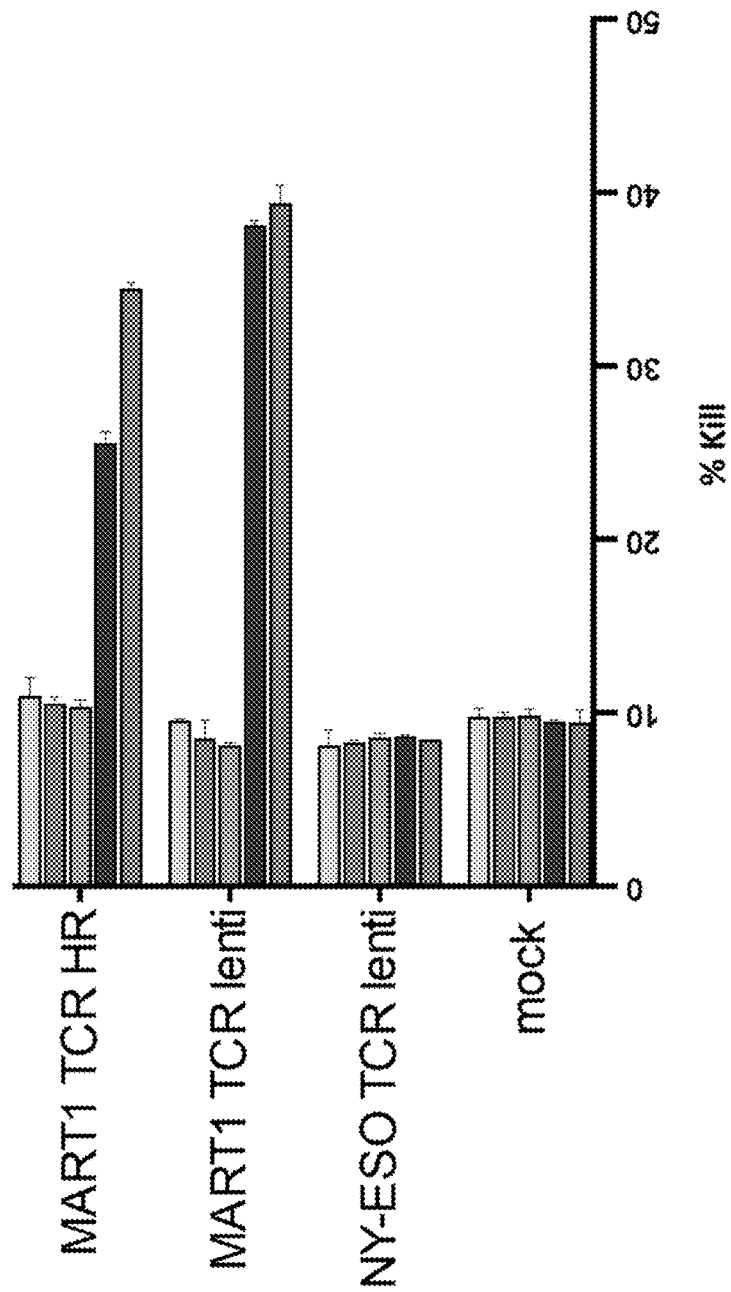
FIG. 12 shows assessment of engineered T cells in an antigen-specific T cell-mediated killing assay. Columns from top to bottom in each group: non-cognate MHC HLA-A01 not pulsed with cognate peptide; non-cognate MHC HLA-A01 pulsed with 10 μM MART1; cognate MHC HLA-A02 not pulsed with cognate peptide; cognate MHC HLA-A01 pulsed with 10 μM MART1; HLA-A02 target cells constitutively expressing a MART-1 cognate antigenic peptide.

Engineered T cells were assessed for antigen-specific T cell-mediated killing. As shown in FIG. 12, HLA-A02 target cells either constitutively expressing (FIG. 12, bottom column in each group) or pulsed with (FIG. 12, second column from bottom in each group) a the MART-1 TCR (F5), cognate antigenic MART-1 peptide, were comparably killed when co-incubated with T cells expressing the MART-1 neoTCR (F5) engineered using either HR-mediated editing (FIG. 12, "MART1 TCR HR") or lentiviral transduction (FIG. 12, "MART1 TCR lenti") (E:T Ratio 2:1). In contrast, minimal death of target cells was observed when co-incubated with T cells expressing a non-cognate NY-ESO TCR (FIG. 12, "NY-ESO TCR lenti") or co-incubated with T cells that underwent a mock editing procedure but were not engineered to express a neoTCR (FIG. 12, "Mock"). Additionally, killing was not observed above background levels when co-incubated with HLA-A02 target cells not pulsed with a cognate peptide (FIG. 12, middle column in each group), or when co-incubated with target cells expressing the non-cognate MHC HLA-A01 (FIG. 12, top two columns in each group, second from top pulsed with 10 μM MART1). Quantification of the data is presented in Table 8 below. Thus, T cells engineered to express a neoTCR following either the standard electroporation-mediated HR editing procedure, or the lentiviral transduction procedure, demonstrated comparable killing.

TABLE 8

Cytotoxic Killing Following Editing by Electroporation or Transduction

| | K562 HLA-A01 no peptide | K562 HLA-A01 10 uM MART1 | K562 HLA-A02 no peptide | K562 HLA-A02 10 uM MART1 | K562 HLA-A02/ MART1 |
|---|---|---|---|---|---|
| Mock | 9.8 | 9.8 | 9.8 | 9.5 | 9.4 |
| NY-ESO TCR lenti | 8.1 | 8.3 | 8.6 | 8.7 | 8.4 |
| MART1 TCR lenti | 9.5 | 8.5 | 8.1 | 38.1 | 39.4 |
| MART1 TCR HR | 11.0 | 10.6 | 10.4 | 25.6 | 34.5 |

Figure 13B:
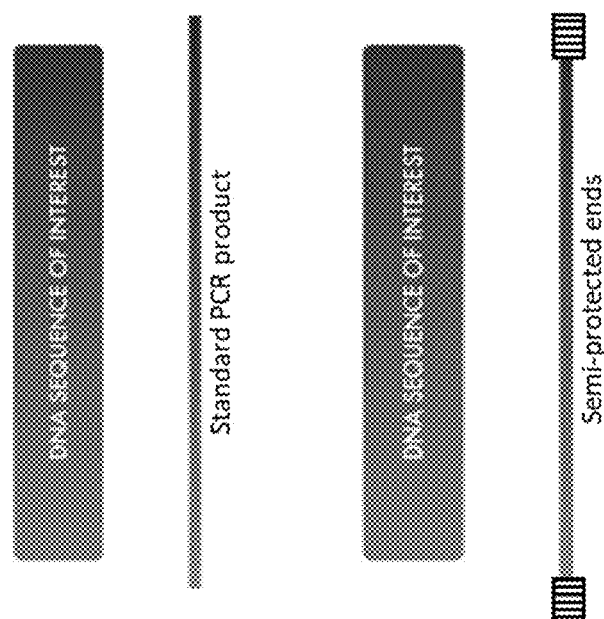
FIGS. 13A-13B show relative HR-mediated editing efficiency of using purified circular plasmid DNA and linear dsDNA generated by PCR as HR templates.
Figure 13A:
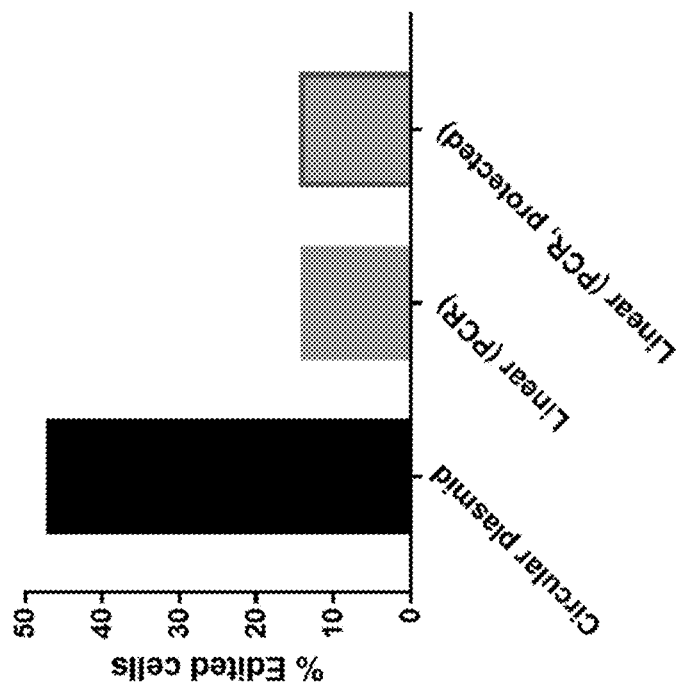

Example 6: Comparison of Editing Efficiency Using Circular or Linear HR Templates The relative HR-mediated editing efficiency of using purified circular plasmid DNA and linear dsDNA generated by PCR as HR templates was tested. A standard PCR product (FIG. 13A top) as well as PCR product generated using primers with nuclease-protected 5' ends (5' terminal phosphorothioate backbone linkages) was used to generate standard linear dsDNA and "semi-protected" linear dsDNA (FIG. 13A bottom). Neo12 neoTCRs were integrated into the TCRα locus. T cells were edited following the standard electroporation-mediated editing procedure and inserting a Neo12 neoTCR construct encoded by either the circular HR template NTC9385R-TRAC(1k)DTS_P2A.neo12.TRBopt.f-P2A.TRA(Va)opt (SEQ ID NO: 13) or the liner HR template Linear TRAC(1k)P2A.neo12.TRBopt.f-P2A.TRA(Va)opt (SEQ ID NO: 12). Editing efficiency was assessed by the percentage of T cells expressing the neoTCR (Neo12) as determined by Neo12 specific dextramer staining. Use of plasmid DNA generated a significantly higher level of editing (47.3%, FIG. 13B left column) as compared to liner HR templates (14.3% and 14.4%, FIG. 13B middle and right columns, respectively), even when tested across a range of concentrations (equal mass shown here). In a separate test, linear covalently closed DNA (dbDNA, Touchlight) was tested and demonstrated a similar profile to the linear open-ended PCR product (data not shown). Thus, the results support the conclusion that circular plasmid DNA HR templates bearing the same HR targeting sequences as linear HR templates supports ~3-fold higher editing efficiency relative to linear PCR-generated DNA.

Figure 14:
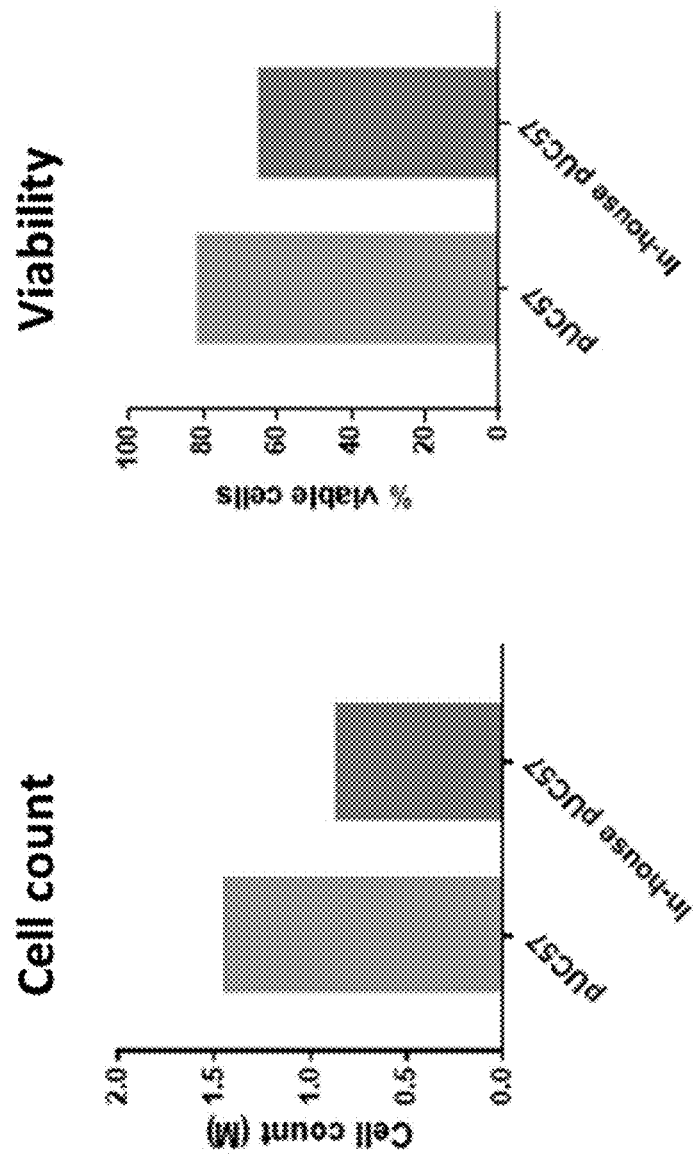
FIG. 14 shows T cell viability using a purchased ("pUC57") or an in-house purified ("In-house pUC57") as assessed by cell count (left) or AOPI staining (right).

Example 7: Comparison of Circular HR Templates Produced from Different Sources Viability was tested in the standard electroporation-mediated editing procedure using circular HR templates produced from different sources. Neo12 neoTCRs were integrated into the TCRα locus. T cells were edited by inserting a Neo12 neoTCR construct encoded by the circular HR template pUCu-Kan TRAC(1k)_P2A.Neo12.TRBC2opt.f-P2A.TRA(Va) (SEQ ID NO: 14) that was either purchased in a purified form (FIG. 14 "pUC57", Nature Technology) or purified in-house with a DNA purification kit (FIG. 14 "In-house pUC57", Maxi kit Macherey Nagel). As shown in FIG. 14, T cells were viable by cell count (FIG. 14 left panel) and as assessed by a viability assay (AOPI, FIG. 14 right panel), with HR template purified in-house achieving greater than 60% viability and purchased HR template achieving greater than 80% viability.

Notably, these results disagree with a recently published report (Roth, et al. [*Nature*. 2018 July; 559(7714):405-4091) that described the use of a circular plasmid HR template in electroporation-mediated editing as leading to reduced T cell viability when compared to linear products.

Example 8: NeoTCR Integration (Neo12)

Figure 15:
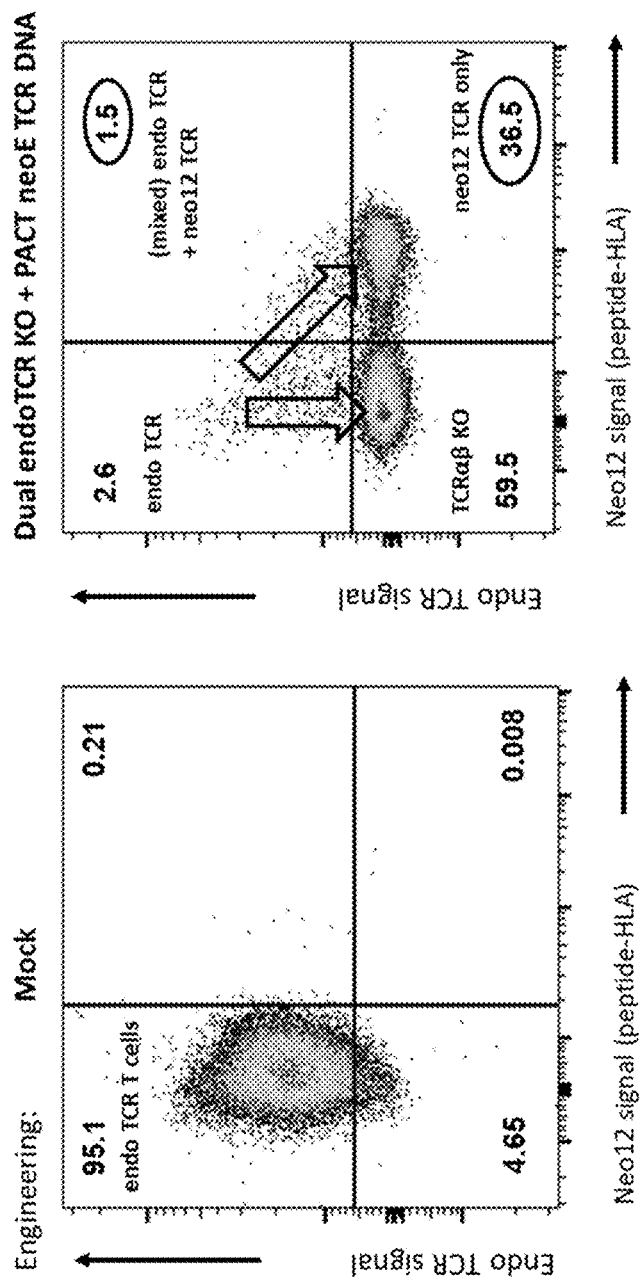
FIG. 15 shows expression of the Neo12 neoTCR as detected by Neo12 specific dextramer staining.

A Neo12 neoTCR was integrated into the TCRα locus. T cells were edited following the standard electroporation-mediated editing procedure and inserting a Neo12 neoTCR construct encoded by the circular HR template NTC9385R-TRAC(1k)DTS_P2A.neo12.TRBopt.f-P2A.TRA(Va)opt (SEQ ID NO: 13). Engineered T cells were assessed for expression of the Neo12 neoTCR by flow cytometry. Expression of the Neo12 neoTCR was detected by Neo12 specific dextramer staining. Of note, the Neo12 construct used was modified such that it was not bound by the pan-TCR antibody. As shown in FIG. 15, 36.5% of T cells expressed the Neo12 neoTCR and did not express the endogenous TCR (FIG. 15 right panel). Additionally, expression of the endogenous TCR was disrupted for the large majority of T cells (96%). Only background levels of neoTCR expression signal was detected when T cell a mock editing procedure (FIG. 15 left panel).

Figure 16:
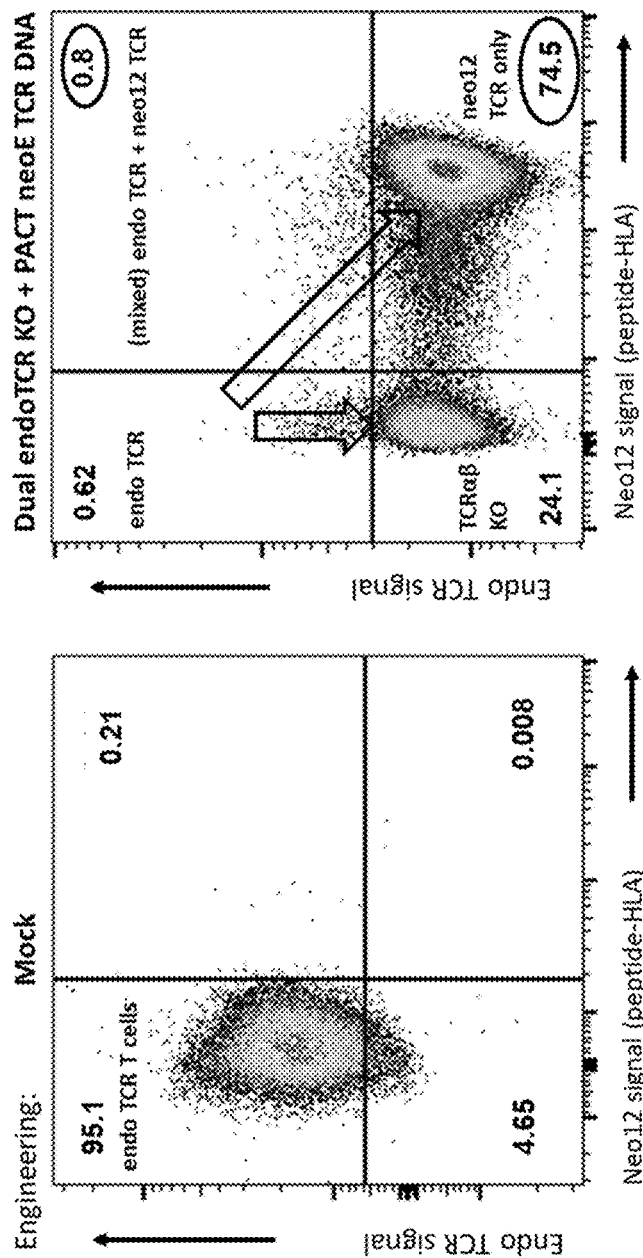
FIG. 16 shows expression of the Neo12 neoTCR as detected by Neo12 specific dextramer staining.

Additional editing experiments were also performed inserting a Neo12 neoTCR construct encoded by the circular HR template NTC9385R-TRAC(1k)DTS_P2A.neo12.TRBopt.f-P2A.TRA(Va)opt (SEQ ID NO: 13). Engineered T cells were assessed as above. As shown in FIG. 16, 74.5% of T cells expressed the Neo12 neoTCR and did not express the endogenous TCR (FIG. 16 right panel). Additionally, expression of the endogenous TCR was disrupted for the large majority of T cells (98.6%). Only background levels of neoTCR expression signal was detected when T cell were mock treated (FIG. 16 left panel).

Example 9: NeoTCR Integration for Various NeoTCRs

Figure 17:
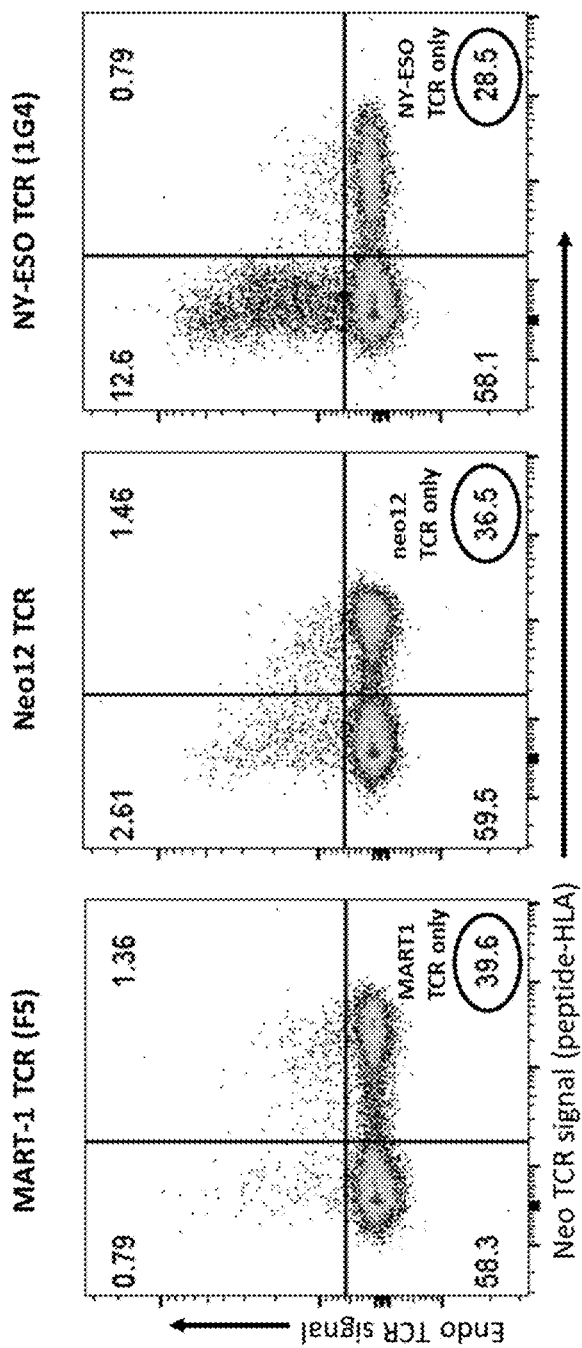
FIG. 17 shows expression of the neoTCRs MART-1, Neo12, and NY-ESO as detected by specific dextramer staining.

Various neoTCRs were integrated into the TCRα locus. T cells were edited following the standard electroporation-mediated editing procedure and inserting either a MART-1 neoTCR (F5) construct encoded by the circular HR template NTC9385R-TRAC(1k)DTS_P2A.F5.TRBopt.f-P2A.TRA(Va)opt (SEQ ID NO: 10) HR template, a Neo12 neoTCR (Neo12) construct encoded by the NTC9385R-TRAC(1k)DTS_P2A.neo12.TRBopt.f-P2A.TRA(Va)opt (SEQ ID NO: 13), or a NY-ESO neoTCR (1G4) construct encoded by the circular HR template NTC9385R-TRAC(1k)DTS_P2A.1-G4.TRBopt.f-P2A.TRAopt.BGHpA (SEQ ID NO: 11). Engineered T cells were assessed for expression of their respective neoTCRs by flow cytometry through neoTCR specific dextramer staining. The neoTCR constructs used here was modified such that it was not bound by the pan-TCR antibody. As shown in FIGS. 17, 39.6%, 36.5%, and 28.5% of T cells expressed the neoTCRs MART-1 (F5), Neo12, and NY-ESO (1G4) respectively, and did not express the endogenous TCR (FIG. 17 left, middle, and right panels respectively) Additionally, expression of the endogenous TCR was disrupted for the large majority of T cells (97.9%, 96%, and 86.6% respectively). Thus, T cell engineering using different neoTCRs generally produced similar editing efficiencies supporting the conclusion that editing efficiencies are reproducible across different TCR expression constructs using the T cell editing methods described herein.

Example 10: NeoTCR Integration in Patient Derived T Cells

Various neoTCRs were integrated into the TCRα locus of either healthy or patient derived T cells (Melanoma, Colorectal Cancer, and Lung cancer typically used from Biooptions and Conversant Bio). T cells were edited following the standard electroporation-mediated editing procedure and inserting either a MART-1 neoTCR construct encoded by the circular HR template NTC9385R-TRAC(1k)DTS_P2A.F5.TRBopt.f-P2A.TRA(Va)opt (SEQ ID NO: 10) HR template, a Neo12 neoTCR construct encoded by the NTC9385R-TRAC(1k)DTS_P2A.neo12.TRBopt.f-P2A.TRA(Va)opt (SEQ ID NO: 13), or a NY-ESO neoTCR construct encoded by the circular HR template NTC9385R-TRAC(1k)DTS_P2A.1G4.TRBopt.f-P2A.TRAopt.BGHpA (SEQ ID NO: 11). Engineered T cells were assessed for expression of their respective neoTCRs by flow cytometry through neoTCR specific dextramer staining.

Figure 18B:
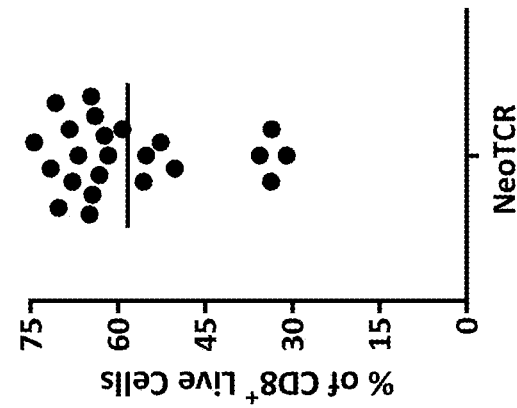
FIGS. 18A-18B show integration of neoTCRs into donor derived T cells.
Figure 18A:
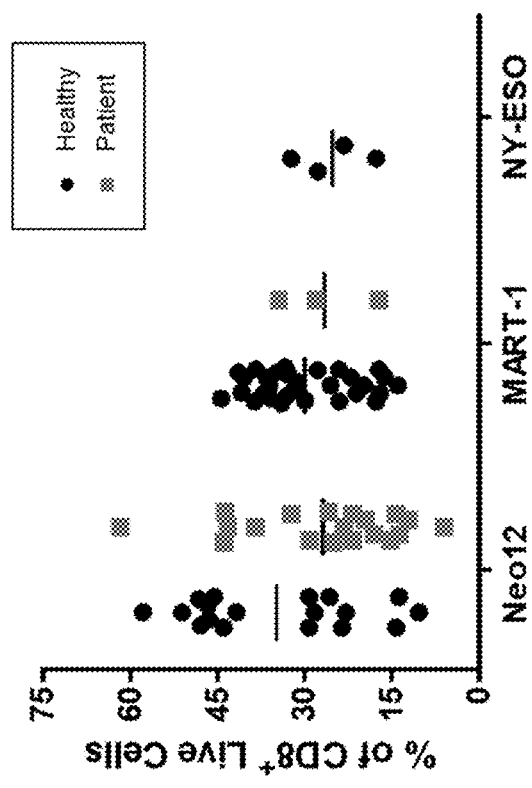

As shown in FIG. 18A, T cells from healthy samples or patient samples were edited with similar efficiency for Neo12 and MART-1 constructs. In addition, editing efficiency was similar across the various neoTCR constructs tested, as well as demonstrating reproducible editing efficiencies between samples. As shown in FIG. 18B, T cells from healthy samples were edited inserting the Neo12 neoTCR at efficiencies approaching 75%.

The Neo12 neoTCR was additionally tested and editing efficiency results are presented in Table 9. In particular, similar editing efficiencies were observed for a duplicate samples of Patient 1 derived T cells (36.2% for replica #1 and 36.4% for replica #2), further demonstrating reproducibility of the T cell editing methods described herein. Thus, the results demonstrate the T cell editing methods described herein are both broadly applicable for various expression constructs and reproducible within a clinical setting.

neoTCR construct encoded by the circular HR template NTC9385R-TRAC(1k)DTS_P2A.1G4.TRBopt.f-P2A.TRAopt.BGHpA (SEQ ID NO: 11). Surface expression of the various neoTCRs and the endogenous TCR was assessed by flow cytometry through staining with anti-CD3.

Figure 20A:
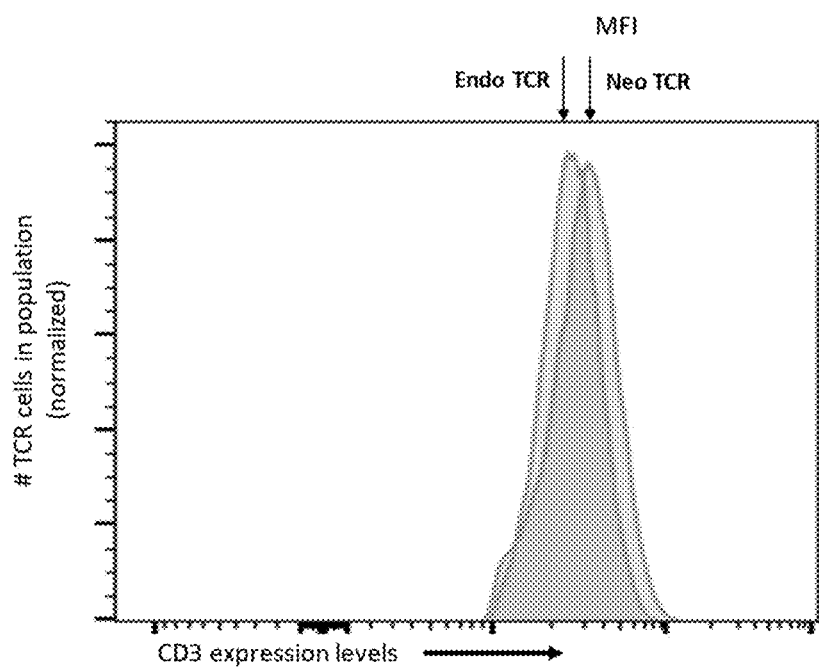
FIGS. 20A-20B show surface expression levels of integrated neoTCRs and endogenous TCRs.
Figure 20B:
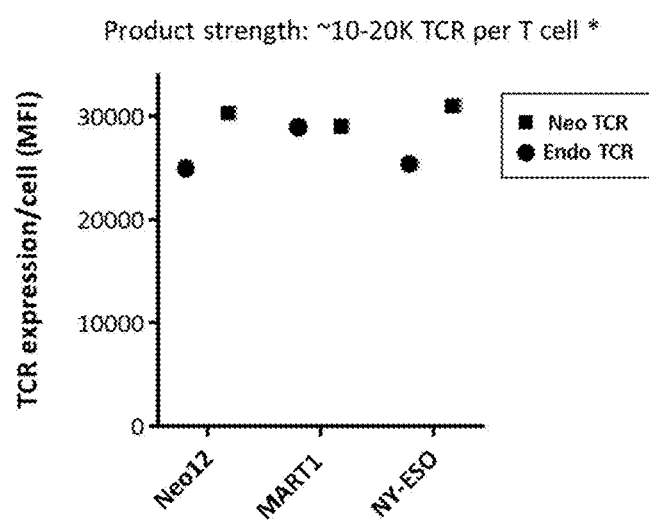

As shown in FIGS. 20A-20B, surface expression of integrated neoTCRs was comparable to endogenous TCR surface expression levels. Mean-fluorescent intensity (MFI) flow-cytometry plots largely overlapped for the endogenous TCR (FIG. 20A, left histogram) and Neo12 neoTCR TCR (FIG. 20A, right histogram) stained using the same antibody (CD3). The MFI calculations for all three neoTCRs tested are quantified in FIG. 20B with each demonstrating surface expression comparable to endogenous TCR levels. Thus, the results demonstrate that the T cell editing methods described herein result in surface expression of the full TCR (i.e., both TCRα and TCRβ) encoded the inserted expression cassette at levels comparable to endogenous.

TABLE 9

Neo12 Editing Efficiencies for Donor-derived Cells

|  | Mock 1 | Mock 2 | Healthy 1 | Healthy 2 | Patient 1 #1 | Patient 1 #2 | Patient 2 |
| --- | --- | --- | --- | --- | --- | --- | --- |
| % WT only | 93.2 | 93.5 | 1.6 | 17.6 | 6.6 | 8.4 | 14.4 |
| % WT + Neo12 | 0.7 | 0.4 | 0.6 | 0.6 | 0.7 | 1.3 | 1 |
| % No TCR | 6.1 | 6.1 | 58.6 | 63.8 | 56.5 | 53.9 | 60.2 |
| % Neo12 only | 0 | 0 | 39.2 | 17.2 | 36.2 | 36.4 | 24.4 |

Mock = underwent mock editing procedure

Example 11: NeoTCR Integration in CD4 and CD8 T Cells

Figure 19:
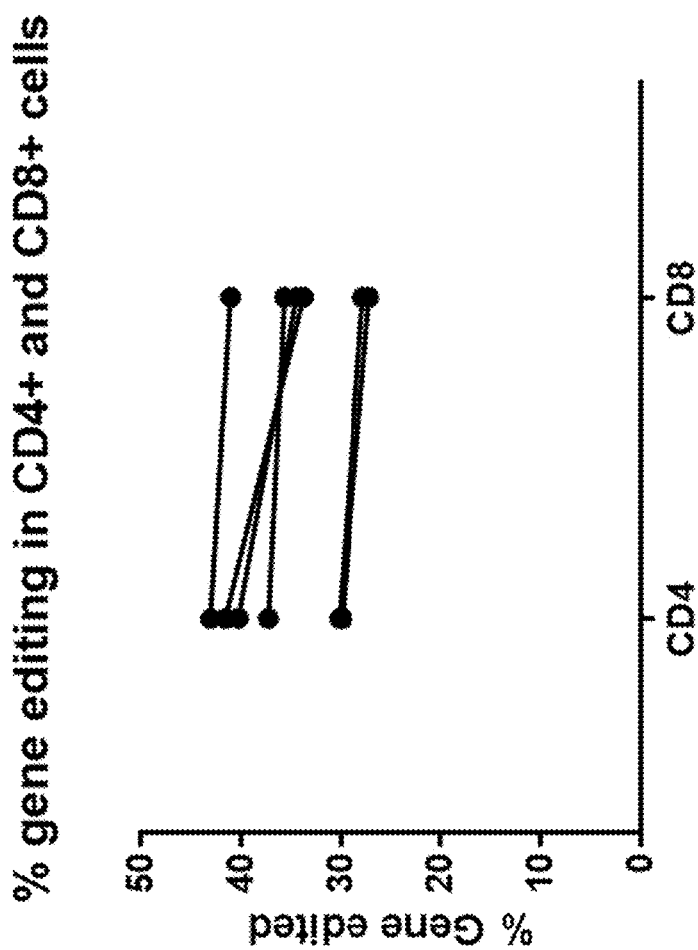
FIG. 19 shows editing efficiency of CD4+ and CD8+ cells as assessed by detection of CD3 complexes that do not bind a pan-TCR antibody.

Editing efficiency of CD4 and CD8 T cells was assessed. A Neo12 neoTCR was integrated into the TCRα locus. T cells were edited following the standard electroporation-mediated editing procedure and inserting a Neo12 neoTCR construct encoded by the circular HR template NTC9385R-TRAC(1k)DTS_P2A.neo12.TRBopt.f-P2A.TRA(Va)opt (SEQ ID NO: 13). Of note, the Neo12 construct used here was modified such that it was not bound by the pan-TCR antibody. Editing of CD8 T cells was assessed by expression of the Neo12 neoTCR (Neo12 specific dextramer staining). Dextramer staining was not sensitive enough to detect neoTCR molecules on CD4 T cells likely due to peptides being presented on MHC class I molecules and CD8 is not present to stabilize MHC-I/TCR interactions. Therefore, editing of CD4 T cells was assessed by detection of CD3 complexes that do not bind the pan-TCR antibody. As shown in FIG. 19, both CD8 and CD4 T cells were edited with similar efficiencies. Thus, the results demonstrate the T cell editing methods described herein are both broadly applicable for different T cell populations.

Example 12: NeoTCR Expression Levels

The surface expression levels of various neoTCRs was tested following integration into the TCRα locus. T cells were edited following the standard electroporation-mediated editing procedure and inserting either a MART-1 neoTCR construct encoded by the circular HR template NTC9385R-TRAC(1k)DTS_P2A.F5.TRBopt.f-P2A.TRA(Va)opt (SEQ ID NO: 10) HR template, a Neo12 neoTCR construct encoded by the NTC9385R-TRAC(1k)DTS_P2A.neo12.TRBopt.f-P2A.TRA(Va)opt (SEQ ID NO: 13), or a NY-ESO Example 13: NeoTCR Integration in Large Format Non-Frozen T Cells Freshly isolated PBMCs (i.e., not frozen) were collected in a leukopak and T cells using the Prodigy platform. T cells were edited by inserting a Neo12 neoTCR construct encoded by the circular HR template pUCu-Kan TRAC(1k)_P2A.Neo12.TRBC2opt.f-P2A.TRA(Va) (SEQ ID NO: 14). Expression of the Neo12 neoTCR was detected by Neo12 specific dextramer staining.

Figure 21:
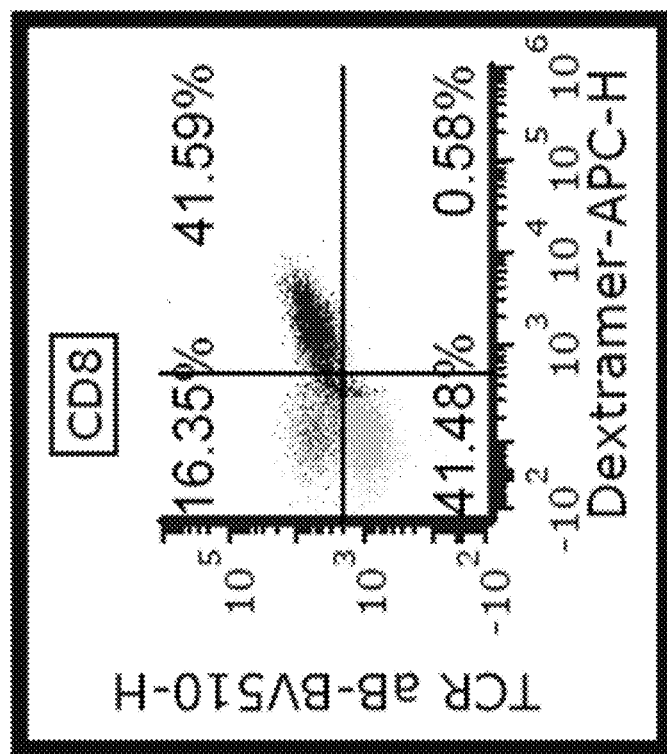
FIG. 21 shows expression of the Neo12 neoTCR as assessed by Neo12 specific dextramer staining using large format editing of T cells from freshly isolated PBMCs and isolated using the Prodigy platform.

As shown in FIG. 21, 41.6% of CD8 positive T cells expressed the Neo12 construct. Thus, the results demonstrate the T cell editing methods described herein are applicable in a clinical setting.

Example 14: Edited T Cells are Functional

Figure 22:
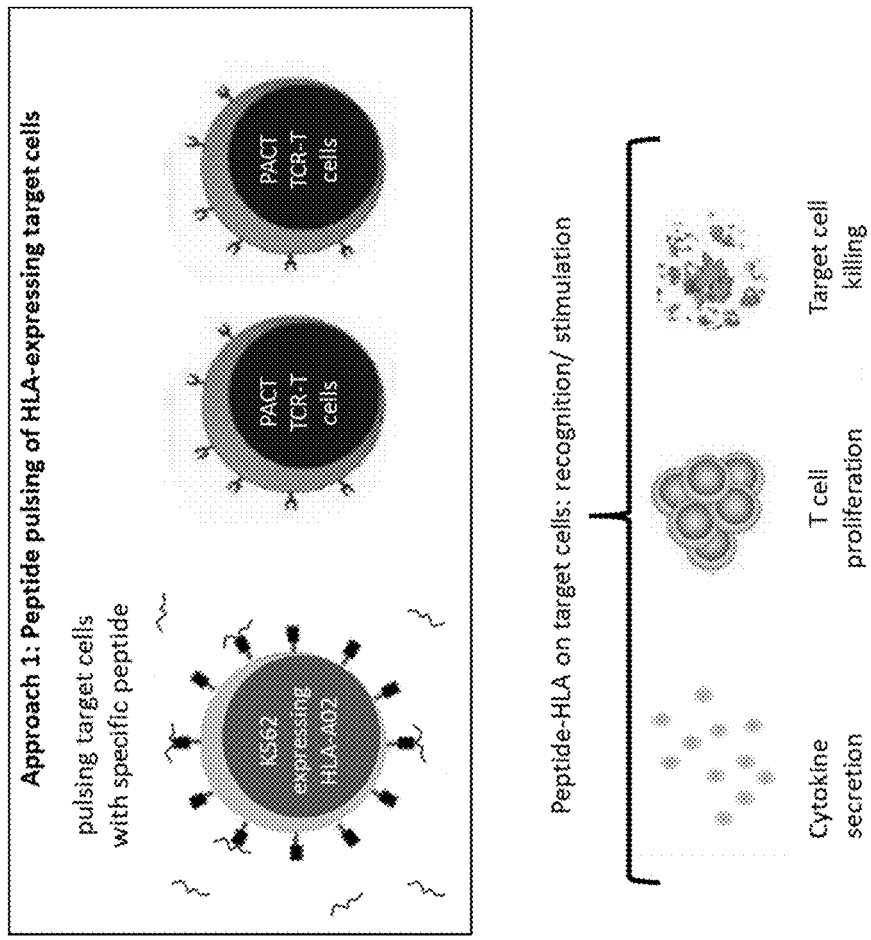
FIG. 22 shows the general strategy for assessing edited T cells using target cells (HLA-A02 expressing K562 cells) pulsed with peptide.
Figure 23:
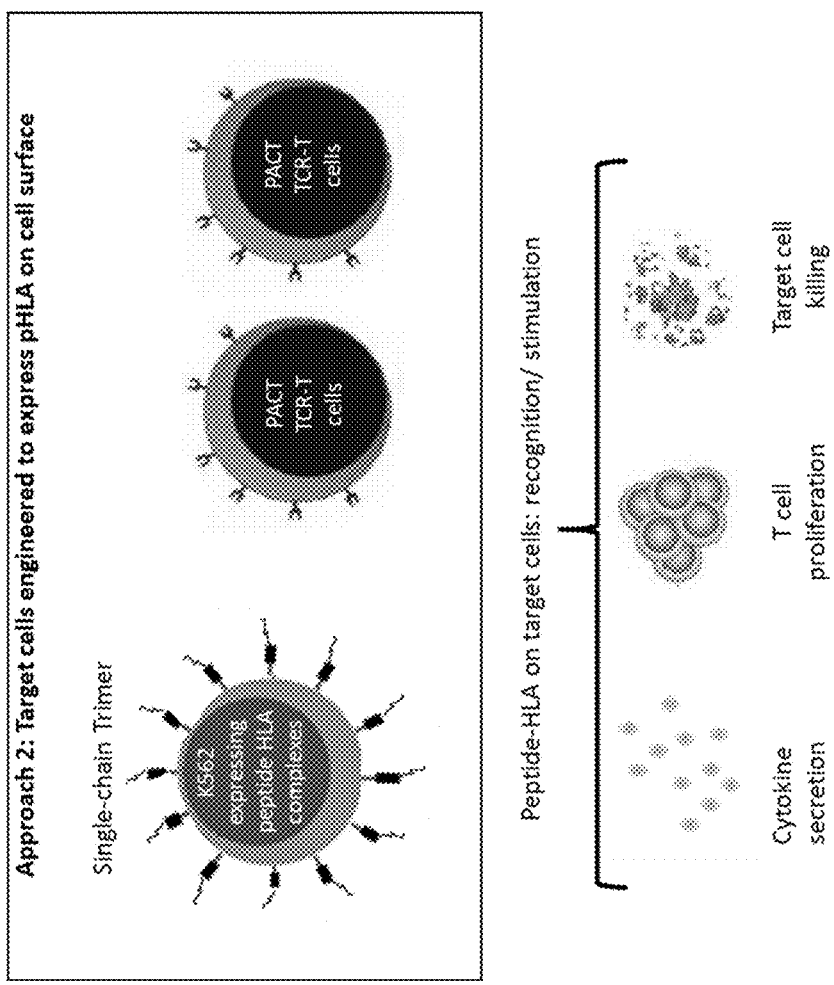
FIG. 23 shows the general strategy for assessing edited T cells using target cells (HLA-A02 expressing K562 cells) engineered to express the peptide preformed in an HLA complex (pHLA).

Edited T cells were assessed for T cell functionality. More specifically, T cells were assessed for cytokine production/secretion, T cell proliferation, and antigen-specific target cell killing using target cells (HLA-A02 expressing K562 cells) either pulsed with peptide (illustrated in FIG. 22) or engineered to express the peptide preformed in an HLA complex (pHLA, illustrated in FIG. 23).

T cells were edited following the standard electroporation-mediated editing procedure and inserting either a MART-1 neoTCR construct encoded by the circular HR template NTC9385R-TRAC(1k)DTS_P2A.F5.TRBopt.f-P2A.TRA(Va)opt (SEQ ID NO: 10) HR template, a Neo12 neoTCR construct encoded by the NTC9385R-TRAC(1k) DTS_P2A.neo12.TRBopt.f-P2A.TRA(Va)opt (SEQ ID NO: 13), or a NY-ESO neoTCR construct encoded by the circular HR template NTC9385R-TRAC(1k)DTS_P2A.1G4.TR Bopt.f-P2A.TRAopt.BGHpA (SEQ ID NO: 11).

Figure 24:
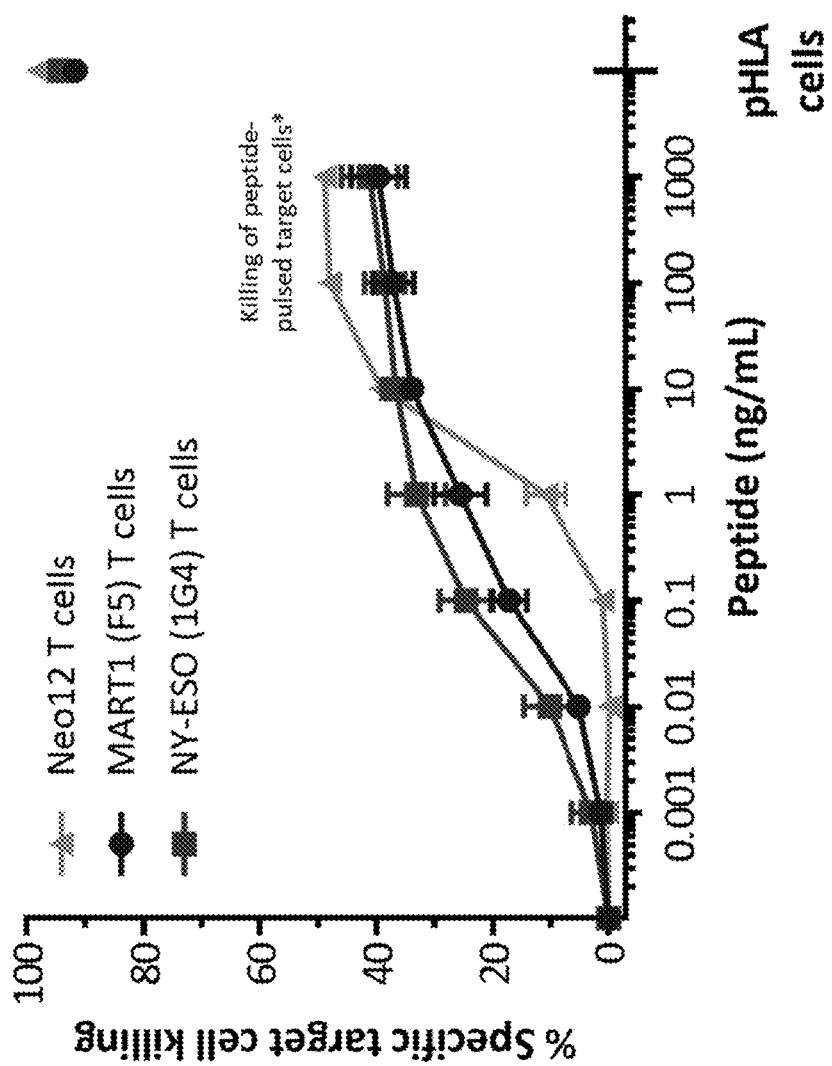
FIG. 24 shows assessment of engineered T cells in an antigen-specific T cell-mediated killing assay. *Pulsed peptides are only briefly displayed on target cells in vitro, in contrast to in vivo tumors that express target neoantigens.

Engineered T cells were assessed for antigen-specific T cell-mediated killing, as described. As shown in FIG. 24, target cells were killed when co-incubated with T cells when target cells were pulsed their respective cognate peptides in a peptide concentration dependent manner (FIG. 24, 0-1000 ng/ml) or engineered to express the peptide/HLA complex (FIG. 24, pHLA) (E:T Ratio 4:1). Notably, target cells engineered to express the peptide/HLA complex demonstrated almost complete killing in contrast to the peptide pulsed cells, likely due to the transient nature of pulsed peptides being presented by HLAs, suggesting more physiologically relevant contexts (e.g., non-transient presentation of antigen peptides) can result in a high level of killing. In addition, antigen-specific killing of T cells was also demonstrated using engineered target cells expressing the peptide/HLA complex co-incubated with Neo12 expressing T cells using an Annexin V cell death assay (E:T Ratio 4:1, data not shown). Thus, engineered T cells demonstrated antigen-specific killing of target cells.

Figure 25A:
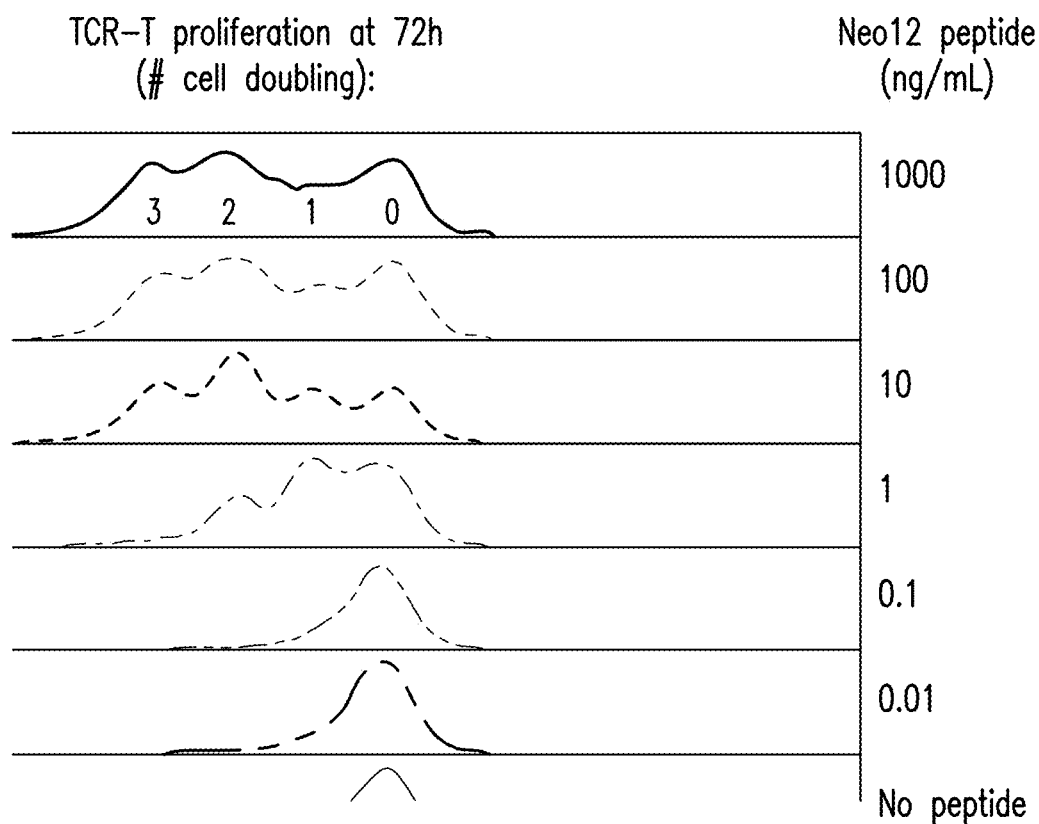
FIGS. 25A-25B show assessment of engineered T cells in an antigen-specific proliferation assay.
Figure 25B:
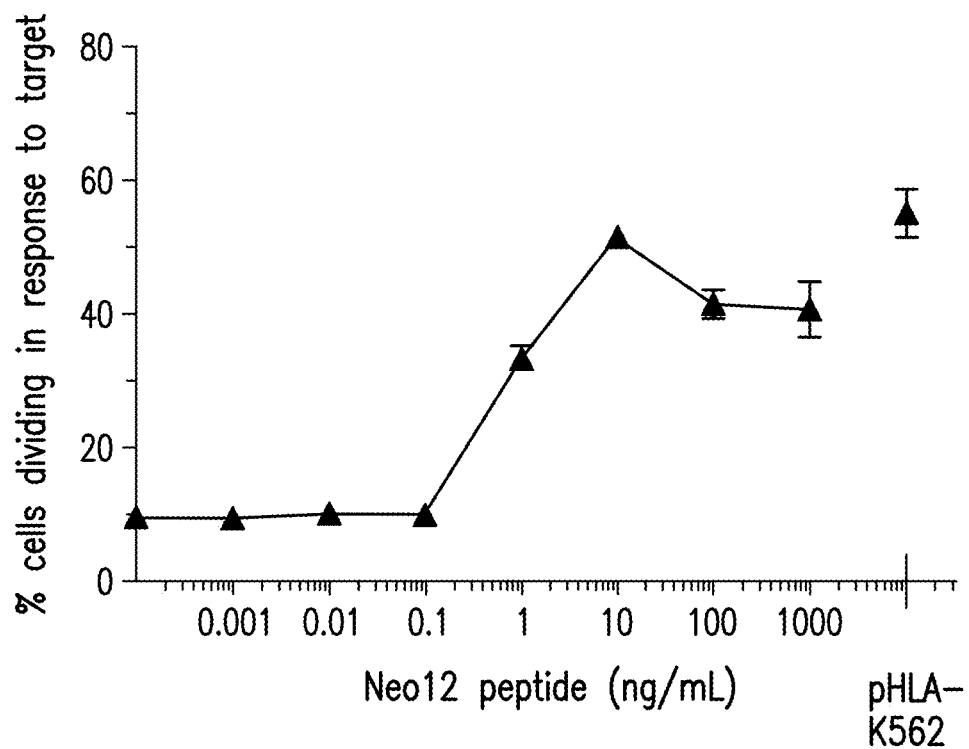
Figures 26C, 26D:
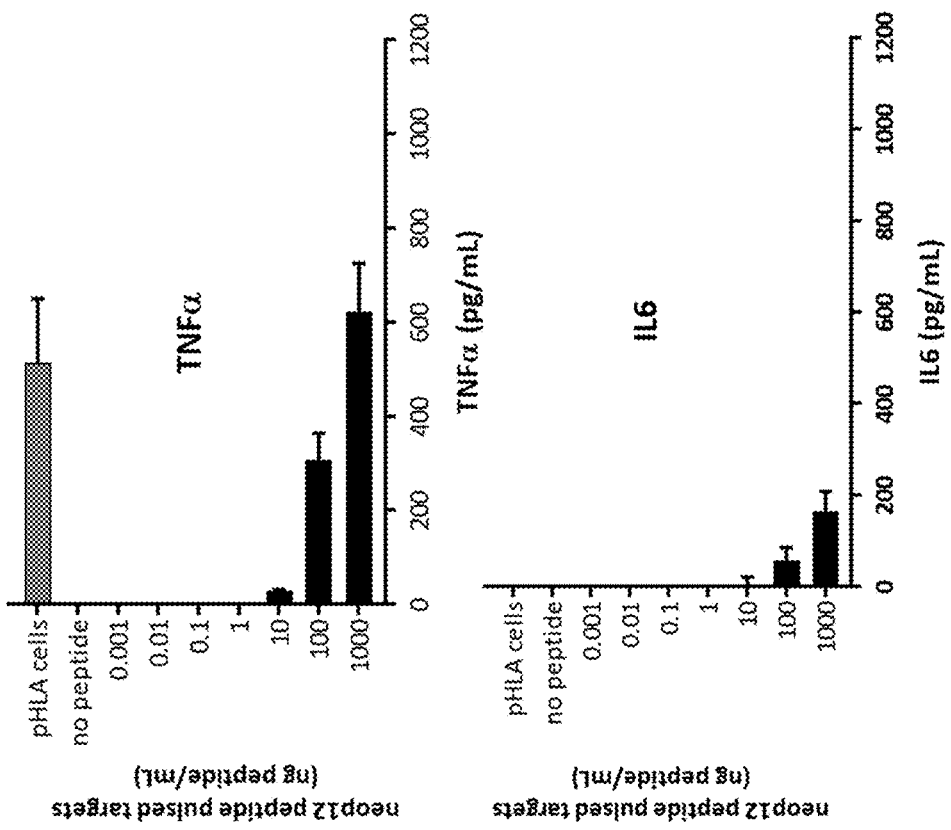

Engineered T cells were assessed for antigen-specific T cell proliferation, as described. As shown in FIG. 25A and FIG. 25B, Neo12 expressing T cells proliferated when co-incubated with target cells pulsed with a Neo12 cognate peptide in a peptide concentration dependent manner (FIGS. 25A and 25B, 0-1000 ng/ml) or engineered to express the peptide/HLA complex (FIG. 25B, pHLA) (E:T Ratio 2:1). FIG. 25A shows a representative histogram plot demonstrating proliferation with percent dividing cells calculated in FIG. 25B. Thus, engineered T cells demonstrated antigen-specific proliferation when co-incubated with target cells presenting cognate peptide.

Engineered T cells were assessed for antigen-specific cytokine production. As shown in FIGS. 26A-26D, Neo12 expressing T cells produced cytokines when co-incubated with target cells pulsed with a Neo12 cognate peptide in a peptide concentration dependent manner (FIGS. 26A-26D, 0-1000 ng/ml) or engineered to express the peptide/HLA complex (FIGS. 26A-26D, pHLA) (E:T Ratio 4:1). Notably, the cytokine profile demonstrated production of Th1 pro-inflammatory cytokines IFNγ, IL-2, TNFα, and little IL-6 (presented in FIGS. 26A-26D respectively), but did not demonstrate production of Th2 cytokines IL-4 or IL-10 (data not shown). Thus, engineered T cells demonstrated an antigen-specific pro-inflammatory Th1 cytokine profile when co-incubated with target cells.

Example 15: Edited Donor-Derived T Cells are Functional

T cells derived from donors were assessed for T cell functionality following editing. A Neo12 neoTCR was integrated into the TCRα locus. T cells were edited following the standard electroporation-mediated editing procedure and inserting a Neo12 neoTCR construct encoded by the circular HR template NTC9385R-TRAC(1k)DTS_P2A.neo12.TRBopt.f-P2A.TRA(Va)opt (SEQ ID NO: 13). Engineered T cells were assessed for editing efficiency by flow cytometry through neoTCR specific dextramer staining. As shown in FIG. 27A, T cells derived from healthy donors and patient donors were edited with similar efficiency.

Figures 27C, 27D:
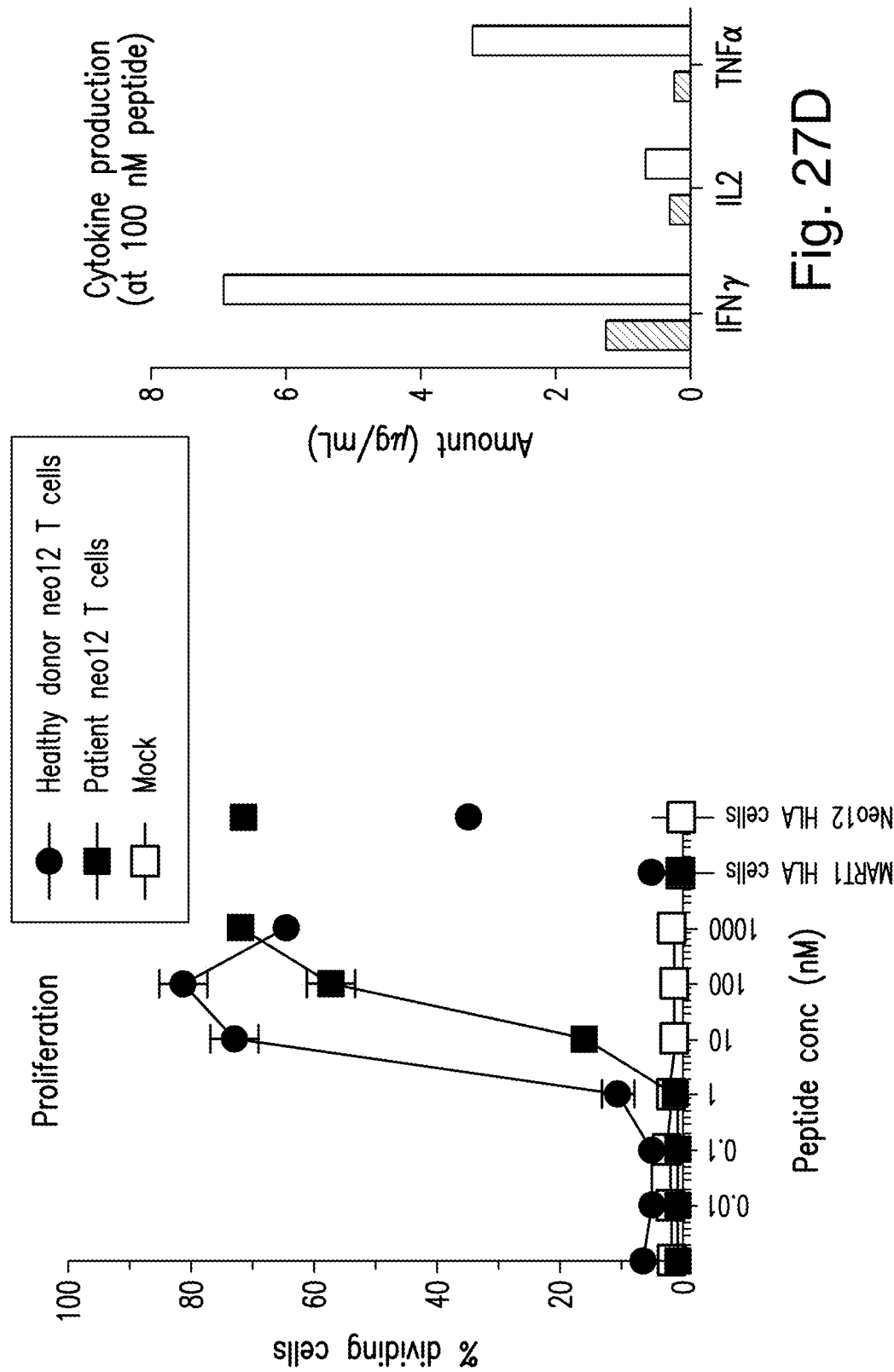

Engineered T cells were assessed for antigen-specific T cell-mediated killing, as described. As shown in FIG. 27B, target cells were killed when co-incubated with edited Neo12 expressing T cells derived from healthy donors and patient donors when target cells were pulsed their respective cognate peptides in a peptide concentration dependent manner (FIG. 27B, 0-1000 ng/ml) or engineered to express the peptide/HLA complex (FIG. 27B, "Neo12 HLA") (E:T Ratio 4:1). Notably, target cells engineered to express a non-cognate peptide/HLA complex did not demonstrate significant killing (FIG. 27B, "MART1 HLA"). In addition, killing was not observed when using T cells that underwent the mock editing procedure. Thus, engineered healthy donor-derived and patient-derived T cells demonstrated antigen-specific killing of target cells demonstrating applicability within a clinical setting Engineered healthy and patient donor-derived T cells were assessed for antigen-specific T cell proliferation, as described. As shown in FIG. 27C, Neo12 expressing donor T cells proliferated when co-incubated with target cells pulsed with a Neo12 cognate peptide in a peptide concentration dependent manner (FIG. 27B, 0-1000 ng/ml) or engineered to express the peptide/HLA complex (FIG. 27C, "Neo12 HLA") (E:T Ratio 4:1). Notably, target cells engineered to express a non-cognate peptide/HLA complex did not demonstrate T cell proliferation (FIG. 27C, "MART1 HLA"). In addition, T cell proliferation was not observed when T cells were mock treated. Thus, engineered healthy and patient donor-derived T cells demonstrated antigen-specific proliferation when co-incubated with target cells presenting cognate peptide.

Engineered healthy and patient donor-derived T cells were assessed for antigen-specific cytokine production. As shown in FIG. 27D, Neo12 expressing T cells produced cytokines when co-incubated with target cells pulsed with 100 nM Neo12 cognate peptide (E:T Ratio 4:1). Notably, the cytokine profile demonstrated production of Th1 pro-inflammatory cytokines IFNγ, IL-2, TNFα, and little IL-6. Thus, engineered healthy and patient donor-derived T cells demonstrated an antigen-specific pro-inflammatory Th1 cytokine profile when co-incubated with target cells.

Notably, the engineered donor-derived T cells were not sorted prior to the assay performed demonstrating that engineered donor-derived T cells were functional without additional enrichment steps.

Example 16: Donor-Derived T Cells Expressing Various neoTCRs are Functional

T cells were assessed for T cell functionality following editing. Both a Neo12 neoTCR and a MART-1 neoTCR was integrated into the TCRα locus. T cells from the same donor were edited following the standard electroporation-mediated editing procedure and inserting either a MART-1 neoTCR construct encoded by the circular HR template NTC9385R-TRAC(1k)DTS_P2A.F5.TRBopt.f-P2A.TRA(Va)opt (SEQ ID NO: 10) HR template or a Neo12 neoTCR construct encoded by the NTC9385R-TRAC(1k)DTS_P2A.neo-12.TRBopt.f-P2A.TRA(Va)opt (SEQ ID NO: 13). Engineered T cells were assessed for editing efficiency by flow cytometry through neoTCR specific dextramer staining. As shown in FIG. 28A, T cells derived from the same donor were edited with similar efficiency for both the Neo12 and MART-1 ("F5") TCR constructs.

These engineered T cells were then assessed for antigen-specific T cell-mediated killing, as described (4:1 E:T ratio). As shown in FIG. 28B, target cells were killed when co-incubated with edited T cells expressing either Neo12 (open squares) or MART-1 (filled squares) when target cells were pulsed their respective cognate peptides in a peptide concentration dependent manner (0-1000 ng/ml) or engineered to express the peptide/HLA complex ("Neo12 HLA" and "MART-1 HLA") (E:T Ratio 4:1). Notably, target cells engineered to express a non-cognate peptide/HLA complex did not demonstrate significant killing, i.e., Neo12 T cells did not kill MART1 HLA expressing cells and MART-1 T cells ("F5") did not kill Neo12 HLA cells. Engineered donor-derived T cells were assessed for antigen-specific T cell proliferation, as described. As shown in FIG. 28C, Neo12 (open squares) or MART-1 (filled squares) expressing donor T cells proliferated when co-incubated with target cells pulsed with their respective cognate peptide in a peptide concentration dependent manner (0-1000 ng/ml) or engineered to express the peptide/HLA complex ("Neo12 HLA" and "MART-1 HLA") (E:T Ratio 4:1). Notably, target cells engineered to express a non-cognate peptide/HLA complex did not demonstrate T cell proliferation, i.e., Neo12 T cells did not proliferate when co-incubated with MART1 HLA expressing cells and MART-1 T cells ("F5") did not proliferate when co-incubated with Neo12 HLA cells. Thus, engineered donor-derived T cells demonstrated antigen-specific proliferation when co-incubated with target cells presenting cognate peptide demonstrating applicability within a clinical setting for multiple TCR constructs.

Notably, the engineered donor-derived T cells were not sorted prior to the assay performed demonstrating that engineered donor-derived T cells were functional without additional enrichment steps.

Example 17: Edited T Cells Maintain Functional Activity

The ability of engineered T cells to maintain their functionality for extended culturing was assessed. Both a Neo12 neoTCR and a MART-1 neoTCR were integrated into the TCRα locus. T cells were edited following the standard electroporation-mediated editing procedure and inserting either a MART-1 neoTCR construct encoded by the circular HR template NTC9385R-TRAC(1k)DTS_P2A.F5.TRBopt.f-P2A.TRA(Va)opt (SEQ ID NO: 10) HR template or a Neo12 neoTCR construct encoded by the NTC9385R-TRAC(1k)DTS_P2A.neo12.TRBopt.f-P2A.TRA(Va)opt (SEQ ID NO: 13).

Figure 29:
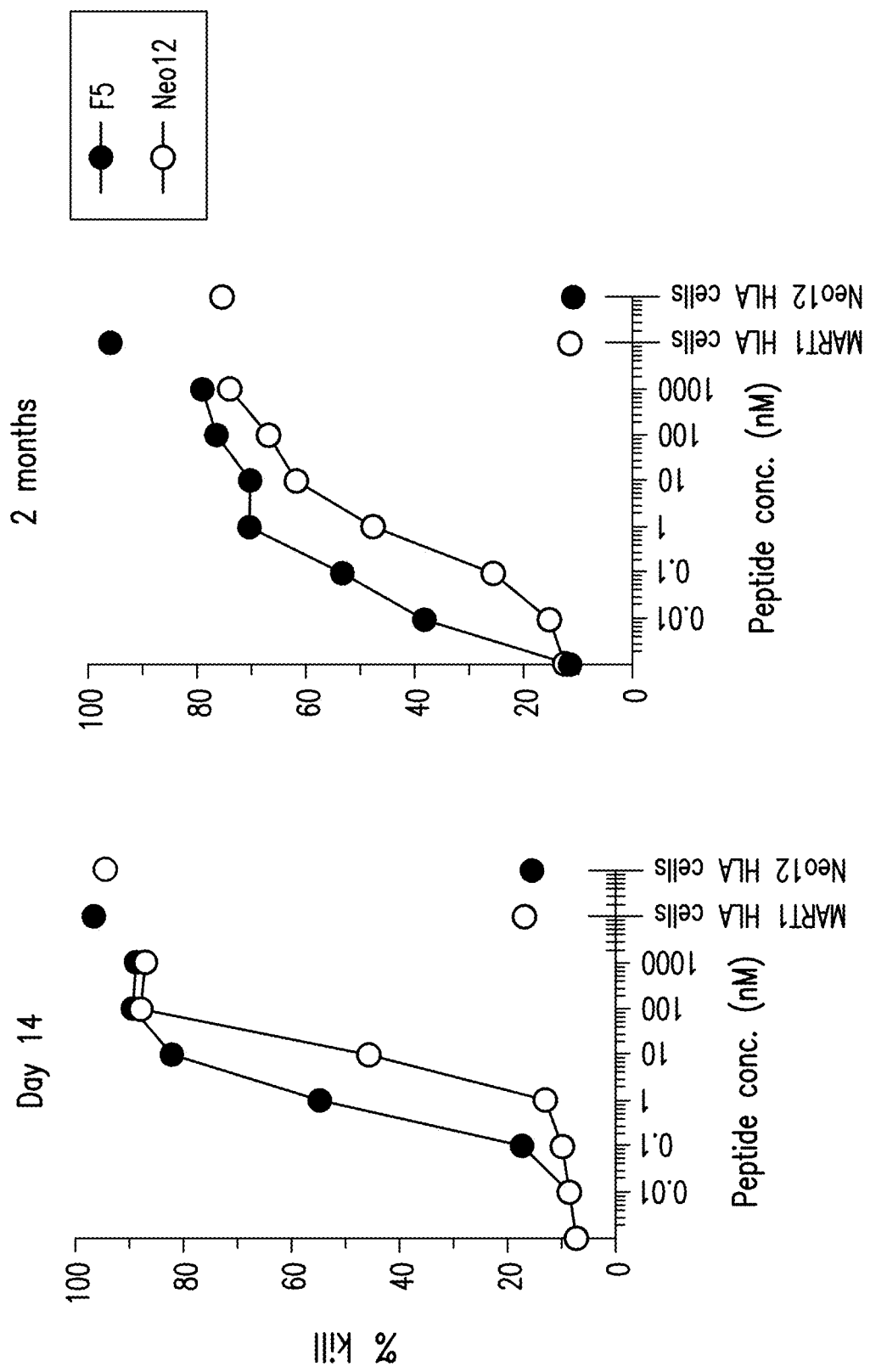
FIG. 29 shows an antigen-specific T cell-mediated killing assay for donor T cells expressing either a Neo12 neoTCR or a MART-1 neoTCR at 14 days (left panel) and 2 months (right panel) after manufacturing with comparable efficiency.

As shown in FIG. 29, Neo12 and MART-1 engineered T cells were able to kill target cells, in an antigen-specific manner, 14 days (FIG. 29 left panel) and 2 months (FIG. 29 right panel) after manufacturing with comparable efficiency. Target cells were killed when co-incubated with edited T cells, derived from the same donor, expressing either Neo12 (open circles) or MART-1 (filled circles) when target cells were pulsed their respective cognate peptides in a peptide concentration dependent manner (0-1000 ng/ml) or engineered to express the peptide/HLA complex ("Neo12 HLA" and "MART-1 HLA") (E:T Ratio 4:1). Notably, target cells engineered to express a non-cognate peptide/HLA complex did not demonstrate significant killing, i.e., Neo12 T cells did not kill MART1 HLA expressing cells and MART-1 T cells ("F5") did not kill Neo12 HLA cells. Cells were kept in medium containing IL7 and IL-15 (without antigen) and were healthy in culture. Thus, edited T cells maintained TCR expression and antigen-specific activity over an extended period of time demonstrating applicability within a clinical setting.

Notably, the engineered T cells were not sorted prior to the assay performed demonstrating that engineered T cells were functional without additional enrichment steps.

Example 18: Characterization of Edited T Cells

Engineered donor-derived (healthy donor) T cells were assessed for T cell functionality following editing. Both a Neo12 neoTCR and a MART-1 neoTCR was integrated into the TCRα locus. T cells were edited following the standard electroporation-mediated editing procedure and inserting either a MART-1 neoTCR construct encoded by the circular HR template NTC9385R-TRAC(1k)DTS_P2A.F5.TRBopt.f-P2A.TRA(Va)opt (SEQ ID NO: 10) HR template or a Neo12 neoTCR construct encoded by the NTC9385R-TRAC(1k)DTS_P2A.neo12.TRBopt.f-P2A.TRA(Va)opt (SEQ ID NO: 13).

Single cell secretome analysis was performed for neoTCR expressing engineered T cells on a per cell basis (Isoplexis). The Isoplexis platform utilized a single-cell 32-plex cytokine assay microdevice (single-cell barcode chip) to delineate the response of T cells to antigen-specific stimulation. CD4+ and CD8+ T-cell subsets were separated using anti-CD4 or anti-CD8 microbeads (Miltenyi Biotec, Bergisch Gladbach, Germany). CD4 and CD8 cells were stimulated separately with specific peptide/target cells (co-cultured with target cells pulsed with 10 or 100 nM specific peptide or with target cells engineered to express the specific peptide/HLA complex) or controls for 19-21 hours at a ratio of 1:2 at 37□C, 5% CO2. Presence of CD4+ or CD8+ T cells was confirmed by staining with Alexa Fluor 647 (Thermo Fisher Cell Therapy Systems, Waltham, Mass.) conjugated anti-CD4 or anti-CD8 antibody at room temperature for 10 minutes, rinsed once with phosphate-buffered saline, and resuspended in medium at a density of $1\times10^6$ cells/mL. Approximately 30 µL of the cell suspension was loaded into the single-cell barcode microchip for single-cell secretomic evaluation. For each sample, a 32-plex assay measured secreted proteins from ~2000 T cells. Raw microscopy and microarray scans of the cell samples loaded onto the single-cell barcode chip and protein secretion data were analyzed using Isoplexis software to determine which combinations of proteins were secreted by each individual cell.

Figure 30A:
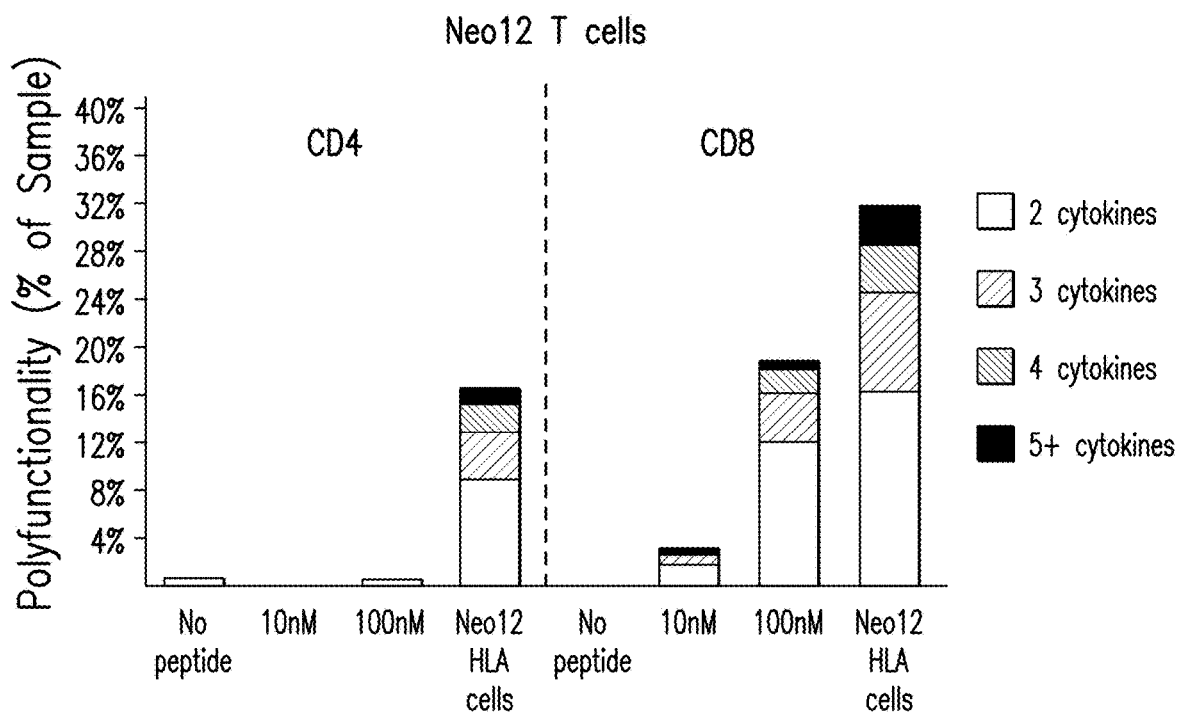
Figure 30B:
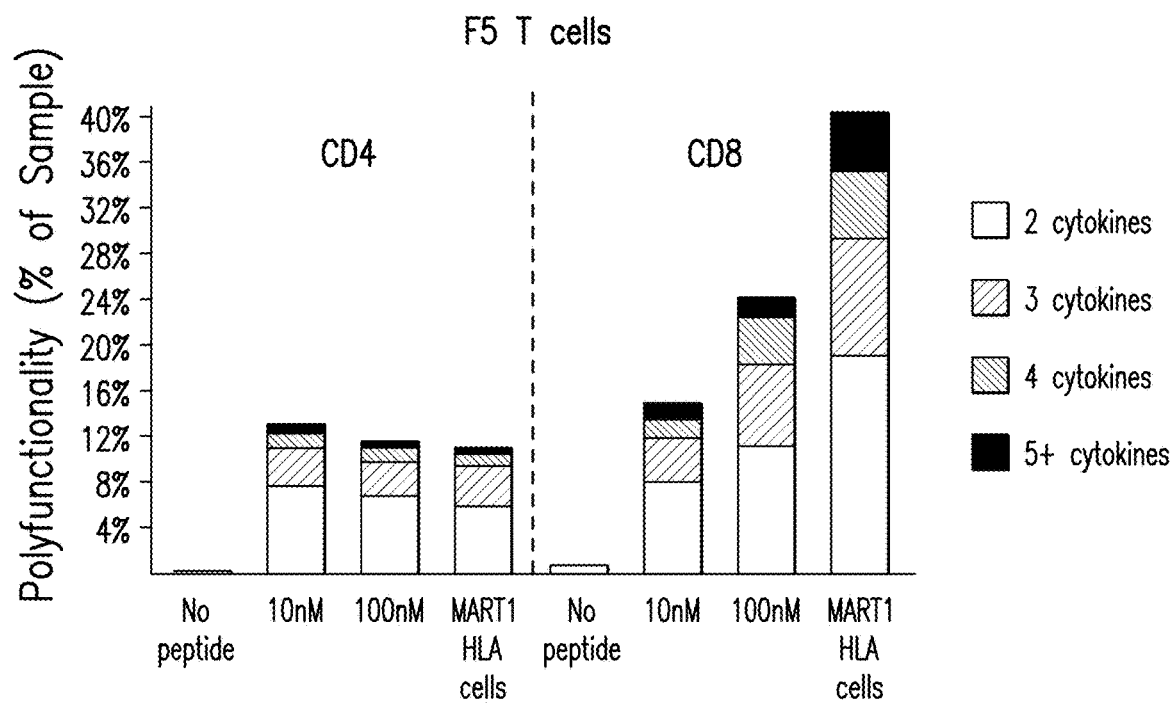

As shown in FIGS. 30A-30C, Isoplexis analysis demonstrated polyfunctional profiles for both CD4 and CD8 T cells. Profiles are shown for CD4 (left panels) and CD8 (right panels) for Neo12 neoTCR expressing engineered T cells (FIG. 30A) and MART-1 neoTCR ("F5") expressing engineered T cells (FIG. 30B). CD8+ T cells demonstrated a dose-dependent polyfunctional profile (secretion of multiple cytokines) with up to 40% of the cells (representing the % of cells that were TCR edited in this experiment, so all edited T cells were polyfunctional) producing more than one cytokine for both Neo12 neoTCR (FIG. 30A, right panel) and MART-1 ("F5") T cells (FIG. 30B, right panel). CD4 responses were overall weaker than CD8 responses, likely due to the absence of CD8 stabilizing the MHC-I/TCR interaction. Notably, CD4+ MART-1 neoTCR ("F5") T cells demonstrated a polyfunctional profile after antigen stimulation with target cells either pulsed with peptide (FIG. 30B, left panel "10 nM" and "100 nM") or engineered to express a MART-1 peptide/HLA complex (FIG. 30B, left panel "MART1 HLA"). In contrast, CD4+ Neo12 T cells demonstrated a detectable polyfunctional profile when stimulated with target cell engineered to express a Neo12 peptide/HLA complex (FIG. 30A, left panel "Neo12 HLA"), but did not demonstrate detectable cytokine production when incubated with target cells pulsed with peptide (FIG. 30A, left panel "10 nM" and "100 nM")), again likely due to the absence of CD8 stabilizing the MHC-I/TCR interaction.

Additionally, as shown in FIG. 30C, while the largest contribution of the engineered T cells is to overall levels of IFNγ (FIG. 30C, left panel), the percentage of T cells producing IFNγ is less than the number of edited cells (FIG. 30C, right panel), as neo12 neoTCR and MART-1 neoTCR (F5) gene editing efficiency for this study was ~45% (data not shown). In contrast, the percentage of T cells producing TNFα better correlates with editing efficiency, i.e., the amount of TNF (~45%) correlated with the amount of gene editing (~45%). (FIG. 30C, right panel and data not shown). Thus, the Isoplexis results demonstrated that TNFα secretion by the engineered T cells may be better predictor of their in vitro killing activity compared to IFNγ secretion.

Thus, Isoplexis analysis demonstrated that engineered neoTCR expressing cell populations possess polyfunctional activity, importantly even in the presence of low antigen stimulation (an important consideration for in vivo efficacy).

Example 19: Electroporation Timing Effects Efficiency

Timing of the incubation step of RNP complexes with cells prior to electroporation was assessed. After activated T cell harvest, centrifugation, and resuspension in electroporation buffer, cells were mixed with RNP complexes and left at room temperature for various time periods (5, 10, 15, 20, 30, 45, 60 minutes and less than 1 minute) before electroporation and subsequent culture. Cells were analyzed by flow cytometry for the percent edited T cells by neoE-specific dextramer staining, and by % viability using a cell counter. Viability ranged from ~20 to ~100% for incubation periods 45 minutes or less, while incubation at 60 minutes was almost 0% (data not shown). The percentage of properly edited T cells (detramer+/endogenous TCR−) was greater than 20% for all time points tested (data not shown).

Example 20: HSC Editing

Figure 31:
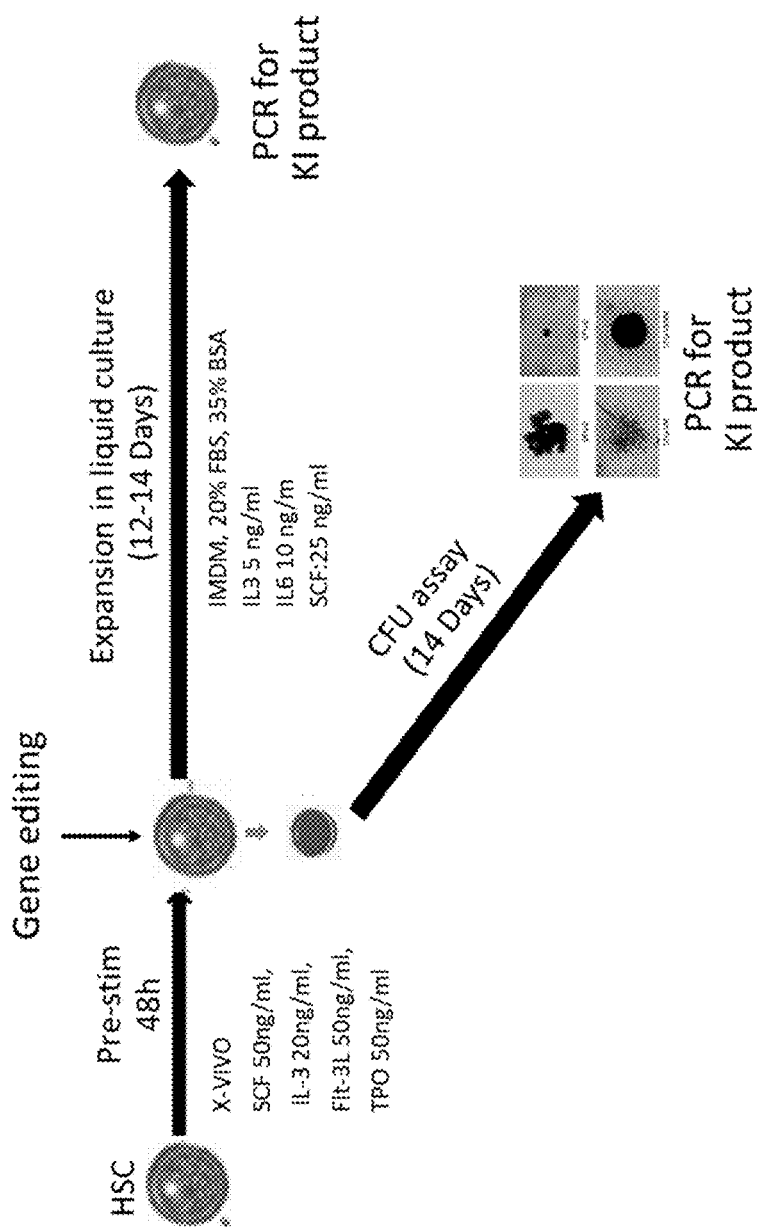
FIG. 31 shows the general work-flow for HSC editing used.

Human HSCs (also referred to as HSPCs) were edited to insert a neoTCR. The general work-flow for HSC editing is presented in FIG. 31. Isolated HSCs (CD34+ cells) CD34+ cells were cultured in pre-stim media for 48 hours (X-VIVO +50 ng/ml SCF, TPO, FL-3L and 20 ng/ml of IL-3). Nucleofection was performed using the conditions described in Table 10 below. Electroporated cells (i.e., modified primary cells) were plated in BBMM media (IMDM, 20% FBS, 35% BSA, IL3 5 ng/ml, IL6 10 ng/ml, SCF:25 ng/ml); media was changed regularly, and cells harvested 16 days post-nucleofection. T cells were edited following the standard electroporation-mediated editing procedure and inserting a Neo12 neoTCR construct encoded by the circular HR template NTC9385R-TRAC(1k)DTS_P2A.neo12.TRBopt.f-P2A.TRA(Va)opt (SEQ ID NO: 13).

TABLE 10

HSC Nucleofection Conditions

| Group | Cells | Volume | Program | RNP (Cas9/sgRNA, pmol) | DNA (ftg) |
|---|---|---|---|---|---|
| 1 | 0.5E6 | 20 μL | DZ100 | 1.33 | 2 |
| 2 | 0.5E6 | 20 μL | DZ100 | 1.33 | 4 |
| 3 | 0.5E6 | 20 μL | DZ100 | 1.33 | 6 |
| 4 | 0.5E6 | 20 μL | DZ100 | 1.33 | 0 |
| 5 | 0.5E6 | 20 μL | EK100 | 1.33 | 2 |
| 6 | 0.5E6 | 20 μL | EK100 | 1.33 | 4 |
| 7 | 0.5E6 | 20 μL | EK100 | 1.33 | 6 |
| 8 | 0.5E6 | 20 μL | EK100 | 1.33 | 0 |
| 9 | 0.5E6 | 20 μL | FA100 | 1.33 | 2 |
| 10 | 0.5E6 | 20 μL | FA100 | 1.33 | 4 |
| 11 | 0.5E6 | 20 μL | FA100 | 1.33 | 6 |
| 12 | 0.5E6 | 20 μL | FA100 | 1.33 | 0 |
| 13 | 0.5E6 | 20 μL | DZ100 | 0 | 0 |
| 14 | 0.5E6 | 20 μL | N/A | 0 | 0 |

Figure 32:
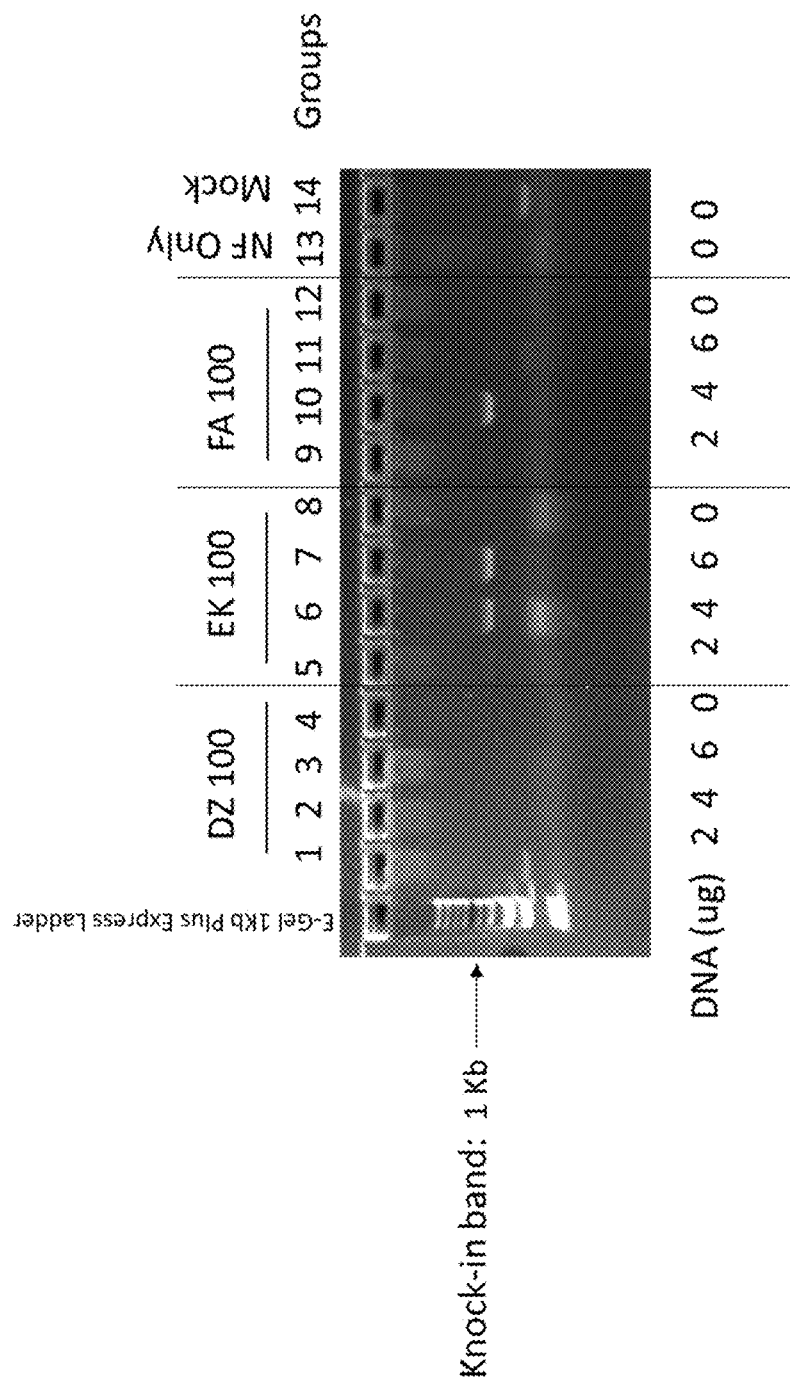
FIG. 32 shows the in-out PCR technique PCR amplification products visualized on an agarose gel used to confirm precise genomic integration of a neo12 neoTCR construct into the TCRα locus of HSCs.

To assess editing, gDNA was extracted and in and out PCR performed. As shown in FIG. 32, groups 5, 6, 7, and 10 demonstrated a 1 Kb amplified PCR band indicative of proper integration. Thus, HSCs were properly edited at the TCRα locus.

To further assess editing in HSCs, the editing procedure was performed as above using 4 μg of a HR template containing a MND promoter driven ZsGreen and truncated LNGRF coding sequence flanked by 1 kb left and right homology arms ("HR Arms") and separated by P2A sequences, encoded in a circular plasmid (pUCu-Kan TRAC (1k)_MNDZsGreen.f-P2A.LNGFRt.P2A; SEQ ID NO: 15). HSCs (0.4×10$^6$) were electroporated using program EK100 in 20 μL using 1.13 pmol of RNP (Cas9/sgRNA). As assessed by brightfield and fluorescent microscopy, methylcellulose colonies at Day 14 expressed ZsGreen (data not shown).

Example 21: HR Arm Length Editing

A MART-1 neoTCR was integrated into the TCRα locus. T cells were edited following the standard electroporation-mediated editing procedure and inserting a MART-1 neoTCR construct encoded by the circular HR template NTC9385R-TRAC(1k)DTS_P2A.F5.TRBopt.f-P2A.TRAopt.BGHpA with HR arm lengths that included 300 base-pairs, 600 base-pairs, 1000 base-pairs (Standard), or 2000 base-pairs.

Engineered T cells were assessed for expression of the MART-1 neoTCR (MART-1 specific dextramer staining) and loss of endogenous TCR expression by flow cytometry. As summarized in Table 11, editing efficiency for generating properly edited T cells (dextramer+/endogenous TCR−) was greater than or equal to 17.6% for all arm lengths tested, and greater than 20% for all arms lengths 600 base-pairs or greater tested.

TABLE 11

Editing Efficiency Using Various HR Arm Lengths

| | TCR+ Dex− | TCR+ Dex+ | TCR− Dex+ | TCR− Dex− |
|---|---|---|---|---|
| 2000 bp HR arms #1 | 3.4 | 1.04 | 26.3 | 69.3 |
| 2000 bp HR arms #2 | 5.81 | 1.18 | 25.5 | 67.5 |
| 1000 bp HR arms (Std.) | 1.64 | 0.6 | 22.7 | 75.1 |
| 600 bp HR arms #1 | 3.94 | 0.84 | 20.9 | 74.3 |
| 600 bp HR arms #2 | 2.32 | 0.87 | 21.5 | 75.3 |
| 300 bp HR arms #1 | 1.59 | 0.43 | 17.6 | 80.3 |
| 300 bp HR arms #2 | 1.1 | 0.52 | 20.4 | 78 |

Example 22: A151 Inhibitor Improves Viability

T cells were edited following the standard electroporation-mediated editing procedure and inserting a Neo12 neoTCR construct encoded by the circular HR template NTC9385R-TRAC(1k)DTS_P2A.neo12.TRBopt.f-P2A. TRA(Va)opt (SEQ ID NO: 13). Engineered T cells were assessed for expression of the Neo12 neoTCR by flow cytometry. Expression of the Neo12 neoTCR was detected by Neo12 specific dextramer staining. Of note, the Neo12 construct used here was modified such that it was not bound by the pan-TCR antibody.

T cells were edited with various concentrations of A151 added pre-incubation. As summarized in Table 12, while editing efficiency for generating properly edited T cells (dextramer+/endogenous TCR−) did not vary significant when A151, cell viability (as assessed by the number of cells) improved with the addition of 0.1 µM or 10 µM A151.

T cells were edited with 0.1 µM A151 added at different stages of the editing procedure. As summarized in Table 13, while editing efficiency for generating properly edited T cells (dextramer+/endogenous TCR−) did not vary significantly when A151 at the different stages tested, cell viability of edited cells (as assessed by the number of edited cells) improved with the addition of A151 during pre-incubation of RNPs and cells, as well as the addition of A151 during both pre-incubation and post-electroporation.

TABLE 12

Editing Efficiency and Viability Using Various Concentrations of A151

| | Dex−TCR+ | Dex+TCR+ | Dex+TCR− | Dex−TCR− | Total Number Editing Cells |
|---|---|---|---|---|---|
| SC | 6.71 | 0.67 | 56.2 | 36.4 | 2.55 |
| 0.01 uM A151 | 3.8 | 0.63 | 57 | 38.6 | 2.47 |
| 0.1 uM A151 | 3.48 | 0.81 | 65 | 30.7 | 2.94 |
| 1 uM A151 | 5.41 | 0.88 | 60.2 | 33.5 | 2.53 |
| 10 uM A151 | 10.6 | 0.71 | 54.6 | 34.1 | 2.77 |

TCR = IP26 antibody, percentages expressed as percentage of CD8+ Cells

TABLE 13

Editing Efficiency and Viability Following A151 Incubation at Various Times

| | Dex−TCR+ | Dex+TCR+ | Dex+TCR− | Dex−TCR− | Total Number Editing Cells |
|---|---|---|---|---|---|
| Standard conditions | 2.98 | 0.63 | 42.4 | 54 | 13.45 |
| | 3.83 | 0.5 | 44.4 | 51.3 | 15.9 |
| | 7 | 0.59 | 40.6 | 51.8 | 13.04 |
| Pre-incubation | 1.02 | 0.51 | 46.1 | 52.4 | 22.8 |
| | 2.75 | 0.53 | 48.4 | 48.3 | 25.2 |
| | 1.98 | 0.53 | 50.3 | 47.2 | 23.41 |
| During EP | 5.84 | 0.37 | 41.9 | 51.9 | 10.65 |
| | 5.33 | 0.63 | 44.1 | 55.0 | 11.88 |
| | 9.4 | 0.4 | 32.8 | 57.4 | 9.16 |
| Post-incubation | 2.53 | 0.52 | 45 | 51.9 | 15.18 |
| | 5.71 | 0.37 | 35.4 | 58.6 | 11.37 |
| | 6.72 | 0.58 | 39.5 | 53.2 | 12.89 |
| Pre + Post-incubation | 4.59 | 0.45 | 36.4 | 58.6 | 18.41 |
| | 2.36 | 0.5 | 42.1 | 55 | 18.8 |

TCR = IP26 antibody, percentages expressed as percentage of CD8+ Cells

Example 23: Engineered T Cell Efficacy in Tumor Models

In vivo efficacy of TCR engineered human T cells is assessed against human tumor cells expressing the specific neoantigen and HLA molecules, such as K562 transduced to constitutively express the specific antigen and HLA or primary human tumor cells that endogenously express specific neoantigen and matched HLA. Tumor cells ($1 \times 10^6$ or $3 \times 10^6$) are subcutaneously inoculated on the flank of 8-weeks old NSG mice (Jackson Laboratory). Tumor growth is monitored by measuring tumor dimensions (using a caliper) 2-3 times per week. Tumor size is calculated by using the following formula: $(Length \times Width^2)/2)$. When the tumors reach ~100 mm$^3$ in size, mice are dosed with $1 \times 10^6$ or $5 \times 10^6$ TCR engineered human T cells (treatment group) or with PBS or mock T cells (electroporated without RNPs or HR template) control groups. Tumor growth is monitored over time and mice are euthanized when tumors reach 2000 mm$^3$ in size. A cohort of mice from each group is sacrificed at early time point (4-7 days after T cells administration). Blood, spleen and tumors are collected. The presence of the edited human T cells in blood is assessed by qPCR and flow cytometry. The presence/infiltration of edited human T cells in the tumor is evaluated by qPCR, flow cytometry and by immunohistochemistry.

The results demonstrate in vivo efficacy of TCR engineered human T cells is assessed against human tumor cells.

Example 24: NK Editing

Human natural killer cells (NK cells) were edited integrating a ZsGreen reporter construct into the TCRα locus. NK cells were isolated by first collecting the flow-through from a CD4/CD8 positive selection isolation (Miltenyi, CliniMACS). Mononuclear cells were isolated using Ficoll (standard procedure) and then NK cells were specifically isolated using an NK Cell Isolation kit (Miltenyi). Isolated NK cells ($1 \times 10^6$) were activated in a culture containing NK MACS Complete Medium (Miltenyi), 5% hABS (Valley Biomedical), 200 ng/mL IL-2 (Miltenyi), 12.5 ng/mL IL-15 (Miltenyi), and Miltenyi NK activation beads (5 uL beads/$10^6$ cells per manufacturer's instructions). On day 3 after activation, activated NK cells ($3 \times 10^6$) were electroporated in 1004 volumes according to the parameters outline in Table 14 below. A homologous repair template containing a MND promoter driven ZsGreen and truncated LNGRF coding sequence flanked by 1 kb left and right homology arms ("HR Arms") and separated by P2A sequences, encoded in a circular plasmid (pUCu-Kan TRAC(1k)_MNDZsGreen.f-P2A.LNGFRt.P2A; SEQ ID NO: 15).

Figure 33:
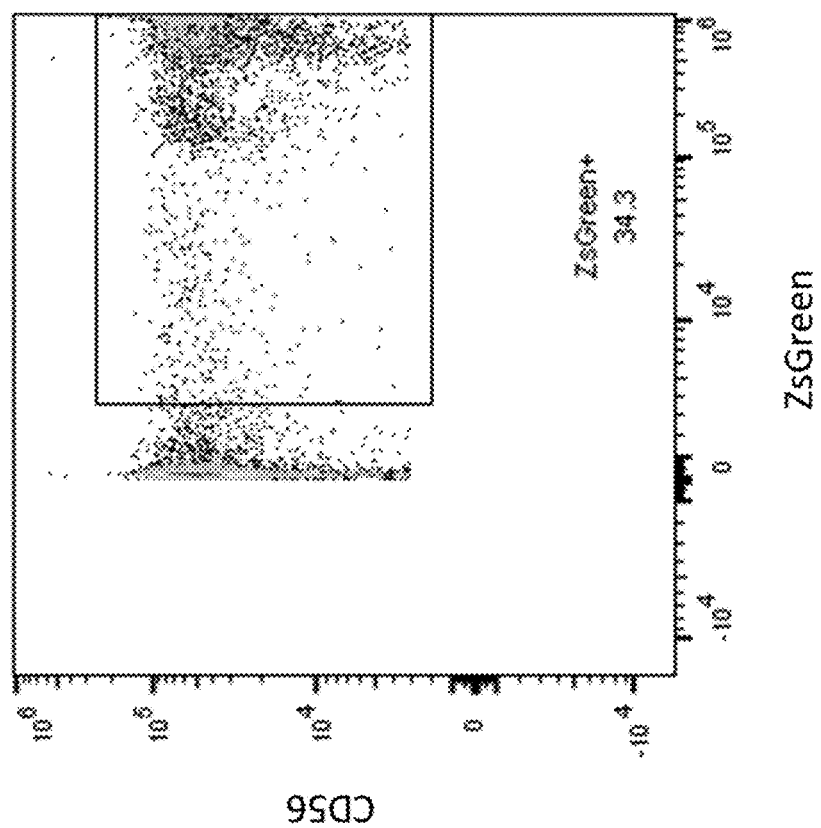
FIG. 33 shows a representative plot demonstrating ZsGreen expression on Day 11 from a ZsGreen reporter integrated into the TCRα locus of NK cells.

Groups were assessed for GFP expression by flow-cytometry on Days 4, 7, and 11. As summarized in Table 14, ZsGreen expression was seen as early as Day 4 (groups 12 and 13). By Day 11, greater than 20% of cells were ZsGreen using programs EN-138 and EK-100 (groups 11, 12, 14, and 15). A representative plot demonstrating ZsGreen expression on Day 11 (Group 12) is shown in FIG. 33.

Figure 34:
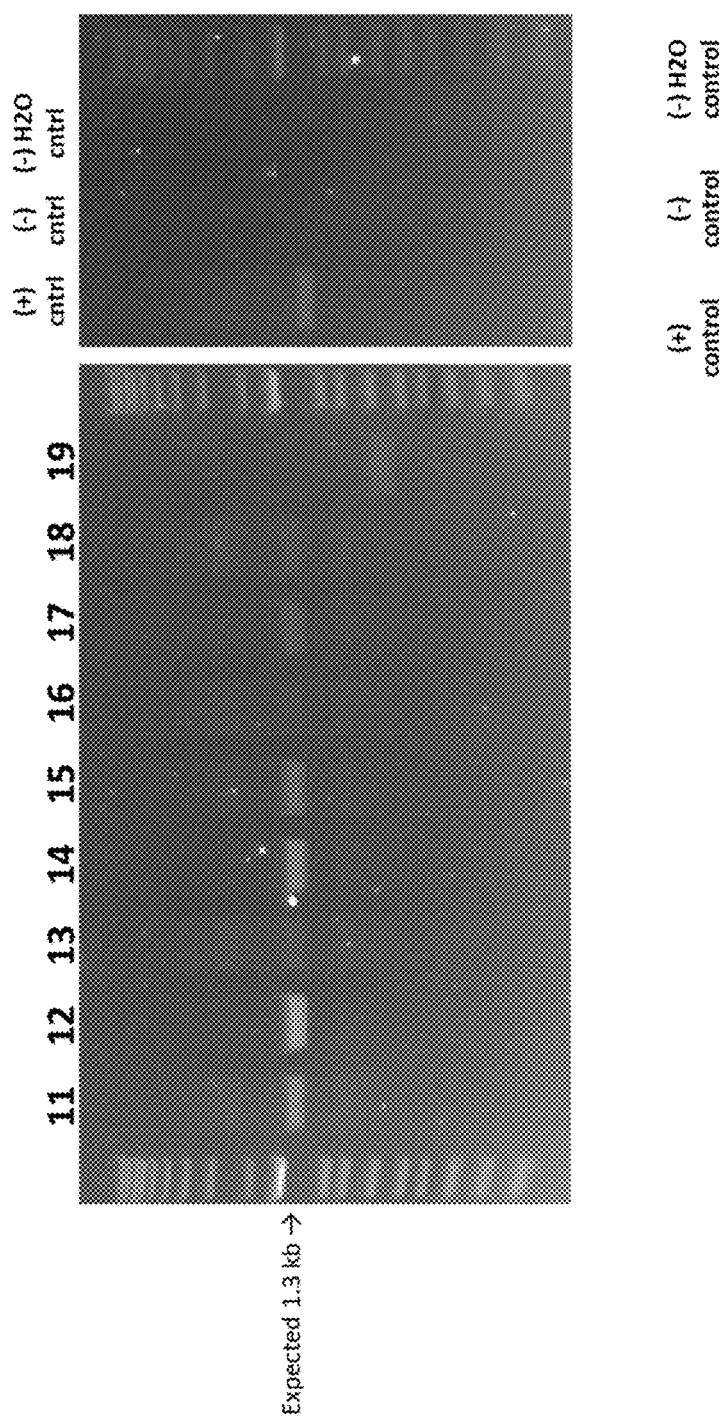
FIG. 34 shows the in-out PCR technique PCR amplification products visualized on an agarose gel used to confirm precise genomic integration a ZsGreen reporter integrated into the TCRα locus of NK cells.

Molecular analysis for integration using the in-out PCR technique was performed to confirm precise genomic integration of the expression construct into the TCRα locus. The PCR used the upstream forward primer used in the previous TCR integration analysis (SEQ ID NO: 1), while an upstream reverse primer specific for an MND insertion was used as the reverse primer (AGGGTCATTTCAGGTCCTT, SEQ ID NO: 23)

except for the positive control which used gRNA from an edited T cell and its respective reverse primer (SEQ ID NO: 2). As summarized in Table 14 and shown in FIG. 34, groups 11-18 demonstrated a 1 Kb amplified PCR band indicative of proper integration. Thus, NK cells were properly edited at the TCRα locus. Notably, PCR band intensity correlated with the percentage of cells expressing ZsGreen, i.e., samples with the highest percentage ZsGreen produced the brightest PCR band.

TABLE 14

Summary of NK Cell Editing

| Group | Program | RNP (Cas9/sgRNA, pmol/reaction) | DNA (ug/reaction) | D4 Flow Analysis % ZsGreen+ | D7 Flow Analysis % ZsGreen+ | D11 Flow Analysis % ZsGreen+ | Molecular Analysis: PCR Band Intensity (D11) |
|---|---|---|---|---|---|---|---|
| 11 | EN-138 | 100/600 | 75 | Not enough cells | 18.4 | 24.5 | +++ |
| 12 | EN-138 | 165/1000 | 75 | 28.3 | 32.8 | 34.3 | ++++ |
| 13 | EK-138 | 165/1000 | 150 | 11.8 | NP | NP | + |
| 14 | EK-100 | 100/600 | 75 | Not enough cells | NP | 45.2 | +++ |
| 15 | EK-100 | 165/1000 | 75 | Not enough cells | NP | 22.7 | ++ |
| 16 | EK-100 | 165/1000 | 150 | Not enough cells | NP | NP | + |
| 17 | FA-100 | 100/600 | 75 | Not enough cells | NP | NP | ++ |
| 18 | FA-100 | 165/1000 | 75 | 0 | NP | 6.14 | ++ |
| 19 | FA-100 | 165/1000 | 150 | Not enough cells | NP | NP | − |
| 20 | FA-100 | no RNPs | 150 | Not enough cells | 0 | Not enough cells | NP |

NP = not performed;
n = 1 for all groups

Example 25: Primary Cell Editing

Primary cells are edited following the procedures described above. The procedure, including but not limited alterations in the electroporation conditions and reagents, are adjusted depending on the exact primary cell to be edited. Primary cells include stem cells, human stem cells, embryonic stem cells, and immune cells. Examples of immune cells include, but are not limited to, B cells, T cells, monocytes, macrophages, dendritic cells, and natural killer cells.

ADDITIONAL EMBODIMENTS AND INCORPORATION OF REFERENCES

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A composition comprising a polynucleotide, wherein the polynucleotide comprises:
   a. first and second homology arms homologous to first and second target nucleic acid sequences;
   b. a TCR gene sequence positioned between the first and second homology arms;
   c. a first P2A-coding sequence positioned upstream of the TCR gene sequence and a second P2A-coding sequence positioned downstream of the TCR gene sequence, wherein the first and second P2A-coding sequences code for the same amino acid sequence that are codon-diverged relative to each other;
   d. a sequence coding for the amino acid sequence Gly Ser Gly positioned immediately upstream of the P2A-coding sequences; and
   e. a sequence coding for a Furin cleavage site positioned upstream of the second P2A-coding sequence.

2. The composition of claim 1, wherein the first and second homology arms of the polynucleotide are each from about 300 bases to about 2,000 bases in length.

3. The composition of claim 1, wherein the first and second homology arms of the polynucleotide are each about 600 bases to about 1,000 bases in length.

4. The composition of claim 1, wherein the polynucleotide further comprises a human growth hormone signal sequence positioned between the first P2A-coding sequence and the TCR gene sequence.

5. The composition of claim 1, wherein the polynucleotide further comprises a second TCR gene sequence positioned between the second P2A-coding sequence and the second homology arm.

6. The composition of claim 5, wherein the polynucleotide further comprises:
   a. a first human growth hormone signal sequence positioned between the first P2A-coding sequence and the first TCR gene sequence; and
   b. a second human growth hormone signal sequence positioned between the second P2A-coding sequence and the second TCR gene sequence,
   wherein the first and the second human growth hormone signal sequences are codon diverged relative to each other.

7. The composition of claim 1, wherein the polynucleotide further comprises an exogenous sequence of interest.

8. The composition of claim 7, wherein the exogenous sequence of interest encodes for a protein useful in autologous cell therapy.

9. The composition of claim 1, wherein the polynucleotide is a circular DNA.

10. The composition of claim 1, wherein the polynucleotide is a linear DNA.

11. The composition of claim 1, wherein the TCR gene sequence encodes for a TCR that recognizes a cancer antigen.

12. The composition of claim 11, wherein the cancer antigen is a neoantigen.

13. The composition of claim 11, wherein the cancer antigen is a patient specific neoantigen.

14. The composition of claim 1, wherein the TCR gene sequence is a patient specific TCR gene sequence.

15. The composition of claim 1, further comprising a nuclease.

16. The composition of claim 15, wherein the nuclease is a Clustered Regularly Interspaced Short Palindromic Repeats (CRISPR) family nuclease or derivative thereof.

17. The composition of claim 16, further comprising an sgRNA.

18. The composition of claim 15, wherein the nuclease targets an endogenous TCR locus.

19. The composition of claim 15, wherein the nuclease targets a TCR-alpha and a TCR-beta loci.

20. The composition of claim 1, wherein the first and second target nucleic acid sequences are positioned within an endogenous TCR locus.

21. The composition of claim 20, wherein the endogenous TCR locus is a TCR-alpha locus.

22. The composition of claim 1, wherein the polynucleotide is non-viral.

23. The composition of claim 1, wherein the polynucleotide is a gene therapy vector.

24. A composition comprising a polynucleotide, wherein the polynucleotide comprises:
   a. first and second homology arms homologous to first and second target nucleic acid sequences;
   b. a TCR gene sequence positioned between the first and second homology arms;
   c. a first P2A-coding sequence positioned upstream of the TCR gene sequence and a second P2A-coding sequence positioned downstream of the TCR gene sequence, wherein the first and second P2A-coding sequences code for the same amino acid sequence that are codon-diverged relative to each other;
   d. a sequence coding for a flexible linker positioned immediately upstream of the P2A-coding sequences; and
   e. a sequence coding for a protease cleavage sequence positioned upstream of the second P2A-coding sequence.

25. A composition comprising a circular polynucleotide, wherein the circular polynucleotide comprises:
   a. first and second homology arms homologous to first and second target nucleic acid sequences;
   b. a TCR gene sequence positioned between the first and second homology arms;

c. a first P2A-coding sequence positioned upstream of the TCR gene sequence and a second P2A-coding sequence positioned downstream of the TCR gene sequence, wherein the first and second P2A-coding sequences code for the same amino acid sequence that are codon-diverged relative to each other;
d. a sequence coding for the amino acid sequence Gly Ser Gly positioned immediately upstream of the P2A-coding sequences; and
e. a sequence coding for a Furin cleavage site positioned upstream of the second P2A-coding sequence.

\* \* \* \* \*